(12) United States Patent
Dai et al.

(10) Patent No.: US 9,501,621 B2
(45) Date of Patent: Nov. 22, 2016

(54) TREATMENT VALIDATION SYSTEMS AND METHODS

(71) Applicant: AMO Development, LLC, Sanata Ana, CA (US)

(72) Inventors: Guang-ming Dai, Fremont, CA (US); Anatoly Fabrikant, Fremont, CA (US); Dimitri Chernyak, Sunnyvale, CA (US); Jayesh Shah, Sunnyvale, CA (US)

(73) Assignee: AMO Development, LLC, Santa Ana, CA (US)

( * ) Notice: Subject to any disclaimer, the term of this patent is extended or adjusted under 35 U.S.C. 154(b) by 185 days.

(21) Appl. No.: 14/536,256

(22) Filed: Nov. 7, 2014

(65) Prior Publication Data

US 2015/0134316 A1   May 14, 2015

Related U.S. Application Data

(60) Provisional application No. 61/901,213, filed on Nov. 7, 2013.

(51) Int. Cl.
*A61B 3/00*   (2006.01)
*G06F 19/00*   (2011.01)

(52) U.S. Cl.
CPC ................ *G06F 19/3437* (2013.01)

(58) Field of Classification Search
USPC ....................................... 351/246
See application file for complete search history.

(56) References Cited

U.S. PATENT DOCUMENTS

| | | |
|---|---|---|
| 7,926,490 B2 | 4/2011 | Dai et al. |
| 8,409,178 B2 | 4/2013 | Dai et al. |
| 8,663,207 B2 | 3/2014 | Dai et al. |
| 2011/0166558 A1 | 7/2011 | Dai et al. |
| 2013/0190736 A1 | 7/2013 | Fabrikant et al. |
| 2014/0095137 A1 | 4/2014 | Dai et al. |

OTHER PUBLICATIONS

U.S. Appl. No. 14/453,068, filed Aug. 6, 2014 for Guang-ming Dai, et al., all pages.

*Primary Examiner* — Jack Dinh
(74) *Attorney, Agent, or Firm* — Abbott Medical Optics Inc.

(57) ABSTRACT

Treatment validation techniques include generating a modified treatment target from an original treatment target using a modification process, and comparing induced aberrations provided by the original and modified treatment targets, so as to verify the modified treatment target or the modification process. In some cases, a modification process may include a deconvolution process, a low pass filter process, a scaling process, or an adjustment process. The induced aberrations may include high order aberrations, such as spherical aberration.

17 Claims, 75 Drawing Sheets

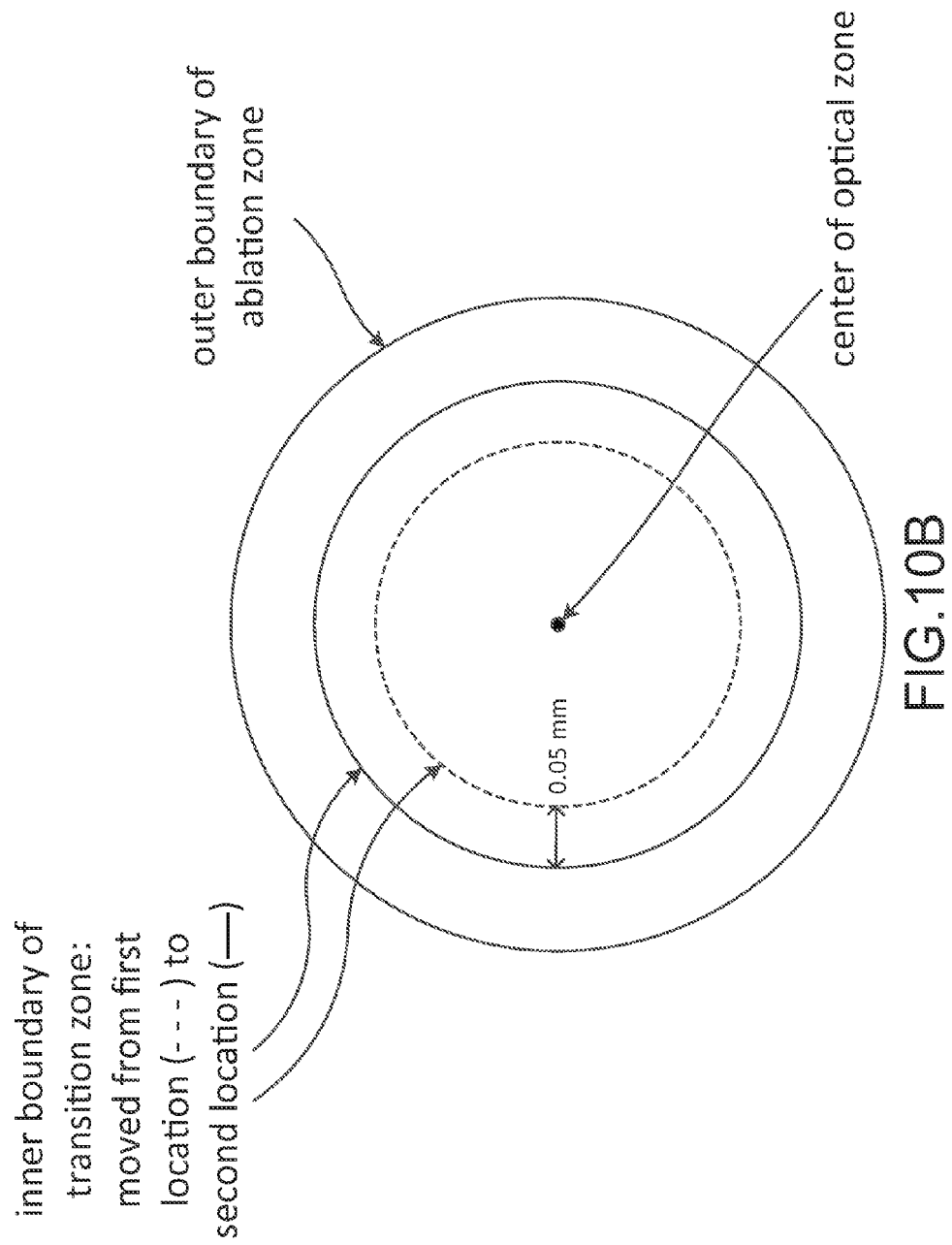

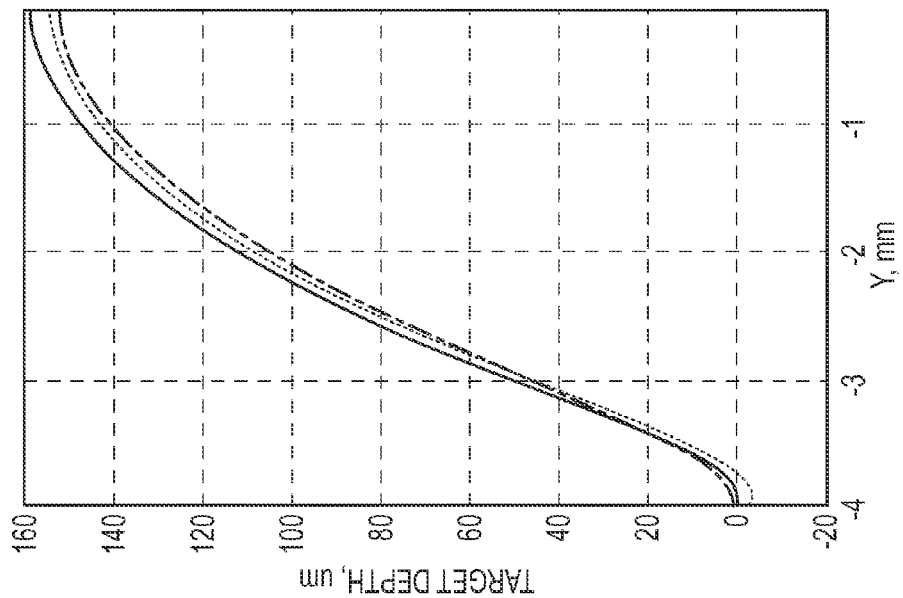
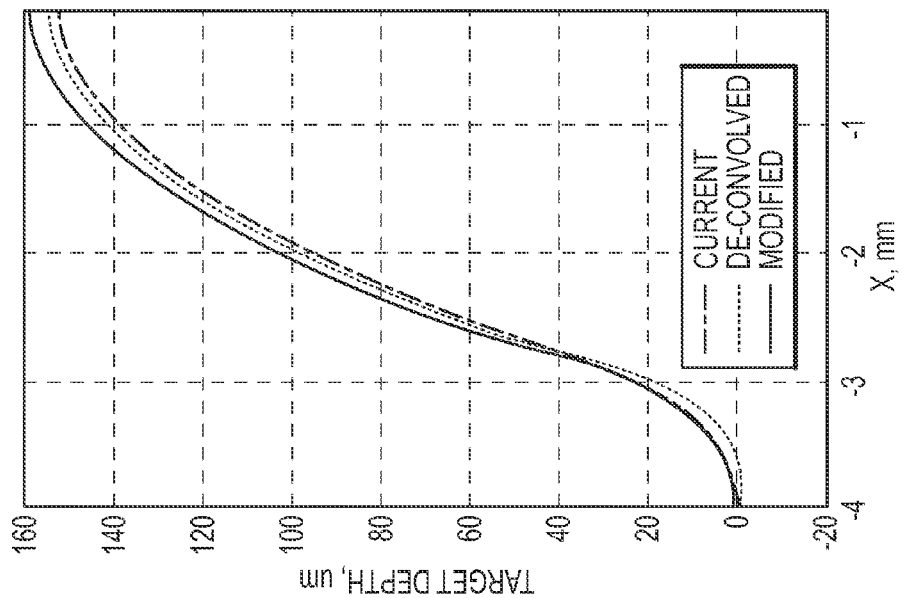

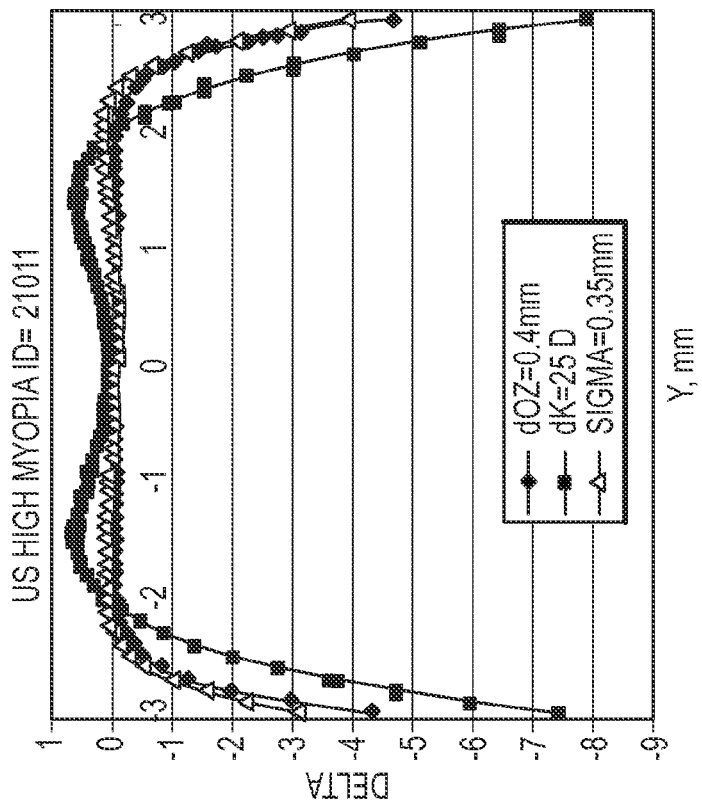
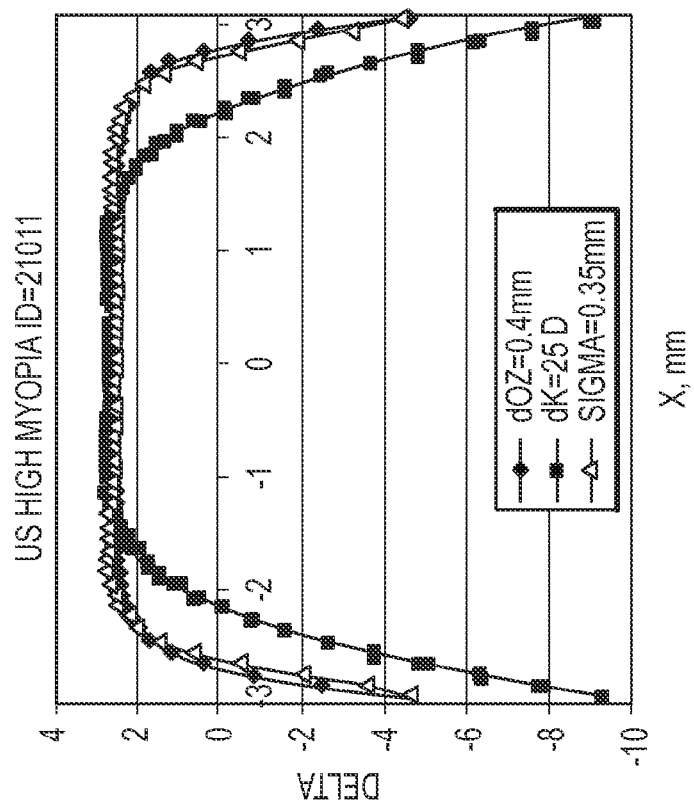
FIG. 20A
FIG. 20B

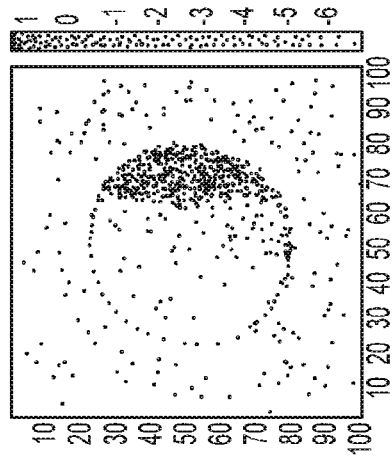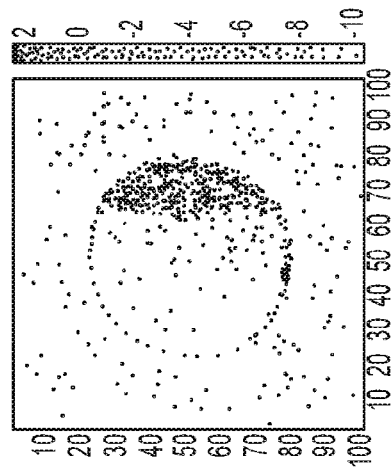
FIG.36A
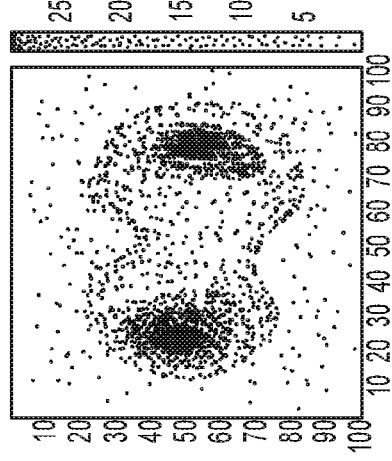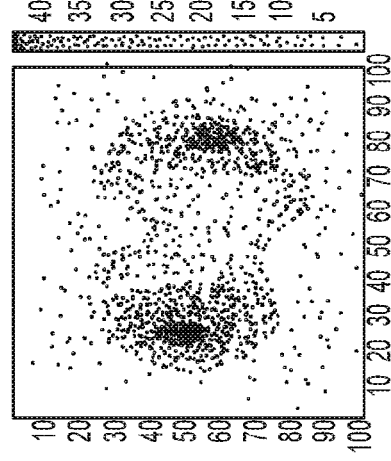
FIG.36B
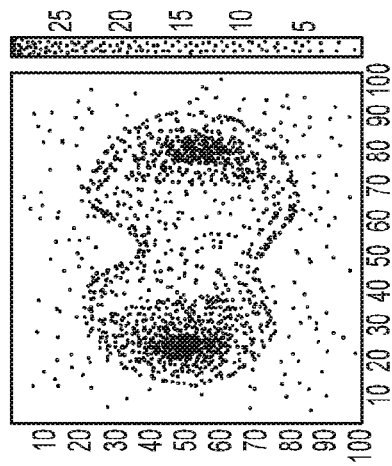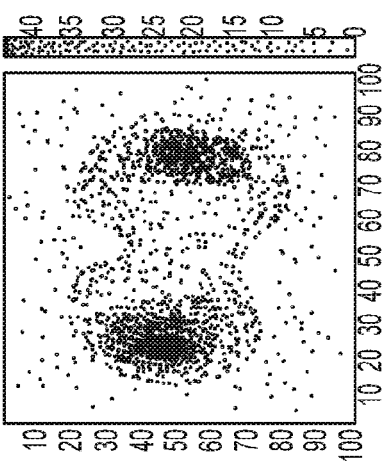

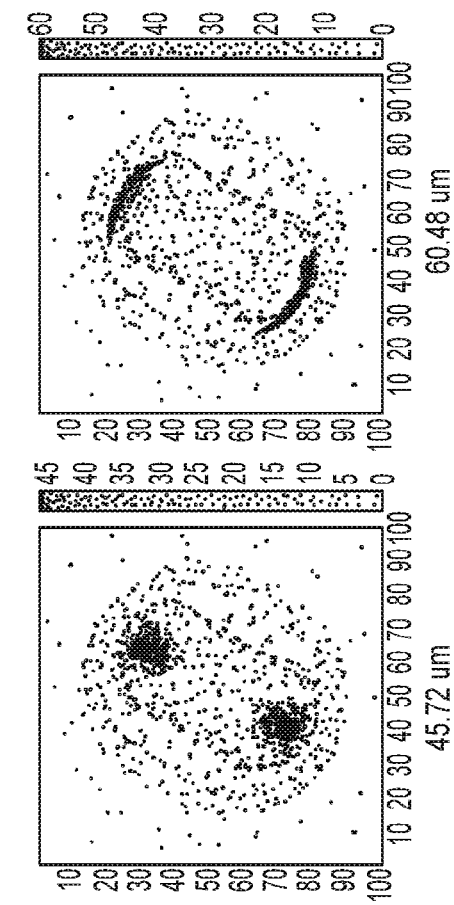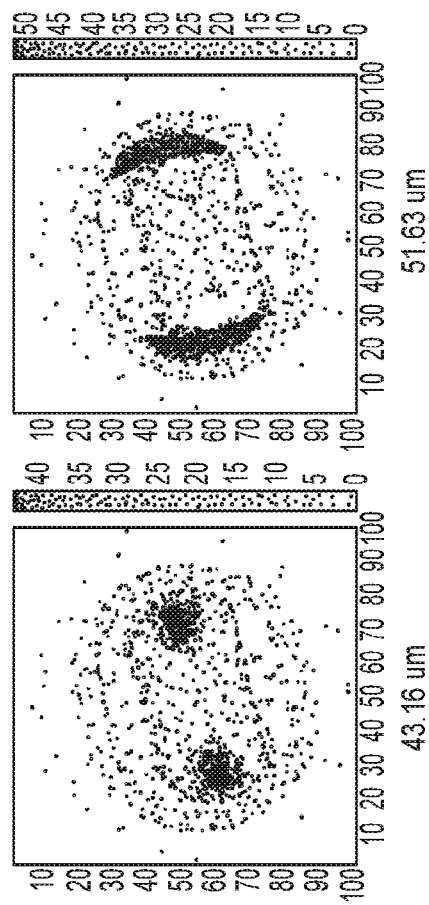
FIG. 39A
FIG. 39B

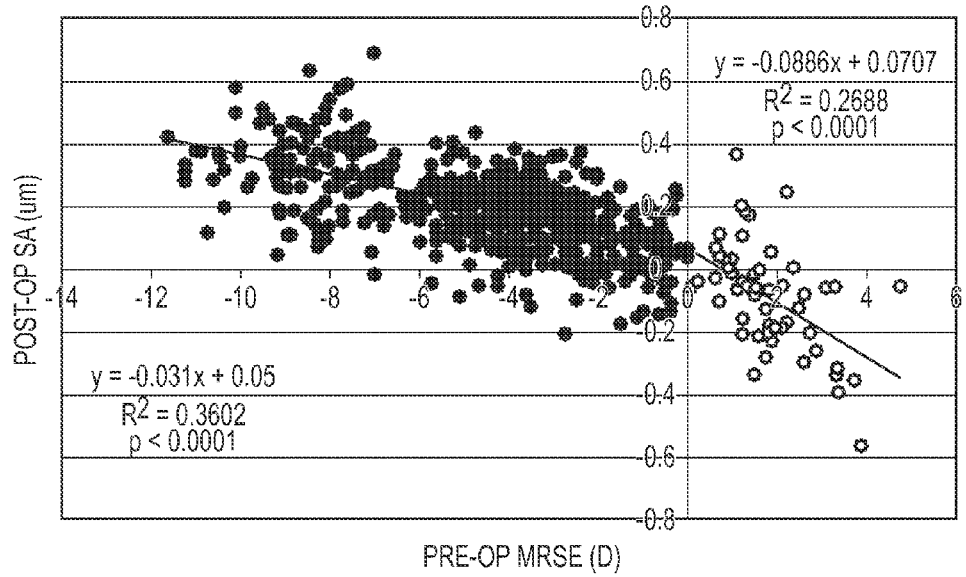
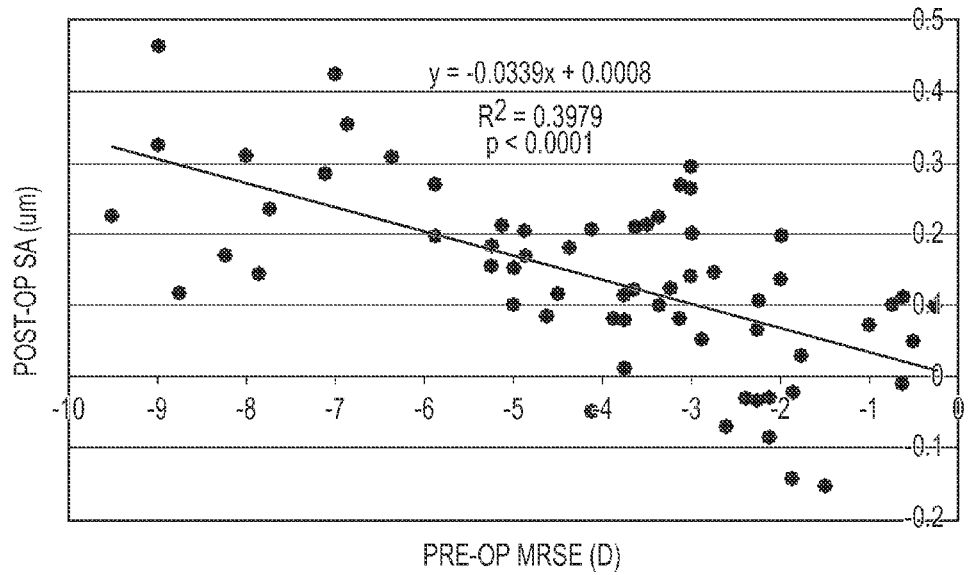
FIG.54

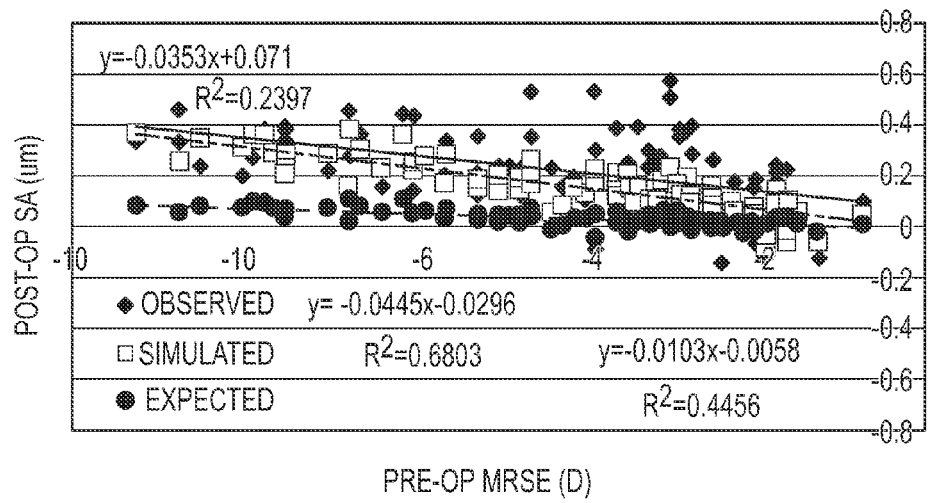
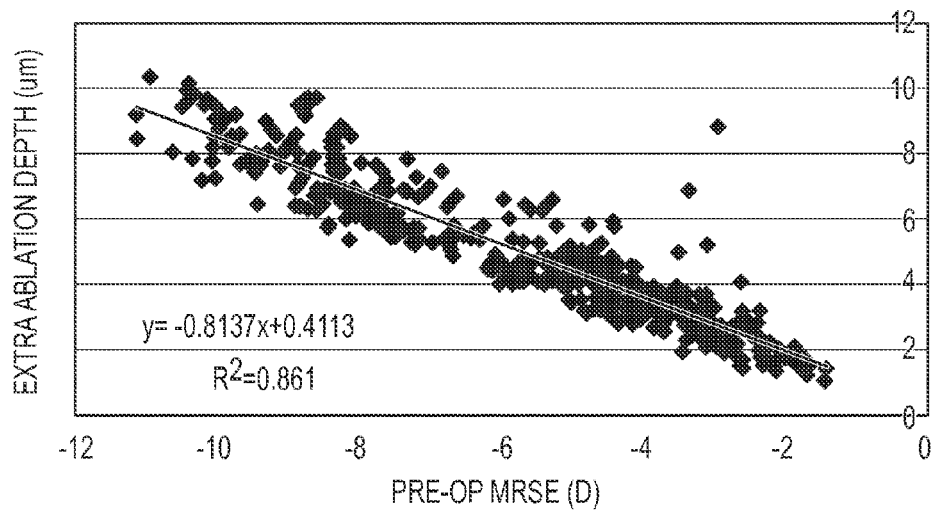
FIG.56

TREATMENT VALIDATION SYSTEMS AND METHODS

CROSS-REFERENCES TO RELATED APPLICATIONS

This application is a non-provisional of and claims the benefit of priority to U.S. Provisional Patent Application No. 61/901,216 filed Nov. 7, 2013. This application is related to U.S. Patent Application No. 61/708,815 filed Oct. 2, 2012, U.S. Patent Application No. 61/871,120 filed Aug. 28, 2013, U.S. patent application Ser. No. 14/044,650 filed Oct. 2, 2013, and U.S. patent application Ser. No. 14/453,068 filed Aug. 6, 2014. This application is also related to U.S. Pat. No. 7,926,490 issued Apr. 19, 2011, U.S. patent application Ser. No. 13/051,452 filed Mar. 18, 2011, and U.S. patent application Ser. No. 13/554,276 filed Jul. 20, 2012. Further, this application is related to U.S. Pat. No. 8,409,178 issued Apr. 2, 2013 and U.S. patent application Ser. No. 13/854,760 filed Apr. 1, 2013 (now U.S. Pat. No. 8,663,207 issued Mar. 4, 2014). The entire content of each of the above filings is incorporated herein by reference for all purposes.

BACKGROUND OF THE INVENTION

Embodiments of the present invention relate generally to the field of optical correction, and in particular encompass methods, devices, and systems for evaluating treatments intended for administration to patients presenting vision conditions.

In a typical refractive surgical procedure, aberrations of the patient's eye are examined with wavefront analysis or other measurement procedures. In turn, the measurement information can be used to generate a treatment for the patient. Laser eye surgery systems and other vision treatment techniques often involve the use of such treatments.

Although current and proposed treatment devices and methods may provide real benefits to patients in need thereof, still further advances would be desirable. For example, there continues to be a need for improved ablation systems and methods that accurately assess, verify, and validate treatments. Embodiments of the present invention provide solutions that address certain limitations which may be associated with known techniques, and hence provide answers to at least some of these outstanding needs.

BRIEF SUMMARY OF THE INVENTION

Embodiments of the present invention encompass systems and methods for validating or qualifying treatments for use in refractive surgery procedures. These techniques ensure that treatments are generated as intended for a particular patient.

Hence, embodiments of the present invention provide improvements in ablation control, laser, ablation profile generation, treatment generation, and process or software verification and validation. Relatedly, techniques for evaluating a treatment as described herein can be used to increase the safety of an ophthalmologic refractive surgery.

In some cases, embodiments of the present invention encompass systems and methods for treatment validation based on the preservation of low order aberrations. In some cases, embodiments of the present invention encompass systems and methods for treatment validation based on sphere-cylinder coupling. In some cases, embodiments of the present invention encompass systems and methods for treatment validation based on high order aberrations, such as the addition of spherical aberration with the use of deconvolution.

The post-operative induction of high-order aberrations (HOAs), especially spherical aberration (SA), remains an important issue for laser vision correction technology. It has been found that post-operative cornea remodeling is a significant root cause of SA induction. One main effect of the cornea remodeling involves the smoothing of epithelium at the anterior surface of the eye, where the epithelium tends to grow thicker and fill in the dips of the cornea surface as created by refractive surgery. Epithelial smoothing can result in regression following refractive surgery, and sometimes leads to induced high-order aberrations that are particularly strong for high myopia and hyperopia cases.

Certain techniques have been proposed for minimizing induced post-operative SA, including linear adjustment of the basis data and nomogram adjustments. Although such techniques can provide benefits to patients in need thereof, further improvements would be desirable. Embodiments of the present invention provide solutions to address such outstanding needs.

In a first aspect, embodiments of the present invention encompass methods of evaluating a treatment table for use in an ophthalmologic refractive surgery for a patient. Methods may include, for example, inputting a treatment table containing laser ablation instructions for treating the patient into a treatment instructions module, determining a simulated ablation for the patient based on the laser ablation instructions with a simulation ablation module, inputting a pupil dimension of the patient into a pupil dimension module, and determining an expected optical refraction for the patient based on the pupil dimension and the simulated ablation with an expected optical refraction module, where the expected optical refraction for the patient is dependent on a sphere ophthalmic term characterized by a set of second radial order polynomial terms, a cylinder ophthalmic term characterized by the set of second radial order polynomial terms, and an axis ophthalmic term characterized by the set of second radial order polynomial terms, and where the expected optical refraction profile is independent of a piston ophthalmic term characterized by a zero radial order polynomial term, an x-tilt ophthalmic term characterized by a set of first radial order polynomial terms, and a y-tilt ophthalmic term characterized by the set of first radial order polynomial terms. Methods may further include inputting an intended optical refraction for the patient into an intended refraction module, where the intended optical refraction for the patient is dependent on a sphere ophthalmic term, a cylinder ophthalmic term, and an axis ophthalmic term, and where the intended optical refraction profile is independent of a piston ophthalmic term, an x-tilt ophthalmic term, and a y-tilt ophthalmic term. Additionally, methods may include evaluating the treatment table by comparing the expected and intended optical refractions for the patient with a comparison module. In some cases, the set of second radial order polynomial terms includes a set of second radial order Zernike polynomial terms, the zero radial order polynomial term includes a zero radial order Zernike polynomial term, and the set of first radial order polynomial terms includes a set of first radial order Zernike polynomial terms. In some cases, the set of second radial order polynomial terms includes a set of second radial order Seidel power series terms, the zero radial order polynomial term includes a zero radial order Seidel power series term, and the set of first radial order polynomial terms includes a set of first radial order Seidel power series terms. Optionally, the expected optical refraction and the intended optical refraction each correspond to a common plane. In some instances, the expected optical refraction and the intended optical refraction each correspond to a corneal plane. In some instances, the pupil dimension of the patient corresponds to a wavefront diameter related to a wavescan of the patient. In some instances, the pupil dimensional of the patient comprises a pupil diameter that is equivalent to the wavefront diameter. According to some embodiments, the pupil dimension of the patient is a pupil diameter of about 4 mm. Methods may also include determining if a difference between the expected and intended optical refractions for the patient is within a pre-defined tolerance. Methods may also include qualifying the treatment table for use in the ophthalmologic refractive surgery for the patient if the difference between the expected and intended optical refractions is within the pre-defined tolerance. Some method may include disqualifying the treatment table for use in the ophthalmologic refractive surgery for the patient if the difference between the expected and intended optical refractions is not within the pre-defined tolerance.

In another aspect, embodiments of the present invention encompass systems for evaluating a treatment table for use in an ophthalmologic refractive surgery for a patient. Exemplary systems may include a treatment instructions module that accepts a treatment table containing laser ablation instructions for treating the patient, a simulation ablation module having a tangible medium embodying machine-readable code that determines a simulated ablation for the patient based on the laser ablation instructions, a pupil dimension module that accepts a pupil dimension of the patient, and an expected optical refraction module having a tangible medium embodying machine-readable code that determines an expected optical refraction for the patient based on the pupil dimension and the simulated ablation, where the expected optical refraction for the patient is dependent on a sphere ophthalmic term characterized by a set of second radial order polynomial terms, a cylinder ophthalmic term characterized by the set of second radial order polynomial terms, and an axis ophthalmic term characterized by the set of second radial order polynomial terms, and where the expected optical refraction profile is independent of a piston ophthalmic term characterized by a zero radial order polynomial term, an x-tilt ophthalmic term characterized by a set of first radial order polynomial terms, and a y-tilt ophthalmic term characterized by the set of first radial order polynomial terms. Systems may further include an intended refraction module that accepts an intended optical refraction for the patient, where the intended optical refraction for the patient is dependent on a sphere ophthalmic term, a cylinder ophthalmic term, and an axis ophthalmic term, and where the intended optical refraction profile is independent of a piston ophthalmic term, an x-tilt ophthalmic term, and a y-tilt ophthalmic term. Additionally, systems may include a comparison module having a tangible medium embodying machine-readable code that evaluates the treatment table by comparing the expected and intended optical refractions for the patient. In some system embodiments, the set of second radial order polynomial terms includes a set of second radial order Zernike polynomial terms, the zero radial order polynomial term includes a zero radial order Zernike polynomial term, and the set of first radial order polynomial terms includes a set of first radial order Zernike polynomial terms. In some systems, the expected optical refraction and the intended optical refraction each correspond to a common plane. In some systems, the expected optical refraction and the intended optical refraction each correspond to a corneal plane. Exemplary systems may also include a validation module having a tangible medium embodying machine-readable code that determines if a difference between the expected and intended optical refractions for the patient is within a pre-defined tolerance, and a qualification module having a tangible medium embodying machine-readable code that qualifies the treatment table for use in the ophthalmologic refractive surgery for the patient if the difference between the expected and intended optical refractions is within the pre-defined tolerance.

In another aspect, embodiments of the present invention encompass a computer program product embodied on a tangible computer readable medium that includes computer code for inputting a treatment table containing laser ablation instructions for treating the patient, computer code for determining a simulated ablation for the patient based on the laser ablation instructions, computer code for inputting a pupil dimension of the patient, and computer code for determining an expected optical refraction for the patient based on the pupil dimension and the simulated ablation, where the expected optical refraction for the patient is dependent on a sphere ophthalmic term characterized by a set of second radial order polynomial terms, a cylinder ophthalmic term characterized by the set of second radial order polynomial terms, and an axis ophthalmic term characterized by the set of second radial order polynomial terms, and where the expected optical refraction profile is independent of a piston ophthalmic term characterized by a zero radial order polynomial term, an x-tilt ophthalmic term characterized by a set of first radial order polynomial terms, and a y-tilt ophthalmic term characterized by the set of first radial order polynomial terms. Computer program products may also include computer code for inputting an intended optical refraction for the patient, where the intended optical refraction for the patient is dependent on a sphere ophthalmic term, a cylinder ophthalmic term, and an axis ophthalmic term, and where the intended optical refraction profile is independent of a piston ophthalmic term, an x-tilt ophthalmic term, and a y-tilt ophthalmic term, and computer code for evaluating the treatment table by comparing the expected and intended optical refractions for the patient with a comparison module. For some computer program products, the set of second radial order polynomial terms includes a set of second radial order Zernike polynomial terms, the zero radial order polynomial term includes a zero radial order Zernike polynomial term, and the set of first radial order polynomial terms includes a set of first radial order Zernike polynomial terms. For some computer program products, the expected optical refraction and the intended optical refraction each correspond to a common plane. For some computer program products, the expected optical refraction and the intended optical refraction each correspond to a corneal plane. Exemplary computer program products may also include computer code for determining if a difference between the expected and intended optical refractions for the patient is within a pre-defined tolerance, and computer code for qualifying the treatment table for use in the ophthalmologic refractive surgery for the patient if the difference between the expected and intended optical refractions is within the pre-defined tolerance.

It has been discovered that deconvolution techniques based on a cornea smoothing model can be used to obtain an ablation target or treatment shape that induces little or no post-operative SA. In some instances, these ablation targets or treatment shapes can provide a post-operative SA that is equal to or below a naturally occurring amount of SA.

Hence, embodiments of the present invention encompass systems and methods for obtaining a modified ablation target that is capable of eliminating, reducing, or minimizing a systematic trend in post-operatively induced spherical aberration. In some cases, the modification of the target shape introduces only a small increase in the required depth for the ablation. Hence, such techniques are helpful in providing safe and effective treatments. In some cases, the modification of the target shape may change the peripheral cornea profile, which can affect the SA without changing the central refractive power.

In some instances, embodiments encompass techniques for determining a vision treatment for an eye of a patient, which may include obtaining an original target profile for the eye of the patient, obtaining a spatial domain kernel filter (e.g. based on an inverse Fourier transform of a Fourier domain noise filter), convolving the original target profile with the spatial domain kernel filter, and determining the vision treatment based on the convolved profile.

In one aspect, embodiments of the present invention encompass systems and methods for determining a vision treatment for an eye of a patient. Exemplary techniques may include, for example, receiving, at an input, an original target profile for the eye of the patient, and convolving the original target profile with the spatial domain kernel filter. The spatial domain kernel filter can be based on an inverse Fourier transform of a Fourier domain noise filter. Techniques may also include determining the vision treatment based on the convolved profile. Optionally, techniques may include administering the treatment to the patient. In some instances, the Fourier domain noise filter is based on a conjugate of a Fourier domain complex matrix. In some instances, the Fourier domain noise filter is based on a modulus of a Fourier domain complex matrix. In some instances, the Fourier domain noise filter is based on a conjugate of a Fourier domain complex matrix and a modulus of the Fourier domain complex matrix. According to some embodiments, the Fourier domain noise filter is characterized by fraction having a numerator comprising a conjugate of a Fourier domain complex matrix and a denominator comprising a modulus of the Fourier domain complex matrix. In some cases, the Fourier domain complex matrix is characterized by the formula $$K(k_x, k_y) = \frac{1}{1 + \frac{\sigma^2(k_x^2 + k_y^2)}{(0.5dL)^2}}$$

where $\sigma$ represents a diffusion coefficient, $k_x$ and $k_y$ represent frequency domain variables, and dL represents a mesh size. In some cases, $\sigma$ has a value of 0.35 mm and dL has a value of 0.1 mm. Optionally, $\sigma$ may have a value within a range from about 0.2 mm to about 0.5 mm. In some cases, $\sigma$ may have a value within a range from about 0.33 mm to about 0.4 mm. Optionally, the denominator can be characterized by the expression $|K(k_x, k_y)|^n$, where n is an integer having a value of 2 or more. In some instances, the denominator can be characterized by the expression $[|K(k_x, k_y)|^n + SNR^2]$ where n is an integer having a value of 2 or more and SNR represents a signal to noise ratio value. In some instances, the convolved profile includes a transition zone radius, and a method may further include zeroing the convolved profile at locations outside of the transition zone radius. In some instances, the original target profile may include an original refractive spherical equivalent value within a 4 mm diameter area, and the convolved target profile may include a target refractive spherical equivalent value within a 4 mm diameter area. Optionally, the method may further include scaling the original refractive spherical equivalent with the target refractive spherical equivalent value. Some methods may also include elevating the convolved profile so that a lowest point on the convolved profile is zero or greater. In some instances, a convolved profile includes a transition zone radius, and methods may include applying a damping multiplier at or near the transition zone radius. In some instances, the target shape includes an optical zone having a periphery, and the convolution effects a change in the target shape near the periphery of the optical zone.

In another aspect, embodiments of the present invention encompass systems for determining a vision treatment for an eye of a patient. Exemplary systems may include an input that receives an original target profile for the eye of the patient, and a convolution module that convolves the original target profile with a spatial domain kernel filter. The spatial domain kernel filter can be based on an inverse Fourier transform of a Fourier domain noise filter. Systems may also include a treatment generation or determination module that determines the vision treatment based on the convolved profile. In some instances, the Fourier domain noise filter is based on a conjugate of a Fourier domain complex matrix. In some instances, the Fourier domain noise filter is based on a modulus of a Fourier domain complex matrix.

In still another aspect, embodiments of the present invention encompass computer program products for determining a vision treatment for an eye of a patient. An exemplary computer program product may be embodied on a non-transitory tangible computer readable medium, and may include computer code for receiving an original target profile for the eye of the patient, computer code for convolving the original target profile with a spatial domain kernel filter, and computer code for determining the vision treatment based on the convolved profile. The spatial domain kernel filter may be based on an inverse Fourier transform of a Fourier domain noise filter.

In one aspect, embodiments of the present invention encompass systems and methods for determining a vision treatment for an eye of a patient. Exemplary methods include receiving, at an input, an original target profile for the eye of the patient, and obtaining a deconvolved target profile based on the original target profile and a low pass filter. In some cases, the low pass filter is an optimized linear filter. Methods may also include obtaining a scale factor, where the scale factor is based on a low order refraction measure of a test eye population and a low order refraction measure of a convolved test eye population profile. In some cases, the convolved test eye population profile is based on a convolution of the test eye population profile. Methods may also include determining a scaled target profile based on the deconvolved target profile and the scale factor, and determining the vision treatment based on the scaled target profile. In some cases, methods may include validating the scaled target profile. In some cases, the scale factor has a value within a range from about 0.4 to about 0.8. In some cases, the scale factor has a value of about 0.7489. In some cases, the low order refraction measure of the test eye population profile includes a first manifest refraction spherical equivalent measure and the low order refraction measure of the convolved test eye population profile includes a second manifest refraction spherical equivalent measure. In some cases, the first manifest refraction spherical equivalent measure is a 4 mm refraction measure and the second manifest refraction spherical equivalent measure is a 4 mm refraction measure.

In another aspect, embodiments of the present invention encompass methods for determining a vision treatment for an eye of a patient, where exemplary methods include receiving, at an input, an original target profile for the eye of the patient, determining a first low order refraction measure based on the original target profile, obtaining a deconvolved target profile based on the original target profile and a low pass filter, determining a second low order refraction measure based on the deconvolved target profile, determining a scale factor based on a comparison between the first and second low order refraction measures, determining a scaled target profile based on the deconvolved target profile and the scale factor, and determining the vision treatment based on the scaled target profile. According to some embodiments, methods may include validating the scaled target profile. In some embodiments, the first low order refraction measure includes a first manifest refraction spherical equivalent measure and the second low order refraction measure includes a second manifest refraction spherical equivalent measure. In some embodiments, the first manifest refraction spherical equivalent measure is a 4 mm refraction measure and the second manifest refraction spherical equivalent measure is a 4 mm refraction measure. In some embodiments, the first low order refraction measure includes a first sphere measure and the second low order refraction measure includes a second sphere measure. In some embodiments, the first low order refraction measure includes a first cylinder measure and the second low order refraction measure includes a second cylinder measure.

In still another aspect, embodiments of the present invention encompass methods of determining a vision treatment for an eye of a patient that include receiving, at an input, an original target profile for the eye of the patient, obtaining a first healed profile based on the original target profile, obtaining a deconvolved target profile based on the original target profile and a low pass filter, obtaining a second healed profile based on the deconvolved target profile, determining a first low order refraction measure based on the first healed profile, determining a second low order refraction measure based on the second healed profile, determining a scale factor based on a comparison between the first and second low order refraction measures, determining a scaled target profile based on the deconvolved target profile and the scale factor, and determining the vision treatment based on the scaled target profile. According to some embodiments, methods may include validating the scaled target profile. In some instances, the first low order refraction measure includes a first manifest refraction spherical equivalent measure and the second low order refraction measure includes a second manifest refraction spherical equivalent measure. In some instances, the first manifest refraction spherical equivalent measure is a 4 mm refraction measure and the second manifest refraction spherical equivalent measure is a 4 mm refraction measure. In some instances, the first low order refraction measure includes a first sphere measure and the second low order refraction measure includes a second sphere measure. In some instances, the first low order refraction measure includes a first cylinder measure and the second low order refraction measure includes a second cylinder measure.

In yet another aspect, embodiments of the present invention encompass methods of determining a vision treatment for an eye of a patient that include receiving, at an input, an original target profile for the eye of the patient, and obtaining a deconvolved target profile based on the original target profile and a low pass filter. Some methods may include obtaining a scale factor, where the scale factor is based on a low order refraction measure of a test eye population and a low order refraction measure of a convolved test eye population profile. In some cases, the convolved test eye population profile is based on a convolution of the test eye population profile. Methods may also include determining a scaled target profile based on the deconvolved target profile and the scale factor, adjusting a sphere parameter of the scaled target profile based on a pre-operative cylinder measurement of the eye of the patient, and determining the vision treatment based on the adjusted target profile. According to some embodiments, methods may include validating the scaled target profile.

In still yet another aspect, embodiments of the present invention encompass methods of determining a vision treatment for an eye of a patient that include receiving, at an input, a pre-operative cylinder value for the eye of the patient, and determining the vision treatment for the eye, where the vision treatment includes a sphere value that is based on the pre-operative cylinder value. In some cases, the pre-operative cylinder value is a manifest refraction measurement. In some cases, the pre-operative cylinder value is a wavefront refraction measurement. In some cases, the sphere value of the vision treatment is determined based on the formula $S=-0.2\,C-0.25$, where S is the sphere value and C is the pre-operative cylinder value.

In another aspect, embodiments of the present invention encompass methods of determining a vision treatment for an eye of a patient that include receiving, at an input, an original target profile for the eye of the patient, and obtaining a deconvolved target profile based on the original target profile and a low pass filter. In some cases, the low pass filter can be an optimized linear filter. Methods may also include obtaining a scale factor, where the scale factor is based on a high order aberration measure of a test eye population and a high order aberration measure of a convolved test eye population profile. The convolved test eye population profile can be based on a convolution of the test eye population profile. Methods may also include determining a scaled target profile based on the deconvolved target profile and the scale factor, and adjusting a spherical aberration parameter of the scaled target profile based on a pre-operative spherical equivalent measurement (or a pre-operative sphere measurement) of the eye of the patient, and determining the vision treatment based on the adjusted target profile. According to some embodiments, methods may include validating the adjusted target profile.

For a fuller understanding of the nature and advantages of the present invention, reference should be had to the ensuing detailed description taken in conjunction with the accompanying drawings.

BRIEF DESCRIPTION OF THE DRAWINGS

FIG. 10A shows post-operative values and FIG. 10B shows aspects of optical and transition zones according to embodiments of the present invention.

FIGS. 16C and 16D illustrate aspects of ablation profile modifications according to embodiments of the present invention.

FIGS. 20A and 20B show aspects of differences between modified targets and original targets according to embodiments of the present invention.

FIGS. 36A, 36B, and 36C depict aspects of expected and inversed convolved targets according to embodiments of the present invention.

FIGS. 39A, 39B, and 39C show aspects of vision condition cases according to embodiments of the present invention.

FIG. 54 depicts aspects of treatment validation systems and methods according to embodiments of the present invention.

FIG. 56 depicts aspects of treatment validation systems and methods according to embodiments of the present invention.

DETAILED DESCRIPTION OF THE INVENTION

Figure 1:
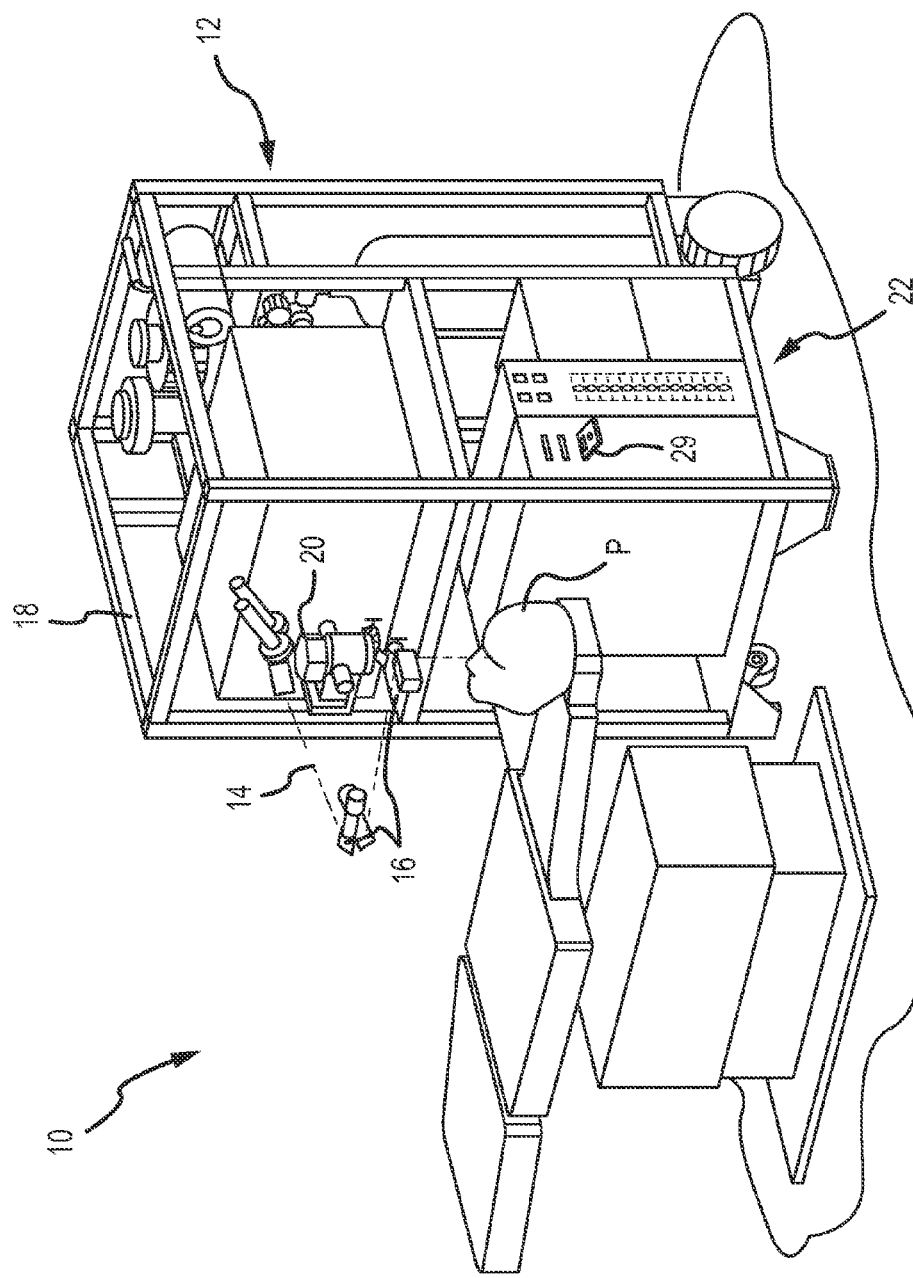
FIG. 1 illustrates a laser ablation system according to an embodiment of the present invention.

Embodiments of the present invention encompass systems and methods for treatment validation based on the preservation of low order aberrations. In some cases, a vision treatment for an eye of a patient can be determined by receiving an original target profile for the eye of the patient, obtaining a deconvolved target profile based on the original target profile and a low pass filter, such as an optimized linear filter, determining a scaled target profile based on the deconvolved target profile and a scale factor, and determining the vision treatment based on the scaled target profile. The scale factor can be based on a low order refraction measure of a test eye population and a low order refraction measure of a convolved test eye population profile, and the convolved test eye population profile can be based on a convolution of the test eye population profile. In some cases, a vision treatment can be determined by receiving an original target profile for the eye of the patient, determining a first low order refraction measure based on the original target profile, obtaining a deconvolved target profile based on the original target profile and a low pass filter, determining a second low order refraction measure based on the deconvolved target profile, determining a scale factor based on a comparison between the first and second low order refraction measures, determining a scaled target profile based on the deconvolved target profile and the scale facto, and determining the vision treatment based on the scaled target profile. In some cases, a vision treatment can be determined by receiving an original target profile for the eye of the patient, obtaining a first healed profile based on the original target profile, obtaining a deconvolved target profile based on the original target profile and a low pass filter, obtaining a second healed profile based on the deconvolved target profile, determining a first low order refraction measure based on the first healed profile, determining a second low order refraction measure based on the second healed profile, determining a scale factor based on a comparison between the first and second low order refraction measures, determining a scaled target profile based on the deconvolved target profile and the scale factor, and determining the vision treatment based on the scaled target profile.

Embodiments of the present invention also emcompass systems and methods for treatment validation based on sphere-cylinder coupling. For example, a vision treatment can be determined by receiving an original target profile for the eye of the patient, obtaining a deconvolved target profile based on the original target profile and a low pass filter, determining a scaled target profile based on the deconvolved target profile and a scale factor, adjusting a sphere parameter of the scaled target profile based on a pre-operative cylinder measurement of the eye of the patient, and determining the vision treatment based on the adjusted target profile. In some cases, the scale factor can be based on a low order refraction measure of a test eye population and a low order refraction measure of a convolved test eye population profile, and the convolved test eye population profile can be based on a convolution of the test eye population profile. In another example, a vision treatment ca be determined by receiving a pre-operative cylinder value for the eye of the patient, and determining the vision treatment for the eye, such that the vision treatment includes a sphere value that is based on the pre-operative cylinder value.

Embodiments of the present invention encompass further systems and methods for treatment validation based on techniques involving high order aberrations, such as spherical aberration. For example, a vision treatment can be determined by receiving an original target profile for the eye of the patient, obtaining a deconvolved target profile based on the original target profile and a low pass filter, such as an optimized linear filter, determining a scaled target profile based on the deconvolved target profile and a scale factor, adjusting a spherical aberration parameter of the scaled target profile based on a pre-operative sphere (or a pre-operative spherical equivalent) measurement of the eye of the patient, and determining the vision treatment based on the adjusted target profile. In some cases, the scale factor can be based on a high order aberration measure of a test eye population and a high order aberration measure of a convolved test eye population profile, and the convolved test eye population profile can be based on a convolution of the test eye population profile.

Embodiments of the present invention include systems and methods which use treatment table content (e.g. laser pulse instructions) to derive or generate an expected optical refraction, and compare that expected refraction with an intended refraction for the patient Typically, optical refractions include sphere, cylinder, and axis components. In addition to the treatment table laser instructions, the derived expected refraction may also take into account the treatment or vertex plane, for example to ensure that the derived refraction plane matches the intended refraction plane. Further, embodiments of the present invention provide systems and methods for treatment table validation that implement a separate, independent set of code to ensure that a planned refraction in the treatment table is consistent with the desired refraction. Thus, an exemplary method may involve inputting an intended refraction for a patient, inputting a treatment table containing laser ablation instructions, calculating an expected optical refraction based on the treatment table and optionally a vertex or treatment plane parameter, comparing the expected optical refraction with the intended refraction, and evaluating the treatment table based on the comparison of the expected optical refraction with the input refraction. If the expected optical refraction deviates significantly from the intended refraction, the treatment table will be disqualified.

In some cases, an intended optical refraction is dependent upon ophthalmic sphere, cylinder, and axis terms that are not based on Zernike values, whereas an expected optical refraction is dependent on sphere, cylinder, and axis terms that are based on Zernike values. Intended optical refractions, such as those dependent on ophthalmic sphere, cylinder, and axis terms, can be related to Zernikes (e.g. wavefront-guided), or physician input (e.g. VSS Refractive™ technique, non-wavefront guided, or manifest refraction). Optionally, wavefront-guided or nonwavefront-guided data can be used on conjunction with a physician adjustment.

Embodiments of the present invention can be readily adapted for use with existing laser systems and other optical treatment devices. Although system, software, and method embodiments of the present invention are described primarily in the context of a laser eye surgery system, it should be understood that embodiments of the present invention may be adapted for use in or in combination with alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom preformed lenses, intraocular lenses, custom contact lenses, custom corneal implants, and the like, which can be configured to treat or ameliorate any of a variety of vision conditions in a particular patient based on their unique ocular characteristics or anatomy. Additionally, the modified ablation target or target shape may be implemented via other non-ablative laser therapies, such as laser-incised custom lenticule shapes and subsequent extraction and laser-based corneal incision patterns.

Exemplary systems and methods disclosed herein can be implemented via a variety of ophthalmic devices or solutions. For example, treatment techniques may be used for any of a variety of surgery modalities, including excimer laser surgery, femtosecond surgery, and the like. A variety of forms of lasers and laser energy can be used to effect a correction or treatment, including infrared lasers, ultraviolet lasers, femtosecond lasers, wavelength multiplied solid-state lasers, and the like. By way of non limiting example, ophthalmic corrections can involve a cornea or lens reshaping procedure, such as, for example using a picosecond or femtosecond laser. Laser ablation procedures can remove a targeted amount stroma of a cornea to change a cornea's contour and adjust for aberrations. In some cases, a treatment protocol can involve the delivery of a series of discrete pulses of laser light energy, with a total shape and amount of tissue removed being determined by a shape, size, location, and/or number of laser energy pulses impinging on or focused within a cornea. In some cases, a surgical laser, such as a non-ultraviolet, ultra-short pulsed laser that emits radiation with pulse durations as short as nanoseconds and femtoseconds (e.g., a femtosecond laser, or a picosecond laser) can be used to treat the eye of a patient. Other pulse widths may be suitable as well. The laser systems can be configured to deliver near infrared light. Other wavelengths may be used as well. The laser systems can be configured to deliver laser light focused at a focus depth (e.g. within corneal or other ophthalmologic tissue) which may be controlled by the system. Laser surgery with ultra-short pulse lasers such as femtosecond lasers can be used to treat the eye. These pulsed lasers can make very accurate incisions of the eye and can be used in many ways to treat the eye. Additional types of incisions that can be performed with the short pulse lasers include incisions for paracentesis, limbal relaxing incisions, and refractive incisions to shape the cornea, for example.

In some cases, vision treatments can include focusing femtosecond laser energy within the stroma so as to ablate a volume of intrastromal tissue. By scanning the focal spot within an appropriate volume of the stromal tissue, it is possible to vaporize the volume so as to achieve a desired refractive alteration. Hence, embodiments of the present invention encompass laser surgical techniques that involve femtosecond laser photodisruption or photoalteration treatments. In some cases, a femtosecond laser can be used to perform the photodisruption, thus providing an easy, precise, and effective approach to refractive surgery According to some embodiments, a femtosecond laser (or other laser) of the optical system can be used to incise the cornea or to cut a flap. A femtosecond laser may be used to make arcuate or other incisions in the cornea, which incisions may be customized, intrastromal, stable, predictable, and the like. Likewise, corneal entry incisions may be made, which are custom, multi-plane, and self-sealing.

Pulsed laser beams include bursts or pulses of light. Pulsed lasers, such as non-ultraviolet, ultra-short pulsed lasers with pulse durations measured in the nanoseconds to femtoseconds range, can be used in ophthalmic surgical procedures as disclosed herein. For example, a pulsed laser beam can be focused onto a desired area of ophthalmologic material or tissue, such as the cornea, the capsular bag, or the lens of the eye, to photoalter the material in this area and, in some instances, the associated peripheral area. Examples of photoalteration of the material include, but are not necessarily limited to, chemical and physical alterations, chemical and physical breakdown, disintegration, ablation, photodisruption, vaporization, a the like. Exemplary treatment systems can include a focusing mechanism (e.g. lens) and/or a scanning mechanism so as to guide or direct a focus of femtosecond energy along a path within the patient's eye.

In some instances, these techniques can be carried out in conjunction with treatments provided by any of a variety of laser devices, including without limitation the WaveScan® System and the STAR S4® Excimer Laser System both by Abbott Medical Optics Inc., the WaveLight® Allegretto Wave® Eye-Q laser, the Schwind Amaris™ lasers, the 217P excimer workstation by Technolas PerfectVision GmbH, the Mel 80™ laser by Carl Zeiss Meditec, Inc., and the like. In some cases, embodiments provide techniques for using laser basis data during refractive surgery treatment procedures which can be implemented in such laser devices.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with an input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
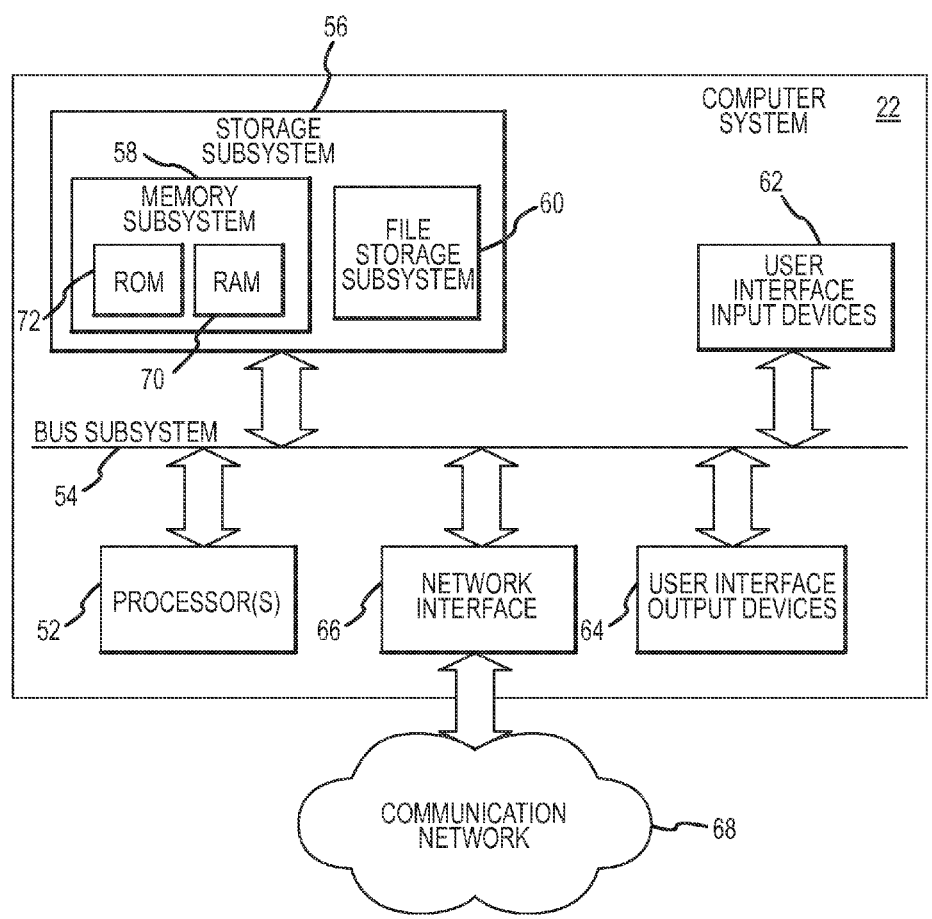
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
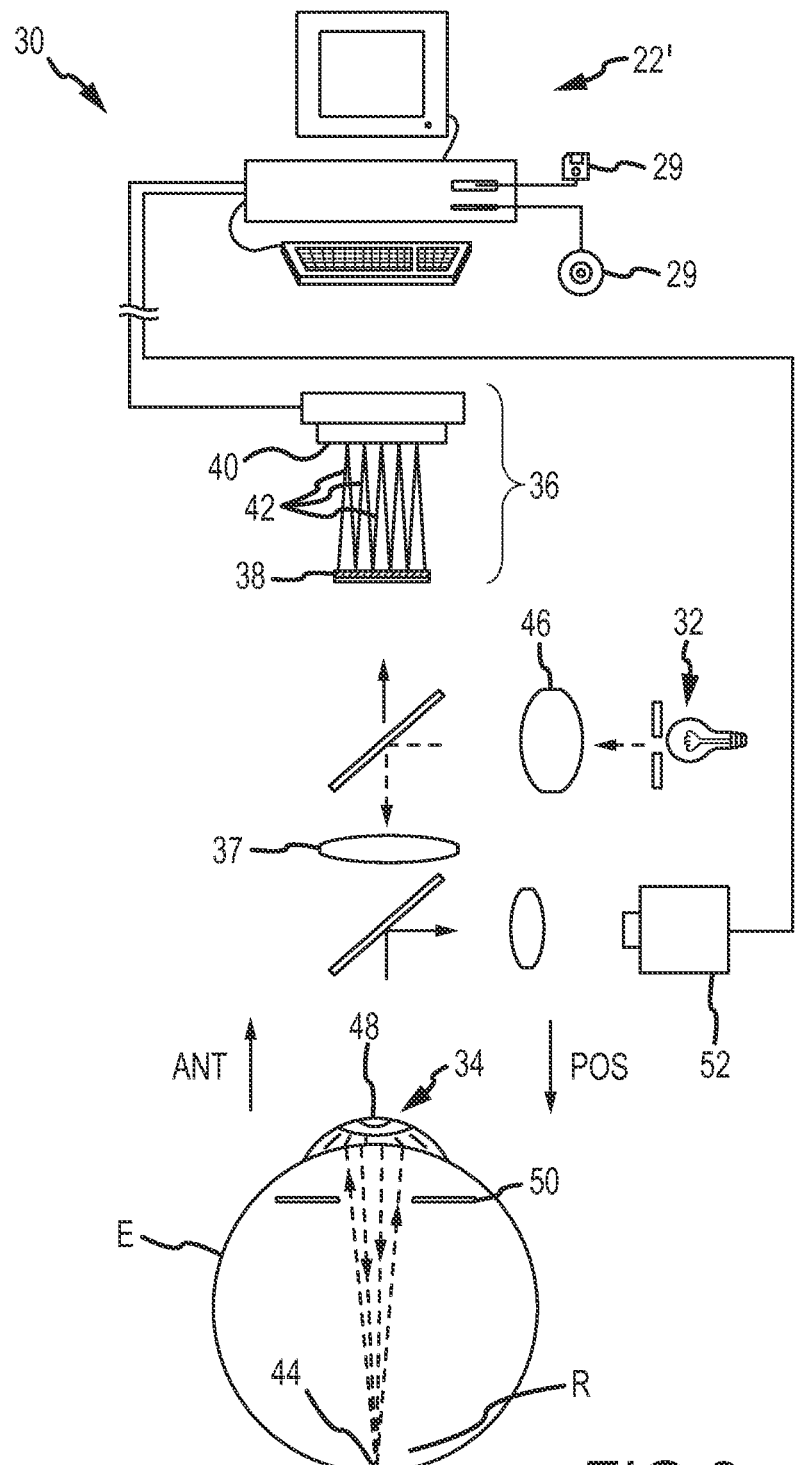
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
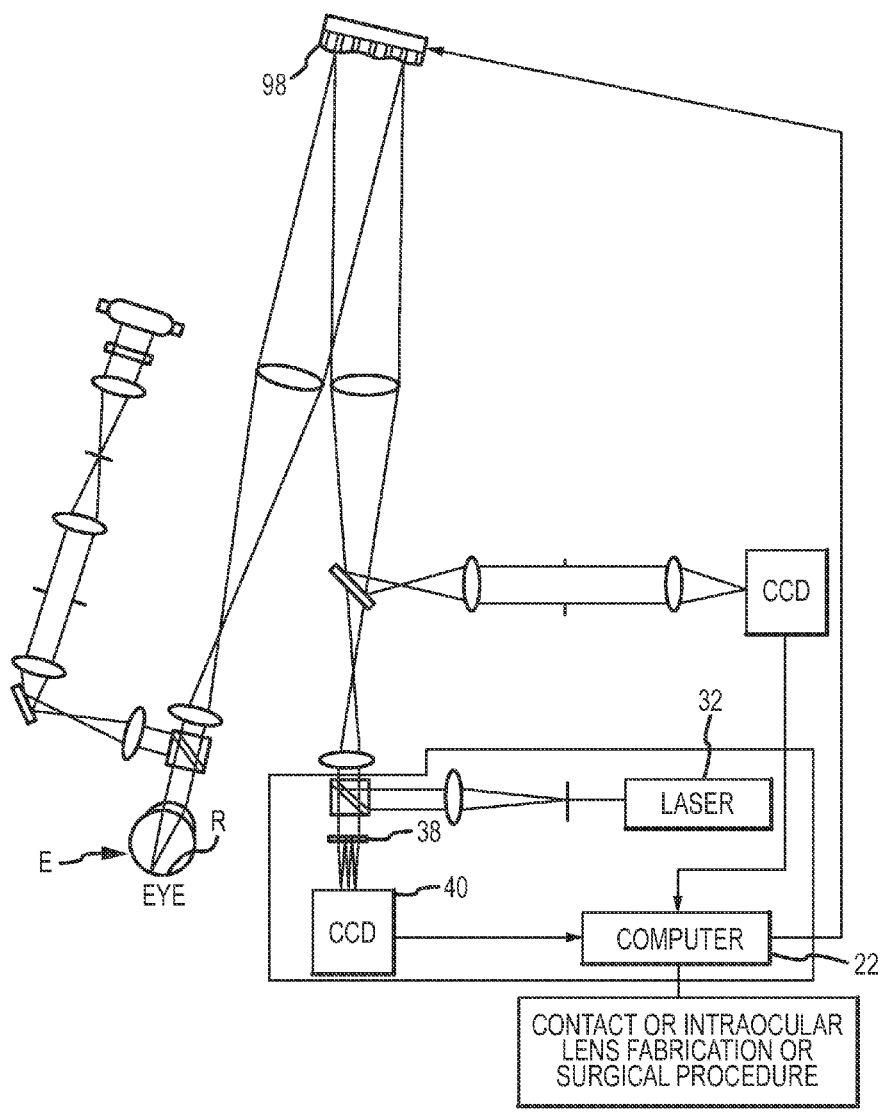
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from AMO MANUFACTURING USA, LLC, MILPITAS, California. One embodiment includes a WaveScan system with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention. Relatedly, embodiments of the present invention encompass the implementation of any of a variety of optical instruments provided by AMO WaveFront Sciences, LLC, including the COAS wavefront aberrometer, the ClearWave contact lens aberrometer, the CrystalWave IOL aberrometer, and the like.

Relatedly, embodiments of the present invention encompass the implementation of any of a variety of optical instruments provided by WaveFront Sciences, Inc., including the COAS wavefront aberrometer, the ClearWave contact lens aberrometer, the CrystalWave IOL aberrometer, and the like. Embodiments of the present invention may also involve wavefront measurement schemes such as a Tscherning-based system, which may be provided by WaveFront Sciences, Inc. Embodiments of the present invention may also involve wavefront measurement schemes such as a ray tracing-based system, which may be provided by Tracey Technologies, Corp.

Figure 4:
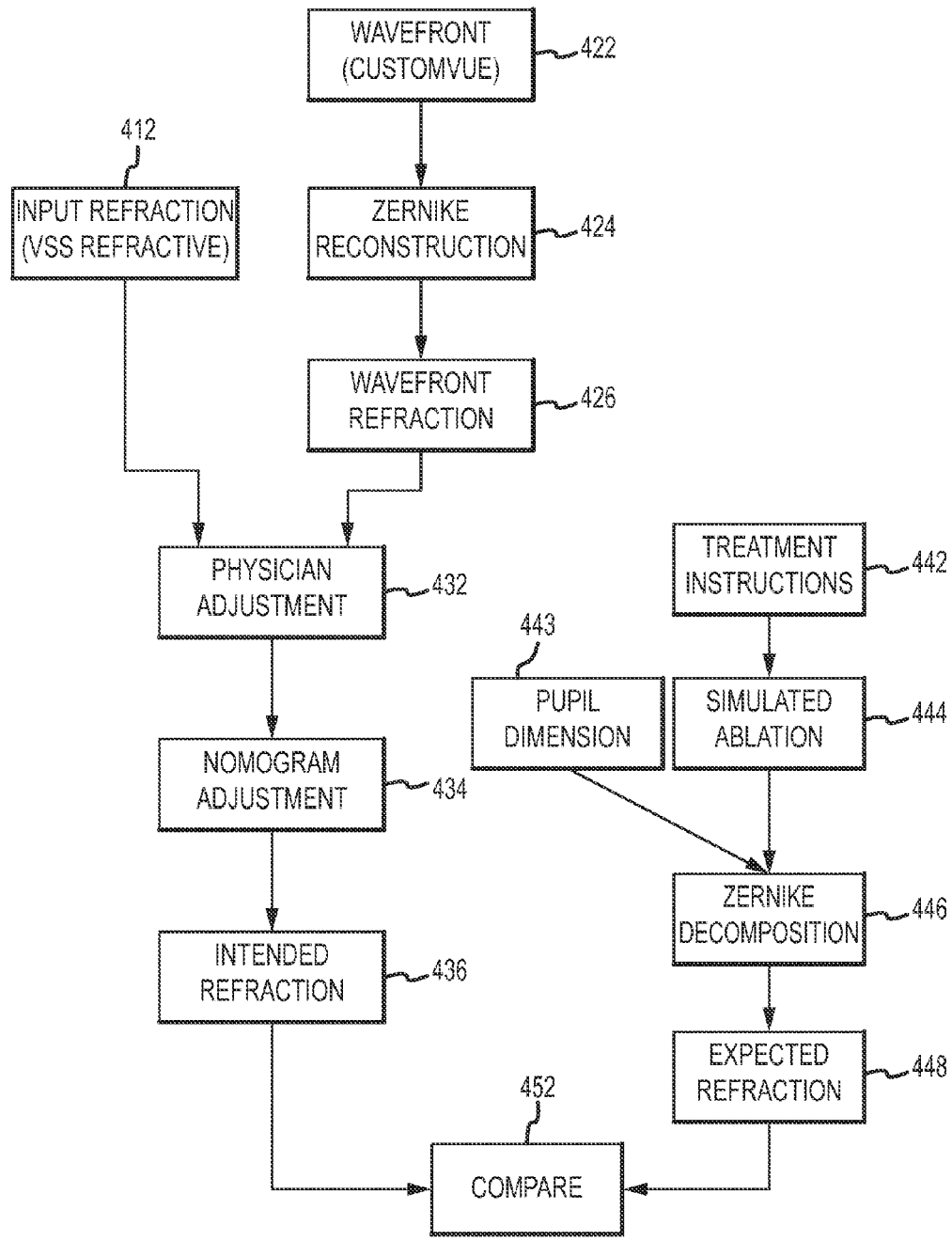
FIG. 4 shows aspects of an evaluation system according to embodiments of the present invention.

FIG. 4 depicts aspects of an evaluation system 400 according to embodiments of the present invention. As shown here, system 400 may include an Input Refraction module 412, a Wavefront module 422, a Zernike Reconstruction module 424, a Wavefront Refraction module 426, a Physician Adjustment module 432, a Nomogram Adjustment module 434, an Intended Refraction module 436, a Treatment Instructions module 442, a Pupil Dimension module 443, a Simulated Ablation module 444, a Zernike Decomposition module 446, an Expected Refraction module 448, and a Comparison module 452.

Input Refraction

The Input Refraction module 412 can operate to receive, process, and transmit information related to original refractions from the patient, such as VSS Refractive™ technology (Variable Spot Scanning) data, or manifest or subjective refraction. This information can correspond to non-wavefront guided data. According to some embodiments, Input Refraction module 412 can be configured to receive information regarding the refractive error of a patient. Such refractive error information may include sphere, cylinder, cylinder axis, and vertex distance data. Hence, low order aberration information can be used. For example, refractive error information may correspond to input cases such as myopia or hyperopia. In some cases, the refractive error information may be obtained at or correlated with a spectacle plane (e.g. 12.5 mm vertex). Input Refraction module 412 can also be configured to convert the input refractive error information to refractive error information relative to the corneal plane. Such plane conversion techniques are discussed in G.-m. Dai, Wavefront Optics for Vision Correction (SPIE Press, 2008), which is incorporated herein by reference. Plane conversion techniques can correspond to a vertex distance change or adjustment. Embodiments of the present invention encompass systems and methods for converting between treatment planes, user-defined or physician-defined planes, spectacle planes, corneal planes, pupil planes, and other planes of interest. Further, Input Refraction module 412 can be configured to output or transmit the corneal plane refractive error information, which may include sphere, cylinder, cylinder axis, and vertex distance components. In some cases, the refractive error information can be presented in the following format: sphere value DS/cylinder value DC x axis value @ vertex distance value. Optionally, Sphere and Cylinder can be represented in terms of diopters of power, Axis can be represented in terms of angle or degrees, and Vertex Distance can be represented in terms of millimeters. Sphere typically presents a measurement of lens power for myopia (negative) or hyperopia (positive), and cylinder typically presents a measurement of lens power for astigmatism. Hence, this refraction information and other eye measurements can be processed, as described herein, and compared with processed treatment table information to qualify the treatment table.

Wavefront

The Wavefront module 422 can operate to receive, process, and transmit information related to CustomVue™ technology or wavefront guided data. According to some embodiments, Wavefront module 422 can be configured to receive information regarding the wavefront error of a patient. Such wavefront error information may include wavefront map and wavefront diameter data. In some cases, the wavefront error information may be obtained at or correlated with a pupil plane. Wavefront module 422 can also be configured to process Hartmann-Shack spot diagram data, for example as described in G.-m. Dai, Wavefront Optics for Vision Correction (SPIE Press, 2008). Hartmann-Shack data can correspond to wavefront map data and wavefront diameter data. Typically, Hartmann-Shack data provides x and y shift information corresponding to array lenslets, and a wavefront data map can be derived from the Hartmann-Shack data. The map may optionally be associated with a particular wavefront diameter, particularly when the map is described with Zernike terms. In some cases, the map may be represented by a discrete matrix. Hence, Wavefront module 422 can be configured to output or transmit wavefront slope data, which may include x- and y-slope information.

Zernike Reconstruction

The Zernike Reconstruction module 424 can operate to receive information such as wavefront slope data, including for example x- and y-slope data. Zernike Reconstruction module 424 can also be configured to process the wavefront slope data with a Zernike reconstruction technique to obtain Zernike coefficient data, for example as described in G.-m. Dai, Wavefront Optics for Vision Correction (SPIE Press, 2008). Further, Zernike Reconstruction module 424 can be configured to output or transmit the Zernike coefficient information.

Wavefront Refraction

The Wavefront Refraction module 426 can operate to receive Zernike coefficient information, such as data related to z3, z4, and z5 Zernike coefficients. Wavefront Refraction module 426 can also be configured to receive wavefront diameter information. What is more, Wavefront Refraction module 426 can be configured to determine or calculate wavefront refraction information, for example based on Zernike coefficients and wavefront diameter, as discussed in G.-m. Dai, Wavefront Optics for Vision Correction (SPIE Press, 2008). The wavefront refraction information can be generated so as to correlated with a pupil plane, or with a corneal plane. Further, Wavefront Refraction module 426 can transmit or output the wavefront refraction information.

Physician Adjustment

The Physician Adjustment module 432 can be configured to receive information related to additional refractive correction at the user vertex or plane which may be selected or desired by a physician or operator. The selected plane can correspond to the pupil plane, the cornea plane, the spectacle plane, or some other user-defined plane. The Physician Adjustment can be applied at the selected or user-defined plane. For example, if the user vertex or plane corresponds to a spectacle plane, the physician can apply the adjustment at the spectacle plane as well. Hence, if the physician desired to add another diopter of treatment, the additional diopter could be applied at the spectacle plane when the physician is planning for a particular treatment. The adjustment is combined with the correction, and the combination can be converted to another plane, for example the corneal plane. Physician Adjustment module 432 can also be configured to convert the physician adjustment to the corneal plane, as described in G.-m. Dai, Wavefront Optics for Vision Correction (SPIE Press, 2008). Moreover, Physician Adjustment module 432 can be configured to transmit or output information relating the physician adjustment at the corneal plane. Such information corresponding to the corneal plane, or another selected plane, can be used for comparison and evaluation as discussed elsewhere herein.

Nomogram Adjustment

The Nomogram Adjustment module 434 can be configured to receive information related to a percentage of a treatment target multiplication factor. Nomogram Adjustment module 434 can also be configured to multiply the nomogram factor. The multiplication factor can be determined by the sum of one plus the nomogram adjustment percentage. For example, if the nomogram adjustment percentage is 8%, the multiplication factor can be calculated as one plus 8/100, or 1.08. According to some embodiments, the nomogram adjustment percentage can be a value within a range from about −10% to about +10%. Relatedly, according to some embodiments, the multiplication factor can be a value within a range from about 0.9 to about 1.1. Further, the Nomogram Adjustment module 434 can be configured to transmit or output information corresponding to a multiplied treatment target.

Intended Refraction

The Intended Refraction module 436 can operate to receive information directly from Wavefront Refraction module 426, or from Physician Adjustment module 432 or Nomogram Adjustment module 434. According to some embodiments, Intended Refraction module 436 can be configured to receive information that is similar to or the same as the input refraction discussed above in relation to the Input Refraction module 412. For example, Intended Refraction module 436 can be configured to receive information regarding the refractive error of a patient. Such refractive error information may include sphere, cylinder, cylinder axis, and vertex distance data. In some cases, the refractive error information may be obtained at or correlated with a spectacle plane. Typically, the refractive error information or intended refraction information is based on a correction that is planned for application to the patient's eye. Such intended or desired refractive correction information can also be represented in terms of ocular or optical refraction data. Intended Refraction module 436 can also be configured to convert the input refractive error information to refractive error information relative to the corneal plane. Such plane conversion techniques are discussed in G.-m. Dai, Wavefront Optics for Vision Correction (SPIE Press, 2008). Further, Intended Refraction module 436 can be configured to output or transmit the corneal plane refractive error information, which may include sphere, cylinder, cylinder axis, and vertex distance components. For example, Intended Refraction module 436 can be configured to transmit refractive information that is dependent upon or correlated with a sphere ophthalmic term, a cylinder ophthalmic term, and an axis ophthalmic term.

In some cases, the intended optical refraction can be related to Zernike terms, and in some cases the intended optical refraction can be related to manifest refraction which is used in VSS refractive. For example, the intended optical refraction can be dependent upon ophthalmic terms such as sphere, cylinder, and axis that are not directly related to Zernike terms. In some instances, the resolution of a wavefront aberrometer device may be greater than that of a phoropter device. Hence, a patient receiving a wavefront aberrometer exam that provides a result of 3.75 diopters, may also receive a phoropter exam that provides a result of 3.50 diopters. Either of the wavefront or manifest refraction results may be used.

Treatment Instructions

The Treatment Instructions module 442 can be configured to receive information related to a treatment target. Further, Treatment Instructions module 442 can operate to process the treatment target information according to a simulated annealing least squares algorithm (SALSA) to obtain a treatment table or set of laser ablation instructions for a patient, as described in G.-m. Dai, Wavefront Optics for Vision Correction (SPIE Press, 2008). The treatment table may include laser instruction parameters such as iris size, x- and y-scanning positions or locations, shot-to-shot or beam pulse delay time, pulse or beam size, and other ablation instruction parameters. The laser parameters can be used to deliver an ablation that corresponds to the Zernike polynomial terms, or other basis function terms such as Seidel series terms. A refraction typically corresponds to a second order polynomial, and basic functions such as Zernike polynomials and Seidel series are well suited for characterizing refractions based on calculation of second order coefficients. Treatment Instructions module 442 may also be configured to transmit or output laser ablation instructions, such as iris size, x- and y-scanning positions, shot-to-shot delay time, and the like. The treatment table may characterize information that has been processed via a table generation engine. When the ablation is simulated based on the ensemble of laser instructions, the resulting volumetric information corresponds to the Zernike terms.

A laser treatment table can include, for example, a listing of coordinate references for delivery of a laser beam during an ablation of the cornea. In some cases, a treatment table includes the value of the discrete radial and angular positions of the optomechanical elements used to scan an image over a portion of the anterior corneal surface. Treatment tables may also contain laser pulse instructions such as size, location, sequence, and the number of laser pulses per position. In order to provide a patient with an effective, predictable, and safe surgical procedure, it is important to generate and implement a treatment table which is accurate.

Pupil Dimension

The Pupil Dimension module 443 can operate to process information related to a pupil dimension of the patient. In some cases, Pupil Dimension module 443 can be configured to receive a selected wavefront or pupil diameter, and to calculate a refraction corresponding to the pupil dimension. Such information can be transmitted to a Zernike Decomposition module, as discussed elsewhere herein. In some cases, a pupil diameter can correspond with a wavefront diameter used during a wavefront exam, for example a wavefront exam which may be performed in conjunction with the operation of Wavefront module 422. The pupil dimension may in some instances have a value within a range from about 3 mm to about 7 mm. In some cases, the pupil dimension is a pupil diameter of about 4 mm. Hence, embodiments encompass techniques that calculate a refraction over a 4 mm pupil diameter, as well as other pupil dimensions. Exemplary aspects of pupil dimension selection are discussed in U.S. Pat. No. 7,460,288, which is incorporated herein by reference.

Simulated Ablation

The Simulated Ablation module 444 can be configured to receive information related to laser ablation instructions, such as iris size, x- and y-scanning positions or tracking distances, shot-to-shot delay time, and the like. Simulated Ablation module 444 can also be configured to process information related to a simulated laser ablation or laser ablation instructions to obtain a simulated volume or tissue volume planned for removal, based on basis data. Often, specific basis data information is available for corresponding specific iris sizes. Hence, for each particular iris size there can be a corresponding basis data information. Further, Simulated Ablation module 444 can be configured to output or transmit the simulated volume or tissue volume intended to be removed.

Zernike Decomposition

The Zernike Decomposition module 446 can be configured to receive information related to a pupil dimension and a tissue volume being removed. Zernike Decomposition module 446 can also be configured to process the pupil dimension and tissue volume information according to a singular value decomposition method to obtain Zernike coefficient and wavefront diameter information. In some cases, Zernike Decomposition module 446 generates data related to a set of second radial order Zernike polynomial terms. The second order Zernike polynomials, z3 z4, and z5 are analytically related to sphere, cylinder, and axis. The group of z3 z4, and z5 terms can be used to determine sphere. Similarly, the group of z3 z4, and z5 terms can be used to determine cylinder. Further, the group of z3 z4, and z5 terms can be used to determine axis. Aspects of a singular value decomposition method are discussed in G.-m. Dai, Wavefront Optics for Vision Correction (SPIE Press, 2008). Further, Zernike Decomposition module 446 can be configured to transmit or output information related to the Zernike coefficients and wavefront diameter. As discussed elsewhere herein, embodiments may encompass techniques that involve other basis function coefficients or second order radial polynomials, for example Seidel power series.

Expected Refraction

The Expected Refraction module 448 can be configured to receive information regarding Zernike coefficients (e.g. z3, z4, and z5 terms) and a pupil dimension. Expected Refraction module 448 can be configured to determine a wavefront refraction based on the Zernike coefficient and pupil dimension information. Aspects of a wavefront refraction determination are discussed in G.-m. Dai, Wavefront Optics for Vision Correction (SPIE Press, 2008). Further, Expected Refraction module 448 can be configured to transmit or output information related to an expected optical refraction for the patient, which may include for example a sphere ophthalmic term characterized by a set of second radial order Zernike polynomial terms, a cylinder ophthalmic term characterized by the set of second radial order Zernike polynomial terms, and an axis ophthalmic term characterized by the set of second radial order Zernike polynomial terms. Optical refraction information typically corresponds to second order wavefront data or low order aberrations, and is distinctly different from a surface shape, height, or topography. For example, when piston is added, the surface shape changes, however the curvature or refraction does not. Similarly, if a surface is tilted, the surface changes, however the curvature or refraction does not. Piston corresponds to a zero order Zernike polynomial, and represents upward or downward displacement of a wavefront. Relatedly, tilt corresponds to a first order Zernike polynomial.

Comparison

The Comparison module 452 can operate to compare intended refraction information with expected optical refraction information. For example, intended spherical equivalent (which corresponds to sphere and cylinder) can be compared with expected spherical equivalent, intended cylinder can be compared with expected cylinder, and intended axis can be compared with expected axis. In some cases, Comparison module 452 can be configured to receive information regarding an intended refraction and an expected or achieved refraction, optionally adjusted to or characterized in terms of a common or user-defined plane such as the corneal plane, pupil plane, or spectacle plane.

Because refractions are typically dependent upon the vertex plane, it may be desirable to compare intended and expected optical refraction information that corresponds to a common or specific vertex plane. Exemplary vertex or refraction conversions which may be used are described in U.S. Pat. No. 7,296,893, incorporated herein by reference. Hence, if the input refraction data corresponds to the spectacle plane, and the wavefront data corresponds to the pupil plane, embodiments of the present invention encompass techniques for converting this data so that it may be compared with data corresponding to a common plane, such as the corneal plane. Comparison module 452 can also be configured to compare the intended refraction and expected optical refraction information. For example, Comparison module 452 can operate to determine an algebraic difference for the sphere, cylinder, and axis ophthalmic terms, and compare the differences with a tolerance for the ophthalmic term. Comparison module 452 can also be configured to qualify or disqualify a treatment table based on the comparison between the respective refraction differences and tolerances.

Typically, comparison module 452 operates to compare low order aberration information related to the intended refraction with low order aberration information related to the expected refraction. Embodiments of the present invention also encompass techniques that involve the comparison of high order aberration information related to the intended refraction with high order aberration information related to the expected refraction.

Hence, comparison techniques can involve comparing an expected optical refraction for the patient, which is based on a pupil dimension and a simulated ablation, with an intended optical refraction for the patient. The expected optical refraction can be dependent on a sphere ophthalmic term characterized by a set of second radial order Zernike polynomial terms, a cylinder ophthalmic term characterized by the set of second radial order Zernike polynomial terms, and an axis ophthalmic term characterized by the set of second radial order Zernike polynomial terms. The expected optical refraction profile can also be independent of a piston ophthalmic term characterized by a zero radial order Zernike polynomial term, an x-tilt ophthalmic term characterized by a set of first radial order Zernike polynomial terms, and a y-tilt ophthalmic term characterized by the set of first radial order Zernike polynomial terms. The intended optical refraction for the patient can be dependent on a sphere ophthalmic term, a cylinder ophthalmic term, and an axis ophthalmic term. Further, the intended optical refraction profile can be independent of a piston ophthalmic term, an x-tilt ophthalmic term, and a y-tilt ophthalmic term.

Scaling

With continued reference to FIG. 4, evaluation techniques can be implemented in various ways. For example, in a VSS refractive treatment, an evaluation technique may be implemented by using a scaling factor to scale down the refraction from the treatment table, without using a scaling factor to boost the treatment target. Such approaches are well suited for use with a Munnerlyn shape which is deeper than a parabolic shape. Relatedly, in a CustomVue® treatment, an evaluation technique may be implemented by using a scaling factor, for example of 1.11, to boost the treatment target, without using a scaling factor to scale down the refraction from the treatment table, for example without a parabolic or Munnerlyn scaling. With regard to the VSS technique, scaling can be applied in a linear fashion, to a Munnerlyn or parabolic shape. In some case, a Munnerlyn shape can be scaled so as to approach or approximate a parabolic shape. A parabolic shape represents a second order shape, and a Munnerlyn represents a second order shape as supplemented with higher orders. Hence, for the same refraction, a Munnerlyn shape and a parabolic shape can differ. A comparison can be performed either at the corneal plane or at the vertex plane, or both. According to some embodiments, the treatment table should qualify or pass if the difference between the refraction from the table and the initial input refraction is smaller than the criteria used for wavefront exam selection during the treatment table creation phase. In some cases, embodiments of the present invention provide systems and methods for qualifying a VSS refractive treatment. Exemplary techniques can implement a treatment qualification validation process whereby a refraction from a simulated tissue ablation is compared with an input refraction, for example to ensure that no abnormal tables have been created. Because the Munnerlyn shape and a parabolic shape may differ, it may be useful to convert a Munnerlyn refraction to a parabolic refraction. Munnerlyn shapes are discussed generally at C. R. Munnerlyn, S. J. Koons, and J. Marshall, "Photorefractive keratectomy: A technique for laser refractive surgery," *J. Cataract Refract. Surg.* 14, 46-52 (1988), the entire content of which is incorporated herein by reference. Embodiments of the present invention encompass different types of scaling. For example, the techniques disclosed herein may include refraction scaling or shape scaling, both of which involve multiplication. In some cases, it is possible to use scaling factors of 1.015 for myopic sphere, 1.025 for hyperopic sphere, and 1.015 for cylinder to scale a refraction, for example as discussed in relation to Eqs. (9) to (11) provided elsewhere herein. In some cases, it is possible to use a scaling factor of 1.11 to scale a shape.

Figure 4A:
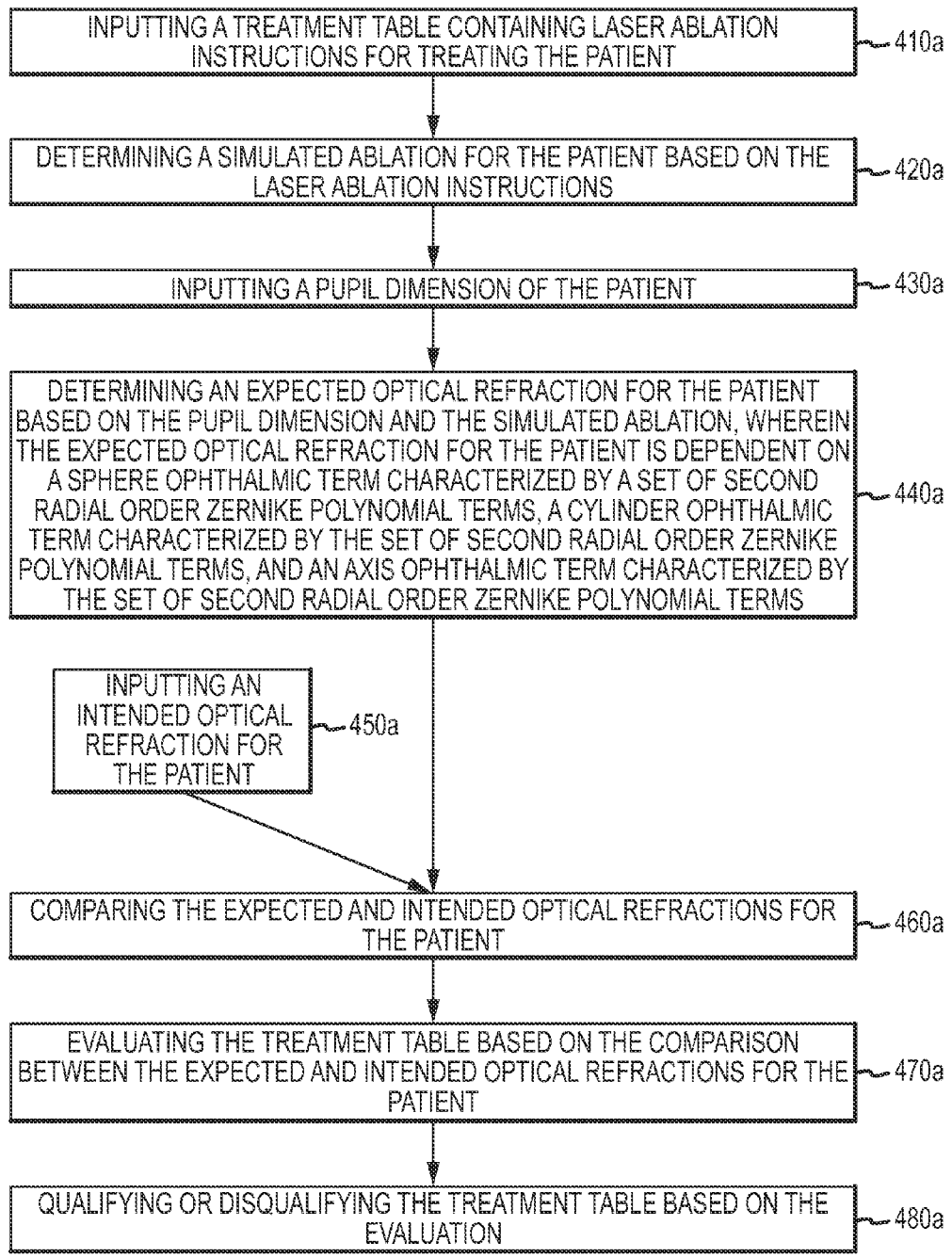
FIG. 4A depicts aspects of an evaluation method according to embodiments of the present invention.

FIG. 4A illustrates an exemplary method 400a of evaluating a treatment table for use in an ophthalmologic refractive surgery for a patient. As shown here, such evaluation, verification, or qualification techniques may include inputting a treatment table containing laser ablation instructions for treating the patient, as depicted by step 410a. Methods may also include determining a simulated ablation for the patient based on the laser ablation instructions as indicated by step 420a, and inputting a pupil dimension of the patient as indicated by step 430a. In an exemplary embodiment, an evaluation method may include determining an expected optical refraction for the patient based on the pupil dimension and the simulated ablations, as indicated by step 440a, wherein the expected optical refraction for the patient is dependent on a sphere ophthalmic term characterized by a set of second radial order Zernike polynomial terms, a cylinder ophthalmic term characterized by the set of second radial order Zernike polynomial terms, and an axis ophthalmic term characterized by the set of second radial order Zernike polynomial terms. Optionally, the expected optical refraction profile can be independent of a piston ophthalmic term characterized by a zero radial order Zernike polynomial term, an x-tilt ophthalmic term characterized by a set of first radial order Zernike polynomial terms, and a y-tilt ophthalmic term characterized by the set of first radial order Zernike polynomial terms. Method embodiments may also include inputting an intended optical refraction for the patient, as indicated by step 450*a*, wherein the intended optical refraction for the patient is dependent on a sphere ophthalmic term, a cylinder ophthalmic term, and an axis ophthalmic term, and wherein the intended optical refraction profile is independent of a piston ophthalmic term, an x-tilt ophthalmic term, and a y-tilt ophthalmic term. Further, methods may include comparing the expected and intended optical refractions for the patient, as indicated by step 460*a*. The refractions can be adjusted to or correlated with a common plane, such as the treatment plane, pupil plane, corneal plane, or spectacle plane, prior to the comparison. In some cases, methods may include evaluating the treatment table based on the comparison between the expected and intended optical refractions for the patient, as indicated by step 470*a*, and qualifying or disqualifying the treatment table based on the evaluation, as indicated by step 480*a*. For example, evaluation methods may include determining a difference between the intended optical refraction and the expected optical refraction, and comparing that difference to a predefined tolerance. If the difference between the intended optical refraction and the expected optical refraction is within the tolerance, the method may include qualifying or passing the treatment table, or otherwise approving the treatment table for use. Such qualification techniques can provide an enhanced level of safety during a patient treatment, for example by helping to ensure that a treatment table has not been altered or hacked.

Information corresponding to any of a variety of inputs may be processed, such as data related to a spectacle plane parameter, a corneal plane, a pupil plane, or any other desired vertex plane or distance parameter.

Figure 5:
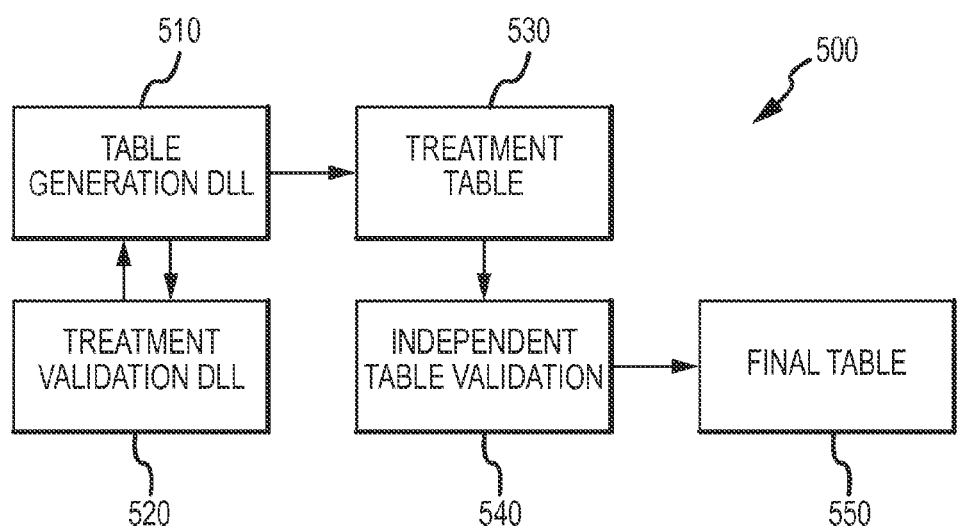
FIG. 5 shows aspects of an evaluation system according to embodiments of the present invention.

FIG. 5 depicts aspects of an evaluation system 500 according to embodiments of the present invention. As shown here, system 500 may include a Table Generation DLL module 510, a Treatment Validation DLL module 520, a Treatment Table module 530, an Independent Table Validation module 540, and a Final Table module 550.

As shown here, for a Table Generation DLL 510 or treatment generation engine, a validation process can be performed by a Treatment Validation DLL 520 whereby a validation is conducted for various possible simulation annealing solutions. Moreover, a process to validate a ready-to-use treatment corresponding to Treatment Table 530 can provide a separate, independent step for validating a treatment table. Such an independent validation technique can operate separately from a treatment table generation engine or a treatment table generation algorithm which may involve a simulated annealing process, and therefore does not incorporate possible error which may result, for example, due to unexpected error from third-party DLLs, from mal-operation of the users that is not captured in the fault tree analysis during the software design phase, or from other possible sources of error. For example, due to possible unknown bugs or errors in the high level software code or embedded in third-party libraries (DLLs), or due to inappropriate operation of the software, it is possible that a software that is verified and validated by Treatment Validation DLL 520 may still produce an unwanted treatment table that can potentially result in a suboptimal treatment. Hence, embodiments of the present invention encompass validation techniques for addressing situations where third party components such as operating systems, computers, or DLL's introduce error or are malfunctioning, and other sources that introduce unforeseeable or incorrect results.

According to some embodiments, the validation of a treatment table can be implemented in connection with the table generation system or software. In some cases, the validation of a treatment table can be implemented in connection with the laser system or software, such as validation software residing in the laser system. For instance, a VSS-based validation as described elsewhere herein, which may optionally be in relation with an aberrometer or wavefront system, can also be implemented in a laser system. Hence, it is possible to validate a treatment table after it is generated and saved, and it is also possible to validate a treatment table prior to use in treating a patient. Hence, if a treatment table has been corrupted for some reason, validation and qualification can be performed prior to laser delivery of the ablation pulses, and the treatment can be canceled if disqualification is appropriate.

According to some embodiments, the validation of a treatment table can be implemented in connection with software residing in a diagnostic device such as WaveScan® and iDesign™ devices. System and method embodiments disclosed herein can also be configured to validate treatment tables for topographic driven treatment, refraction driven or conventional treatment, and wavefront driven treatment.

Table Generation DLL module 510 can operate to process information related to treatment table generation, Treatment Validation DLL module 520 can operate to process information related to treatment validation, Treatment Table module 530 can operate to process information related to a treatment table, and Table Validation module 540 can operate to process information related to table validation. In some instances, Table Validation module 540 is configured to embody or implement techniques described elsewhere herein in relation to Comparison module 452. Final Table module 550 can operate to process information related to a final table. According to some embodiments, a final table corresponding to Final Table module 550 will be the same as a treatment table corresponding to Treatment Table module 530, in the event that the treatment table corresponding to Treatment Table module 530 is validated or qualified by Table Validation module 540.

Passing Criteria for Treatment Table Qualification

Any of a variety of exam selection criteria can be used to qualify a treatment table generated by the VSS Refractive™ technique. Numerous Monte Carlo simulations have been performed which support the suitability of such exam selection criteria for treatment table qualification.

According to some embodiments, the difference in spherical equivalent (SE), cylinder, and cylinder angle can be set or predetermined to satisfy the following qualification conditions.

$$|dSE|=|dS+0.5dC|=|S_1-S_0+0.5C_1-0.5C_0|<0.625 \quad (1)$$

$$|dC|=|C_1-C_0|\leq 0.5 \quad (2)$$

$$|dA|\leq -1.1538(|C_0|+|C_1|)/2+15.577 \text{(for } |C_0|>0.5 \text{ and } |C_1|>0.5, \text{ or ignore)} \quad (3)$$

As described here, Eq. 1 represents a comparison or difference between spherical equivalent, Eq. 2 represents a comparison or difference between cylinder, and Eq. 3 represents a comparison or difference between axis.

For example, if $C_0=0.55$ D, $C_1=0.5$ D, then according to Eq. 1, the cylinder difference is less than 0.5, and thus there may be no need to check cylinder angle. For another example, if $C_0=0.9$ D, $C_1=0.8$ D, then dA must be smaller than 14.6 degree in order to qualify. Also note that for Eq. (2), it is generally desirable that both use the same cylinder notation before the difference can be taken. For example, it is desirable that both $C_0$ and $C_1$ be positive, or that both $C_0$ and $C_1$ be negative.

Evaluation and Monte Carlo Simulation

Treatment qualification systems and methods according to embodiments of the present invention can be implemented in a variety of ways. There is typically inter-correlation between sphere and cylinder as well as the vertex correction. A scaling factor between a Munnerlyn power and a parabolic power may in some cases depend not only upon the sphere refraction, but also upon on the cylinder refraction. As described in G.-m. Dai, *Wavefront Optics for Vision Correction* (SPIE Press, 2008), the Munnerlyn shape may differ from a parabolic shape. For example, as described at page 90, supra, the Munnerlyn shape can be 11% deeper than parabolic shape, when a spherical myopia is considered.

Embodiments of the present invention encompass empirically adjusted and theoretically based systems and methods for implementing a treatment qualification technique. Such approaches can include processing a set of input refractions (e.g. with sphere between −15 D and +7 D and cylinder between −6 D and +6 D) with Munnerlyn shapes, decomposing the data into Zernike polynomials. Zernike decomposition may involve processing pupil dimension and tissue volume information to obtain Zernike coefficient and wavefront diameter information, such as data related to a set of second radial order Zernike polynomial terms, and determining the refractions based on the Zernike information. In this way, it is possible to determine an expected refraction, based on the Zernike coefficient and pupil dimension information.

Further, these approaches can include regressing the input Munnerlyn refraction against a calculated parabolic refraction using multivariate linear and quadratic parameters to obtain theoretical scaling factors for both sphere and cylinder. Still further, these approaches can include using a theoretical algorithm to test in a full implementation with vertex correction, cosine effect using random keratometry values, and the like, using Monte Carlo simulation with multiple (e.g. 5000) samples. Moreover, these approaches can include refining the theoretical algorithm based on the Monte Carlo simulation. What is more, these approaches can include retesting the revised algorithm for a new set of Monte Carlo simulation with multiple (e.g. 5000) samples. According to some embodiments, such approaches may be implemented in a production software.

The following formulas give an algorithm for sphere ($f_s$) and cylinder ($f_c$) scaling:

$$f_s=1.028-0.00275S-0.00448C(S<0) \quad (4)$$

$$f_s=1.028-0.00326S-0.00018C(S\geq0) \quad (5)$$

$$f_c=1.011-0.00574S-0.00142C \quad (6)$$

As indicated here, both S and C can be refractions on the corneal plane. In some cases, it may be desirable to convert the input refractions on vertex plane to the corneal plane before these equations are used. Supposing the refractions on the vertex plane are $S_0$ and $C_0$, respectively, it is possible to write:

$$S = \frac{S_0}{1-0.001S_0 d} \quad (7)$$

$$C = \frac{S_0+C_0}{1-0.001(S_0+C_0)d} - S \quad (8)$$

When $f_s$ and $f_c$ are calculated, they can be applied to refractions on the corneal plane. For example, suppose the input refractions are −15 DS/−5.75 DC×64 @ 12.5 mm vertex. They are used to generate the Munnerlyn shape, which has more power than the corresponding parabolic shape. From Equations (7) and (8), it is possible to obtain the refractions on the corneal plane as −12.63 DS/−3.84 DC×64 @ 0 mm vertex. Using Equations (4) and (6), it is possible to obtain $f_s=1.0799$ and $f_c=1.0889$. These are scaling factors which may be determined via Monte Carlo simulation. Further, such scaling factors can be applied to an input refraction. It can be assumed that the Zernike decomposed refractions from the treatment table are −13.68 DS/−4.09 DC×64 @ 0 mm vertex.

According to some embodiments, for the CustomVue® technique or Wavefront input data, there may be no need to use a scaling factor for refractions, however it may be beneficial to scale the treatment shape 11% to achieve a similar target depth corresponding to that of conventional or VSS Refractive™ input data.

The scaling factors for these refractions can be applied to obtain −12.67 DS/−3.76 DC×64 @ 0 mm vertex, which may correspond to a scaled refraction on the treatment plane or corneal plane. It is possible to convert these refractions to a 12.5 mm vertex using Equations (7) and (8), setting d=−12.5 mm. Such conversion corresponds to propagation to the spectacle plane. Hence, −12.67 DS/−3.76 DC×64 @ 0 mm vertex propagated to the spectacle plane is −15.05 DS/−5.62 DC×64 @ 12.5 mm vertex. Conversions are useful when comparing refractions, such as an intended refraction and an expected refraction, and this example illustrates that it is possible to compare refractions in, for example, a user vertex (e.g. spectacle) plane. Hence, a treatment table power of −13.68/−4.09×64 at 0 mm vertex can be vertex corrected to obtain the refraction as −15.05DS/−5.62 DC×64 at 12.5 mm vertex. This leaves a residual error of −0.05 DS/0.13 DC.

The difference in SE can be calculated as (−15.05−5.62/2+15+5.75/2)=0.02D, the difference in Cylinder can be calculated as −5.62+5.75=0.07D, and the difference in axis can be calculated as 0. If the tolerance for SE is 0.625D and the tolerance for cylinder is 0.5D, then these SE and Cylinder values are within the tolerances, and hence the treatment can be approved for release to treat the patient.

Figure 6:
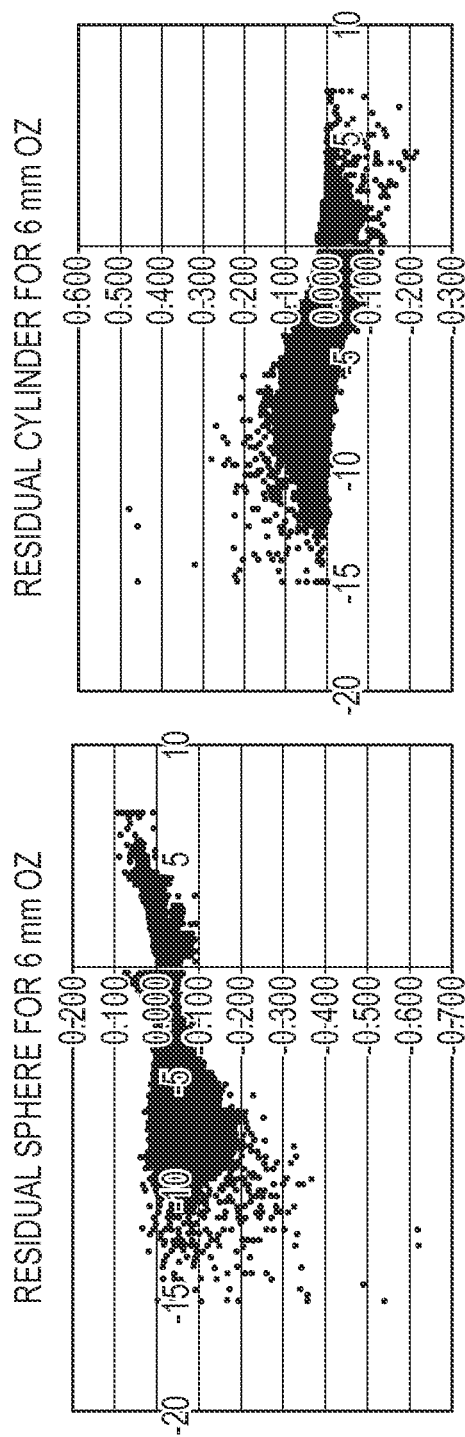
FIG. 6 illustrates aspects of residual error according to embodiments of the present invention.

FIG. 6 shows a residual error for 5000 simulated cases with 6 mm OZ. The left panel shows residual sphere, and the right panel shows residual cylinder, after correction of the scaling factors for 5000 simulated realistic cases. If the four outliers are excluded, the spread of sphere is within (−0.4D, +0.1D) and that of cylinder is within (−0.2D, +0.3D), both are in about half a diopter range. Without the exclusion, the range is still within the criteria listed in Eqs. (1) to (3).

Table 1 provides the residual error or residual refractions (in diopters) from a Monte Carlo simulation after implementing the algorithm shown in Eqs. (4) to (6), for optical zones of 7 mm, 6 mm, 5 mm, and 4 mm.

TABLE 1

| OZ | 7 (mm) | | 6 (mm) | | 5 (mm) | | 4 (mm) | |
|---|---|---|---|---|---|---|---|---|
| Rx<br>N | Sphere<br>5000 | Cylinder<br>5000 | Sphere<br>5000 | Cylinder<br>5000 | Sphere<br>5000 | Cylinder<br>5000 | Sphere<br>5000 | Cylinder<br>5000 |
| Mean | −0.043 | 0.015 | −0.043 | 0.014 | −0.045 | 0.016 | −0.013 | 0.017 |
| Stdev | 0.054 | 0.044 | 0.054 | 0.044 | 0.057 | 0.047 | 0.045 | 0.035 |
| Max | 0.206 | 0.480 | 0.090 | 0.476 | 0.149 | 0.432 | 0.132 | 0.265 |
| Min | −0.564 | −0.330 | −0.622 | −0.215 | −0.610 | 0.245 | −0.376 | −0.171 |

For the criteria for treatment table qualification, because the residual errors shown in Table 1 are within the exam selection criteria, it may be desirable to use the exam selection criteria to qualify treatment tables in terms of the refraction check. Embodiments of the present invention encompass techniques for qualifying an exam, which may involve the application of treatment table qualification criteria, and selecting the exam for treatment generation, which may involve the application of exam selection criteria.

Verification with Production Code and Revised Formulas

Eqs. (4) to (6) were implemented in a production code, and tested with about 1000 cases with each pupil sizes of 4 mm, 5 mm, 6 mm, and 7 mm. Occasional discrepancies were discovered, and it was determined that such discrepancies may be due to some implementation differences between the C++ code and the Matlab code. Subsequently, a set of new examples were generated and regression ran. Results for the new examples were much more linear, and the nonlinear behavior previously observed was absent.

Table 2 shows the linear factor for different pupil sizes. Scaling factor data for sphere (t) and cylinder ($f_c$) was regressed from data obtained with the production code for various pupil sizes.

TABLE 2

| Pupil | Minus Sph | Plus Sph | Cylinder |
|---|---|---|---|
| 4 mm | 0.999 | 1.022 | 1.010 |
| 5 mm | 1.014 | 1.037 | 1.023 |
| 6 mm | 1.026 | 1.026 | 1.014 |
| 7 mm | 1.023 | 1.014 | 1.014 |
| Average | 1.015 | 1.025 | 1.015 |

Based on the information in Table 2, the original Eqs. (4) to (6) were adjusted as follows. These equations can override equations (4)-(6).

$$f_s = 1.015 (S<0) \quad (9)$$

$$f_s = 1.025 (S>0) \quad (10)$$

$$f_c = 1.015 \quad (11)$$

Figure 7:
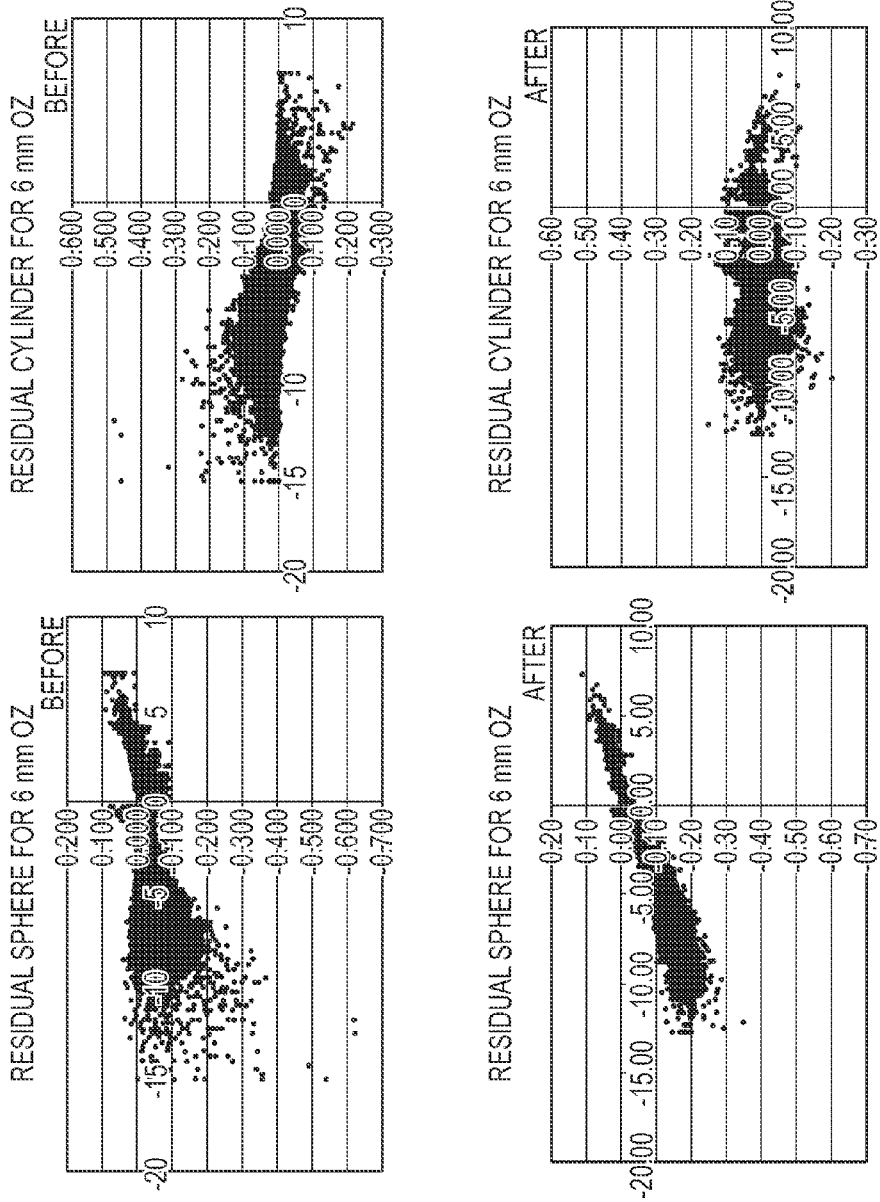
FIG. 7 illustrates aspects of residual sphere and cylinder according to embodiments of the present invention.

As a verification that this new implementation narrows the spread of the residual error both in sphere and cylinder, the same 5000 samples for each pupil which were used before, were again used running with the production code. This is the revised code based on the adjustments described above. FIG. 7 shows the results obtained for a 6 mm pupil using the revised code, compared with the previous results obtained using the original code. Specifically, the upper panels of FIG. 7 show the residual sphere (left panel) and residual cylinder (right panel) for a 6 mm pupil after correction of the scaling factors for 5000 simulated realistic cases using the original Eqs. (4) to (6). In comparison, the lower panels of FIG. 7 show the residual sphere (left panel) and cylinder (right panel) for a 6 mm pupil after correction of the scaling factors for 5000 simulated realistic cases using the revised Eqs. (9) to (11). From FIG. 7, it can be seen that after the scaling factor revision, the spread of the residual error in sphere and cylinder becomes tighter. Therefore, in a normal condition, it is not expected that any treatment would fail. However, if a treatment does not satisfy a validation test, it can be inferred that something unexpected may have happened. In such instances, the treatment table can be disqualified, and the treatment will not be applied to the patient. Hence, this example illustrates that for validating treatment tables, a set of numerical formulas can be developed and validated with multiple Monte Carlo simulations of 5000 cases for each optical zone of 4, 5, 6, and 7 mm.

Embodiments of the present invention encompass systems and methods for estimating or determining a scaling factor. Such techniques may involve constructing a theoretical Munnerlyn shape for all refractive cases covered by the VSS Refractive™ technique (e.g. S and C with increment of 0.25 D), calculating a decomposed refraction over a 4 mm diameter, and regressing using a multivariate quadratic regression model. Embodiments may also include calculating a wavefront refraction over a pupil dimension (e.g. assuming the wavefront diameter is not smaller than the pupil dimension), and converting the refraction to a vertex distance. Embodiments may also include calculating a 2D Munnerlyn shape, decomposing a surface into Zernike coefficients, calculating Zernike polynomials of each term, calculating Zernike polynomials of arbitrary size and returning a 2-D surface mesh.

Embodiments of the present invention further encompass systems and methods based on validation with a Monte Carlo Simulation. Exemplary techniques may involve performing a validation using Monte Carlo simulation which ensures that implementation of a validation technique passes all regular cases within a proposed range, for example a proposed −15 to +7 DS and −6 to +6 DC range for the VSS Refractive™ procedure. Such approaches can be based on a proposed tolerance that is the same as or similar to a an exam qualification, such as 0.625 D for SE and 0.5 D for cylinder. For example, for a 6 mm optical zone (OZ) and 12.5 mm vertex, it is possible to input sphere, cylinder, and axis data corresponding to a vertex plane, and sphere, cylinder, and axis data corresponding to a corneal plane. Similarly, it is possible to output sphere, cylinder, and axis data corresponding to a corneal plane. Embodiments also encompass determining scaling factors for sphere, cylinder, and axis, and calculating scaled sphere, cylinder, and axis values for corneal and vertex planes. Further, embodiments include determining differences between sphere, cylinder, and axis values at a corneal plane. A Monte Carlo simulation can be run with multiple (e.g. 1000) random refractions. Embodiments include calculating a predicted refraction versus a decomposed refraction from the treatment targets. Embodiments may also include calculating a refraction on the corneal plane. In some cases, embodiments encompass determining sphere and cylinder scaling factors. Embodiments may also include determining an empirical scaling factor for Munnerlyn power, where S and C represent the refraction on a corneal surface. Refractions can be converted to the corneal plane, and scaling factors can be calculated based on corneal refractions.

Post-Operative Aberrations

Refractive procedures may, in some cases, induce certain aberrations in an eye of a patient. For example, it is believed that laser-assisted in situ keratomileusis (LASIK) surgeries can induce high order aberrations, and in particular spherical aberration (SA). Spherical aberration is a special type of high order aberration that can affect night vision, and involves off-axis rays entering the eye with different heights of focus at different locations.

Embodiments of the present invention encompass systems and methods for reducing, eliminating, or otherwise compensating for such post-operative inductions. For example, whereas an original target shape applied to the eye may lead to induced aberrations, it is possible to deconvolve the original target shape so as to obtain a modified target shape, such that when the modified target shape is applied to the eye, there are fewer or less pronounced induced aberrations.

Figure 8:
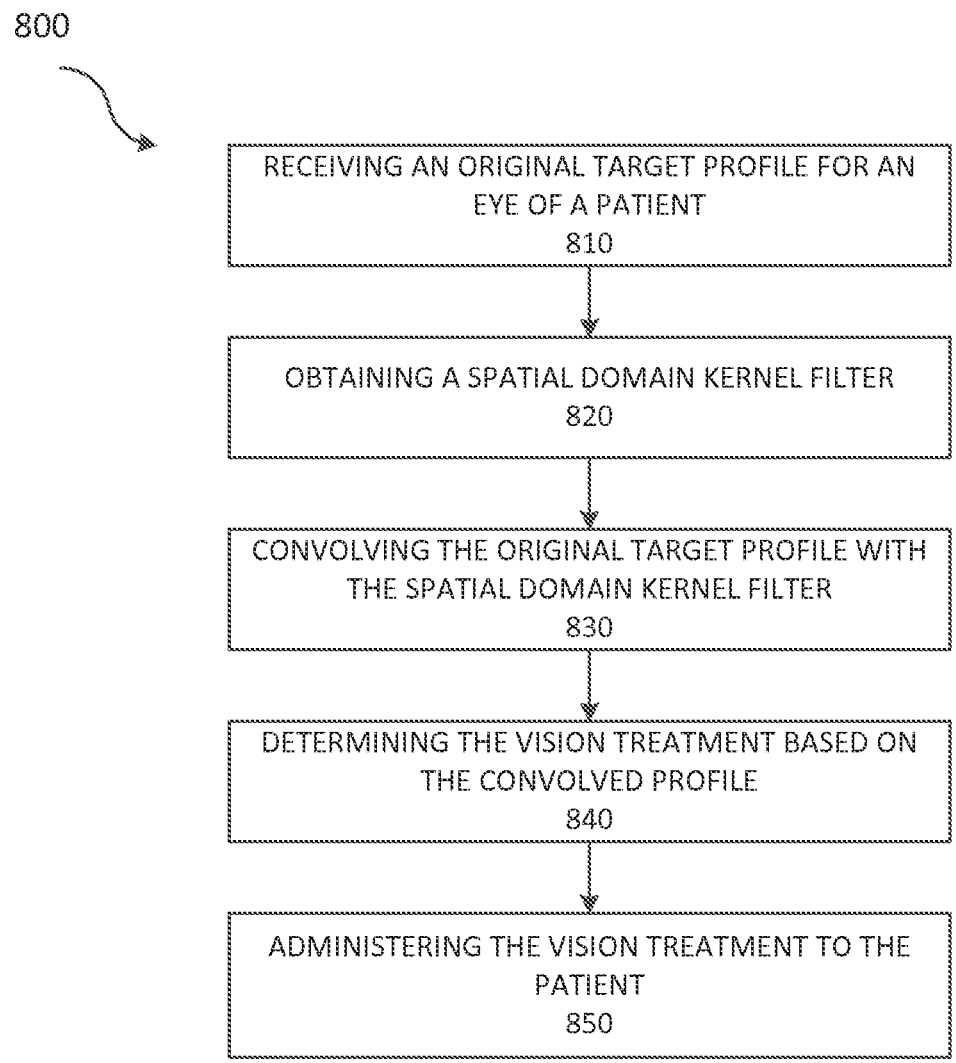
FIG. 8 depicts aspects of a method for determining a vision treatment for an eye, according to embodiments of the present invention.

FIG. 8 depicts aspects of a method 800 for determining a vision treatment for an eye of a patient As shown here, the method includes receiving (e.g. at an input) an original target profile for the eye of the patient as indicated by step 810. Method 800 also includes obtaining a spatial domain kernel filter as indicated by step 820. The spatial domain kernel filter can be based on an inverse Fourier transform of a Fourier domain noise filter. Further, the method may include convolving the original target profile with the spatial domain kernel filter as indicated by step 830. As illustrated here, method 800 also may include determining the vision treatment based on the convolved profile as indicated by step 840. According to some embodiments, methods may include administering the vision treatment to the patient as indicated by step 850.

Figure 9:
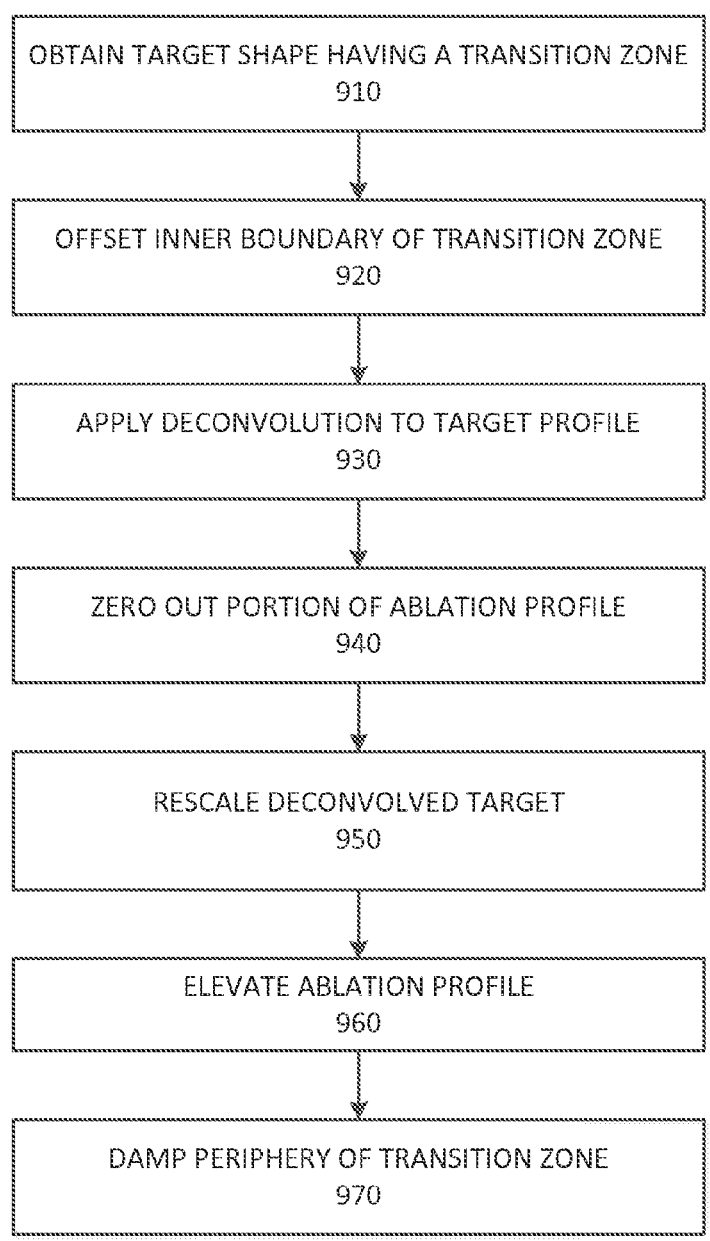
FIG. 9 depicts aspects of a method for modifying a target shape according to embodiments of the present invention.

FIG. 9 depicts aspects of a method for modifying a target shape according to embodiments of the present invention. As shown here, a modification method 900 includes obtaining a target shape as indicated by step 910. Often, the target shape or profile will have an optical zone and a transition zone. In some cases, a target shape may refer to an intended optical surface designed to achieve a given refractive correction. A method 900 for modifying or deconvolving a target shape may also include offsetting an inner boundary of the transition zone (e.g. by about 0.1 mm in diameter), as indicated by step 920. Further, the method may include inputting, receiving, or reading in an inverse smoothing kernel as described elsewhere herein. As illustrated by step 930, methods may include applying a deconvolution to a target profile, for example as a low pass filter multiplied with the target profile as discussed below with reference to Equation 25. Methods may also include zeroing out an ablation profile at distances greater than the transition zone radius, as indicated by step 940. In some cases, methods may include rescaling a deconvolved target, for example as indicated by step 950, so that its Zernike defocus term within the 4 mm diameter is the same as for the original target. In some instances, the rescaling factor can be 1.0. In some embodiments, the rescaling process described in step 950 can incorporate scaling or rescaling techniques disclosed elsewhere herein, such as those described in FIGS. 22, 24, 41, and 42 and the corresponding specification text descriptions. Optionally, methods may include elevating the entire ablation profile, as depicted by step 960, so that the lowest point on the ablation profile is zero. This elevation technique can help to ensure that the ablation profile does not have negative heights. In some instances, methods may include applying a damping multiplier (e.g. Equation 28) to the periphery of the transition zone, as indicated by step 970. Optionally, a modification or deconvolution method can be implemented before application of a cosine compensation step.

Post-Operative Epithelial Smoothing And Spherical Aberration

As noted above, cornea remodeling following treatment with a refractive target shape can induce SA, for example due to smoothing of epithelium at the anterior surface of the eye. To develop techniques that compensate for such remodeling, it is helpful to simulate the post-operative epithelium smoothing process with a model. An exemplary model may define the shape of the post-operative cornea surface as a convolution of an ablation target profile with a low-pass filter (LPF), as follows:

$$h_{post\text{-}op} = h_{pre\text{-}op} - K \otimes T \qquad \text{Equation 12}$$

where T is the ablation target profile. K=K(x,y) is the LPF kernel, which has the following Fourier transform:

$$K(k_x, k_y) = \frac{1}{1 + \sigma^2(k_x^2 + k_y^2)} \qquad \text{Equation 13}$$

K(x,y), the LPF kernel, can be considered as a spatial domain representation. The Fourier transform of K(x,y) (i.e. K($k_x$, $k_y$) or F[K]), can be considered as a frequency or Fourier domain representation.

According to some embodiments, the Fourier transform F[K], or K($k_x$, $k_y$), may be a squared Butterworth low-pass filter of the first order, which can be applied to the treatment target T in order to obtain the wavefront change due to corneal smoothing. In some instances, the Fourier transform of the LPF kernel can be defined by or based on a single diffusion coefficient σ, which has a unit of length.

In some instances, the post-operative induced spherical aberration can be computed with a Zernike decomposition of the simulated post-operative cornea surface after the smoothing, as follows:

$$SA_{post\text{-}op} = SA_{pre\text{-}op} - SA(K \otimes T) \qquad \text{Equation 14}$$

The spherical aberration computed by Zernike decomposition of a given target can be represented by the function SA(T), where SA(T) refers to SA from the target T.

According to an exemplary experimental embodiment, a target for each eye in a clinical study was computed as follows:

$$T = \text{scale} \cdot T_{controller} \qquad \text{Equation 15}$$

According to some embodiments, $T_{controller}$ may refer to a target created by production code. Such a target can be created according to various options. For example, the target shape can be generated based on input such as measured pre-operative Zernike coefficients with added flap-induced spherical aberration (e.g. flapSA). The target shape can also be generated with or without applying a cosine correction (e.g. warping adjustment). In some cases, the target can be generated based on scaling and/or physician adjustments. Target shapes may also be generated based on keratometry parameters. For example, if available, keratometry parameters k1, k2, k2a may be used. Optionally, for example if keratometry parameters are not available, default values of k1=43.5, k2=43.5, k2σ=0 may be used.

Figure 11:
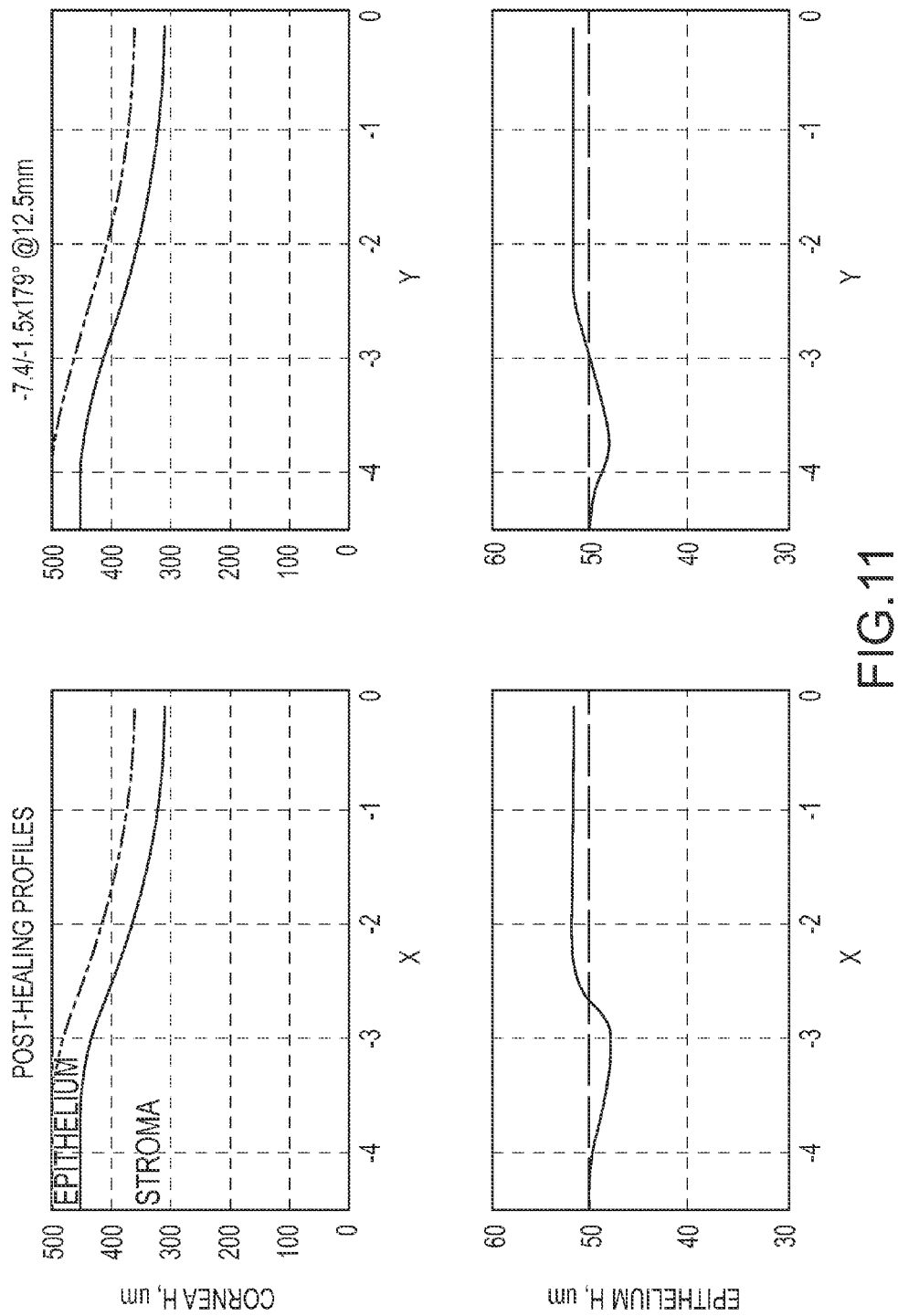
FIG. 11 shows aspects of simulated epithelium thickness profiles according to embodiments of the present invention.

It is possible to simulate the cornea thickness after smoothing using an LPF model. For example, FIG. 11 shows simulated epithelium thickness profiles after smoothing (High Myopia study, case ID=21011 OD, −7.4D/−1.5D×179). For this illustration, pre-operative epithelium was assumed uniform and 50 um thick. Corneal smoothing after a myopic ablation may lead to epithelium diffusion, from high curvature areas on the peripheral transition zone, toward the center where the curvature is smaller. As a result, the epithelium may become thicker in the center and thinner on the periphery of the ablation target. This effect may help explain partial regression after myopia refractive surgery.

Using available clinical data, a smoothed target was compared with the observed 6M corneal change within 6 mm and 5.5 mm diameter optical zone. A diffusion coefficient σ was estimated based on the comparison. In some cases, the comparison can be performed with a linear least-square fit of the model to the observed SA change, as described elsewhere herein. According to some embodiments, the fitting procedure yielded an estimation of σ and its confidence interval for each value of flapSA.

Figure 12A:
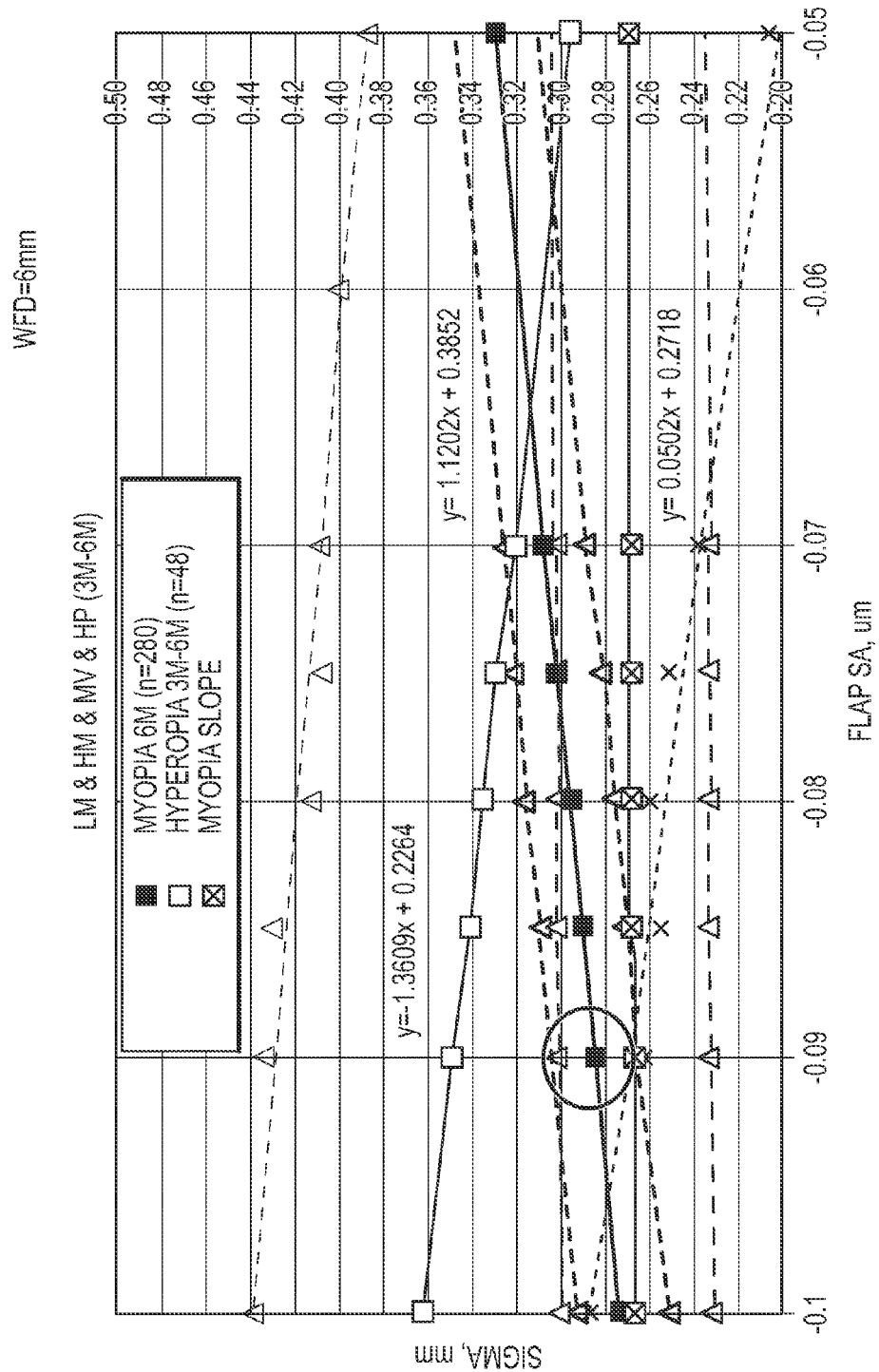
FIGS. 12A and 12B show aspects of flap SA and sigma relationships according to embodiments of the present invention.
Figure 12B:
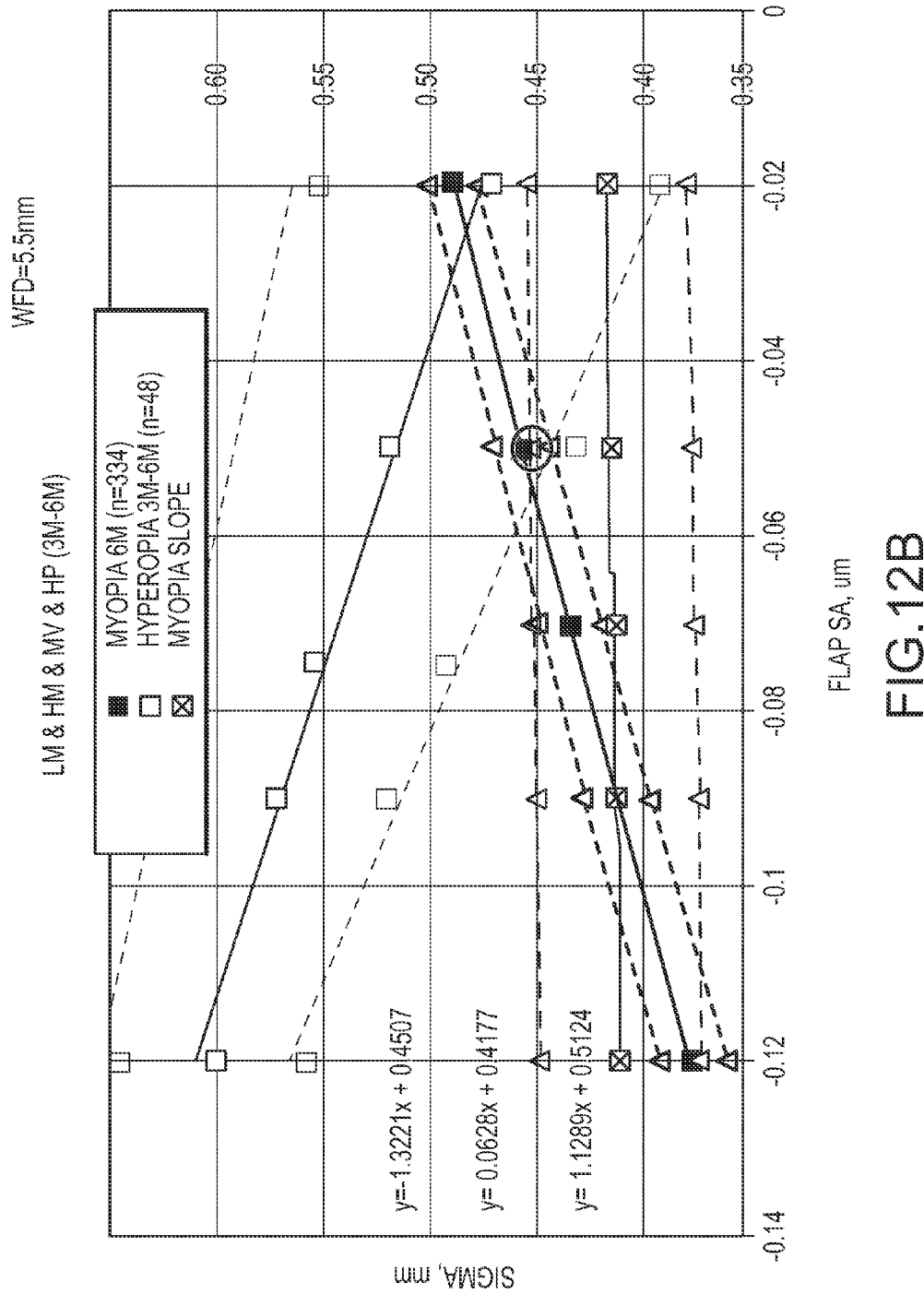

Various independent estimations of σ were used, including (a) RMS match for low and high Myopia (6M), (b) and Hyperopia (6M-9M), and (c) slope-based estimation for low Myopia (6M). For example, FIGS. 12A and 12B depict optimized sigma vs. flap induced SA (simulations for clinical studies) for WFD=6 mm and WFD=5.5 mm, respectively. The dashed lines represent confidence intervals. WFD refers to a wavefront diameter.

As flap-induced aberrations typically do not depend on the type of the subsequent treatment, it is possible to assume that the optimal values for flapSA and σ can be chosen within the crossing of confidence intervals for these three estimates (e.g. circled data points in FIGS. 12A and 12B). These points can define optimal values approximately σ=0.3 mm, flapSA=0.09 um for 6 mm wavefront and σ=0.45 mm, flapSA=0.05 um for 5.5 mm wavefront. Some clinical observations for a flap incision without a subsequent ablation show close values for the flap induced SA (e.g. flapSA≅0.07 um).

Figure 13A:
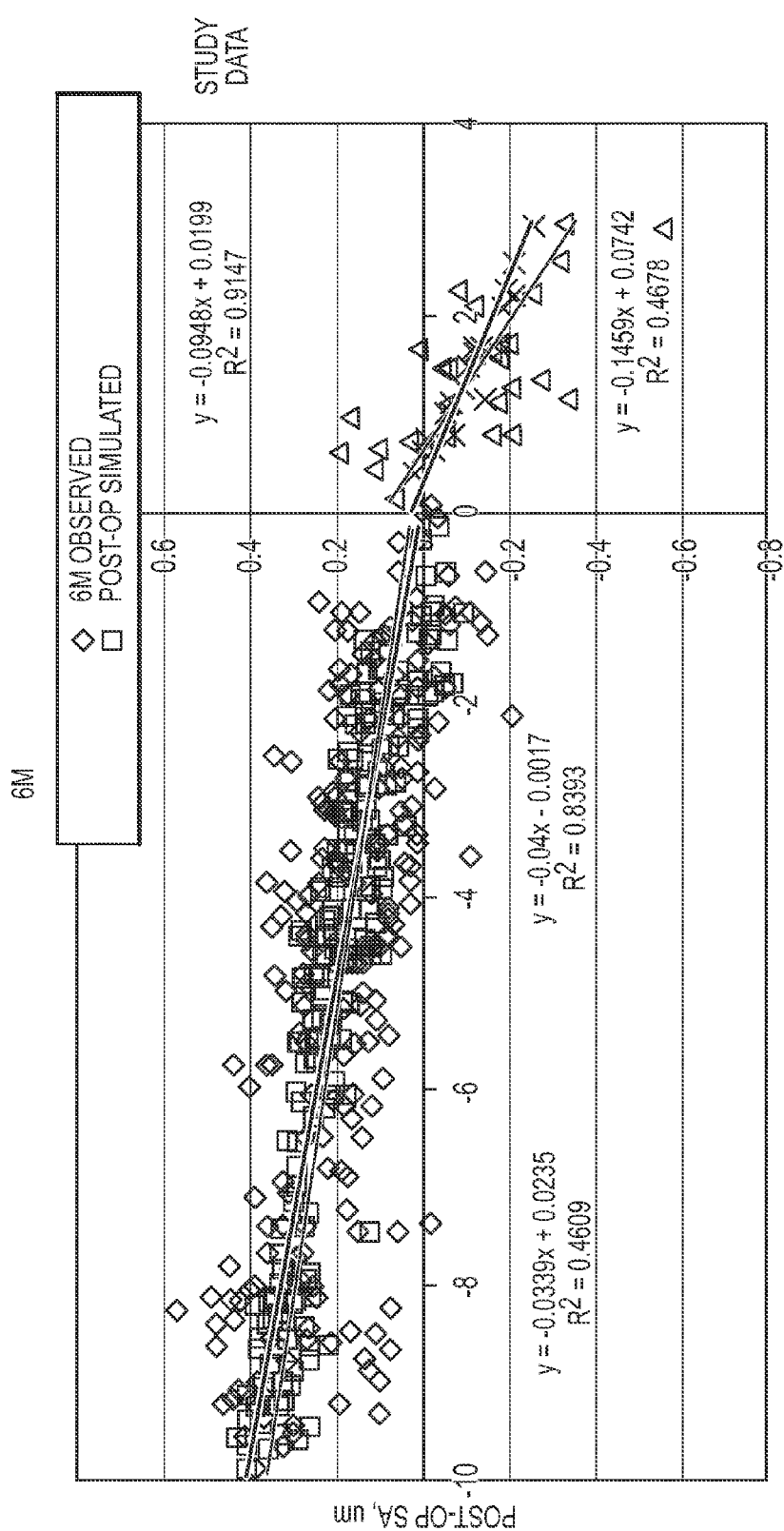
FIGS. 13A to 13C depict aspects of post-operative SA and pre-operative MRSE or SE relationships according to embodiments of the present invention.
Figure 13B:
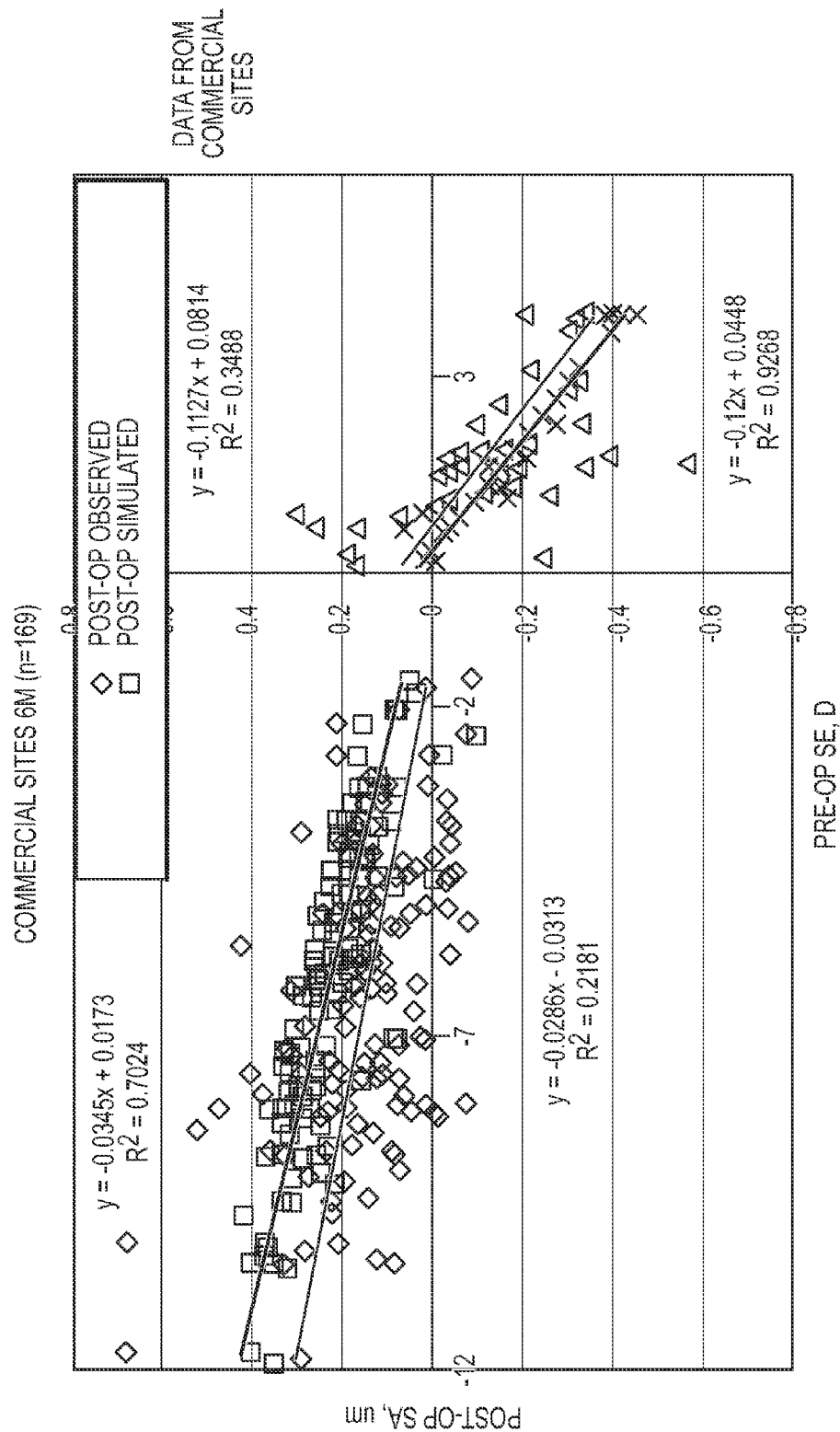
Figure 13C:
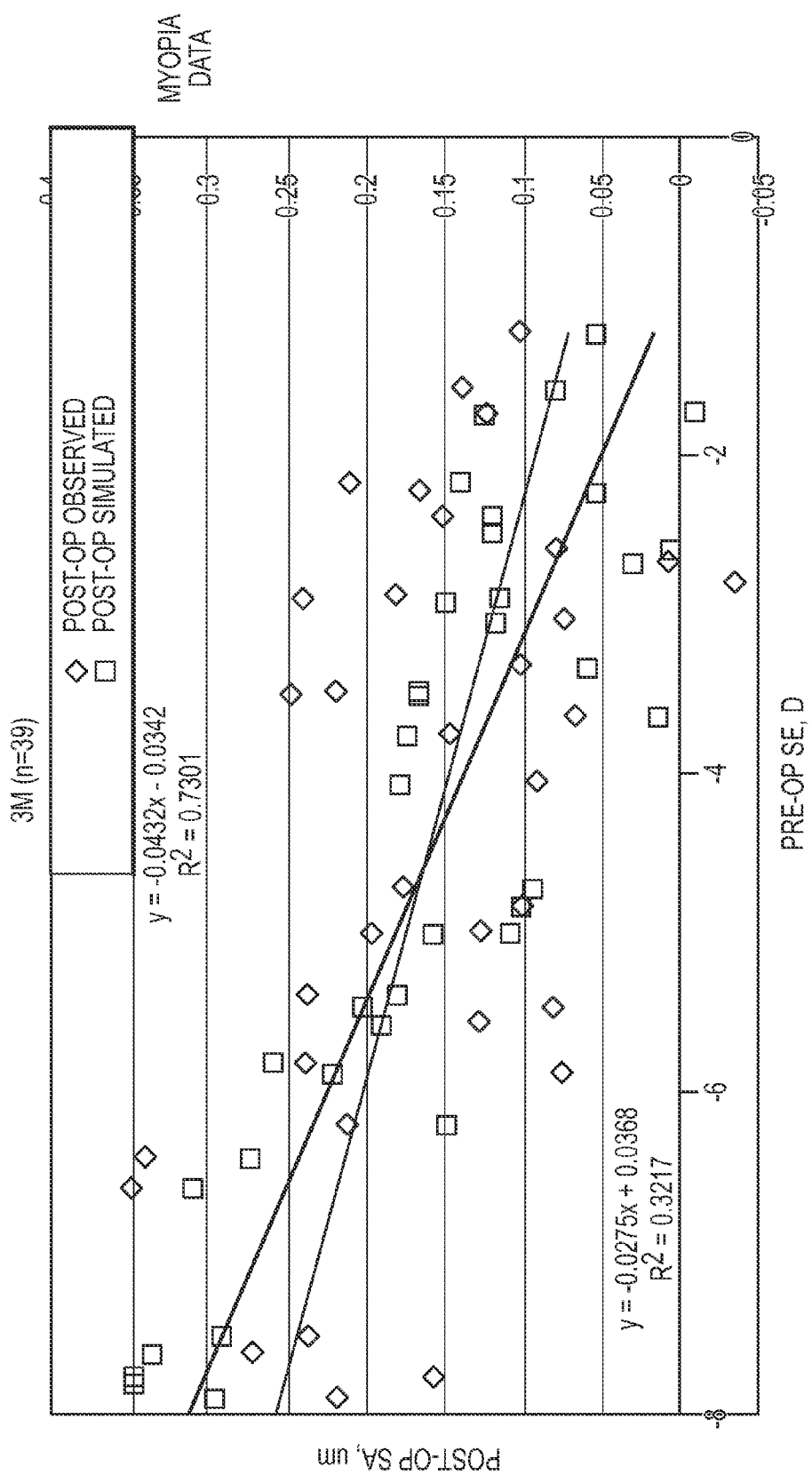

It is possible to compare simulated and observed post-operative SA (e.g. with WFD=6 mm). For example, as depicted in FIGS. 13A, B, and C, an estimated diffusion coefficient σ=0.3 mm for 6 mm wavefront diameter may be validated by comparison of simulated post-operative operative SA with the actual observed values. A flapSA=0.09 um was assumed for all data sets. In some embodiments, this value might be different for mechanical microkeratome and IntraLase® femtosecond laser treatments. As illustrated here, trend lines for simulated and observed data can be almost identical for myopia and high myopia data and rather close for other data sets.

Hence, it is understood that epithelial smoothing subsequent to refractive surgery can induce SA, and that simulation of smoothing can be helpful in developing approaches that compensate for the smoothing. In some cases, it is possible to define the shape of the post-operative cornea surface as a convolution of an ablation target profile with a low-pass filter (LPF).

In some cases, the post-operative epithelium smoothing process can be simulated by defining the shape of the post-operative cornea surface as a convolution of the ablation target profile with a low-pass filter (LPF) as follows (spatial domain):

$$h_{post-op} = h_{pre-op} - K(x,y) \otimes T(x,y) \quad \text{Equation 16}$$

where h stands for the elevation maps, ⊗ denotes a convolution, T(x, y) is the ablation target profile and K(x, y) is a low pass filter (LPF) kernel, which has the following Fourier transform:

$$K(k_x, k_y) = \cfrac{1}{1 + \cfrac{\sigma^2(k_x^2 + k_y^2)}{(0.5 dL)^2}} \quad \text{Equation 17}$$

Equation 17, which is in the Fourier domain, represents a squared Butterworth low-pass filter of the first order, which can be applied to the treatment target in order to obtain the wavefront change due to the corneal smoothing. It can be defined by a single diffusion coefficient σ, which has a unit of length. For some discrete case embodiments, the 101×101 mesh size can be dL=0.1 mm. Based on optimizations using data from certain clinical trials, a sigma of 0.35 mm was determined to best explain that observed data.

According to some embodiments, K(x, y) is in the spatial domain, and is a Fourier transform of $K(k_x, k_y)$. Here, $k_x$ and $k_y$ are Fourier domain or frequency domain variables. According to some embodiments, K(x, y) is an LPF kernel that can be exemplified by a 101×101 matrix or by a 3-D surface expressed in matrix form where x and y are spatial domain variables.

Matching Simulation Results Vs. Observed Data

According to some embodiments, it is possible to match or compare simulated post-operative SA with observed 6M post-operative SA using linear least-square fit of the model to the observed SA change by minimizing the following function:

$$F = \sum_{all\_eyes} \frac{[flapSA + SA(K \otimes T) - (SA_{post-op} - SA_{pre-op})]^2}{N} \quad \text{Equation 18}$$

Here $SA_{pre-op}$ and $SA_{post-op}$ are spherical aberration values for pre-operational and 6M post-operative wavefront measurements, flapSA is the immediate flap-induced SA value before the smoothing, and N is the number of eyes. It is possible to compute this function (F) for different flapSA and diffusion coefficients, σ, and for each flapSA to find the value σ min where fitting residual is minimal. SA (K⊗T) refers to the SA of the target T after LPF.

The confidence interval for the optimized σ can be roughly estimated as:

$$\Delta \sigma = \frac{std([SA(K \otimes T) - (SA_{post-op} - SA_{pre-op})]^2)}{\sqrt{N}} \cdot \frac{d\sigma}{dSA} \quad \text{Equation 19}$$

Here std is a standard deviation, computed for the ensemble of eyes with the optimized value $\sigma = \sigma_{min}$.

Both optimized σ and its confidence interval can depend on the value of flapSA. This dependence can be computed separately for myopic (6M) and hyperopic (6M-9M) eyes, for example as depicted in FIGS. 12A and 12B. Hence, it is possible to have two independent estimations for optimized flapSA and σ.

An alternative estimation of these values can be obtained from matching the simulated vs. observed trend slopes, as follows:

$$\left(\frac{d\Delta SA^{(sim)}}{dSE_{pre-op}}\right)_{all\_eyes} = \left(\frac{\Delta SA^{(exp)}}{dSE_{pre-op}}\right)_{all\_eyes} \quad \text{Equation 20}$$

Here $\Delta SA = SA(K \otimes T) - (SA_{post-op} - SA_{pre-op})$. The optimized σ can provide a simulated slope that is the same as the observed slope. A confidence interval for this estimate can be defined as 95% confidence interval for the slope of linear regression, as follows:

$$\Delta \sigma = \frac{d\sigma}{dSA} \cdot \frac{t_{0.025} \cdot s}{s_x \sqrt{N-1}} \quad \text{Equation 21}$$

Here $t_{0.025} = 1.96$, $$s^2 = \frac{N-1}{N-2} \cdot \left(s_y^2 - s_x^2 \frac{dSA_{post-op}}{dSE_{pre-op}}\right),$$

$s_x = \text{stdev}(SE_{pre-op})$, $s_y = \text{stdev}(SA_{post-op})$. The slope-based estimation was calculated for a Myopia study.

Offset Transition Zone

In some instances, a target shape or ablation target profile will include an optical zone and a transition zone. The aggregate of the optical zone and transition zone may be referred to as an ablation zone, corresponding to the entire corneal region covered by a laser ablation. The optical zone may refer to a corneal region which received a full intended refractive treatment. A transition zone may refer to a corneal region outside of the optical zone but inside of the ablation zone. Often, a transition zone receives a treatment that is not strictly optically correct. With returning reference to FIG. 9, exemplary methods may also include offsetting an inner boundary of the transition zone, as indicated by step 920. According to some embodiments, an original target shape may include a transition zone starting at about 0.25 mm inside the boundary of the optical zone. It is possible that such a target may induce some post-operative SA, independent of any effect cornea smoothing may have on post-operative SA. Hence, a total induced SA may include a target-induced SA combined with a subsequent smoothing-induced SA.

Figure 10A:
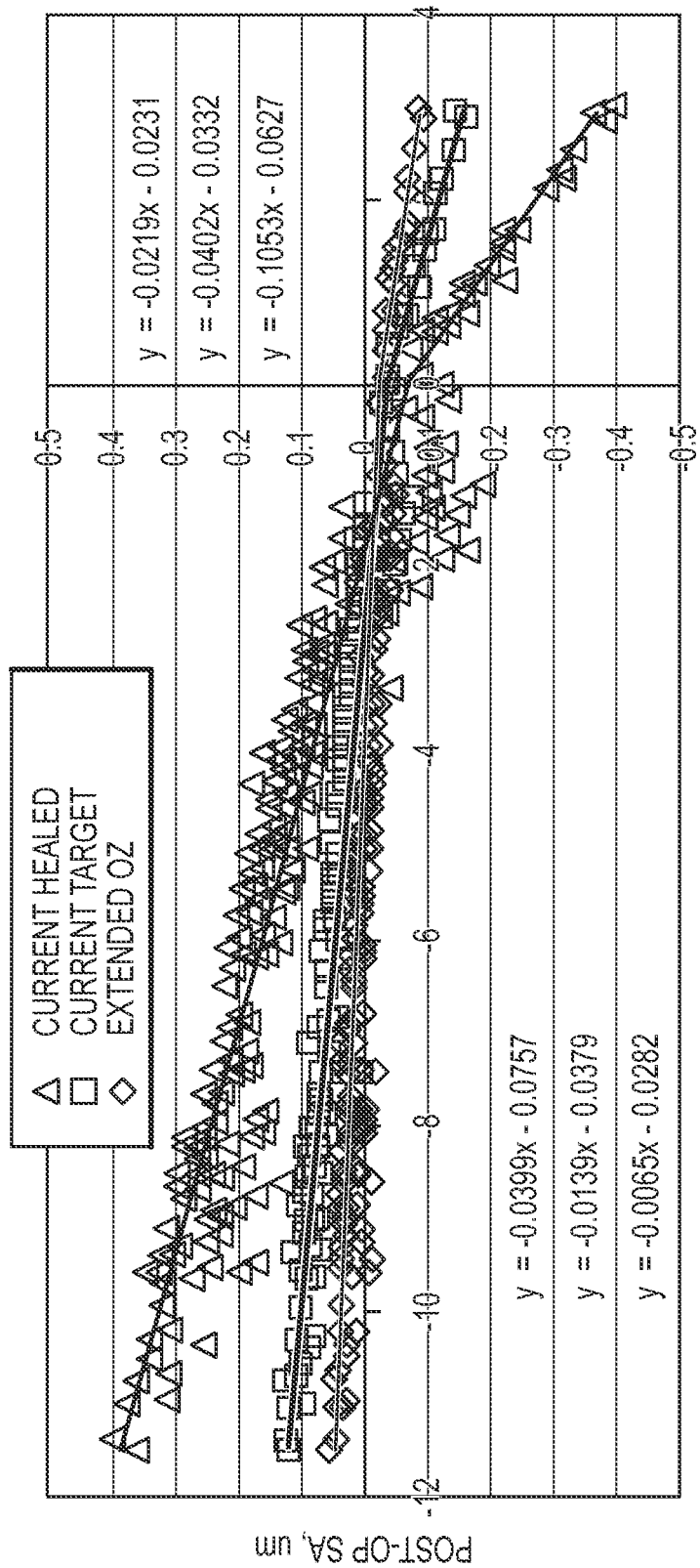

For example, FIG. 10A depicts post-operative values, in microns, simulated with σ=0.3 mm for study data (n=340), for SA as indicated in Table 3.

TABLE 3

| Symbol | Source of induced SA |
|---|---|
| □ | Original target shape, no corneal smoothing (i.e. immediately after ablation) |
| Δ | Original target shape, and corneal smoothing |
| ◊ | Modified target shape (transition zone extended by 0.1 mm), no corneal smoothing |

As shown here, a target-induced SA (□) may be reduced or even completely eliminated with a small offset of the transition zone (◊). In some cases, the offset of the transition zone may cause sharper gradients in the peripheral target. A 0.05 mm radial shift of the inner boundary of the transition zone away from the center of the optical zone, for example as shown in FIG. 10B, (corresponding to a diameter change of 0.1 mm), can make the trend slope for target-induced SA vs. pre-operative SE about twice as small and bring the magnitude of target-induced SA (◊) below 0.1 um level, which may be considered negligible. In some instances, by offsetting the inner boundary of the transition zone (e.g. by about 0.1 mm in diameter), the target induced SA can be reduced by about 50% (e.g. 0.1 mm change in diameter). As depicted here, correcting the target induced SA can be effective to remove post-operative SA.

Deconvolution

With returning reference to FIG. 9, a method of modifying a target shape can also include applying a deconvolution to the target profile or shape, as indicated by step 930. For example, methods may include applying a low pass filter (LPF) deconvolution (e.g. with σ=0.35 mm) to the target profile. Sigma (σ) can refer to a diffusion coefficient related to the strength of an LPF process.

According to some embodiments, the application of a deconvolution transformation to an original target can operate to compensate for the area of high curvature, which can be a significant cause of post-operatively induced SA.

In some instances, an LPF kernel for a deconvolution may be the same as the one optimized to fit an observed induced post-operative SA, for example such as those described above in connection with the post-operative epithelial smoothing and spherical aberration. Corneal smoothing, simulated as convolution with an identical or similar LPF kernel, can bring the cornea back to the desired shape.

In some instances, high-frequency variations may be suppressed by diffusion or LPF convolution. Restoration of such suppressed variations by deconvolution may introduce inaccuracies, which may also be influenced by a signal-to-noise level.

Embodiments of the present invention encompass the use of deconvolution techniques which can reduce the degree to which suppressed variations may introduce such inaccuracies. For example, deconvolution techniques may involve the use of a deconvolution filter, combining an LPF kernel, K, and a signal-to-noise ratio, SNR. The Fourier transform of such a filter can be expressed as follows:

$$DK(\vec{k}) = \frac{K * (\vec{k})}{|K(\vec{k})|^2 + SNR^2} \quad \text{Equation 22}$$

Here K(k) represents a Fourier transform of a LPF kernel, the asterisks refers to a complex conjugate, SNR is the signal-to-noise ratio, and k represents a vector variable. According to some embodiments, the SNR is assumed to be constant. The value of SNR can define which scales will be restored by the deconvolution, reversing diffusion effect on them. In some instances, SNR can be 0.1. If the SNR is excessively small, many small features may be amplified. If the SNR is excessively large, only relatively large features will be amplified. In exemplary embodiments of the present invention, SNR has a value within a range from 0 to 0.1.

If there are no noises and SNR=0, deconvolution should bring back exactly the original target, which existed before the LPF was applied. Where finite noises are present, small features may be irreversibly lost after low-pass filtering and, therefore, deconvolution may restore the original target only with a finite accuracy. The error of restoration can be estimated with applying a LPF to a target and then using deconvolution to restore it and compare it with the original target.

Figure 14A:
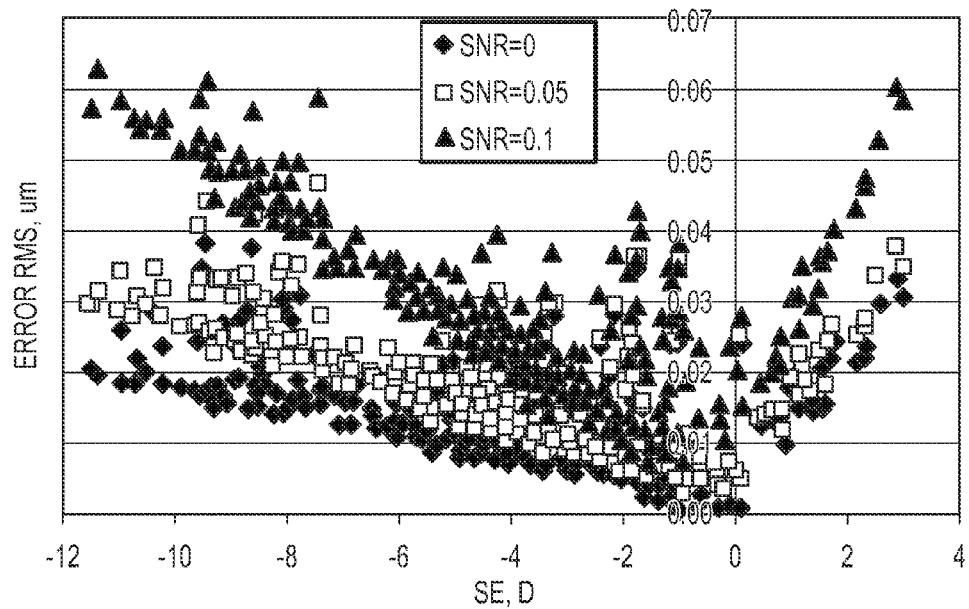
FIGS. 14A and 14B illustrate aspects of spherical aberration errors for deconvolution according to embodiments of the present invention.
Figure 14B:
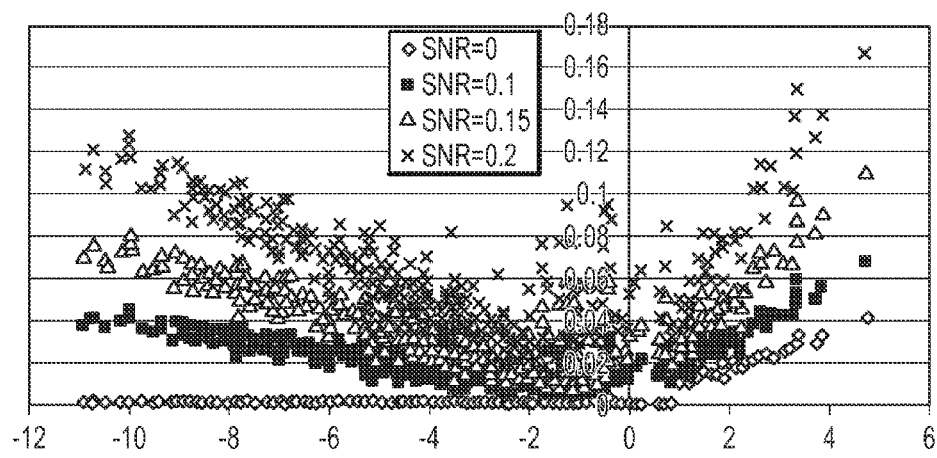

FIG. 14A shows spherical aberration RMS errors for deconvolution for different SNR values, estimated for study targets (n=340) with σ=0.3 mm, where WFD=6 mm. As depicted here, with SNR=0.1, all SA RMS errors are below 0.07 um level. FIG. 14B shows SA errors for a similar deconvolution, estimated for study targets (n=515) with σ=0.28 mm.

Any small and narrow dips in the measured pre-operative wavefront may be amplified by the deconvolution. This may result in small-size features that are too narrow to resolve with laser pulses, which are often restricted to a width of about 1 mm.

In some cases, it is not necessary or desirable to ablate these very narrow features, as they may be flattened by the smoothing process. What is more, these features may also have little influence on the vision quality. In some cases, it is possible to effect the deconvolution so as to neglect or minimize these features and amplify only relatively large-scale features of the ablation target. For example, this can be done by optimizing the SNR value in a deconvolution process. It has been found that by using SNR≥0.1, for example, any features smaller than 0.5 mm are not amplified by deconvolution. Hence, SNR=0.1 may be used a default parameter.

A deconvolved target typically has an oscillating profile at the periphery. These oscillations may be mainly caused by boundaries between the optical zone, transition zone, and an edge of the finite-size target, where either the target profile or its derivatives have sharp changes.

Embodiments of the present invention encompass the use of deconvolution and related techniques to compensate for the post-operative induction of high order aberrations (HOAs), and in particular spherical aberration (SA). Accordingly, the visual quality of patients receiving treatments according to these techniques provides desirable results, particularly in the management of night vision symptoms. Often, deconvolution procedures will result in treatment target shape changes near the periphery of the optical zone. For example, within a central 4 mm area, the refraction of a modified target shape may be similar or identical to that of an original target shape.

According to some embodiments, to obtain a new or modified target shape, a deconvolution process can be employed as follows:

$$T_{new} = K_{INV} \otimes T_{current} = F\left[\frac{K*(k_x, k_y)}{|K(k_x, k_y)|^2 + SNR^2}\right] \otimes T_{current} \quad \text{Equation 23}$$

where F(•) stands for a Fourier transform, * denotes a complex conjugate, $T_{current}$ is an original treatment target, $T_{new}$ is the new target that is intended to remove the post-operative SA, and $K_{INV}$ is the inverse kernel of K. The SNR can be used to prevent or inhibit noise amplification and oscillation at the edge. In some instances, a SNR value of 0.1 may be suitable for practical purposes. To prevent or as a substitute for real-time calculation of the Fourier transforms, the inverse kernel $K_{INV}$ can be pre-calculated and applied in real-time as a look-up table or a resource file. A suitable SNR value can prevent the denominator from being zero or excessively small, which may otherwise results in the matrix quotient being unreasonably large.

According to some embodiments, an inverse kernel can be exemplified as a convolution kernel that operates like a deconvolution procedure. In this sense, a deconvolution operation may be considered to be an inverse procedure of a convolution operation.

Embodiments of the present invention encompass techniques for calculating an inverse smoothing kernel $K_{INV}$. Whereas a low pass filter (e.g. Butterworth kernel) such as K(x, y) is in the Fourier domain, the inverse kernel is in the spatial domain. Instead of implementing a Fourier transform, it is possible to perform a spatial convolution implemented as multiplication.

Figure 23:
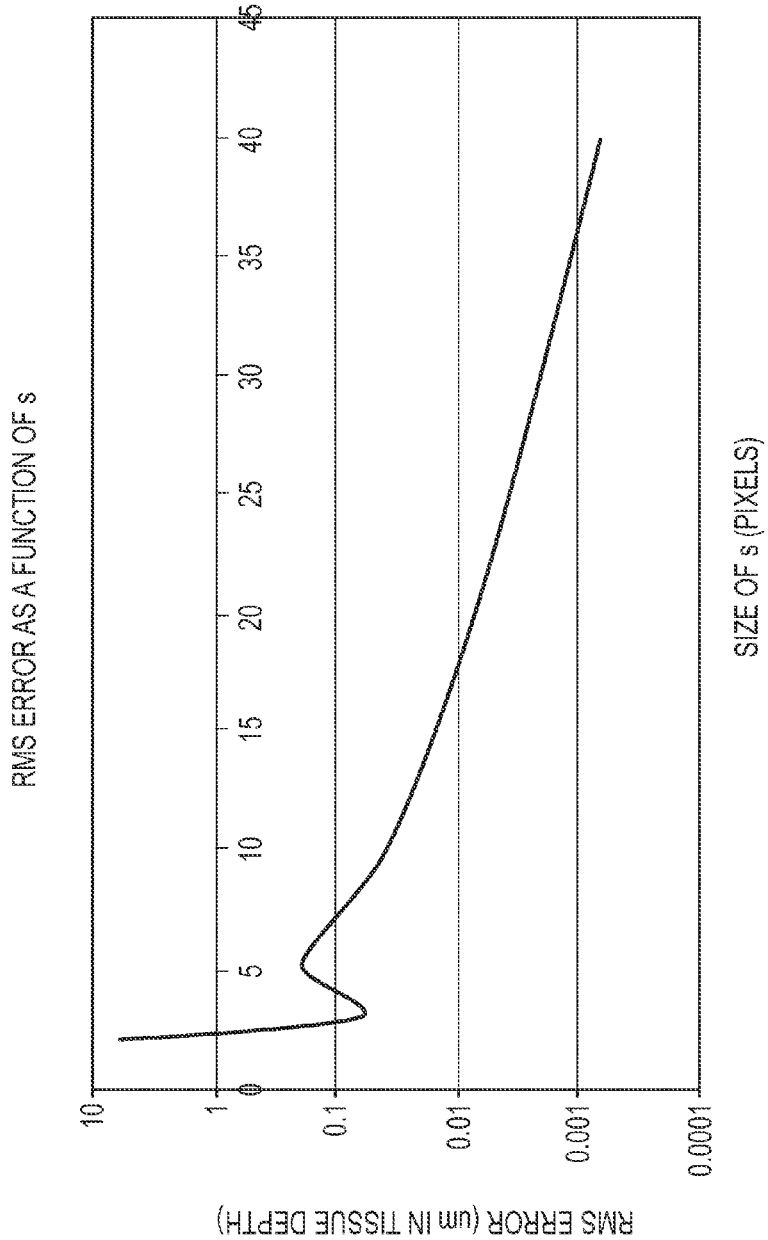
FIG. 23 depicts aspects of relationships between RMS error and size of s (pixels), according to embodiments of the present invention.

In some cases, embodiments encompass rapid convolution calculations (e.g. in the order of several milliseconds) for UI (user interface) manipulation, in a practical implementation. A normal implementation for a spatial 2-D convolution may involve four netted loops each with 101 elements. Such embodiments may be related to the 101×101 mesh size cases discussed above in the paragraph following Equation 17. A 2-D spatial convolution can be written as follows:

$$T_{new}(i, j) = T_{current} \otimes K_{INV} = \sum_{k=-\infty}^{\infty} \sum_{l=-\infty}^{\infty} T_{current}(i-k, j-l) K_{INV}(k, l) \quad \text{Equation 24}$$

where $K_{INV}$ is the 2-D inverse smoothing kernel. In some cases, $K(k_x, k_y)$ may be a Butterworth of the first kind, and its inverse may have an actual size that is only a few pixels wide. Therefore, Equation 24 may be rewritten as follows:

$$T_{new}(i, j) = T_{current} \otimes K_{INV} = \sum_{k=-s}^{s} \sum_{l=-s}^{s} T_{current}(i-k, j-l) K_{INV}(51+k, 51+l) \quad \text{Equation 25}$$

where the inverse kernel size is treated as (2s+1)×(2s+1) in size. When s=17, or the inverse kernel frame size of 35×35, RMS error using Equation B is about 0.01 microns. With s=37, use of Equation 25 may be about 7 times faster than Equation 24, but the error is within 0.001 microns. FIG. 23 shows the relationship between the RMS error and the size of s (pixels), with a simulation of 515 eyes. This figure depicts the RMS error as a function of s when Equation 25 is used (e.g. in contrast to Equation 28 as discussed below).

Zero Out

With returning reference to FIG. 9, a method of modifying a target shape can also include zeroing out an ablation profile at distances greater than the transition zone radius, as indicated by step 940.

Typically, no ablation is performed beyond the end of transition zone. Hence, it is possible to zero-out the ablation profile at distances greater than the transition zone outer radius, $R_{TZ}$, as discussed elsewhere herein, for example with regard to FIGS. 16C and 16D.

A zeroing-out procedure can be included, so as to prevent artifacts and the like that might occur as a result of performing convolution or deconvolution. For example convolution or deconvolution may inadvertently or unintentionally introduce nonzero or negative values at positions outside of the transition zone. A zeroing-out operation can be instituted as a safeguard, so as to ensure that such non-zero or negative values are removed, which could otherwise cause complications for a tissue ablation protocol.

Rescaling Deconvolved Target

As shown in FIG. 9, a method of modifying a target shape can also include rescaling a deconvolved target, as indicated by step 950. For example, a deconvolved target can be rescaled so that its Zernike defocus term within a 4 mm diameter is the same as that for an original target. In this way, the spherical equivalent refraction of a modified or deconvolved target can be the same as that for an original target. In some instances, a rescaling procedure can be performed to ensure that the refractive power for a deconvolved target is the same as that for an original target. In some cases, the refractive power for a deconvolved target is the same as that for an original target and no rescaling step is performed.

According to some embodiments, an original target shape may perform adequately for correcting or treating refraction errors, and hence a modified target shape based on the original target shape may be generated so that the refraction of the modified target is the same as for the original target. This can be achieved, for example, by rescaling of the deconvolved target so that its defocus Zernike term within the 4 mm area (which defines wavefront-based SE) is the same as for the current target. A rescaling coefficient, which is the ratio of the defocus terms for the current and deconvolved targets, may be expressed as follows:

$$\text{rescale} = \frac{SE_{current}}{SE_{de-conv}} \qquad \text{Equation 26}$$

Figure 15A:
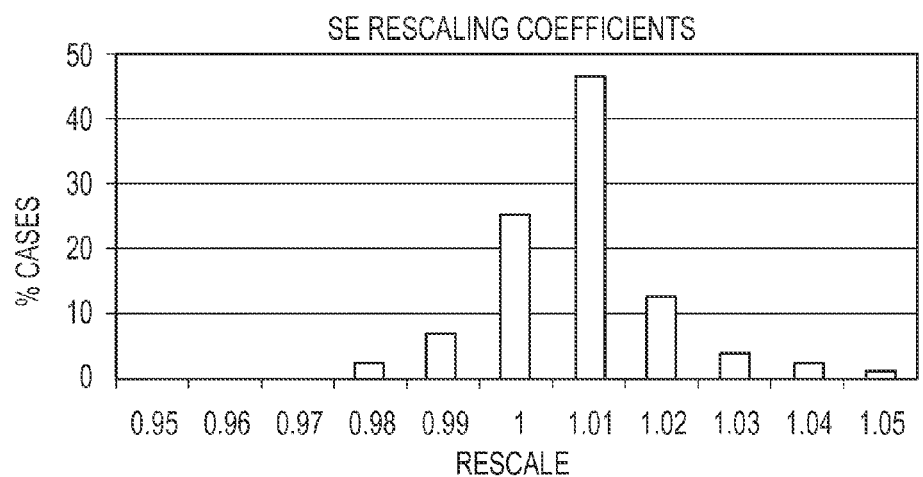
FIGS. 15A and 15B show aspects of rescaling coefficients and refraction errors, respectively, according to embodiments of the present invention.
Figure 15B:
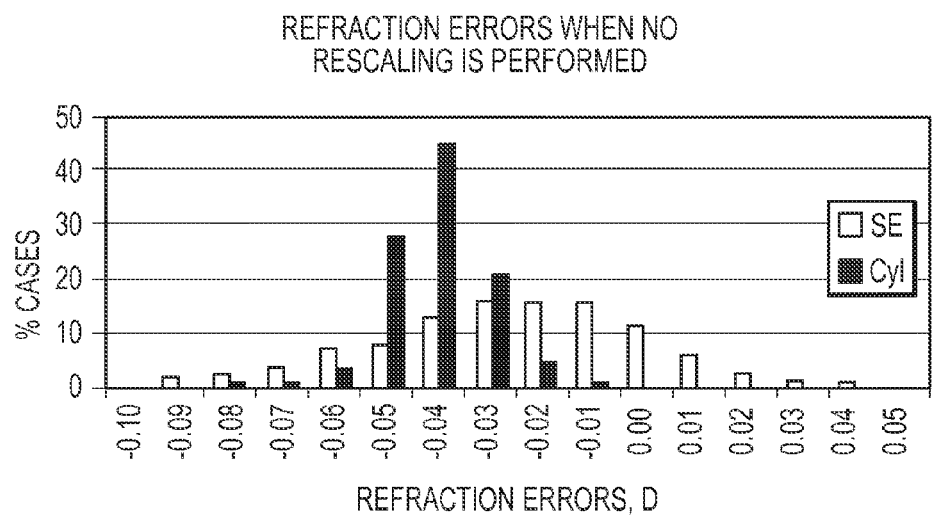

The rescaling coefficient may be close to 1, and distributed as shown in FIGS. 15A and 15B. For example, a rescaling coefficient may have a mean value of 1.003, such as that which was found for certain studies. In such instances, rescaling may not be needed, in practical terms. In no rescaling is performed, then resulting refraction errors may be below 0.1 D, for example as shown in FIG. 15A. Hence, it may be possible to neglect or ignore such small values. FIG. 15B shows a distribution of SE re-scaling coefficients and refraction errors without rescaling for the studies (n=340).

Figure 16B:
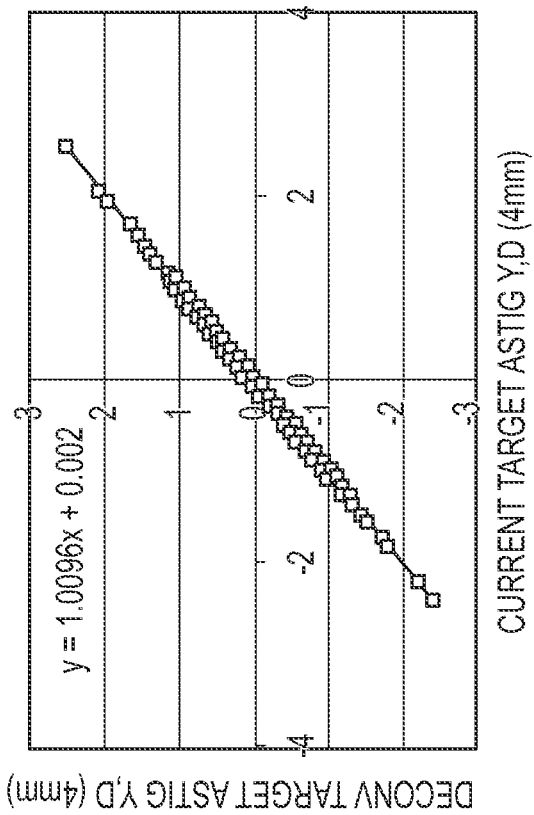
FIGS. 16A and 16B depict aspects of effects of deconvolution on cylinder refraction according to embodiments of the present invention.
Figure 16A:
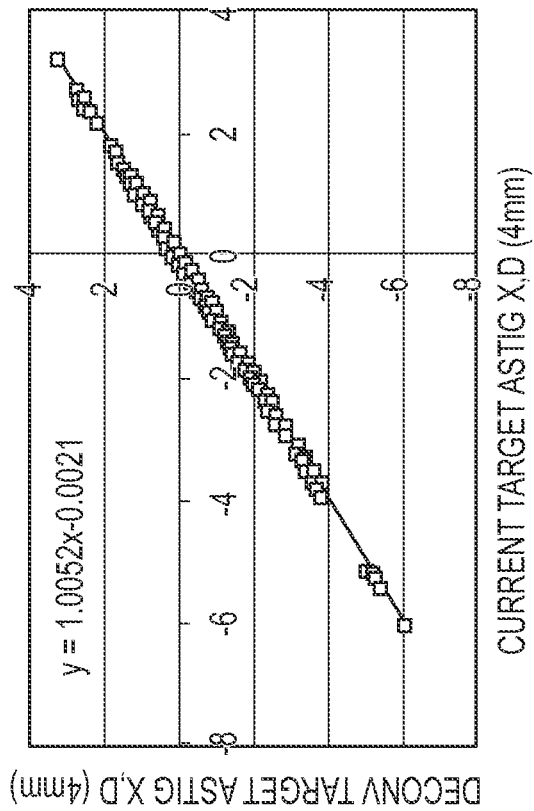

According to some embodiments, deconvolution may also affect the cylinder refraction. A magnitude of this effect is illustrated in FIGS. 16A and 16B. Here, it is possible to see a comparison of X, Y components of astigmatism for an original target and a deconvolved target (simulated for the studies, n=340). The deconvolved targets show slightly higher astigmatism, as compared with the original targets, although the difference is less than 1%.

According to some embodiments, a current or original target $T_{current}$ yields good matching to low order aberrations, and a scaling can be performed such that the refractive spherical equivalent over 4 mm of the new or modified target is the same as that of the current or original target. Exemplary studies have shown that such a scaling factor is about unity. Therefore, a scaling factor of 1.0 can be assumed in some cases.

In some embodiments, the rescaling process can incorporate scaling or rescaling techniques disclosed elsewhere herein, such as those described in FIGS. 22, 24, 41, and 42 and the corresponding specification text descriptions.

Elevating Ablation Profile

As shown in FIG. 9, a method of modifying a target shape can also include elevating an ablation profile, as indicated by step 960. For example, in order to make all ablation values be non-negative, it is possible to elevate the entire ablation profile so that the lowest point on the ablation profile is zero or otherwise non-negative. In this way, the ablation profile can be generated so that it does not have negative heights.

Damping Periphery Of Transition Zone

As shown in FIG. 9, a method of modifying a target shape can also include damping a periphery of a transition zone, as indicated by step 970. For example, a damping multiplier or multiplication factor may be applied which suppresses the fluctuations of the periphery of the target shape. In some embodiments, after certain adjustments are made (e.g. such as the adjustment discussed above), a peripheral part of the ablation profile may have a small bump, which may be the result of a cut-off at the end of the transition zone. Ablating such a bump may require a sequence of many small laser pulses around the transition zone periphery. In some cases, this may cause a substantial reduction of speed in the entire ablation process. In some cases, the bump may not be needed because it lies away from the optical zone and its influence on the wavefront within the optical zone after smoothing may be very limited. Embodiments of the present invention encompass the application of a damping multiplier to the periphery of the transition zone, starting from the distance $R_b = R_{TZ} - 0.5$ mm, as Follows:

$$T = T \cdot \begin{cases} \frac{R_{TZ} - R}{R_{TZ} - R_b} & R > R_b \\ 1 & R <= R_b \end{cases} \qquad \text{Equation 27}$$

Such a damping multiplier or factor can be used to eliminate or diminish the bump.

FIG. 16C shows an X cross-section of modifications of an ablation profile, and FIG. 16D shows a Y cross-section of modifications of an ablation profile. In some embodiments, modifications of an ablation profile (e.g. high myopia study, case ID=21011 OD) may include target deconvolution with $\sigma=0.35$ mm, as well as an elevation modification, or a cut-off beyond the transition zone.

Figure 17A:
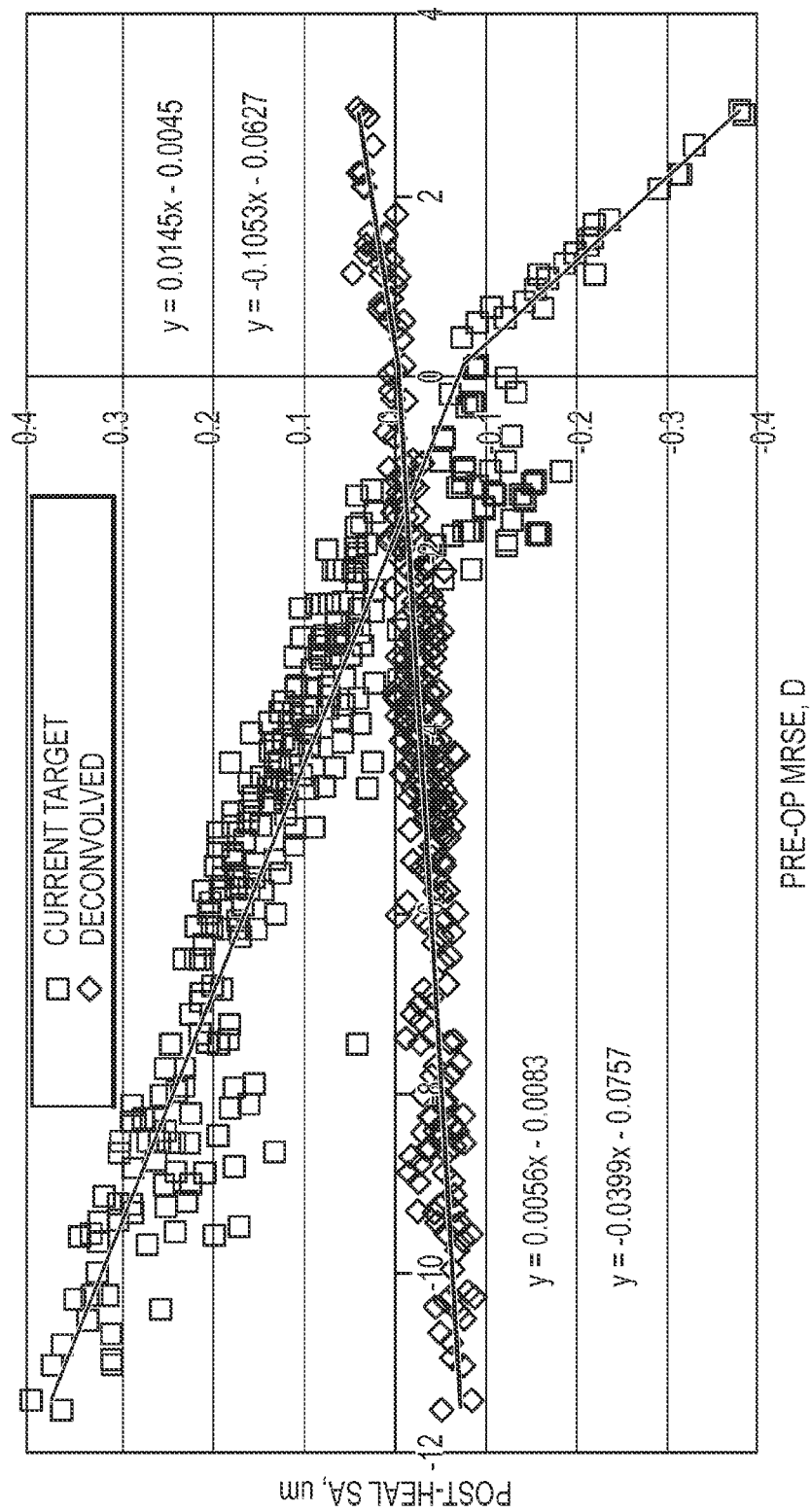
FIGS. 17A to 17C depict aspects of pre-operative MRSE (Manifest Refraction Spherical Equivalent) according to embodiments of the present invention.
Figure 17B:
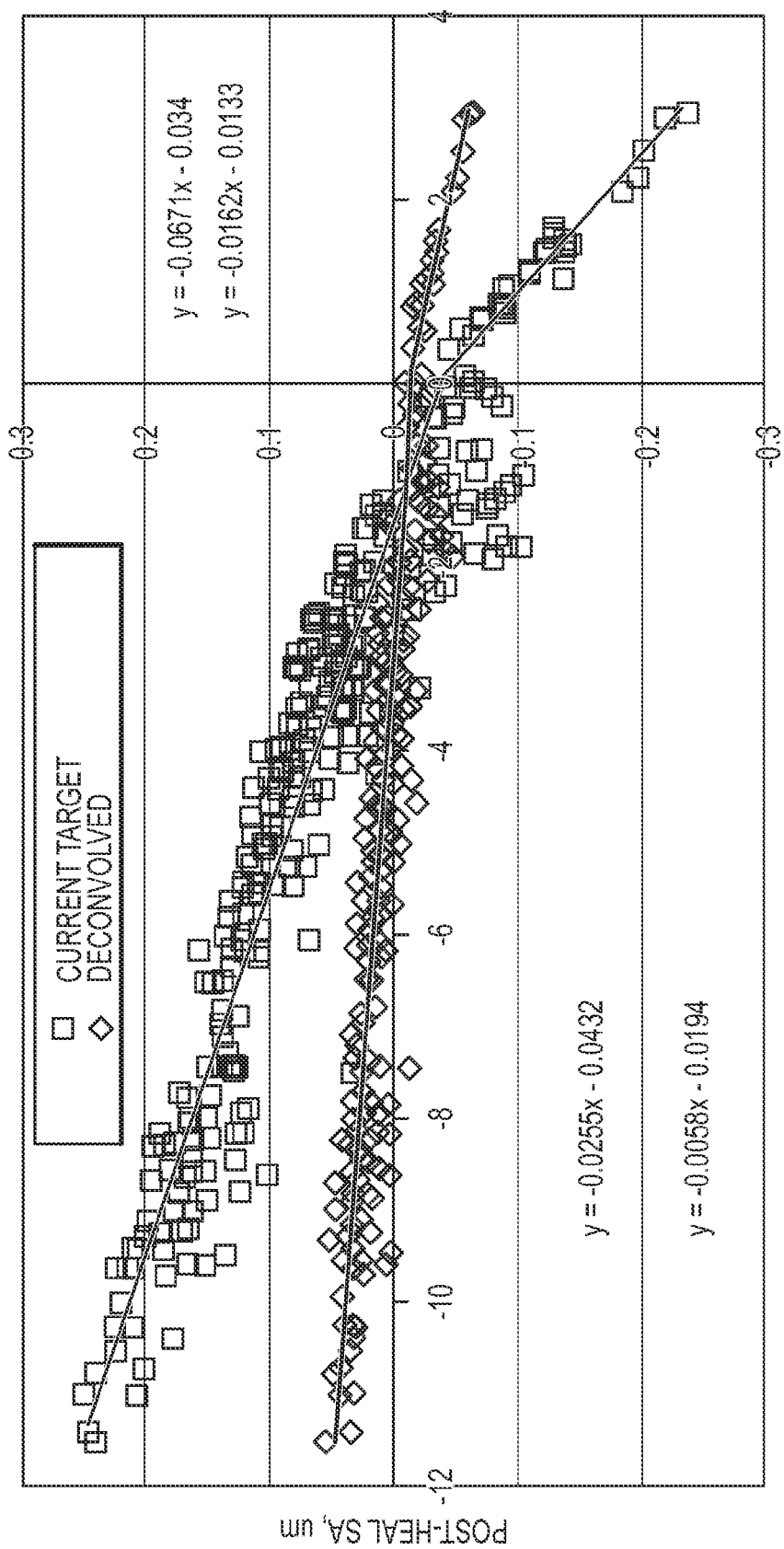
Figure 17C:
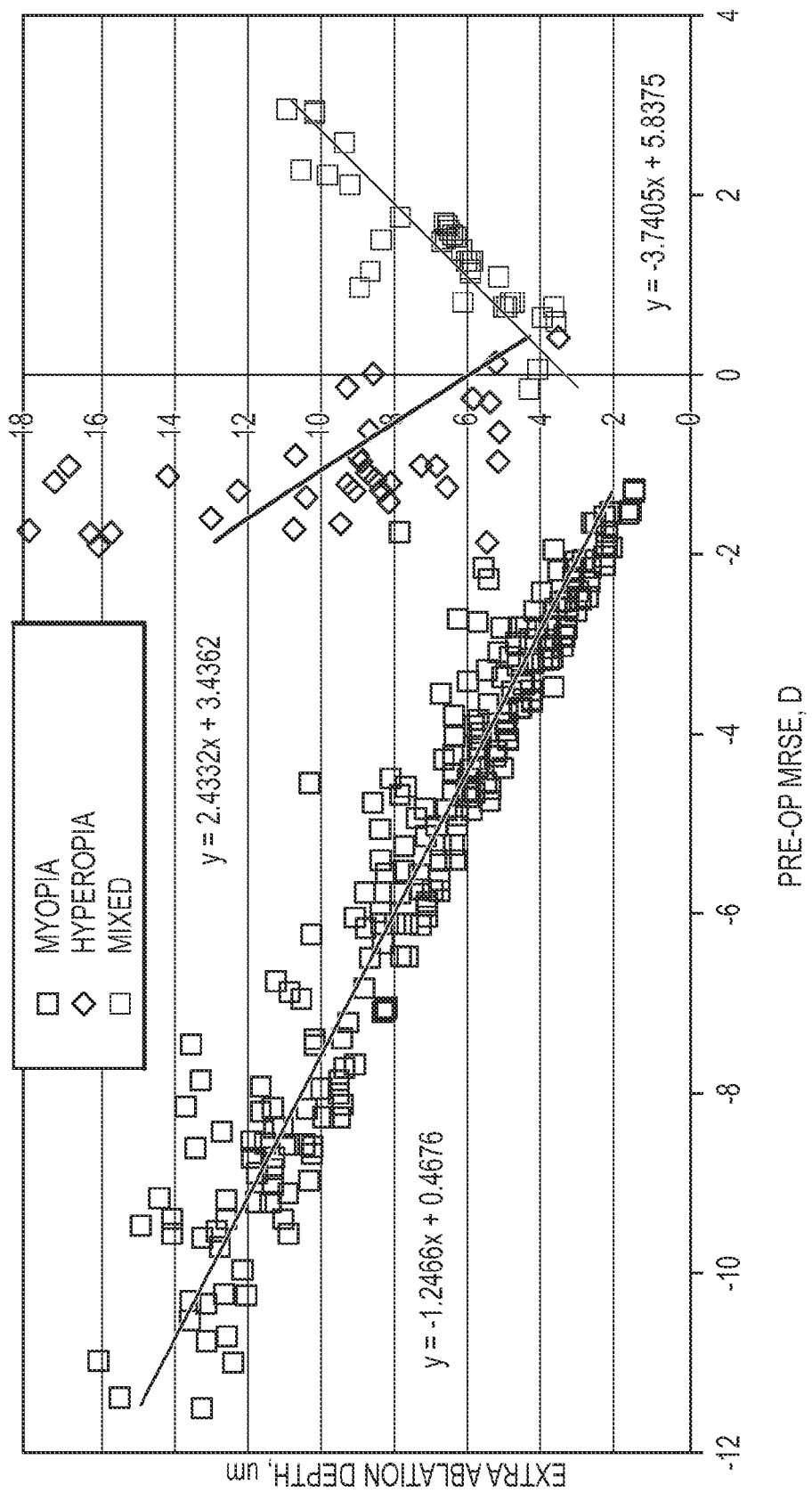

In some cases, a different wavefront diameter may use or benefit from a different diffusion coefficient (e.g. for an LPF model) to match post-operative measurements. In some cases, it is possible to use an approximated value of $\sigma=0.35$ mm, which is between optimized values for 6 mm and 5.5 mm wavefront diameters, as discussed elsewhere herein. Using a diffusion coefficient such as this for the target deconvolution, it is possible to predict or calculate a substantial reduction of induced SA for both WFD=6 mm and WFD=5 mm and also additional ablation depth requirement. For example, FIG. 17A depicts a simulated post-operative SA for a 6 mm wavefront, FIG. 17B depicts a simulated post-operative SA for a 5.5 mm wavefront, and FIG. 17C depicts an extra ablation that may benefit a deconvolved target. As such, these figures demonstrate the effect of deconvolution on post-smoothing SA and on additional maximum ablation depth.

Because deconvolution may amplify noises, the tail or outer periphery of the ablation profile may have some bumps. To remove such bumps, a damping multiplier can be applied as $$T' = T \cdot \begin{cases} 2(R_{TZ} - R) & R > R_b \\ 1 & R \le R_b \end{cases} \qquad \text{Equation 28}$$

where T' is the new target after damping, T is the target after Equation 14 and R is a variable in radius. $R_{TZ}$ is the transition zone radius, and the cutoff radius $R_b = R_{TZ} - 0.5$ mm. This damping multiplier can effectively and substantially eliminate the bumps.

Results And Data Analysis

Based on certain codes for treatment target creation, the following two phases of simulation studies were conducted. A first phase involved optimizing a one-parameter diffusion coefficient such that it best explains the clinically observed 6M post-operative spherical aberrations with the same surgical parameters as these eyes were treated. A second phase involved verifying that with the use of an optimized diffusion coefficient, the expected post-operative spherical aberration is significantly reduced when a deconvolution algorithm is used.

Optimization of a diffusion coefficient was based on data from various clinical studies and trials, as well as data from commercial sites. Only eyes with pre-operative and 6M (3M for iDesign™ system) post-operative wavefront measurements with at least 6 mm diameter were used. As such, 340 eyes were from the study, 169 eyes from the commercial sites, and 39 eyes from iDesign™ system based study. Of the 340 eyes from a study, 158 were in the low to moderate myopia cohort, 75 in the high myopia cohort, 26 from hyperopia cohort, 47 from the monovision cohort (dominant eyes only), and 34 from the mixed astigmatism cohort.

As explained elsewhere herein, a comparison between a simulated and an observed post-operative spherical aberration can be performed for a given diffusion coefficient. An optimization process was chosen such that the simulated post-operative spherical aberration has a substantially identical slope as compared with a pre-operative spherical equivalent to that of the observed post-operative spherical aberration.

Because of variations of the sample size in different cohorts, the 95% confidence bands are different for different cohort. A small overlap area can be identified for these 95% confidence bands. The optimized diffusion coefficient of 0.35 mm was obtained from the overlap area.

According to some embodiments, deconvolution, which can be used to reduce post-operative spherical aberrations, is a physical-model-backed approach. It is based on the smoothing effect observed from the clinical data. Therefore, not only can it account for the increase of the post-operative spherical aberration, but it can also account for the induction of other high order aberrations, such as coma, secondary astigmatism, and secondary spherical aberration. Furthermore, as discussed elsewhere herein, it provides a smaller ablation depth as compared with other techniques (e.g. larger optical zone, larger keratometric values) used to target the same level of spherical aberration reduction.

Many of the target shape modification discussed herein can operate to change a peripheral area of the target so as to reduce the induction of SA. It is possible to compare such methods, for example when their parameters are selected to generate a small slope of SA vs. SE trend, as indicated in Table 4. The parameters in this table were selected for the simulation to achieve a slope of SA vs. SE trend that is about the same as the slope from the observed clinical data.

Table 4 provides a comparison of three methods of target modifications, simulated for data from the studies. Parameters for each modification method were chosen to bring the magnitude of simulated slope of post-operative SA vs SE trend line down to 0.01. The simulated average post-op SA ($<SA>$), the worst case SA (max $|SA|$), the average extra ablation depth ($<extraH>$), and the worst case (max extraH) are also shown. Sigma ($\sigma$) is a diffusion coefficient related to the strength of an LPF process, described elsewhere herein. As shown in Table 4, a deconvolution method (sigma) can virtually eliminate both the mean SA and the SA vs. SE trend slope. Similarly, a widened optical zone method (dOZ) and a cosine correction adjustment method (dK) can also virtually eliminate both the mean SA and the SA vs. SE trend slope. Compared with widened optical zone and cosine adjustment methods, deconvolution techniques often require lower amounts of ablation, and hence can provide useful solutions where saving or maintaining more tissue is desired.

Figure 18A:
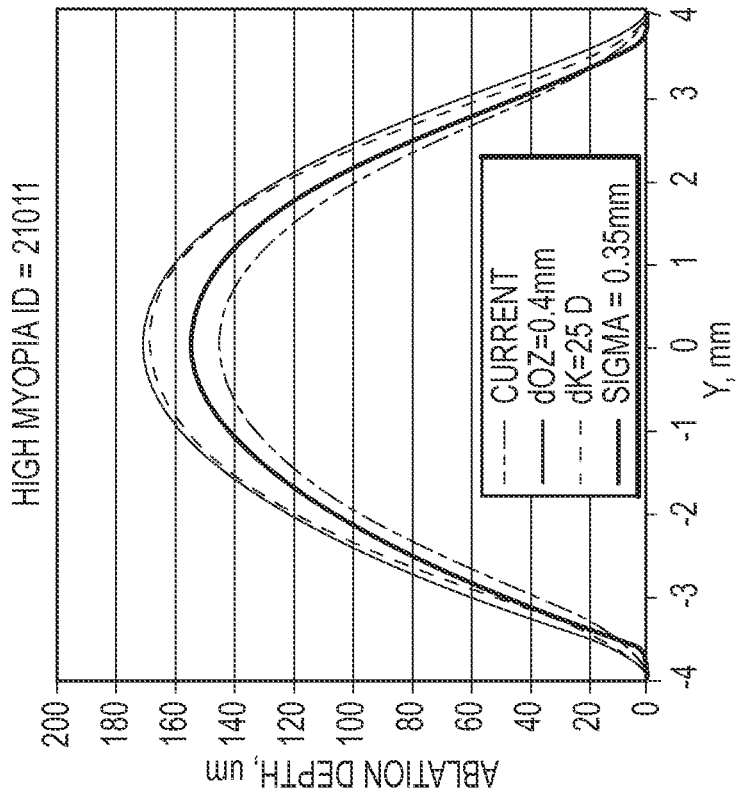
FIGS. 18A and 18B illustrate aspects of ablation profile modifications according to embodiments of the present invention.
Figure 18B:
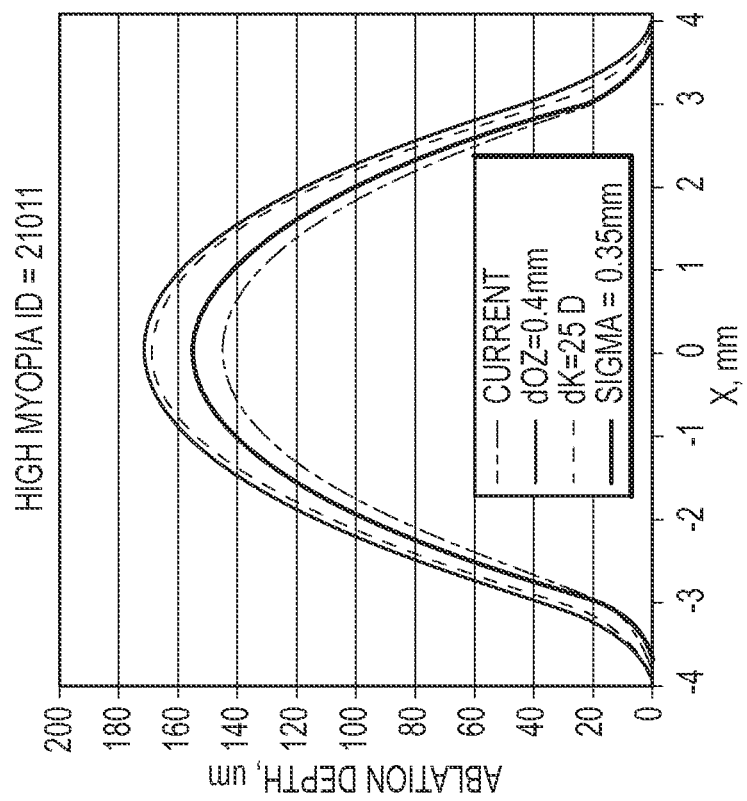

FIG. 18A shows an X cross-section of modifications of an ablation profile, and FIG. 18B shows a Y cross-section of modifications of an ablation profile. These modifications of an ablation target are simulated for a high myopia study (study ID=21011 OD, −7.4D/−1.5D×179°). Simulation was performed for a wider optical zone approach (dOZ=0.4 mm), an adjusted cornea curvature for cosine correction approach (dK=25D), and a deconvolution approach ($\sigma$=0.35 mm). When evaluating the expected post-operative SA, it may be helpful to consider that simulations may only show the changing SA vs SE trend line after the target modification. In reality the post-operative SA may deviate from the trend line due to some other factors which are not accounted for. These deviations can be estimated for the current target as follows:

$$\delta SA = SA_{observed}^{(6M)} - SA_{stimulated}^{(post-op)} \quad \text{Equation 29}$$

Figure 19A:
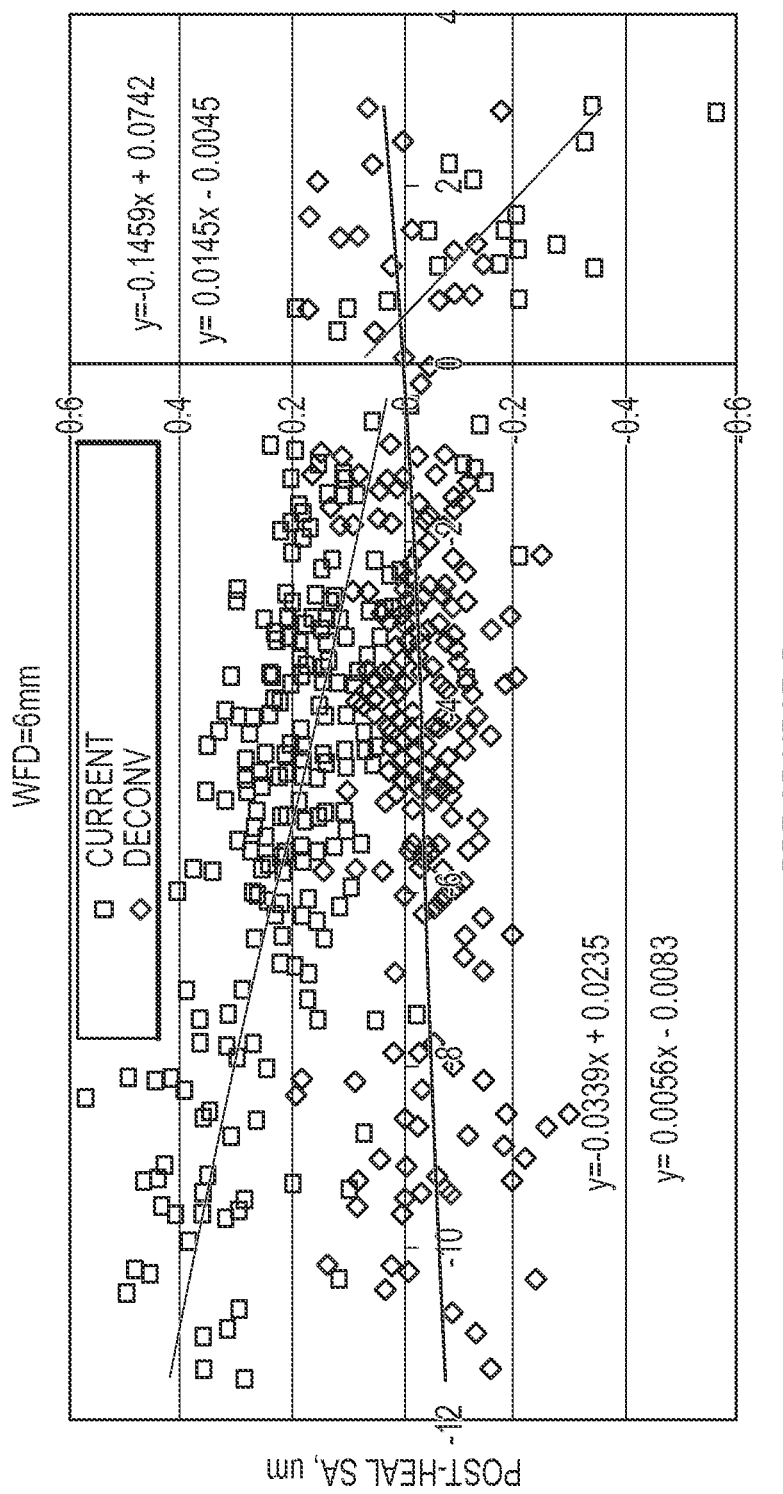
FIGS. 19A and 19B show aspects of pre-operative MRSE according to embodiments of the present invention.
Figure 19B:
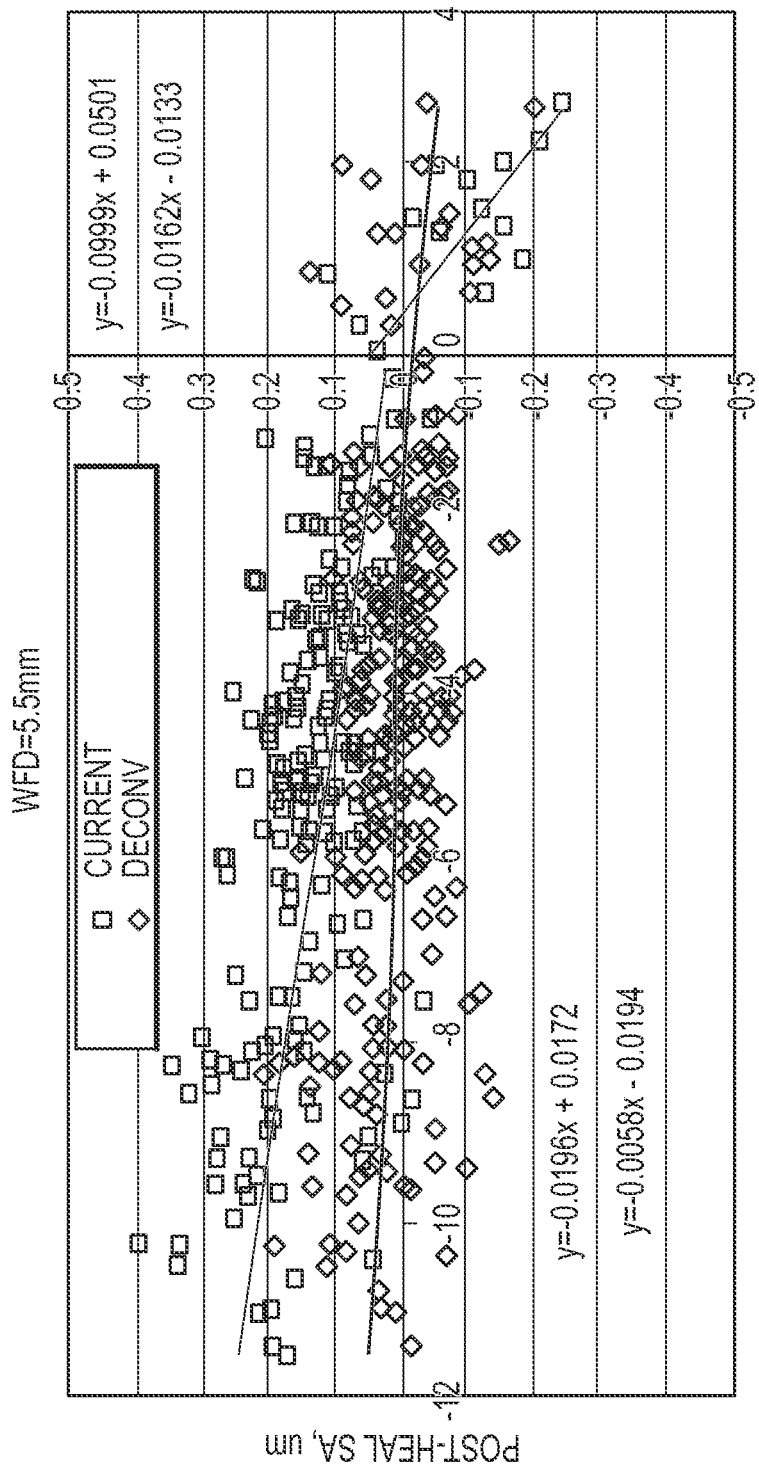

Assuming that the same deviations from the trend line can apply to a modified target, it is possible to add $\delta SA$ to the simulated post-operative SA values of every modified target, which can provide a realistic estimate of post-operative distribution of SA. For example, FIGS. 19A and 19B, depict post-operative SA for observed study data (n=340) and expected post-operative SA for de-convolved targets, simulated with $\sigma$=0.35 mm for the same eyes, for a 6 mm wavefront and 5.5 mm wavefront, respectively.

In addition to piston differences which may be present between the original and modified targets, there may be other shape differences as well. According to some embodiments, the following metrics can be used to compare shape differences:

$$\Delta = (H - \max(H)) - (H_{current} - \max(H_{current})) \quad \text{Equation 30}$$

where H refers to ablation depth or target height.

As illustrated in FIGS. 20A and 20B, target shapes subsequent to smoothing for two modification methods, namely widening optical zone (dOZ) and deconvolution (sigma) are almost identical within the 6 mm optical zone.

TABLE 4

|  | Modification parameter | SA vs.SE trend slope | $<SA>$ um | std(SA) um | max $|SA|$ um | $<extraH>$ um | max extraH um |
| --- | --- | --- | --- | --- | --- | --- | --- |
| Current target |  | −0.04 | 0.16 | 0.16 | 0.58 | 0.0 | 0.0 |
| dOZ, mm | 0.4 | −0.01 | −0.01 | 0.10 | 0.31 | 11.02 | 26.0 |
| dK, D | 25 | −0.01 | −0.04 | 0.11 | 0.33 | 9.90 | 25.9 |
| sigma, mm | 0.35 | 0.01 | −0.03 | 0.09 | 0.29 | 7.24 | 17.9 |

These figures show the differences (i.e. X and Y cross-sections, respectively) between a modified target and an original target, subsequent to smoothing, simulated for a high myopia case (ID=21011 OD, −7.4D/−1.5D×179°). Simulations were performed for a wider optical zone (dOZ=0.4 mm), an adjusted corneal curvature for cosine correction (dK=25 D), and a deconvolution (σ=0.35 mm).

Figure 21:
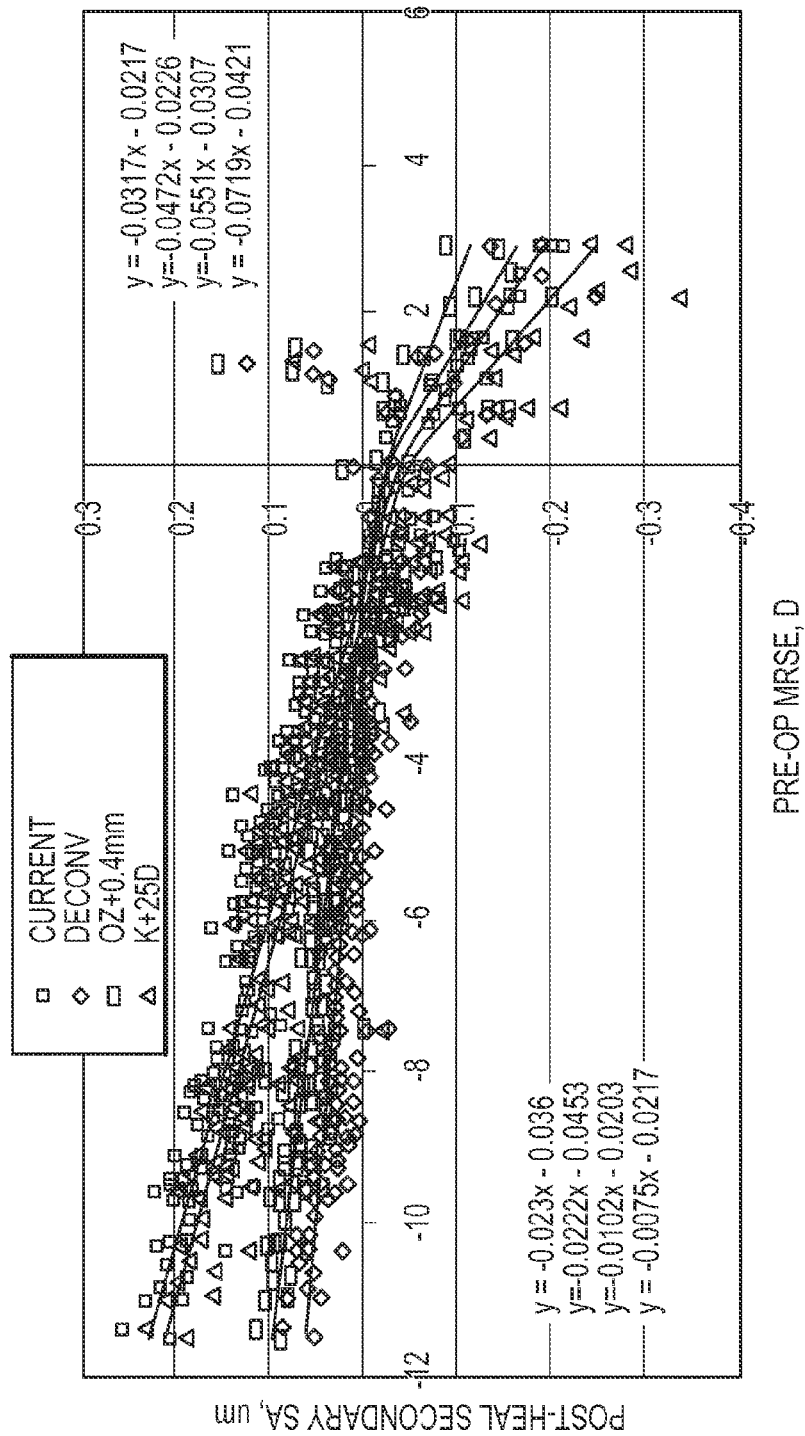
FIG. 21 depicts aspects of shows post-operating secondary spherical aberration according to embodiments of the present invention.

A cosine adjustment can make a different shape with a substantially higher secondary spherical aberration, as depicted in FIG. 21. In some cases, software or systems may allow both a user-defined optical zone and a user-defined adjustment of corneal curvature (e.g. defining the cosine correction), and these two adjustments can be used for validation for a deconvolution technique. In some cases, a wider optical zone, may provide a closer approximation than a curvature adjustment. FIG. 21 shows a post-operating secondary spherical aberration (WFD=6 mm), simulated for study data (n=340). Simulation was performed for original targets and for modified targets with a wider optical zone (dOZ=0.4 mm), an adjusted corneal curvature for cosine correction (dK=25 D), and a deconvolution (σ=0.35 mm).

In sum, the three methods for modification of an ablation target (widening optical zone, adjusting cosine correction, and deconvolution) are capable of eliminating a systematic trend in post-operatively induced spherical aberration. As shown here, the ablation profiles for these modifications can present different depths, and deconvolution can provide a technique which results in a maximum of tissue retention. That is, the amount of ablation associated with deconvolution is smaller than that of the other methods. In some instances, widened optical zone and deconvolution techniques may yield almost identical corneal shapes after smoothing. In some cases, a widened optical zone technique (e.g. based on a user-defined optical zone) may be used as a validation for a deconvolution technique.

Treatment Target Creation

Figure 22:
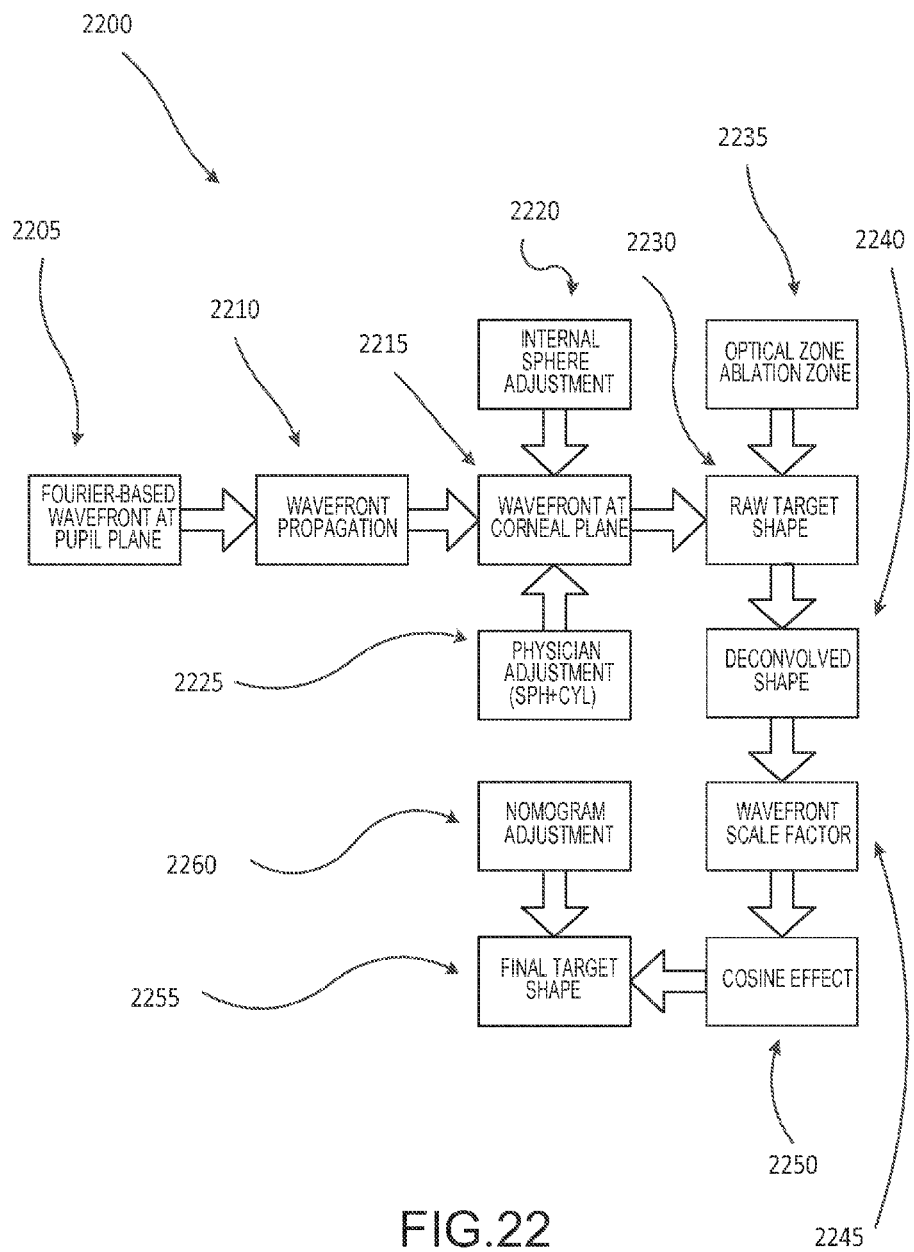
FIG. 22 depicts aspects of methods for generating a target shape, according to embodiments of the present invention.

As noted elsewhere herein, a treatment target shape may represent or correspond to an intended optical surface that is designed to achieve a particular refractive correction. FIG. 22 depicts a method 2200 for generating a target shape, according to embodiments of the present invention. Method 2200 may include obtaining a wavefront corresponding to a pupil plane, as indicated by module 2205. For example, for target creation, the input can be a Fourier-based wavefront, which represents the ocular aberrations on the pupil plane. Typically, a laser ablation is performed on the corneal surface, and hence to obtain the target shape the ocular aberrations are propagated from the pupil plane to the corneal surface. Accordingly, methods may include propagating the wavefront, as indicated by step 2210, and obtaining a wavefront corresponding to a corneal plane, as indicated by step 2215. Any physician adjustments or nomogram adjustments can also be represented on the corneal surface first before they are combined with the ocular aberrations. Hence, the process of obtaining a wavefront at the corneal plane may also be based on an internal sphere adjustment, as indicated by step 2220, or on a physician adjustment (e.g. Sph+Cyl), as indicated by step 2225, or both.

In some instances, parameters such as optical zone size and the ablation zone size, which may be user-defined, can be used to determine the ablation or target shape within such zones. Thus, the process of obtaining a raw or original target shape, as indicated by step 2230, may be based on a selection or definition of an optical zone, an ablation zone, or both, as indicated by step 2235.

A deconvolution technique can be used to deconvolved the raw or original shape, so as to obtain a deconvolved shape, as indicated by step 2240. Such a deconvolution can operate to reduce post-operative spherical aberration. Once the deconvolved shape is obtained, a scaling factor can be applied, as indicated by step 2245, and a cosine effect modification that compensates for the loss of energy due to the curved cornea can be applied, as indicated by step 2250. In some embodiments, the scaling process described in step 2245 can incorporate scaling or rescaling techniques disclosed elsewhere herein, such as those described in FIGS. 9, 24, 41, and 42 and the corresponding specification text descriptions. Hence, the final target shape can be determined based on the deconvolved shape, as indicated by step 2255, optionally considering a scaling factor, a cosine effect, or both.

In some instances a nomogram adjustment can be applied, as indicated by step 2260, when obtaining the final target shape. Following creation of the final or modified target shape, as indicated by step 2255, the target shape can be transmitted to a treatment table generation engine.

Exemplary Techniques for Target Shape Deconvolution

As explained elsewhere herein, treatment target shapes can lead to induced aberrations, and deconvolution can be applied to such treatment target shapes so as to reduce or inhibit the induced aberrations.

Figure 24:
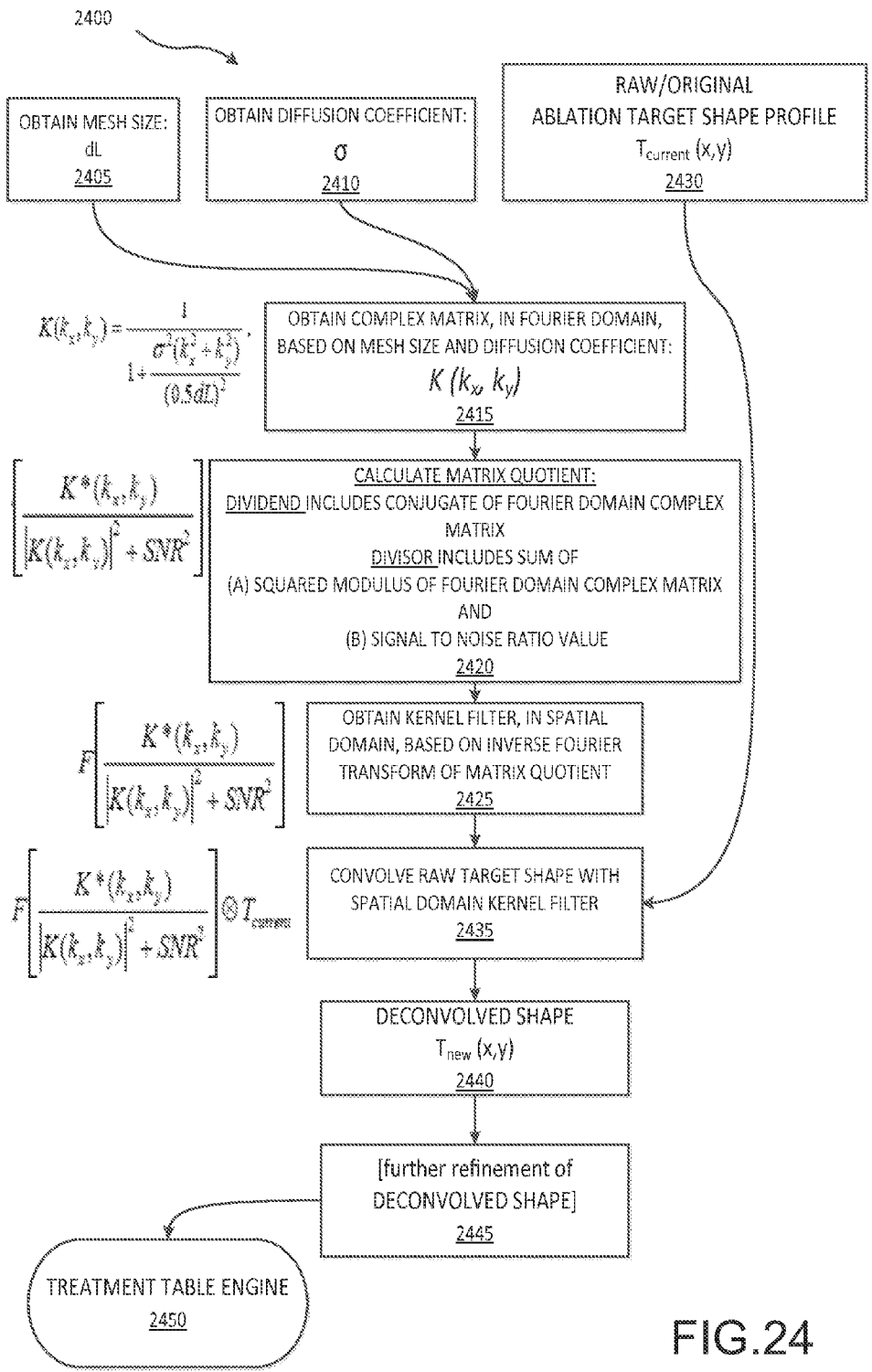
FIG. 24 illustrates aspects of deconvolution methods according to embodiments of the present invention.

FIG. 24 depicts aspects of a deconvolution method 2400 for a target shape, according to embodiments of the present invention. As illustrated here, method 2400 of deconvolving a target shape may include obtaining a mesh size as indicated by step 2405 and obtaining a diffusion coefficient as indicated by step 2410. Method 2400 may also include obtaining a complex matrix, in Fourier domain, based on a mesh size and diffusion coefficient as indicated by step 2415.

Complex Matrix

According to some embodiments, a complex matrix $K(k_x, k_y)$ can be applied to a treatment target to obtain a wavefront change due to corneal smoothing. The complex matrix can be considered to represent a three dimensional matrix in a Fourier or frequency domain. In some cases, the complex matrix may be a squared Butterworth low-pass filter of the first order. Other types of low-pass filters may be suitable for use with embodiments of the present invention. In some cases, a low-pass filter may refer to a function or operation that makes details smoother by suppressing high spatial frequency information.

In some instances, the Fourier domain complex matrix can be expressed as follows:

$$K(k_x, k_y) = \frac{1}{1 + \frac{\sigma^2(k_x^2 + k_y^2)}{(0.5 \, dL)^2}} \qquad \text{Equation 31}$$

where σ represents a diffusion coefficient, $k_x$ and $k_y$ represent frequency domain variables, and dL represents a mesh size. Optionally, the diffusion coefficient σ can have a value of 0.35 mm and the mesh size dL can have a value of 0.1 mm. In some instances, the diffusion coefficient can have a value with a range from about 0.2 to about 0.5 (see, e.g. FIG. 12A). In some instances, the diffusion coefficient can have a value with a range from about 0.33 to about 0.4 (see, e.g. FIG. 37).

In some instances, the term Fourier transform as used herein may refer to a transform operation. In some instances, the term Fourier transform as used herein may refer to a complex valued function produced by a transform process.

Mesh Size

In an exemplary discrete case, a complex matrix K ($k_x$, $k_y$) can be based on a 101×101 mesh size of dL=0.1 mm. Often, such matrix formats (e.g. 101×101) are used when characterizing treatment planning. In some cases, a mesh size or dL may refer to the spacing or spatial distance between two neighboring pixels. In some cases, dL may refer to the pixel resolution in the kernel, which can be 101×101 in pixel frame size or 10 mm×10 mm in space. When a discrete Fourier transform is involved, it is possible to represent the frame in 101×101, although it may no longer be 0.1 mm because it is in frequency domain (more like cycles per degree). Hence, dL may involve a 0.1 mm spacing in the spatial domain.

In some instances, selection of a kernel or matrix format may represent a balance between accuracy and speed concerns. For example, a larger kernel or matrix format such as 101×101 may provide greater relative accuracy and lower relative speed, whereas a smaller kernel or matrix format such as 25×25 may provide lower relative accuracy and greater relative speed.

Diffusion Coefficient

As noted above, a complex matrix can also be based on a diffusion coefficient σ. Typically, a diffusion coefficient σ has a unit of length. This parameter can describe the strength of corneal smoothing during and after a refractive surgical procedure, and as such can be considered as a biologically related parameter. The parameter can be used to characterize a single individual, or a group of individuals. Based on the analysis of results from several clinical trials, it has been discovered that a diffusion coefficient σ of 0.35 mm is consistent with such observed data. In some instances, a diffusion coefficient can have a value within a range from about 0.2 mm to about 0.5 mm. In some instances, a diffusion coefficient can have a value of about 0.3 mm.

Because a Fourier domain complex matrix can be based on the mesh size, the diffusion coefficient, or both, it follows that a corresponding spatial domain kernel filter, as discussed elsewhere herein can also be based on the mesh size, the diffusion coefficient, or both.

According to some embodiments, an LPF can be used to emulate the diffusion of corneal tissue cells. Exemplary techniques may involve estimating or receiving a diffusion coefficient value, and using that value to effect a compensation for a high order aberration before administering a treatment such as a laser vision corrective procedure. By pre-compensating for high order aberrations, it is possible to obtain an outcome with a reduced amount of high order aberrations.

Diffusion coefficients may be evaluated based on simulations. For example, a diffusion coefficient σ value can be selected for application to clinical data in a deconvolution procedure as described herein, and the expected outcome (e.g. deconvolved target shape) can be compared to the actual outcome (e.g. clinical data). The diffusion coefficient can be adjusted or optimized so as to reduce or minimize variance or a standard deviation in the comparison results. Exemplary adjustment or optimization techniques are described elsewhere herein, for example in connection with FIGS. 29 to 32A.

Relatedly, embodiments encompass systems and methods for adjusting refractive surgery parameters, which may include a diffusion coefficient, for use in a vision treatment. An exemplary method may include inputting or receiving a refractive case, determining a model optical surface shape based on the refractive case and a set of refractive surgery system parameters, comparing the refractive case and the model optical surface shape to determine an aberration induced by the set of refractive surgery system parameters, adjusting the set of refractive surgery system parameters so as to inhibit the induced aberration, and administering the refractive treatment to a patient. The refractive treatment can be based on the adjusted set of refractive surgery system parameters.

Matrix Quotient

As depicted by step 2420, methods may include calculating a matrix quotient, where the dividend includes a conjugate of a Fourier domain complex matrix (e.g. K*($k_x$, $k_y$), and the divisor includes the sum of a squared modulus of the Fourier domain complex matrix and a signal to noise ratio value. In some cases, the signal to noise ratio value may be a squared value. An exemplary matrix quotient can be expressed as follows:

$$\left[\frac{K*(k_x, k_y)}{|K(k_x, k_y)|^2 + SNR^2}\right], \quad \text{Equation 32}$$

In some cases, the denominator or divisor of the matrix quotient can be characterized at least in part by the expression $|K(k_x, k_y)|^n$, where n is an integer having a value of 2 or more. In some cases, the denominator or divisor of the matrix quotient can be characterized at least in part by the expression $[|K(k_x, k_y)|^n + SNR^2]$ where n is an integer having a value of 2 or more and SNR represents a signal to noise ratio value. Equation 32 may refer to a filtering process that is in the frequency domain. A complex conjugate may be part of the filtering process.

Spatial Domain Kernel Filter

As depicted by step 2425, methods may also include obtaining a kernel filter, in the spatial domain, based on an inverse Fourier transform of the matrix quotient. An exemplary kernel filter can be expressed as follows:

$$F\left[\frac{K*(k_x, k_y)}{|K(k_x, k_y)|^2 + SNR^2}\right] \quad \text{Equation 33}$$

In some cases, the kernel filter of Equation 33 can be provided as a pre-calculated or pre-defined matrix, and can be used or saved as a lookup table. As discussed elsewhere herein, this kernel filter can also be referred to as an inverse kernel $K_{INV}$. Optionally, this kernel filter can be referred to as K (x, y). This spatial domain filter or inverse kernel can also be provided as a low pass filter, such as a Butterworth or Gaussian filter. Optionally, the spatial domain kernel filter can present a grid or matrix that reflects how the filtered value of a pixel depends on neighboring pixel values, and is independent of the target shape.

Convolving Raw Target

As depicted by step 2435, methods may include convolving a raw or original target shape with the spatial domain kernel filter. Optionally, methods may include receiving, at an input, an original target profile or shape for the eye of the patient, as indicated by step 2430. As shown here, the spatial domain kernel filter can be based on an inverse Fourier transform of a Fourier domain noise filter, for example, which may be based on a conjugate of a Fourier domain complex matrix, on a modulus of a Fourier domain complex matrix, or on a combination thereof. In some instances, a Fourier domain noise filter can be characterized by fraction having a numerator comprising a conjugate of a Fourier domain complex matrix and a denominator comprising a modulus of the Fourier domain complex matrix. Method 2400 indicates that an original target shape $T_{current}(x, y)$ can be convolved with a spatial domain kernel filter so as to obtain a deconvolved shape $T_{new}(x, y)$, as indicated by step 2440. In some instances, the deconvolved shape 2440 emphasizes curvature changes, or corners, sharp edges, sharp transitions, and the like. In some cases, methods may involve the application of a low pass filter deconvolution to a target profile having a slightly extended optical zone. In some instances, parameters of a low pass filter can be optimized by comparing an LPF model prediction against observed clinical data.

According to some embodiments, the systems and methods disclosed herein can implement dual scale kernel techniques, triple scale kernel techniques, and other multi-scale kernel techniques (e.g. multiple parameters in a healing kernel), such as those disclosed in U.S. Provisional Patent Application No. 61/871,120 filed Aug. 28, 2013, U.S. patent application Ser. No. 14/453,068 filed Aug. 6, 2014, and U.S. patent application Ser. No. 14/523,467 filed Oct. 24, 2014, the content of each of which is incorporated herein by reference. According to some embodiments, such kernel scale techniques can be implemented in a healing kernel, such as that shown in step 2415 of FIG. 24.

Other Refinements

As depicted by step 2445, methods may include additional refinements of a shape prior to transmitting the shape to a treatment table engine. For example, a convolved profile may include a transition zone radius, and exemplary techniques may include zeroing the convolved profile at locations outside of the transition zone radius. In some cases, an original target profile may have an original refractive spherical equivalent value within a 4 mm diameter area, and the convolved target profile may have a target refractive spherical equivalent value within a 4 mm diameter area, and method 2400 may include scaling the original refractive spherical equivalent with the target refractive spherical equivalent value. In some embodiments, the scaling process can incorporate scaling or rescaling techniques disclosed elsewhere herein, such as those described in FIGS. 9, 22, 41, and 42 and the corresponding specification text descriptions. In some cases, methods may include elevating the convolved profile so that a lowest point on the convolved profile is zero or greater. In some cases, a convolved profile may include a transition zone radius, and methods may involve applying a damping multiplier at or near the transition zone radius. In some instances, refinement can be performed prior to, or subsequent to, deconvolution, with an equivalent effect.

As discussed elsewhere herein, a deconvolved target may have an oscillating profile at the periphery. Such oscillations may be caused by boundaries between the optical zone, transition zone, and edge of the finite-size target, where either the target profile or its derivatives have sharp changes. In some instances, it may be helpful to elevate the entire ablation profile so that the lowest point on the ablation profile is zero, or so that all ablation values are non-negative. What is more, it may be helpful to zero-out the ablation profile at distances greater than the transition zone radius, $R_{TZ}$, where no ablation is desired beyond the end of the transition zone. Such refinements are illustrated in the X and Y target cross-sections of FIG. 25A, which depicts modifications of an ablation profile (high myopia study, case ID=21011 OD) including deconvolution ($\sigma$=0.28 mm), elevation, and cut-off beyond the transition zone. In some cases, after such refinements or adjustments are made, only the peripheral curvature will be changed, for example as depicted in FIG. 25B, which shows a change of ablation profile after target deconvolution (High Myopia study, case ID=21011, OD, −7.4D/−1.5D×179 deg).

In some instances, an original target shape may operate to effectively address refraction errors, and hence it may be desirable to maintain the refraction of the modified target at the same value as the refraction of the original target. This can be done with rescaling of the deconvolved target so that its defocusing term within the 4 mm area is the same as for the original target. In some embodiments, the rescaling process can incorporate scaling or rescaling techniques disclosed elsewhere herein, such as those described in FIGS. 9, 22, 24, 41, and 42 and the corresponding specification text descriptions.

Figure 25A:
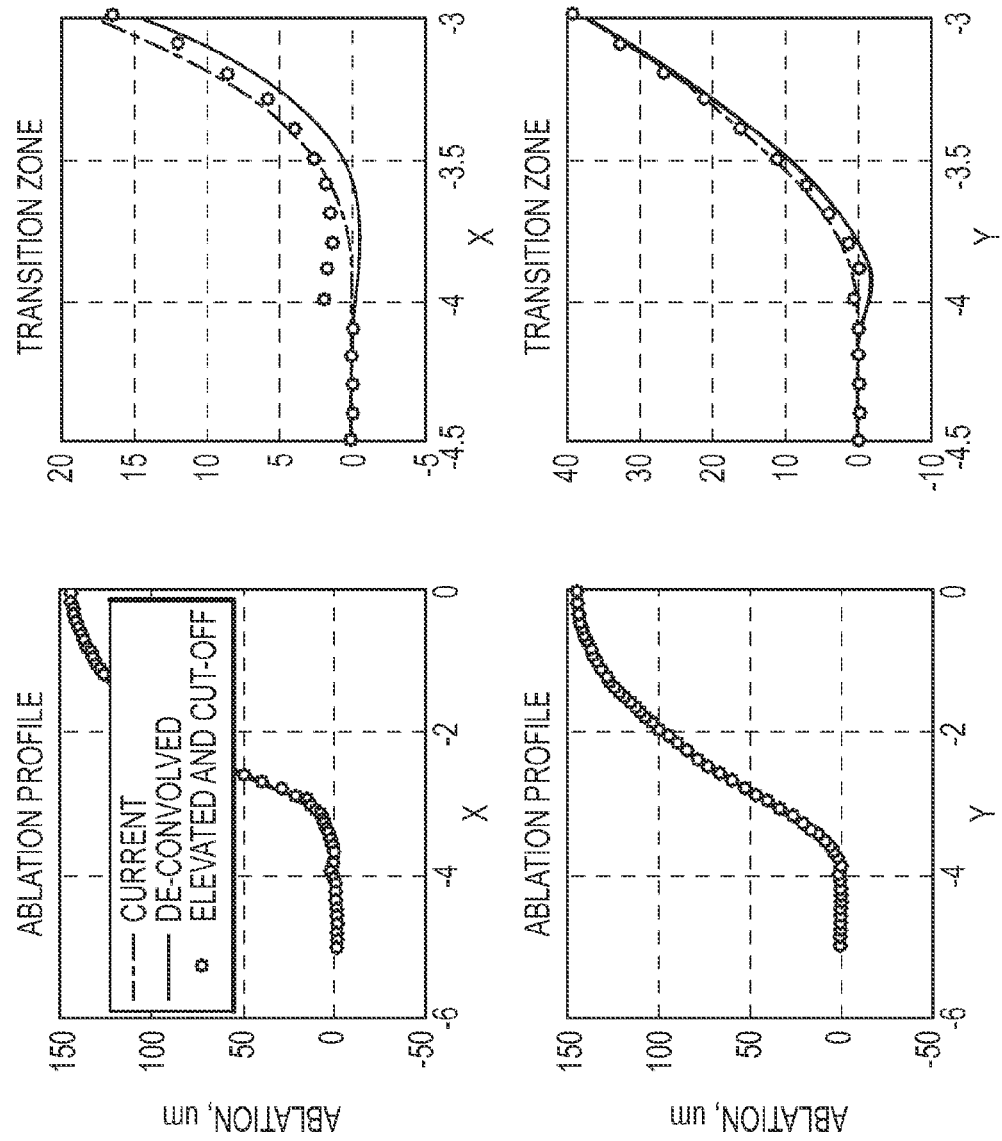
FIGS. 25A and 25B show aspects of ablation profile changes or modifications according to embodiments of the present invention.
Figure 25B:
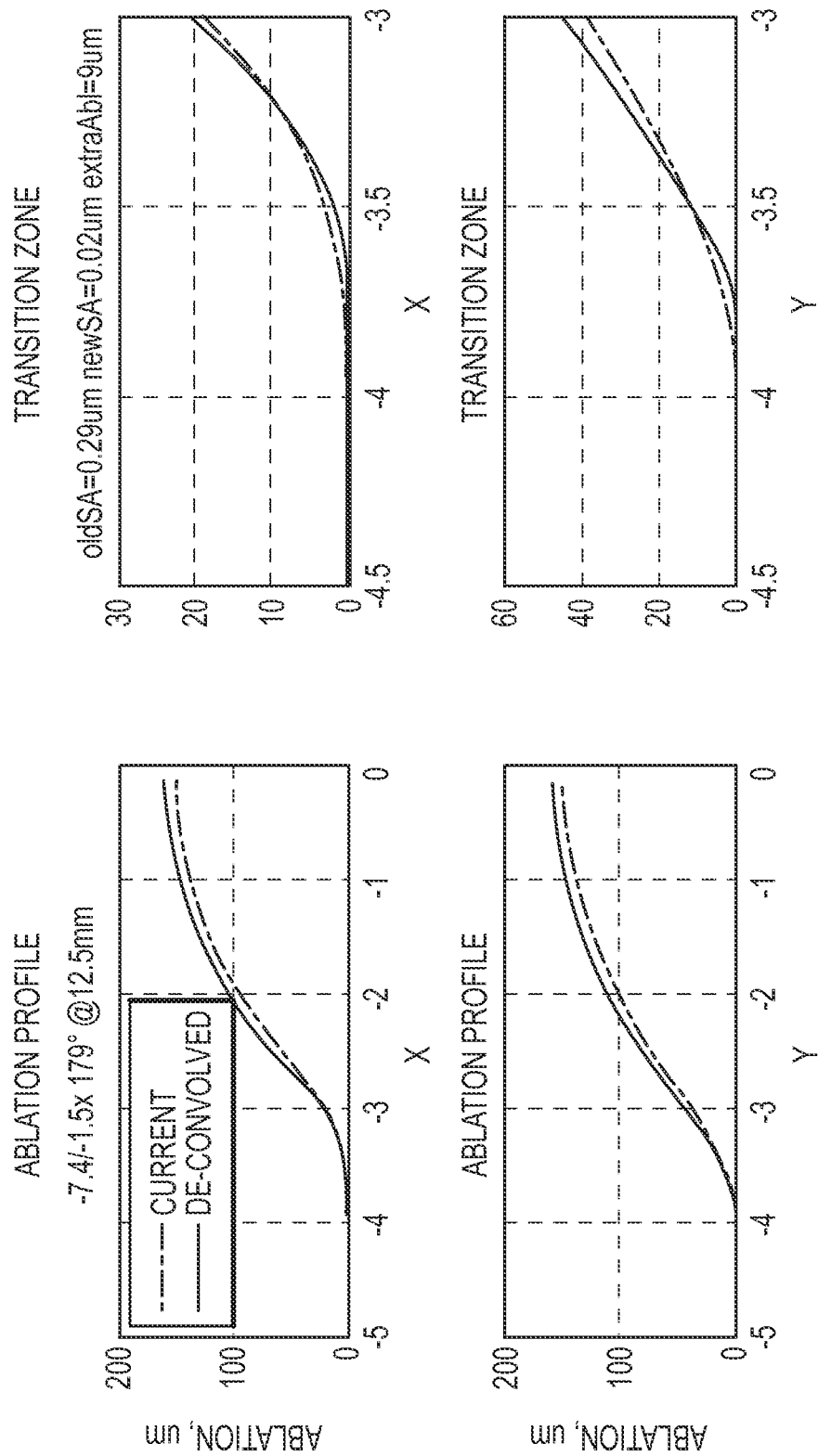

In addition to, or following some or all of the above mentioned adjustments, the peripheral part of the ablation profile may have a small bump, which results mainly from the cut-off at the end of the transition zone, for example as depicted in FIG. 25A. Ablating such a bump may involve application of a sequence of many small laser pulses around the transition zone periphery. In some instances, this may lead to a substantial slow-down of the entire ablation process. Yet this bump may be unnecessary, because it lies away from the optical zone and its influence on the wavefront within the optical zone shall be rather small after healing. With this consideration, it is possible to apply a damping multiplier to the periphery of the transition zone, as described elsewhere herein.

Spherical Aberration and Related Topics

As discussed elsewhere herein, spherical aberration (SA) may be induced by a target shape, a healing effect, or a combination thereof. In some cases, it is possible to reduce or even completely eliminate target-induced SA by implementing a small offset of the transition zone. In some original target shapes, the inner boundary of the transition zone is located within the optical zone, e.g. at about 0.25 mm from the edge of the optical zone. In addressing target-induced SA, it may be helpful to shift the transition zone boundary, by moving it farther from the center of the optical zone. In this way, the target-induced SA can be decreased, although squeeze the transition zone and cause sharper gradients in the peripheral target. In some instances, this may mean there will be a narrower transition zone band. In some instances, shifting the inner boundary of the transition zone away from the center of the optical zone by a distance of about 0.1 mm can operate to reduce the target-induced SA to a level below 0.1 um, which may be considered negligible.

Figure 26:
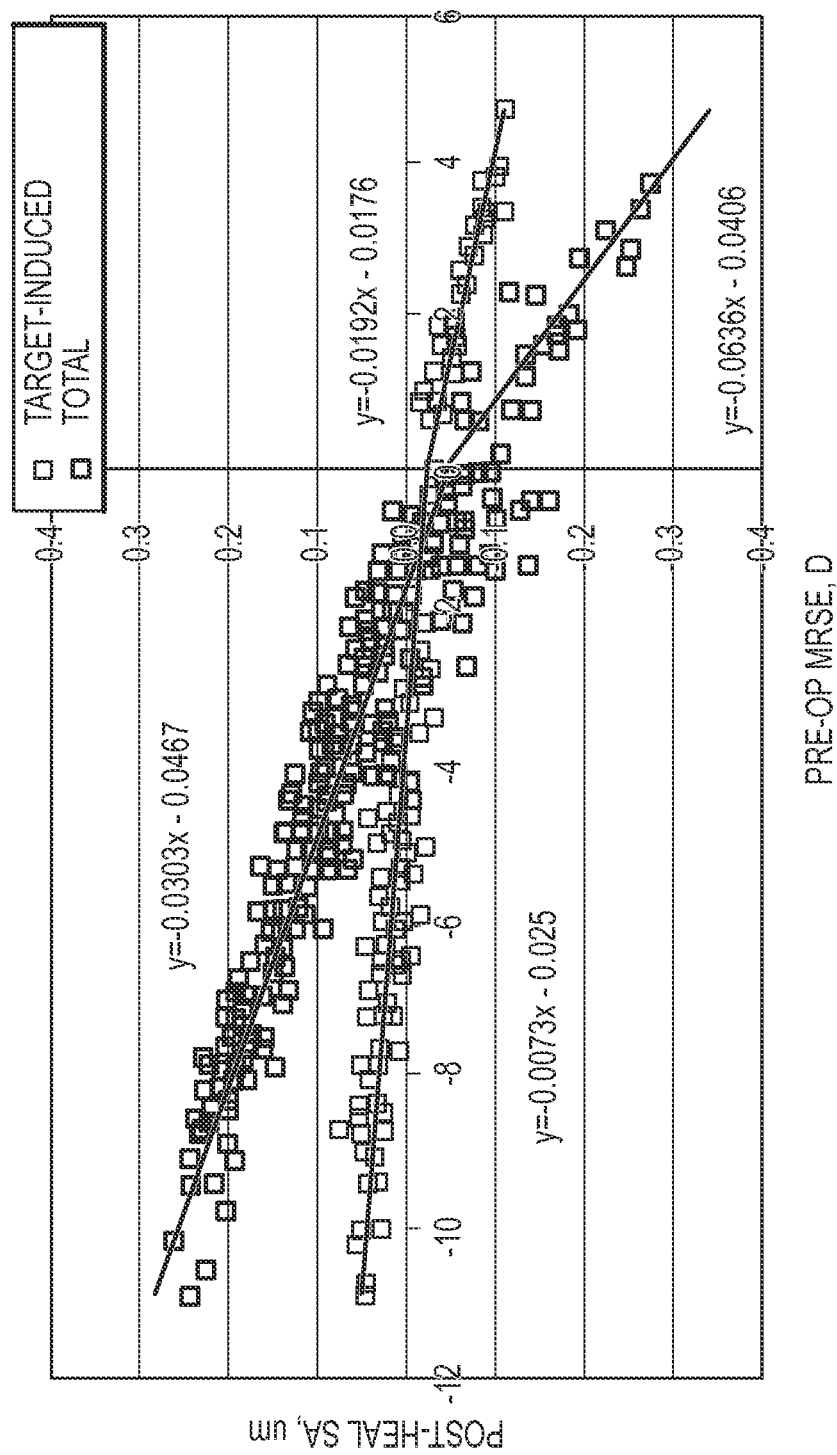
FIG. 26 illustrates aspects of induced SA according to embodiments of the present invention.

FIG. 26 shows a simulated induced SA immediately after ablation (target-induced) and after healing (total) for a target with an inner boundary of the transition zone shifted outward by 0.1 mm, using a healing model where $\sigma$=0.28 mm. As shown here, after healing, the total SA reached a level of about 0.3 um.

In order to compensate for the spread of the high curvature, which is a main cause of post-healing induced SA, it is helpful to apply a deconvolution transformation to the original target. In some cases, the LPF core for deconvolution is the same as the one optimized to fit observed induced post-operative SA. Then healing, simulated as convolution with the same LPF core, can bring the healed cornea back to the desired shape.

Figure 27:
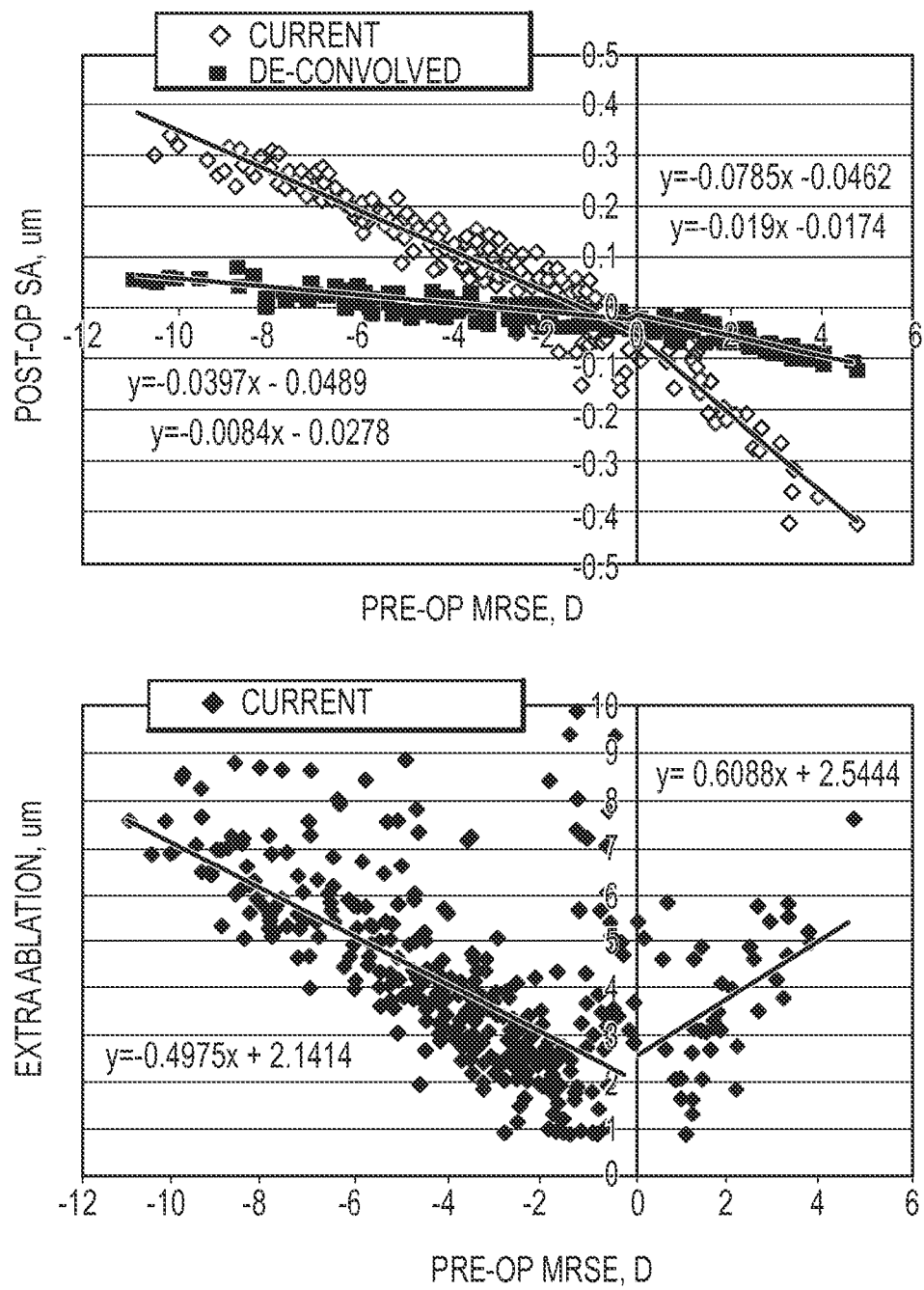
FIG. 27 illustrates aspects of deconvolution effects according to embodiments of the present invention.

FIG. 27 shows the effect of deconvolution on post-healing SA (left panel) and additional maximum ablation depth (right panel) simulated with $\sigma$=0.28 mm for studies (n=515). Relatedly, Table 5 shows simulated changes in post-healing SA and extra ablation, caused by deconvolution and additional adjustments of an original target. Statistics for studies: Myopia and High Myopia (n=327), Hyperopia (n=43), and all studies together (n=515).

TABLE 5

|  | old SA(SE) Slope | new SA(SE) Slope | <SA> | max \|SA\| | <extra Abl> | max extAb |
| --- | --- | --- | --- | --- | --- | --- |
| Myopia & HM | −0 04 | −0.01 | 0.01 | 0.08 | 4.3 | 8.9 |
| Hyperopia | −0.05 | −0.02 | −0.05 | 0.11 | 3.5 | 7.6 |
| All US IDE | −0.04 | −0.01 | 0.00 | 0.11 | 4.2 | 9.9 |

Figure 28:
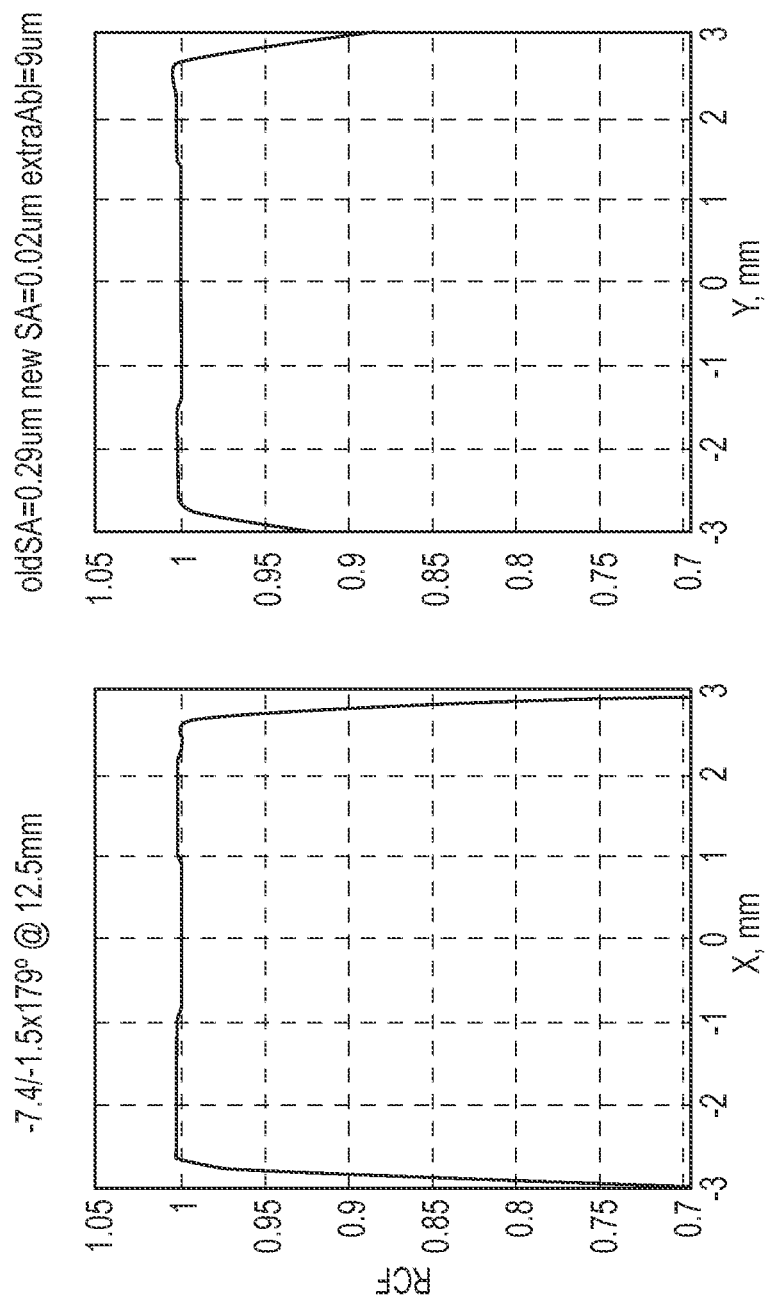
FIG. 28 illustrates aspects of radial compensation function according to embodiments of the present invention.

FIG. 28 depicts a radial compensation function (RCF) for a deconvolved target in a high myopia case, according to embodiments of the present invention. Specifically, a radial compensation function was calculated for a deconvolved target corresponding to a High Myopia study (case ID=21011 OD, −7.4D/−1.5D×179 deg.). As shown here, the RCF is almost flat in the central part and decreases in the periphery.

Figure 29:
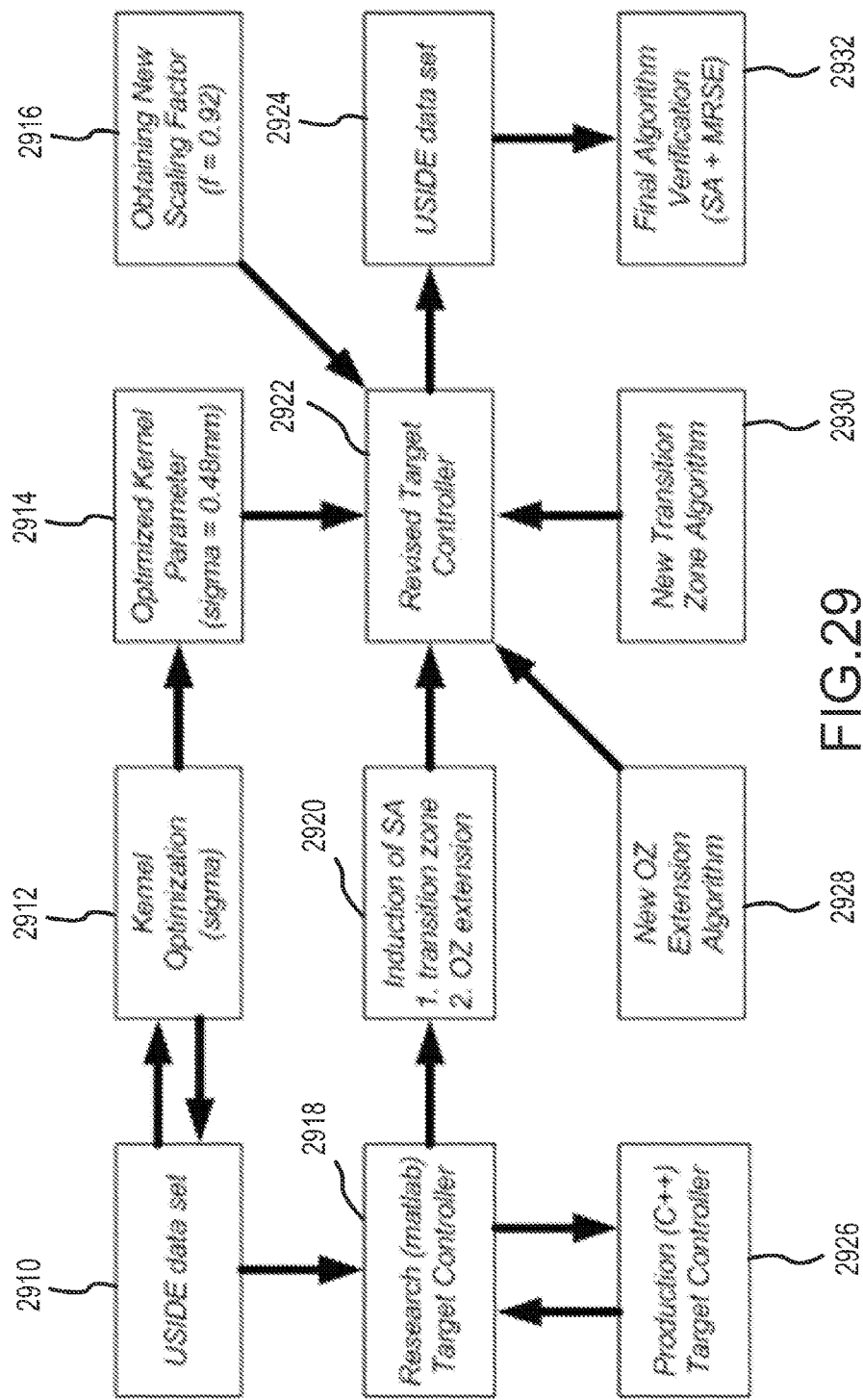
FIG. 29 illustrates aspects of target shape modification according to embodiments of the present invention.

FIG. 29 schematically illustrates techniques for obtaining and implementing a modified target shape, according to embodiments of the present invention. As shown here, study data can be used to derive parameters of a kernel for simulating a low-pass filtering process, for corneal healing and the like. Embodiments may also include optimizing the parameters by using a clinical data set. These techniques may also involve evaluating the extent to which observed spherical aberration is attributed to error, due to an imperfect optical treatment shape. In some instances, methods may also include addressing target shape induced SA by providing transition zone adjustments, optical zone extension adjustments, or both. In some cases, a deconvolution (e.g. inverse of low pass filter) may boost the total treatment depth. Techniques may also involve running a revised target controller (e.g. without a cosine effect) with a low-pass filter, to evaluate the extent to which SA for a clinical data set correlates with observed SA, or to evaluate the extent to which post-operative refractions correlate with what is expected based on the clinical data. The Optimized Kernel Parameter can be related to LPF, and sigma can represent the diffusion coefficient. Hence, as shown in FIG. 29, with a clinical data set 2910, a kernel optimization process 2912 can be employed such that simulation can be performed to obtain the optimized kernel parameter (sigma) 2914. According to some embodiment, the value of sigma=0.35 was found to correspond to an optimized kernel parameter. For a practical implementation, the clinical data 2910 can be sent to a research version of Target Controller 2918 (in matlab), which is identical to the production Target Controller 2926 (in C++). It can be derived from the Target Controller 2918 that induction of spherical aberration (SA) 2920 occurs in the target so a removal of a target-induced SA can be implemented in a revised Target Controller 2922. The revised Target Controller 2922 can implement a new optical zone (OZ) extension algorithm 2928, and a new Transition Zone algorithm 2930. With all the revisions, the Revised Target Controller 2922 can be tested with data set 2924, which can be the same as (or different from) data set 2910. The Revised Target Controller 2922 can then be verified with SA and MRSE (manifest refraction in spherical equivalent) in 2932.

Shape Induced SA

Figure 30:
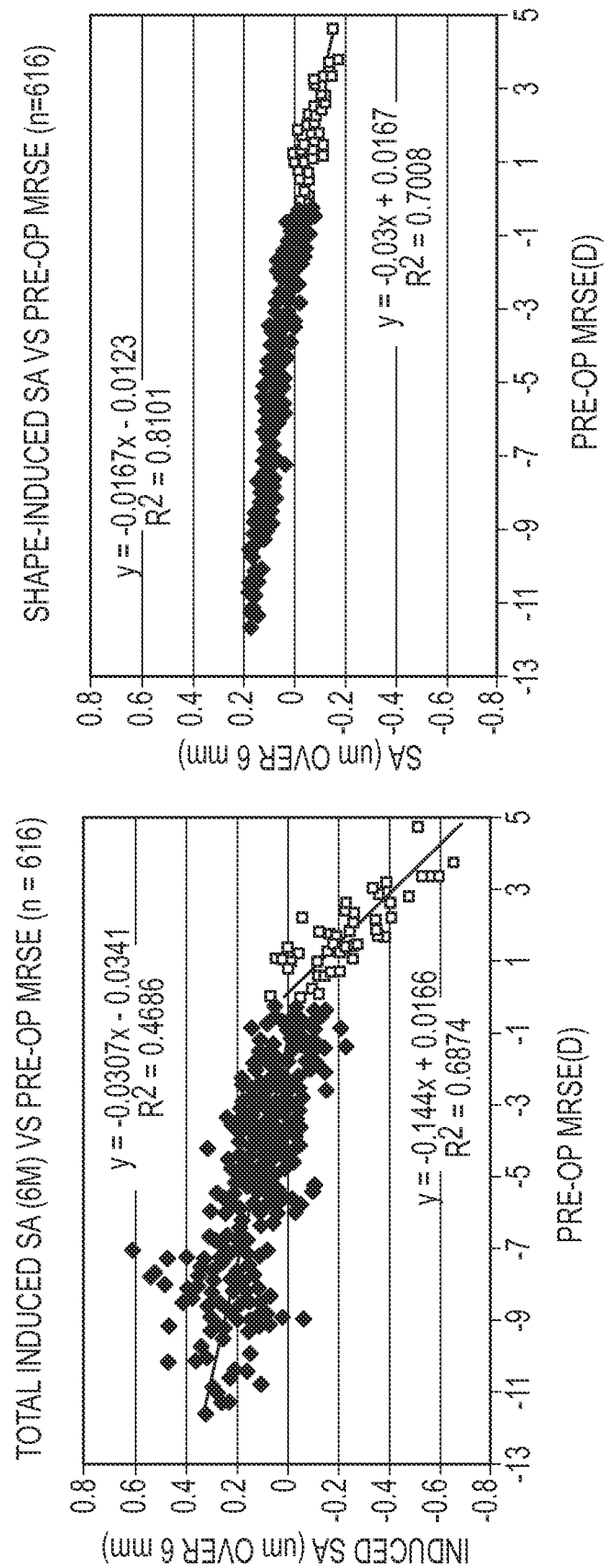
FIG. 30 shows aspects of induced SA according to embodiments of the present invention.

FIG. 30 shows a total induced SA (left panel, 0.188±0.139 for myopia and −0.110±0.179 for hyperopia) and a shape-induced SA (right panel, 0.064±0.049 for myopia and −0.071±0.038 for hyperopia) after taking into account a low-pass filtering effect, according to embodiments of the present invention. When considering the mean, it is possible to observe that shape-induced SA consists of ⅓ of the total SA for myopia and more than ½ for hyperopia. When considering the trend line slope, it is possible to observe that shape-induced SA consists of more than ½ for myopia and less than ¼ for hyperopia. Therefore, a shape-induced SA can be a significant component for an observed post-surgery spherical aberration. For the data presented in FIG. 30, the healing effect for the shape-induced SA was included in the simulation.

Low Pass Filter

Figure 31:
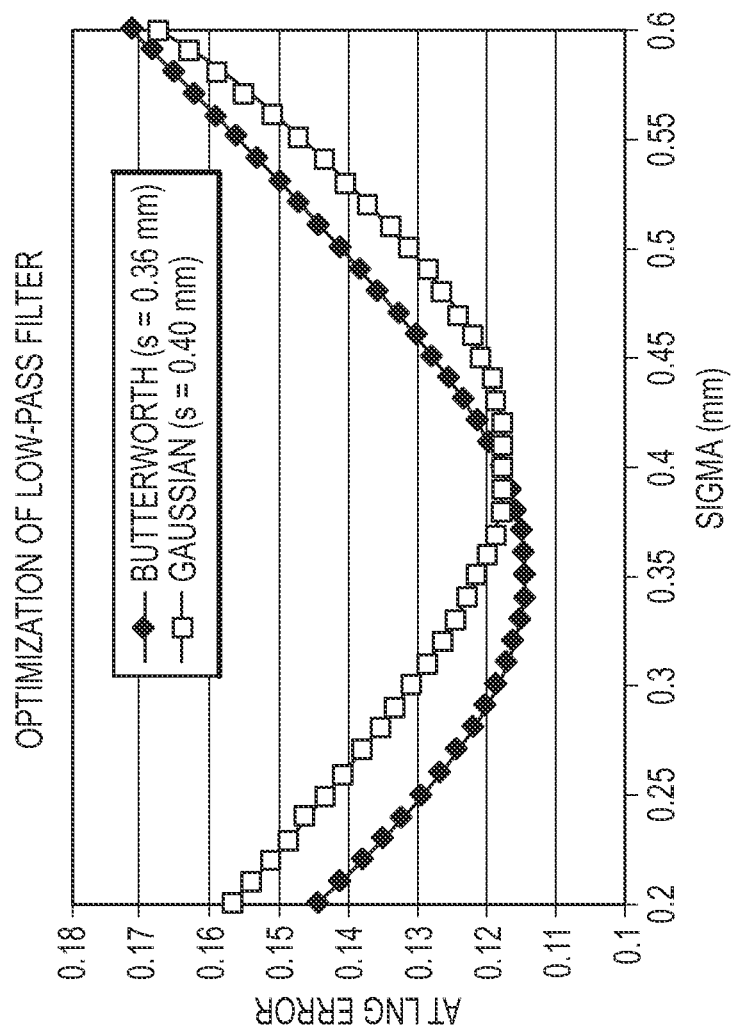
FIG. 31 illustrates aspects of low pass filter according to embodiments of the present invention.
Figure 32A:
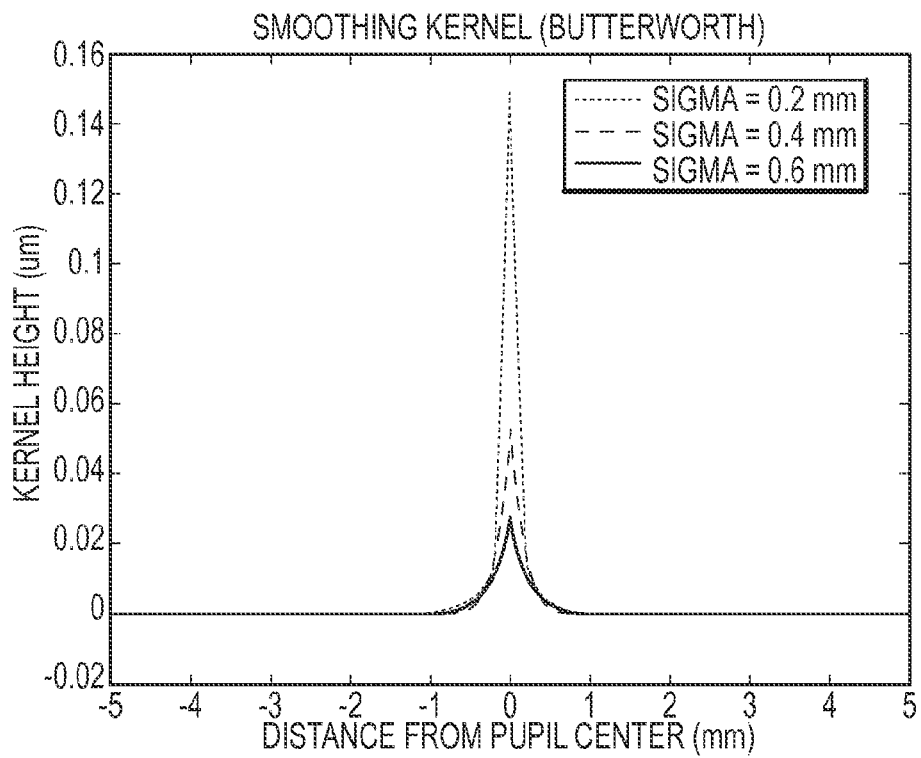
FIGS. 32A and 32B illustrate aspects of kernel and inverse kernel according to embodiments of the present invention.
Figure 32B:
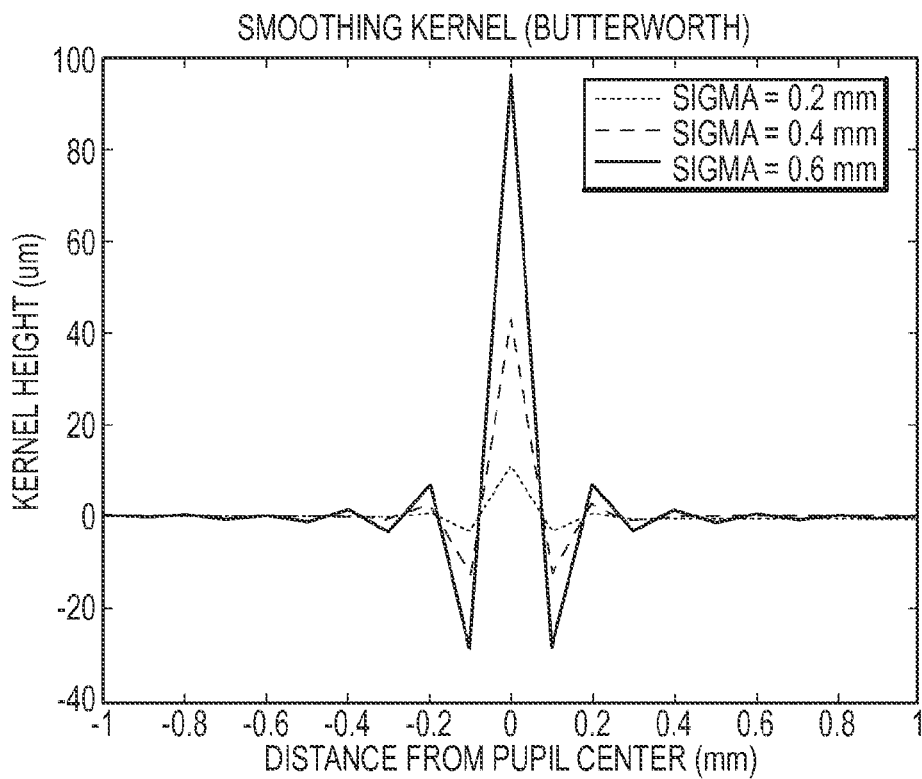

Assuming that a particular theoretical target shape provides a best fit for low order correction it is possible to perform an optimization as follows. First, an ablation target for an eye (e.g. an eye from a study) can be calculated according to a respective scaling factor and sphere adjustment. Second, a low pass filter (e.g. Butterworth or Gaussian) can be applied to obtain a healed shape. Third, a residual shape can be obtained by subtracting the healed shape from a pre-operative CV (CustomVue®) treatment shape. Fourth, a residual error in SA (e.g. predicted SA) can be calculated. Fifth, a merit function can be calculated. For example, the merit function may be the square root of the average sum of the square difference between the observed SA and the predicted SA. FIG. 31 shows aspects of optimization of a low pass filter, according to embodiments of the present invention. FIGS. 32A and 32B show aspects of a kernel and an inverse kernel, according to embodiments of the present invention.

Shape Deconvolution and Verification

Figure 33:
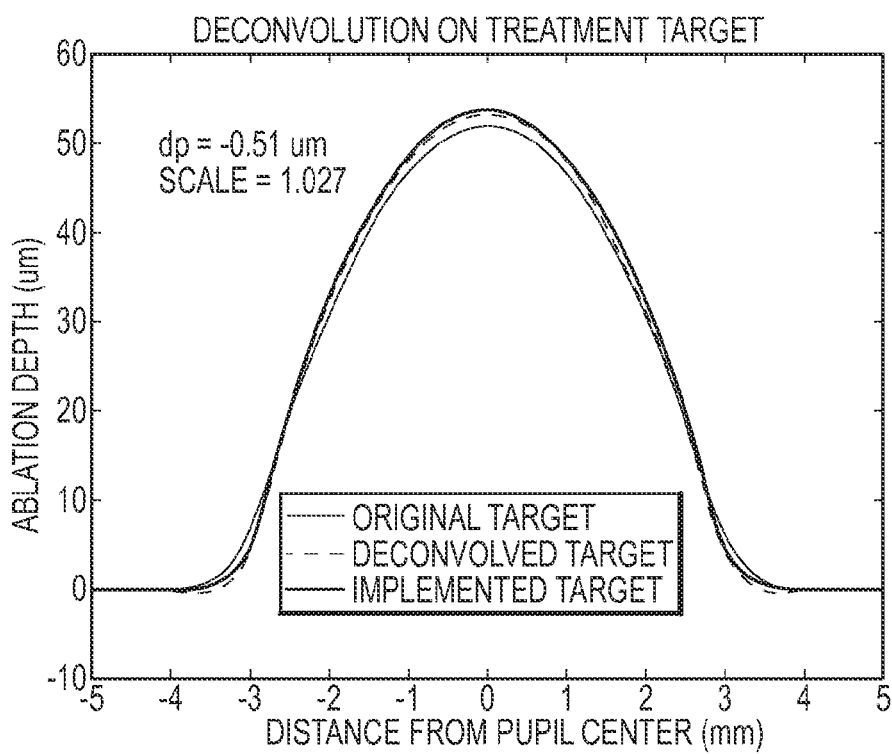
FIG. 33 illustrates aspects of treatment target deconvolution according to embodiments of the present invention.

According to some embodiments, it is possible to process a target shape as follows. First, a theoretical target is created, optionally using a zone-extended target algorithm. The target shape is then convolved with an inverse kernel. The convolved shape is them lifted to avoid negative ablation. A scaling factor can then be applied to preserved SE over a 4 mm zone. Subsequently, a cosine effect can be applied. FIG. 33 depicts aspects of a treatment target deconvolution according to embodiments of the present invention.

Figure 34:
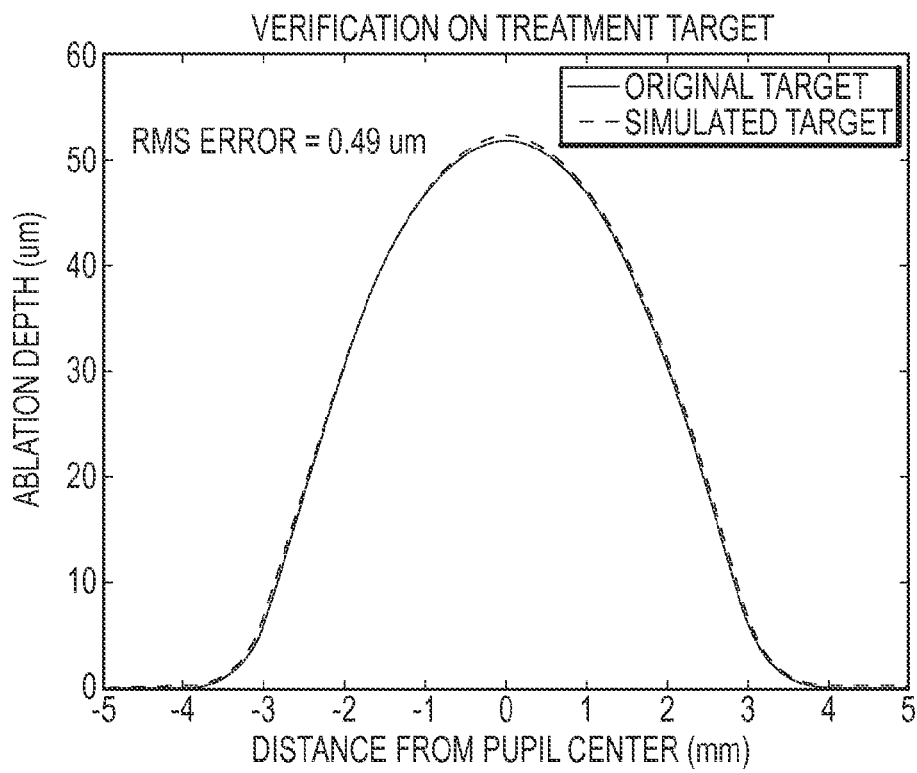
FIG. 34 depicts aspects of target verification according to embodiments of the present invention.
Figure 35A:
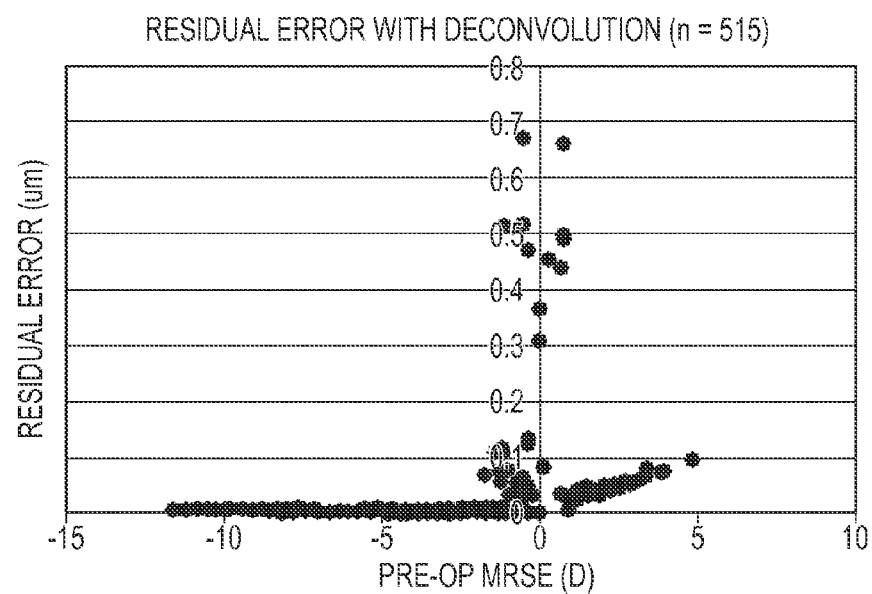
FIGS. 35A to 35C illustrate aspects of residual error with deconvolution according to embodiments of the present invention.
Figure 35B:
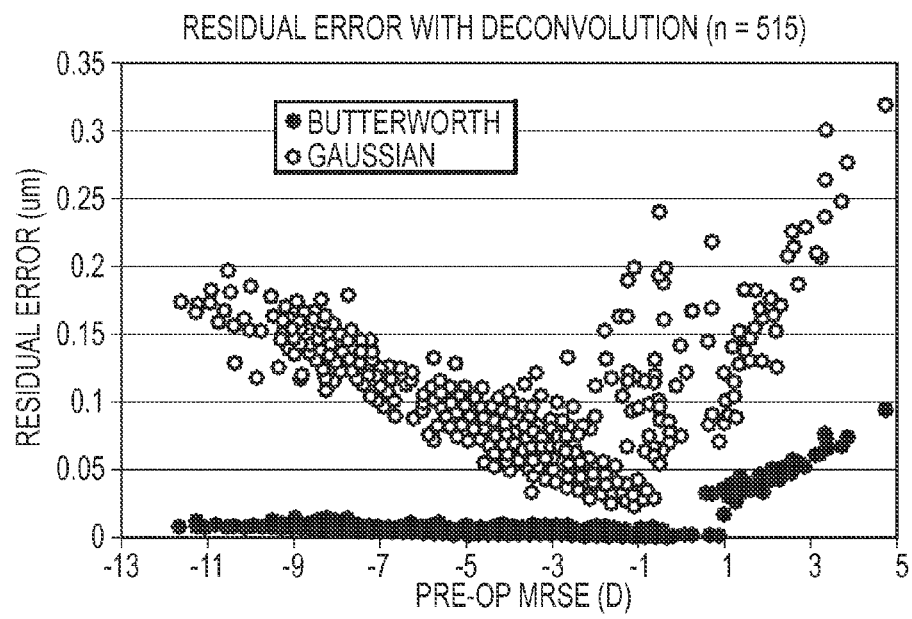
Figure 35C:
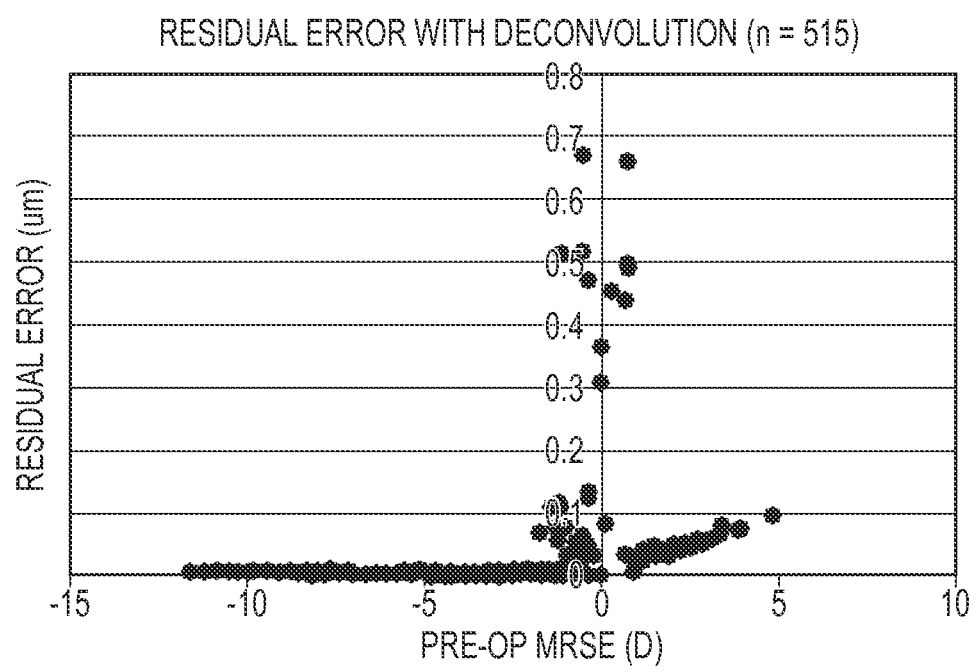

According to some embodiments, it is possible to verify such target shape procedures as follows. First, obtain a theoretical target shape for an eye (e.g. each eye from a study set). Second, obtain a deconvolved target by convolving the target shape with an inverse kernel. Third, convolve the target with a determined kernel (e.g. healed target). Fourth, calculate the difference between the theoretical target and the simulated healed target (e.g. healed target subtracted from theoretical target). FIG. 34 depicts aspects of a target verification procedure according to embodiments of the present invention. FIGS. 35A, 35B, and 35C depict residual error with deconvolution, according to embodiments of the present invention.

Figure 36C:
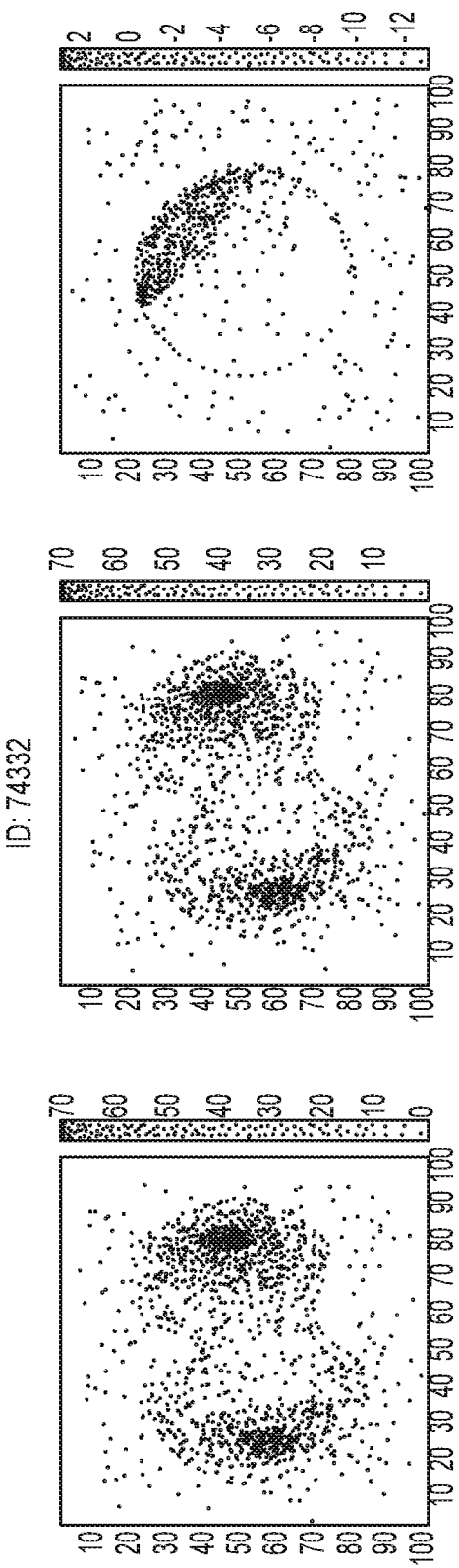

FIGS. 36A, 36B, and 36C depict expected targets (left column), inversed convolved targets (middle column), and the difference between expected and inversed convolved targets (right column), according to embodiments of the present invention.

Optimization of Kernel

Figure 37:
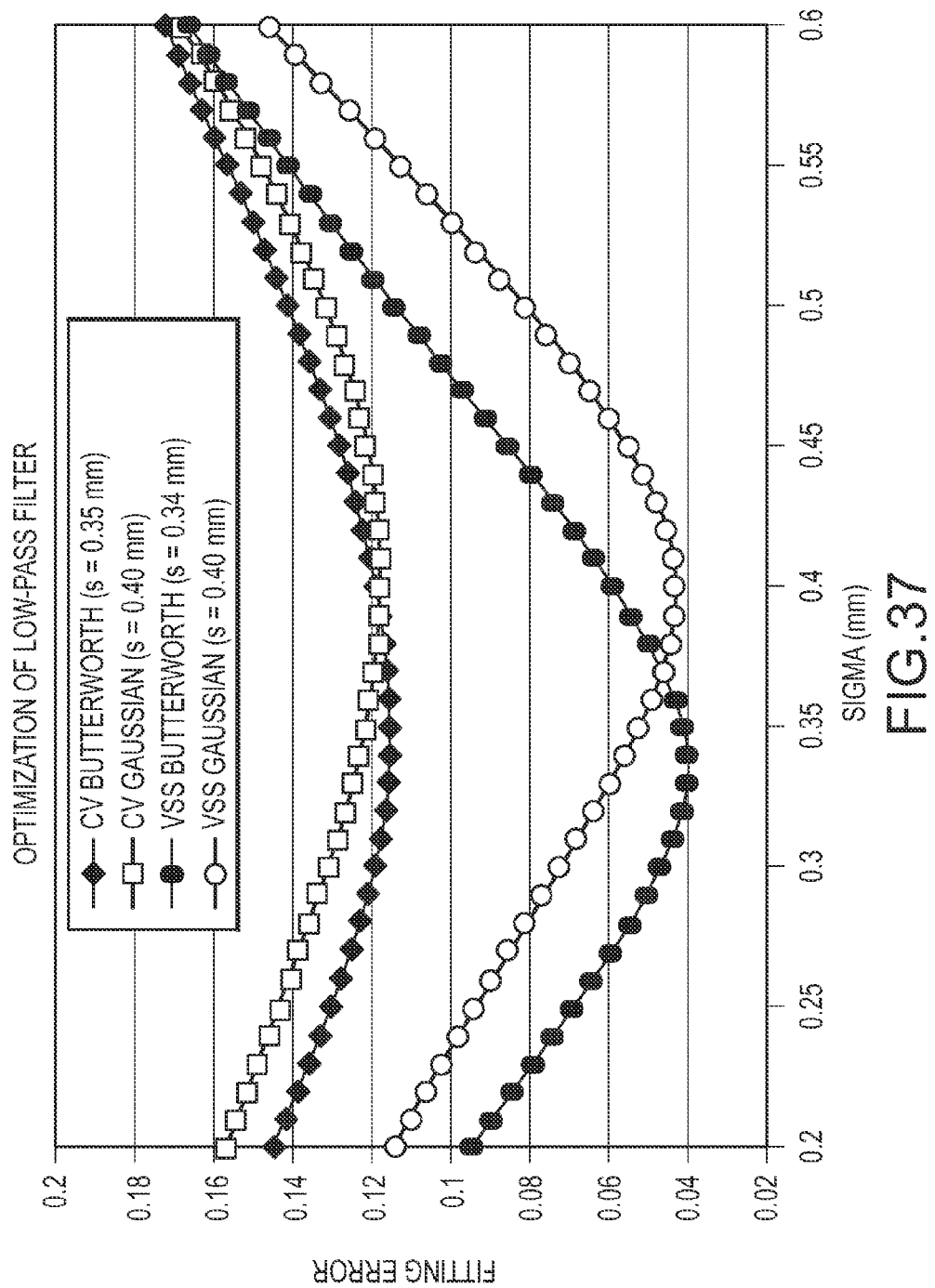
FIG. 37 illustrates aspects of low pass filter according to embodiments of the present invention.

FIG. 37 depicts CV data from a study (515 eyes, including myopia, hyperopia, high myopia, and mixed cases, as well as VSS-R™ treatment data from a Canadian study (77 eyes, including myopia [mostly], and a few hyperopia and mixed cases). FIG. 37 indicates that the optimized sigma for various data sets suggests a range between about 0.33 mm and about 0.40 mm.

Post-Operative SA (Expected vs. Actual)

Figure 38:
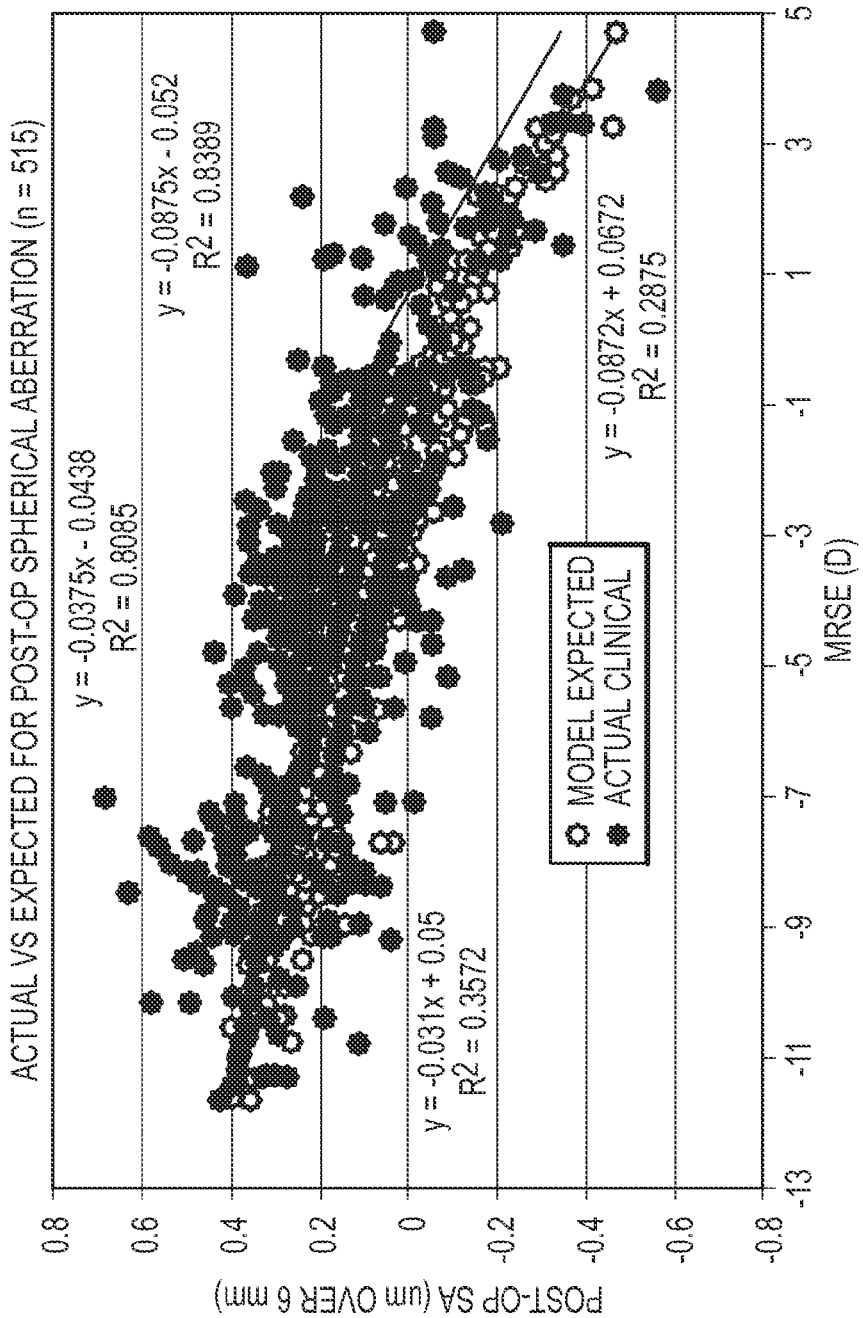
FIG. 38 illustrates aspects of post-operative SA according to embodiments of the present invention.

FIG. 38 depicts actual vs. expected post-operative spherical aberrations.

Other Features

Figure 39C:
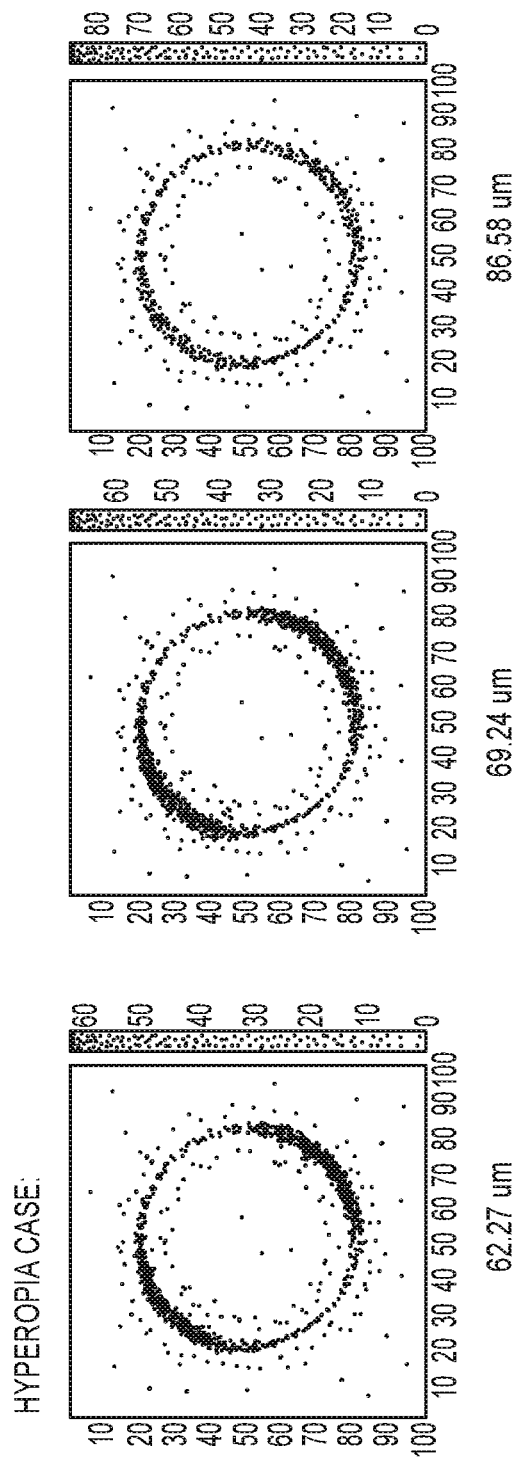

FIG. 39A depicts cylinder like cases (top row), FIG. 39B depicts mixed cases (middle row), and FIG. 39C depicts hyperopia cases (bottom row), according to embodiments of the present invention.

Treatment Validation

Embodiments of the present invention encompass systems and methods for treatment validation based on low order aberrations. In some cases, embodiments of the present invention encompass systems and methods for treatment validation based on sphere-cylinder coupling. In some cases, embodiments of the present invention encompass systems and methods for treatment validation based on high order aberrations.

As discussed elsewhere herein, various deconvolution techniques can be implemented so as to remove or reduce LASIK-induced spherical aberration. Embodiments of the present invention encompass treatment validation systems and methods to ensure that treatments can provide a desired clinical outcome. For example, validation techniques can be implemented to ensure that low order and high order aberrations associated with a developed treatment are consistent with the desired production target shape features. Various verification techniques are disclosed, including approaches related to the preservation of low order aberrations, approaches involving cylinder coupling, and approaches related to the addition of spherical aberration with the use of deconvolution.

Treatment Validation (Low Order Aberrations)

Various clinical studies have been performed, for example to treat low to moderate myopia, high myopia, hyperopia, mixed astigmatism, and monovision, using wavefront guided treatments. In some cases, desired clinical outcomes were achieved using basis data and related adjustment techniques, such as those described in U.S. Provisional Patent Application Nos. 61/724,111 and 61/765,567 filed Nov. 8, 2012 and Feb. 15, 2013, respectively, as well as those described in [KT 91288-868098 (043800US)], the contents of each of which are incorporated herein by reference. In some cases, desired clinical outcomes were achieved using internal sphere adjustment techniques.

Figure 40:
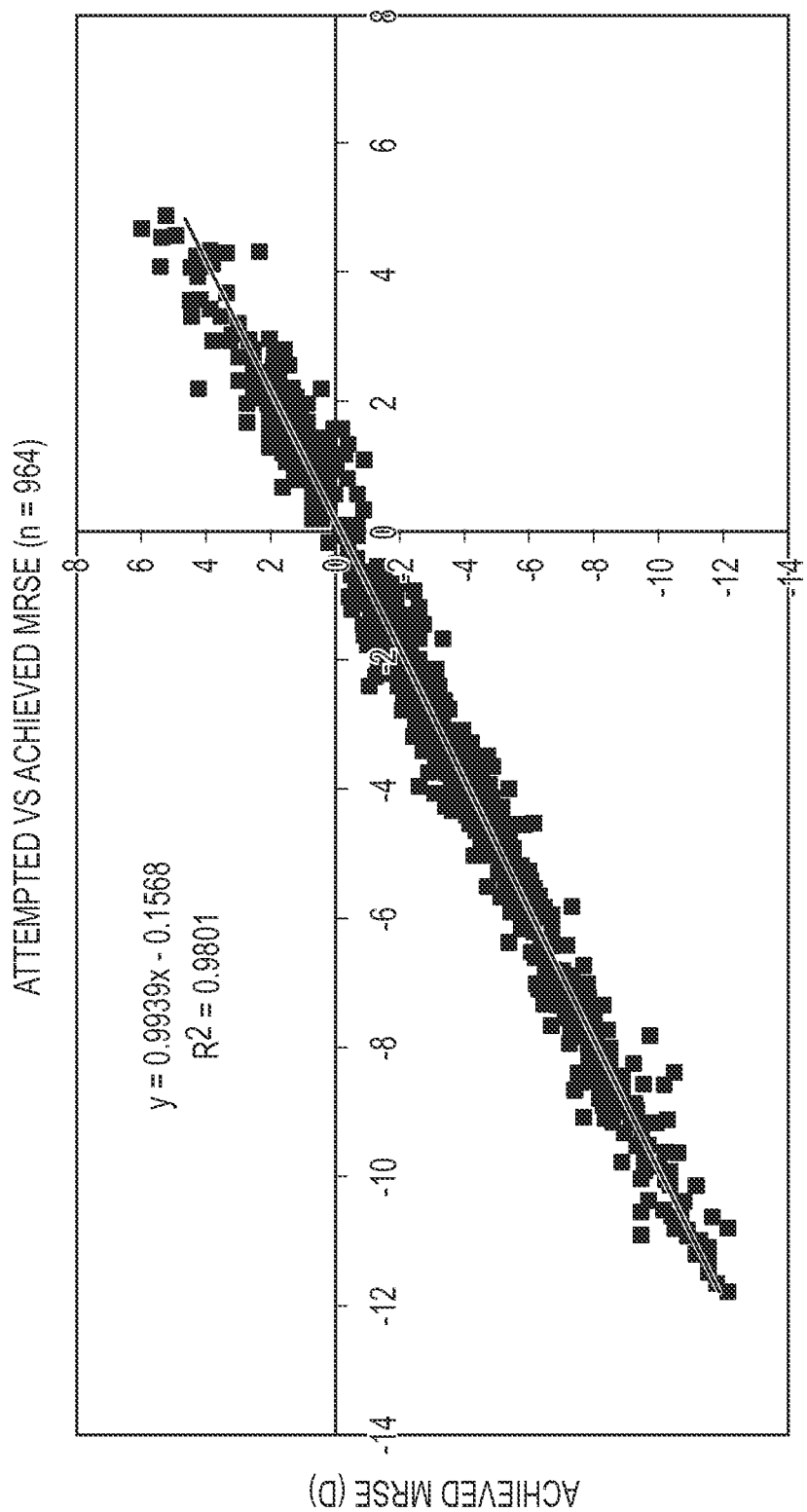
FIG. 40 illustrates aspects of treatment validation systems and methods according to embodiments of the present invention.

The graph in FIG. 40 illustrates attempted (or intended) MRSE versus achieved MRSE (Manifest Refraction Spherical Equivalent) for eyes in several clinical trials. As depicted here, there is a good match between the achieved MRSE and the attempted MRSE, with little deviation.

According to some embodiments, the attempted MRSE can refer to a target, and the achieved MRSE can refer to a clinical outcome. In some cases, the attempted MRSE can be considered to be analogous or equivalent to the raw target shape of step 2230 in FIG. 22. In some cases, the attempted MRSE can be considered to be analogous or equivalent to the existing target 4110 in FIG. 41.

According to some embodiments, the term attempted MRSE can be used interchangeably with the term intended MRSE. In some cases, the term expected MRSE can refer to an expected post-operative MRSE or an expected achieved MRSE. The term expected achieved MRSE can refer to a pre-operative MRSE minus a post-operative MRSE.

Figure 41:
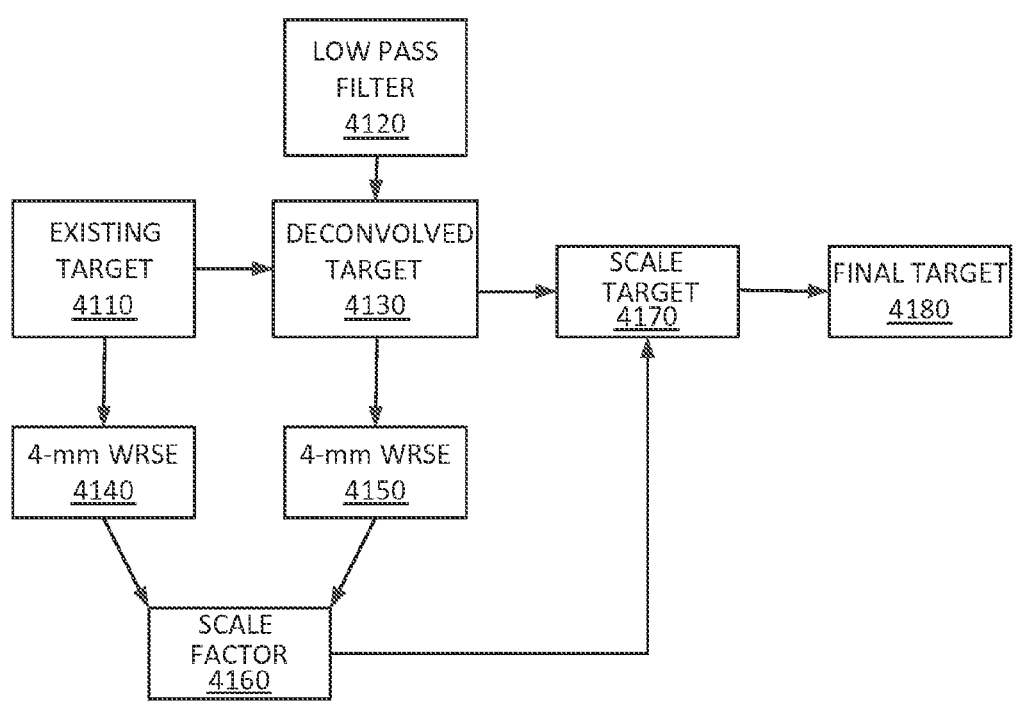
FIG. 41 illustrates aspects of treatment validation systems and methods according to embodiments of the present invention.

FIG. 41 depicts aspects of a target development process, according to embodiments of the present invention. As shown here, the process may involve SE scaling for a deconvolved treatment target. Exemplary techniques may involve obtaining an existing target 4110, and deconvolving the target 4110 with a low pass filter 4120 to obtain a deconvolved target 4130. In some cases, a low pass filter can be referred to as an optimized linear filter. Hence, a low pass filter (or optimized linear filter) can be applied to the existing target to obtain the deconvolved target. Refraction measures, such as wavefront spherical equivalents, can be obtained. For example, a refraction measure 4140 (e.g. 4 mm refraction or 4 mm WRSE) of the existing target 4110 can be obtained, and a refraction measure 4150 (e.g. 4 mm refraction or 4 mm WRSE) of the deconvolved target 4130 can be obtained. The term MRSE can refer to manifest refraction spherical equivalent, and the term WRSE can refer to wavefront refraction spherical equivalent. The terms MRSE and WRSE are similar in that they both refer to measurements of refraction. According to some embodiments, the existing target 4110 depicted here is analogous or equivalent to the $T_{current}$ discussed elsewhere herein (e.g. depicted in FIG. 24). According to some embodiments, the existing target 4110 depicted here is analogous or equivalent to the raw or original target shape discussed elsewhere herein (e.g. depicted in FIG. 22).

A scale factor or ratio 4160 can be obtained based on the existing target refraction measure 4140 and the deconvolved target refraction measure 4150. For example, a factor can be determined based on the ratio of the 4-mm WRSE of the existing target to the 4-mm WRSE of the deconvolved target. As shown here, techniques may also involve applying the scale factor 410 to the deconvolved target 4130 to obtain a scale target 4170. A final target 4180 can be obtained based on the scale target 4170.

According to some embodiments, a desired objective may involve having an existing target refraction measure 4140 that matches or approximates the deconvolved target refraction measure 4150. For example, preservation of the refractive power of the target following convolution can provide an indication of a good clinical outcome.

The relationship between attempted MRSE and achieved MRSE shown in FIG. 40 is based on actual data analysis of clinical observations. It is possible to perform modeling using an intended (or attempted) MRSE (or WRSE) versus an expected MRSE (or WRSE). The scaling techniques discussed herein, for example in FIGS. 9, 22, 24, 41, and 42, can be implemented to achieve an "attempted" versus "achieved MRSE (or WRSE) correlation, for example with a unity slope. Relatedly, with regard to FIG. 41, the measured refraction 4140 can be analogous to the attempted refraction, and the measured refraction 4150 can be analogous to the achieved refraction. In this sense, a process of ensuring that the outcome is good (e.g. a good match between refraction measures 4140 and 4150) can be referred to as validation. For example, as the treatment target shape is changed by deconvolution, steps can be taken to ensure that the refraction measure (e.g. 4 mm WRSE) of the new deconvolved target is the same as or approximates the refraction measure (e.g. 4 mm WRSE) of the existing target. Hence, the objective of obtaining a good clinical outcome, in terms of low order aberrations, can be achieved. Techniques for obtaining a good clinical outcome in terms of high order aberrations are discussed elsewhere herein.

According to some embodiments, validation may involve determining a treatment target based on a treatment table, comparing the treatment target to a wavefront refraction, and evaluating whether the comparison is within a certain tolerance.

According to some embodiments, the low pass filter 4120 or deconvolution technique can be validated, based on whether there is a good or sufficient match between the existing target refraction measure 4140 and the deconvolved target refraction measure 4150. For example, low order aberrations of the existing target are sufficiently close to low order aberrations of the deconvolved target, then the low pass filter can be considered to exhibit the desired performance.

According to some embodiments, the low pass filter 4120 can provide an approximation or simulation of how a laser will deliver a treatment. Hence, by constructing an optical surface and calculating the corresponding refraction, it is possible to compare the refraction to an intended refraction, to validate the low pass filter.

As explained elsewhere herein, a target (or a deconvolved target) can be processed using simulated annealing techniques or other methods to obtain a sequence of laser instructions for a patient eye treatment. According to some embodiments, if the difference between the existing target refraction measure 4140 and the deconvolved target refraction measure 4150 exceeds a certain threshold or amount, then a decision may be made to not proceed with administration of the treatment to the patient.

Figure 42:
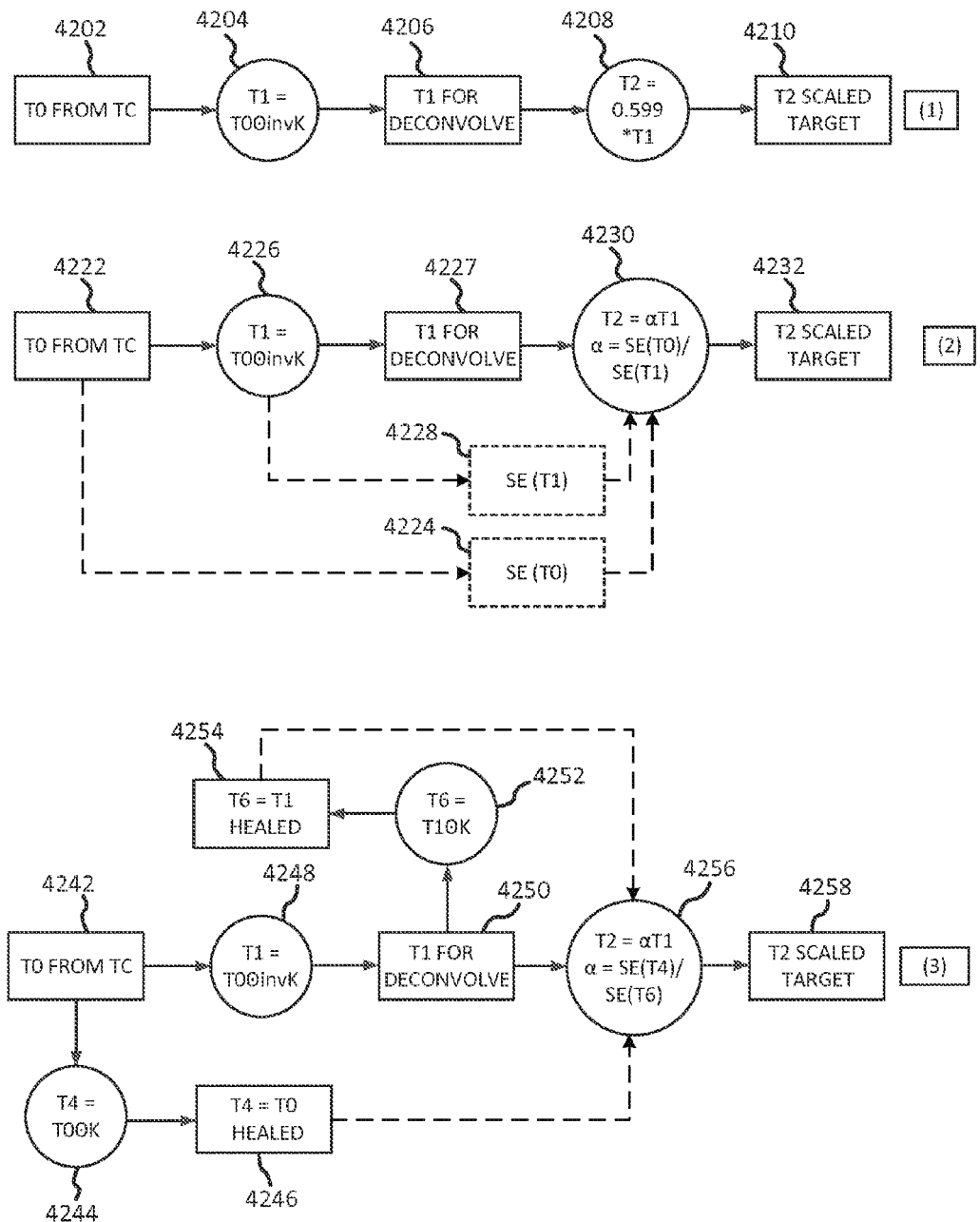
FIG. 42 illustrates aspects of treatment validation systems and methods according to embodiments of the present invention.

For a given low pass filter (LPF), a scaling factor can be determined for each eye. Various techniques can be used to determine a scaling factor. For example, as depicted in FIG. 42, a scaling factor can be determined (1) using a population mean, (2) using individual scaling based on the target refraction, or (3) using individual scaling based on "healed" target refraction. The scaling methods depicted here encompass techniques for low order refraction scaling.

The term T0 can refer to the original or existing treatment target. The term TC can refer to a Target Controller, which may include a software and/or hardware module that generates the original or existing treatment target. The term T1 can refer to a deconvolved target. The term T2 can refer to a scaled target of T1.

As depicted in version (1) here, an exemplary method of determining a vision treatment for an eye of a patient can include receiving, at an input, an original target T0 or target profile for the eye of the patient. The existing target can be obtained from or generated by a target controller, as shown in step 4202. Exemplary methods may also include obtaining a deconvolved target T1 or target profile based on the original target profile and a low pass filter. For example, target T1 can be determined by deconvolving target T0 with a low pass filter (or optimized linear filter). As shown at step 4204, T1 can be processed with an inverse kernel $K_{INV}$. As discussed elsewhere herein, an inverse kernel can be exemplified as a convolution kernel that operates like a deconvolution procedure. In this sense, a deconvolution operation may be considered to be a convolution procedure using an inverse kernel. Step 4206 indicates that a deconvolved target T1 can be obtained via a deconvolution process. Further, exemplary methods may include obtaining a scale factor, where the scale factor is based on a low order refraction measure of a test eye population and a low order refraction measure of a convolved test eye population profile, and where the convolved test eye population profile is based on a convolution of the test eye population profile. In some cases, the scale factor is a constant. As shown here in step 4208, the scale factor can be 0.599. In some embodiments, the scale factor can be 0.7489. According to some embodiments, the scale factor can have a value within the range from about 0.4 to about 0.8. As indicated in step 4210, methods may include determining a scaled target T2 or target profile based on the deconvolved target T1 or target profile and the scale factor. Exemplary methods may also include determining the vision treatment based on the scaled target T2 or target profile.

As noted above, a scale factor can be based on a low order refraction measure of a test eye population and a low order refraction measure of a convolved test eye population profile. In some cases, the low order refraction measure of the test eye population profile includes a first manifest refraction spherical equivalent measure and the low order refraction measure of the convolved test eye population profile includes a second manifest refraction spherical equivalent measure. In some cases, the first manifest refraction spherical equivalent measure is a 4 mm refraction measure and the second manifest refraction spherical equivalent measure is a 4 mm refraction measure.

In addition to the population mean scaling factor approach depicted in version (1), embodiments of the present invention also encompass other low order refraction scaling approaches, such as individual scaling techniques that involve scaling factors based on targets. As depicted in version (2) here, an exemplary method of determining a vision treatment for an eye of a patient can include receiving, at an input, an original target profile T0 for the eye of the patient. The existing target T0 can be obtained from or generated by a target controller, as shown in step 4222. Methods may also include determining a first low order refraction measure, for example SE (T0), based on the original target profile T0, as indicated by step 4224. Further, methods may include obtaining a deconvolved target profile based on the original target profile and a low pass filter. For example, target T1 can be determined by deconvolving target T0 with a low pass filter (or optimized linear filter). As shown at step 4226, T1 can be processed with an inverse kernel $K_{INV}$. Step 4227 indicates that a deconvolved target T1 can be obtained via a deconvolution process. Methods may also include determining a second low order refraction measure based on the deconvolved target profile. For example, a second low order refraction measure, such as SE (T1), can be determined based on the deconvolved target profile T1, as indicated by step 4228. According to the embodiment depicted in version (2), methods may also include determining a scale factor based on a comparison between the first and second low order refraction measures. For example, a scale factor $\alpha$ can be determined based on a comparison between first low order refraction measure SE (T0) and second low order refraction measure SE (T1). As shown here in step 4230, the scale factor $\alpha$ can include a ratio of the first low order refraction measure SE (T0) and the second low order refraction measure SE (T1). Further, methods may include determining a scaled target profile based on the deconvolved target profile and the scale factor. For example, as depicted in step 4232, methods may include determining a scaled target profile T2 based on a deconvolved target profile T1 and a scale factor $\alpha$. Methods may also include determining the vision treatment based on the scaled target profile.

As depicted here, the first low order refraction measure can include a first manifest refraction spherical equivalent (SE) measure. Relatedly, the second low order refraction measure can include a second manifest refraction spherical equivalent (SE) measure. In some instances, the first low order refraction measure (e.g. first manifest refraction spherical equivalent measure) is a 4 mm refraction measure. In some instances, the second low order refraction measure (e.g. second manifest refraction spherical equivalent measure) is a 4 mm refraction measure. In some instances, the first low order refraction measure includes a first sphere measure. In some instances, the second low order refraction measure includes a second sphere measure. In some instances, the first low order refraction measure includes a first cylinder measure. In some instances, the second low order refraction measure includes a second cylinder measure.

Hence, the embodiment depicted by version (2) in FIG. 42 encompasses techniques where T1 represents a target T0 as convolved with an inverse kernel. The ratio $\alpha$ may be different for different eyes. Hence, in comparison to the population approach of version (1), this version can be used for an individualized or customized approach. The ratio $\alpha$ can be determined for individual persons, on a per eye basis.

In addition to the population mean scaling factor approach depicted in version (1), and the individual scaling technique depicted in version (2), embodiments of the present invention also encompass other low order refraction scaling approaches, such as individual scaling techniques that involve scaling factors based on healed target refractions. As depicted in version (3) here, an exemplary method of determining a vision treatment for an eye of a patient can include receiving, at an input, an original target profile T0 for the eye of the patient.

According to some embodiment, T0 can refer to the target (e.g. corresponding to tissue ablation depth over a 101×101 space). TC can refer to a target controller, and may include a software and/or hardware module that generates the treatment target. T1 can refer to a deconvolved target. T2 can refer to a scaled target of T1. T4 can refer to a convolved target (e.g. simulating the healed target of T0). T6 can refer to a healed target of T1 (e.g. the deconvolved target healed).

The existing target T0 can be obtained from or generated by a target controller, as shown in step 4242. Methods may also include obtaining a first healed profile based on the original target profile. For example, a first healed profile T4 can be determined based on an original target profile T0 as indicated by step 4246. The healing can be represented by a healing kernel K. When a target is convolved with K, the target becomes a healed target (i.e. simulating the healing process). A deconvolution is a reverse process of convolution. Further, a deconvolution can be treated as a convolution process, by obtaining an inverse kernel invK. For example, if the healed target is convolved with invK, it is possible to obtain the original target T0. Put another way, if A*K=B, it is possible to have B*invK=A, where * stands for convolution and invK is the inverse kernel of K. Accordingly, Target T4 can be determined based on original target (e.g. T0) and convolution with kernel K. As such, T4 can be considered a healed case for T0, where the healed outcome is considered to be approximated by the convolution. Further, methods may include obtaining a deconvolved target profile based on the original target profile and a low pass filter. For example, target T1 can be determined by deconvolving target T0 with a low pass filter (or optimized linear filter). As shown at step 4248, T1 can be processed with an inverse kernel $K_{INV}$. Step 4250 indicates that a deconvolved target T1 can be obtained via a deconvolution process. Exemplary methods may also include obtaining a second healed profile based on the deconvolved target profile, as indicated by step 4254. For example, a second healed profile T6 can be determined based on the deconvolved target profile T1. Accordingly, based on the discussion above, Target T6 can be determined based on a target (e.g. T1) and convolution with kernel K. As such, T6 can be considered a healed case for T1, where the healed outcome is considered to be approximated by the convolution.

As shown here, methods may include determining a first low order refraction measure, such as SE (T5), based on the first healed profile T5, and a second low order refraction measure, such as SE (T6), based on the second healed profile T6. As shown in step 4256, methods may include determining a scale factor $\alpha$ based on a comparison (e.g. a ratio) between the first low order refraction measure and the second low order refraction measure. Further, methods may include determining a scaled target profile based on the deconvolved target profile and the scale factor. For example, as depicted in step 4258, methods may include determining a scaled target profile T2 based on a deconvolved target profile T1 and a scale factor $\alpha$. Methods may also include determining the vision treatment based on the scaled target profile.

In some cases, the first low order refraction measure can include a first manifest refraction spherical equivalent measure. In some cases, the second low order refraction measure can include a second manifest refraction spherical equivalent measure. In some cases, the first manifest refraction spherical equivalent measure can include a 4 mm refraction measure. In some cases, the second manifest refraction spherical equivalent measure can include a 4 mm refraction measure. In some cases, the first low order refraction measure can include a first sphere measure. In some cases, the second low order refraction measure can include a second sphere measure. In some cases, the first low order refraction measure can include a first cylinder measure. In some cases, the second low order refraction measure can include a second cylinder measure.

Figure 43:
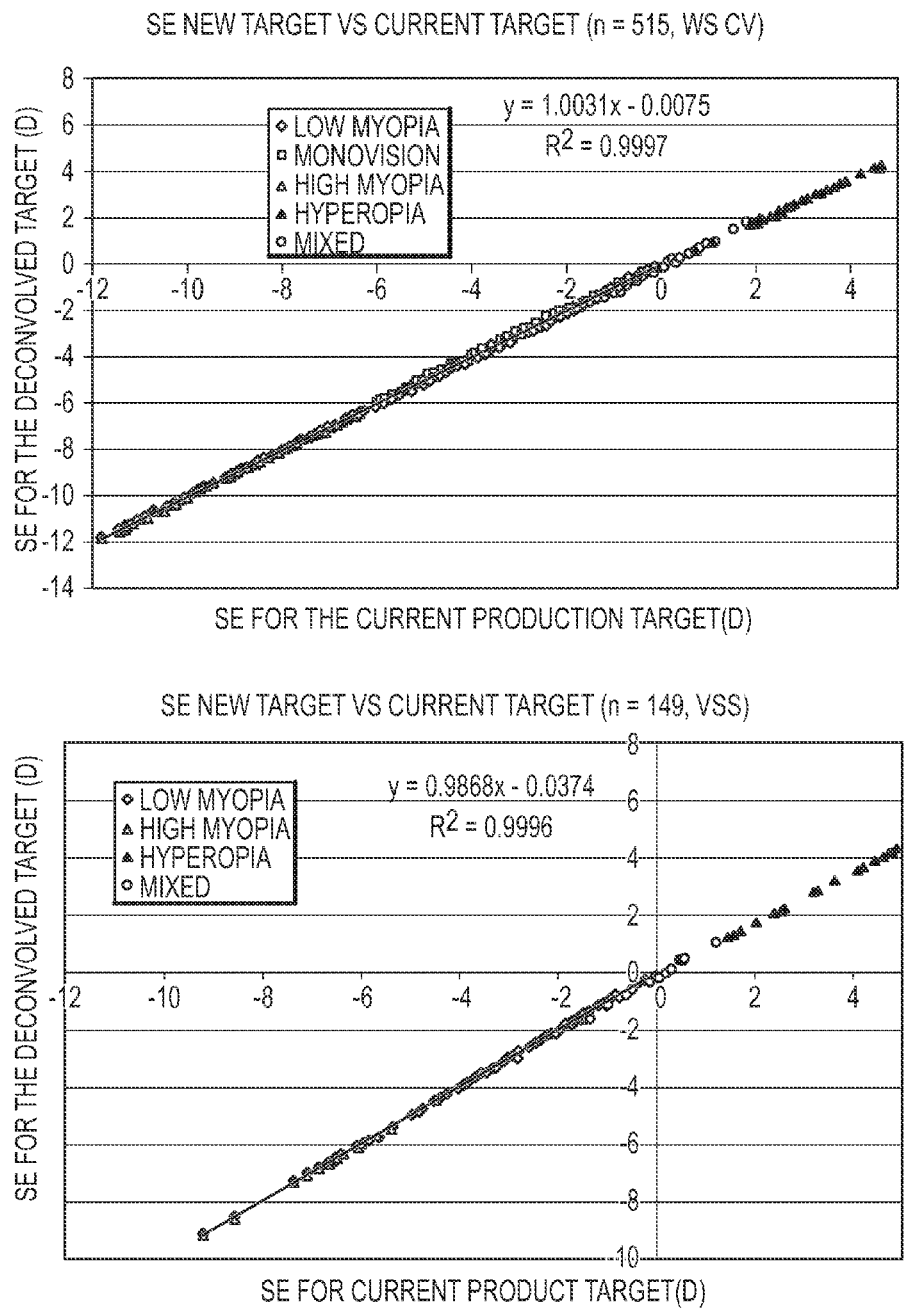
FIG. 43 illustrates aspects of treatment validation systems and methods according to embodiments of the present invention.

Hence, according to version (1) depicted in FIG. 42, a number of test eyes (e.g. eyes from previously performed clinical trials) can be used. Treatment targets can be determined and their associated 4-mm WRSE values can be calculated. What is more, respective deconvolved targets for the same eyes can be determined and their associated 4-mm WRSE values can be calculated. For each eye, a ratio of the existing target WRSE over the deconvolved target WRSE can be calculated. A mean value can be calculated such that it can be used to be implemented in the deconvolved target to scale the target before it is finally generated. With the implemented scaling, those same eyes can be used to verify that the WRSE for the deconvolved scaled targets is the same as the WRSE for the existing target over a 4-mm pupil. FIG. 43 provides results for a wavefront based LASIK (e.g. using WaveScan®, CustomVue®) in the upper panel and a refraction based LASIK (e.g. using VSS Refractive™) in the lower panel, where a scaled deconvolved target SE is compared with an existing target SE. As shown here, the results confirm that a constant scaling factor approach such as that described in version (1) of FIG. 42 (e.g. using a scaling factor of 0.599) can provide a good match for the deconvolved scaled target versus the existing target. To the extent that the terms MRSE and WRSE are interchangeably used, it is understood that both terms refer to types of spherical equivalent (SE), and hence the usage refers to that common aspect, while acknowledging the difference between the wavefront nature of WRSE and the manifest nature of MRSE. Accordingly, there the terms WRSE and/or MRSE are used, it is also possible to replace those terms with the more generic term SE.

As noted above with regard to version (2), a scaling technique can be based on an individualized approach, in contrast to the fixed constant approach provided in version (1). According to some embodiments, when using version (2), when the deconvolved target has a very low SE (e.g. which may occur in cases with mixed astigmatism), any noise can be amplified. In such instances, a different formula, such as sphere or cylinder can be used instead.

As noted above, version (3) also pertains to a scaling technique that is based on an individualized approach. According to version (3), the calculation can be performed using a "healed" target determination.

Figure 44:
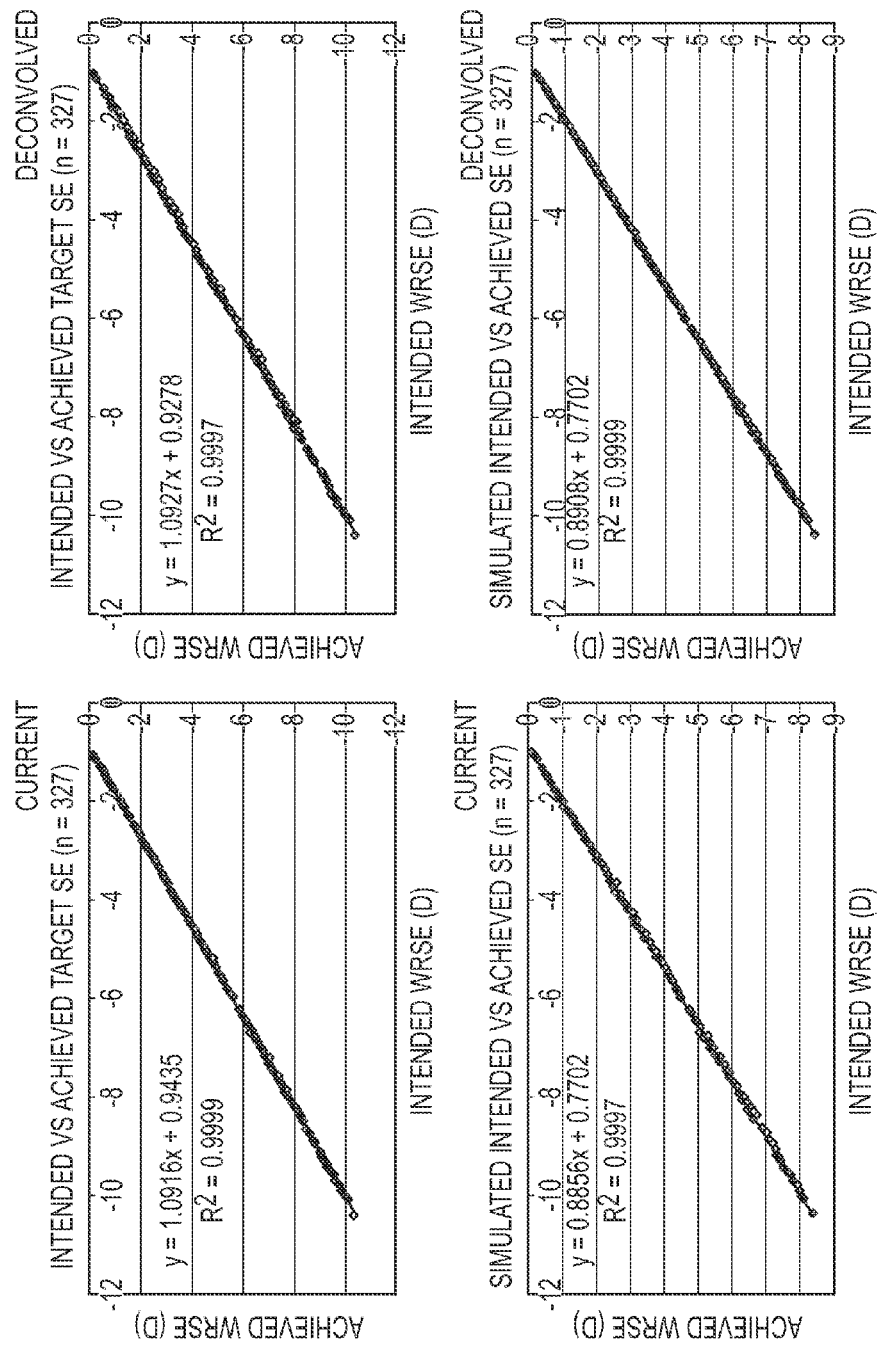
FIG. 44 illustrates aspects of treatment validation systems and methods according to embodiments of the present invention.
Figure 45:
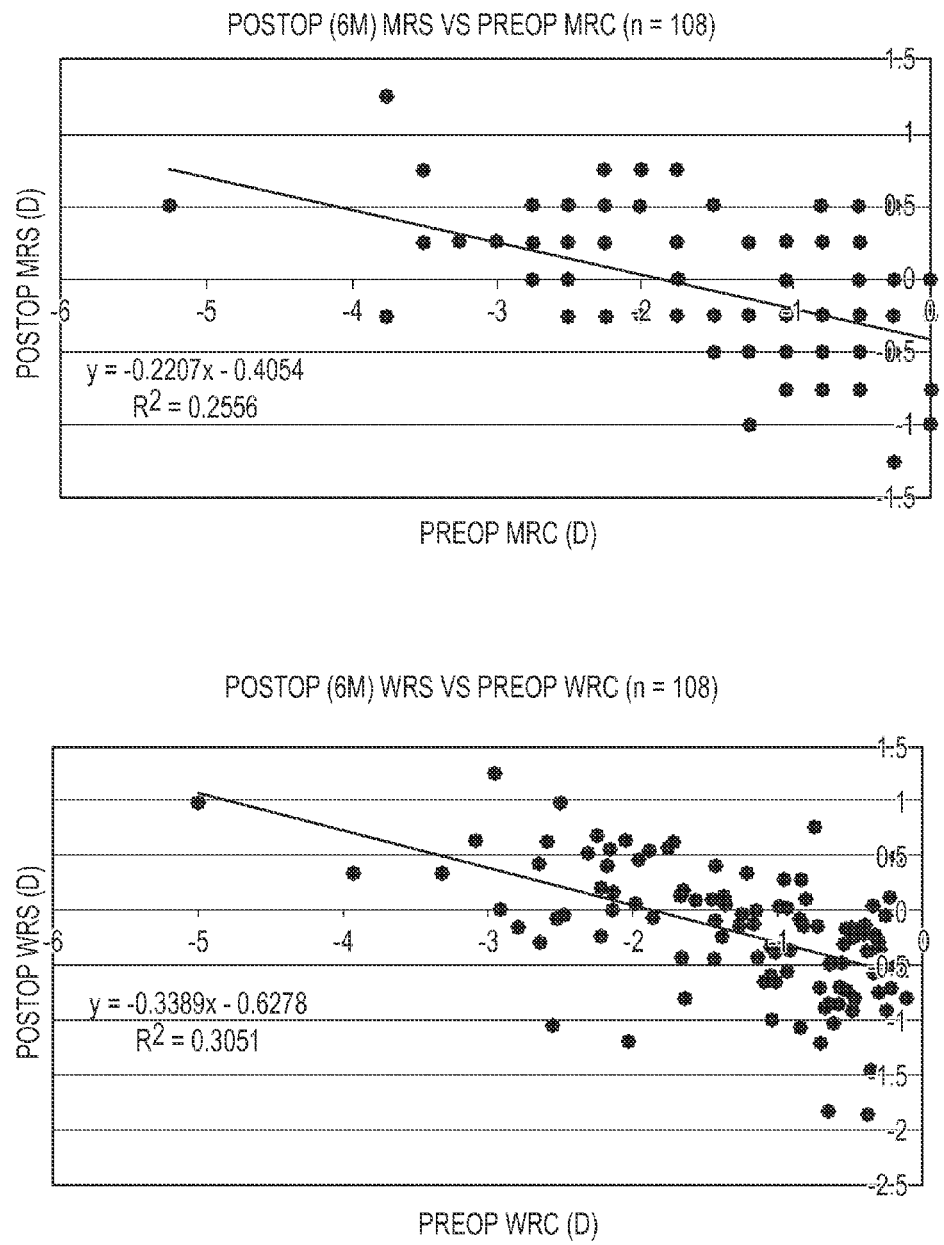
FIG. 45 illustrates aspects of treatment validation systems and methods according to embodiments of the present invention.

To confirm the outcome, in particular for myopia, 327 myopic eyes were used for simulation. Use of a scaling factor shows that the deconvolved target is expected to have the same 4-mm refraction as the original treatment target. The three versions (1), (2), and (3) of FIG. 42 depict three ways of obtaining a reasonable scaling factor. An LPF kernel was used to simulate the low pass filtering or "healing" process. When a treatment target is convolved with the kernel, a post-operative shape (e.g. convolved or healed shape) can be determined. FIG. 44 shows the 4-mm refraction for the intended versus achieved from the treatment target, for both the current (upper left panel) and the deconvolved (upper right panel) targets. In the lower panels, the 4-mm refraction from the simulated post-operative shapes are used to compare to the pre-operative wavefront refraction, again for both the current (lower left panel) and the deconvolved (lower right panel) targets. Because the deconvolved target has the same regression slope as the current target from both the target view point and from the "healed" target, it can be concluded that a significant amount of low order aberration is preserved.

According to some embodiments, the scaling technique disclosed therein can help to ensure that the post-operative patient does not exhibit an undue amount of sphere and cylinder. In some cases, reduction of sphere, cylinder, or both can be enhanced using a nomogram adjustment. Nomogram adjustments can be implemented in manual or automated processes. In some cases, the convolution (or healing) techniques disclosed herein can explain the effects of epithelial remodeling. In some case, as further discussed herein, the convolution techniques can be used to explain effects associated with the sphere and cylinder coupling.

Sphere-Cylinder Coupling

As depicted in FIG. 40, the techniques disclosed herein can produce near optimal clinical outcomes (e.g. a good match between the achieved MRSE and the attempted MRSE). In some instances, target development techniques may produce an amount of under-correction in cylinder. In some instances, target development techniques (e.g. using a low pass filter) may produce an amount of sphere-cylinder coupling. For example, the pre-operative cylinder may affect the post-operative sphere, although the spherical equivalent value is maintained. A higher cylinder in minus notation pre-operatively may cause a higher shift in the hyperopic direction in sphere post-operatively. This can be observed in FIG. 105, when the sphere and cylinder are measured in manifest and wavefront refractions. Cross-coupling phenomenon can be measured as post-operative sphere as a function of the pre-operative cylinder for manifest (upper panel) and wavefront (lower panel).

To help ensure that both the sphere and cylinder are close to zero post-operatively, a nomogram is proposed to be used by the physicians to enter into the "Physician Adjustment" for the sphere correction based on the pre-operative wavefront cylinder. According to some embodiments, this Physician Adjustment can be used at module 2225 in FIG. 22. The nomogram provided in Table 6 (using absolute value of negative cylinder) can be used:

TABLE 6

| Pre-Operative Wavefront Cylinder (diopters) | Physician Adjustment in Sphere (diopters) |
|---|---|
| 0.00 to 0.25 | −0.25 |
| 0.26 to 0.75 | −0.13 |
| 0.76 to 1.00 | 0.00 |
| 1.01 to 2.00 | 0.20 |
| 2.01 to 3.00 | 0.40 |
| 3.01 to 4.00 | 0.60 |
| 4.01 to 5.00 | 0.80 |
| 5.01 to 6.00 | 1.00 |
| 6.01 to 7.00 | 1.20 |
| 7.01 to 8.00 | 1.40 |

According to some embodiments, a formula such as $S=-0.2C-0.25$ can be used, where S represents a sphere adjustment, and C represents a pre-operative wavefront cylinder in minus notation, both in diopters.

Figure 46:
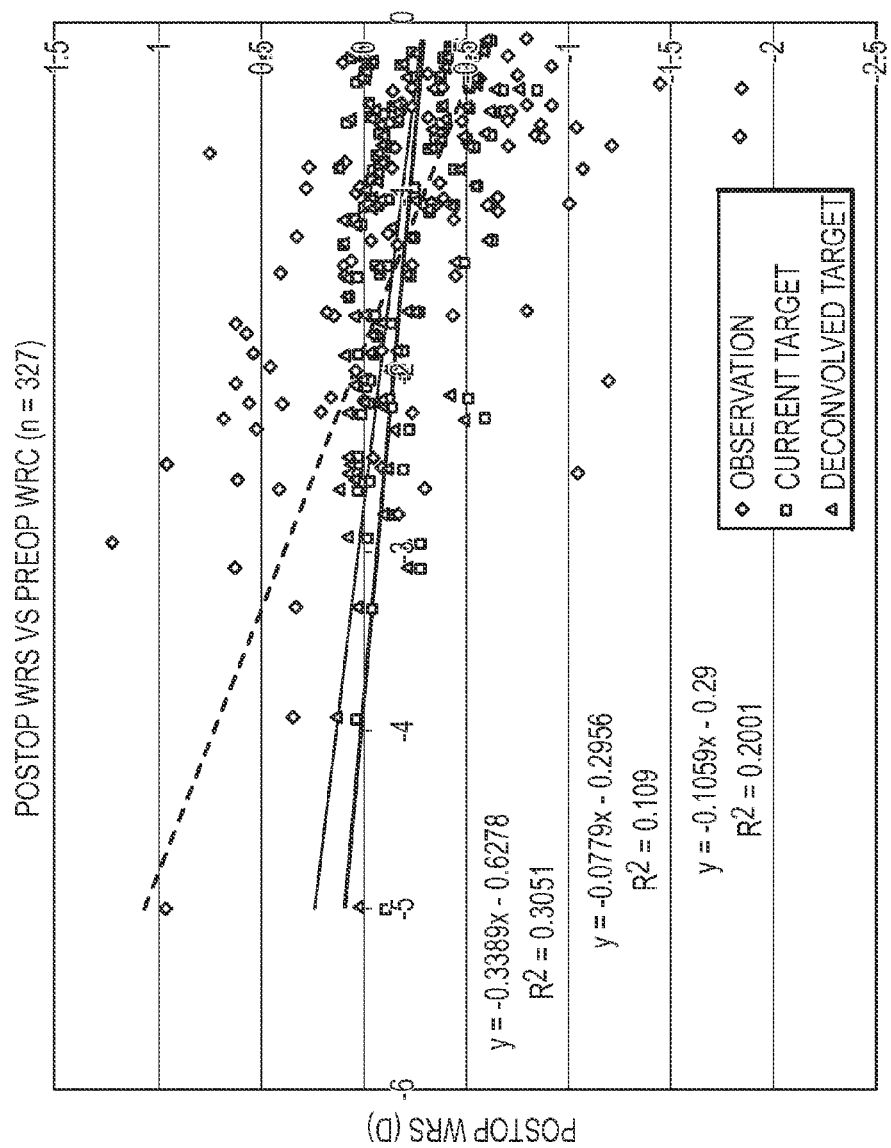
FIG. 46 illustrates aspects of treatment validation systems and methods according to embodiments of the present invention.

According to some embodiments, it is possible to observe and/or predict cylinder coupling results. FIG. 46 depicts low order results, where WRS represents sphere, and WRC represents cylinder. To assess effects due to a low pass filter, a set of patient eyes were used. The targets were smoothed with an LPF using a 2D convolution and the predicted post-operative outcome was calculated. Based on FIG. 46, it can be seen that about 25% of the cylinder coupling may be explained due to the smoothing. When the deconvolution is implemented, about 33% of the cylinder coupling may be explained. The difference between the two is only 2.8%, which is well too small compared to the 34% coupling from the observation (in terms of wavefront refraction, only about 22% in terms of manifest refraction).

These numbers (25%, 33%, 2.8%, 34%, and 22%) can relate to the slopes in the graph. For example, the slope for an original (or current) target can be about 8% (0.0779) which is about 25% of the observed coupling of about 34% (0.3389). The difference of slopes between the current and the deconvolved target is about 2.8% (0.1059−0.0779). The 22% value is also from the slope, but from a different graph (not shown here), and is related to the formula (S=−0.2C−0.25). The 22% value can be approximated with 0.20. Therefore, it may be desirable to use no additional adjustment to the nomogram for cylinder coupling. Hence, the formula mentioned above, $S=-0.2C-0.25$ can be used.

Figure 46A:
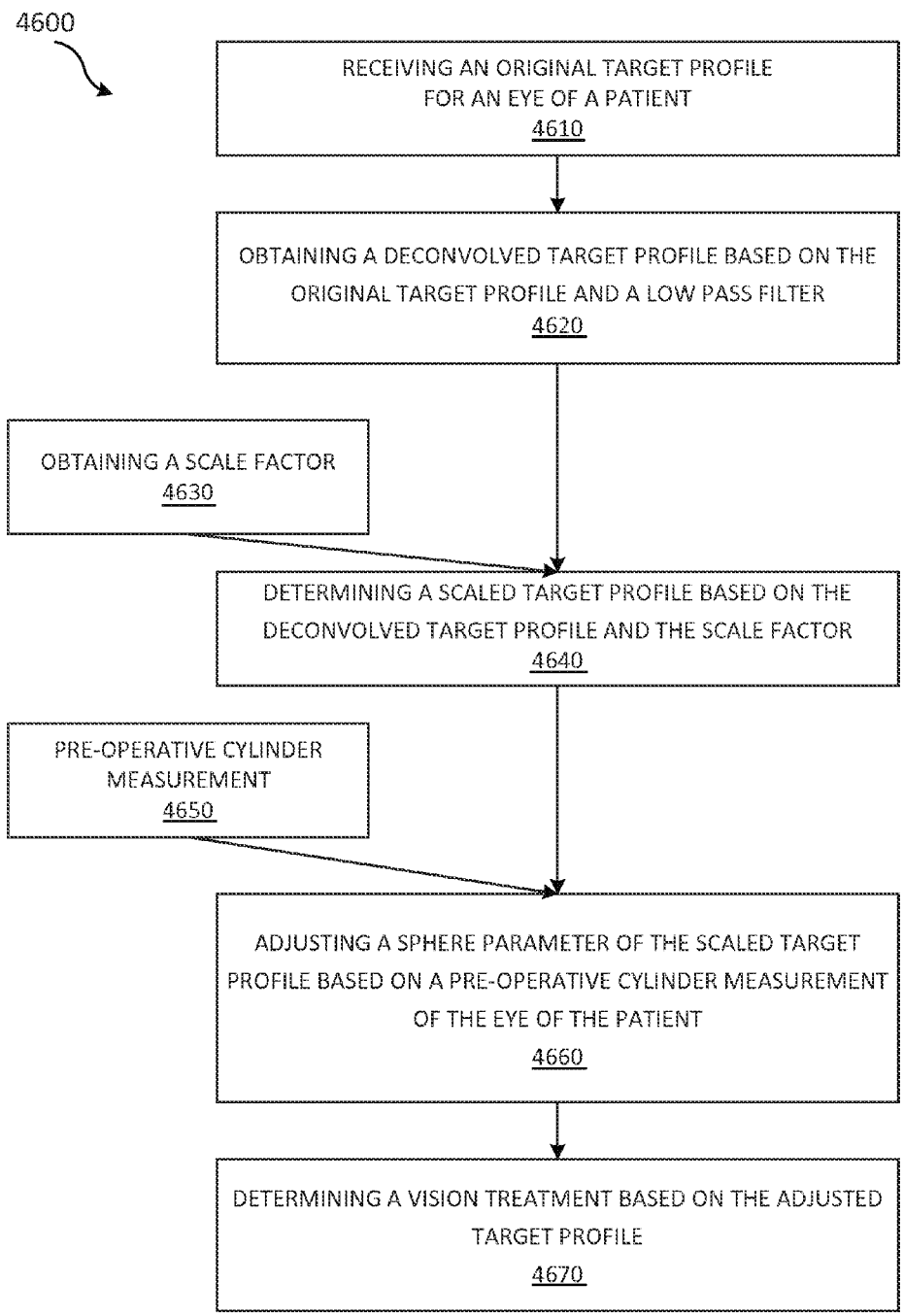
FIG. 46A illustrates aspects of treatment validation systems and methods according to embodiments of the present invention.

Embodiments of the present invention encompass systems and methods for determining a vision treatment which involve adjusting a sphere parameter of a treatment based on a pre-operative cylinder measurement. For example, as shown in FIG. 46A, an exemplary method 4600 may include receiving, at an input, an original target profile for the eye of the patient, as indicated by step 4610. Methods may also include obtaining a deconvolved target profile based on the original target profile and a low pass filter, as indicated by step 4620. Further, methods may include obtaining a scale factor, as indicated by step 4630. The scale factor can be based on a low order refraction measure of a test eye population and a low order refraction measure of a convolved test eye population profile. The convolved test eye population profile can be based on a convolution of the test eye population profile. Methods may also include determining a scaled target profile based on the deconvolved target profile and the scale factor, as indicated by step 4640. Further, methods may include adjusting a sphere parameter of the scaled target profile based on a pre-operative cylinder measurement 4650 of the eye of the patient, as indicated by step 4660. In some cases, methods may also include determining the vision treatment based on the adjusted target profile, as indicated by step 4670. According to some embodiments, methods for determining a vision treatment for an eye of a patient may include obtaining a pre-operative cylinder value for the eye of the patient, for example by receiving, at an input, a pre-operative cylinder value for the eye of the patient, and determining the vision treatment for the eye, where the vision treatment includes a sphere value that is based on the pre-operative cylinder value. In some cases, a pre-operative cylinder value can correspond to a manifest refraction measurement. In some cases, a pre-operative cylinder value can correspond to a wavefront refraction measurement. In some cases, the sphere value of the vision treatment is determined based on the formula S=−0.2 C−0.25, where S is the sphere value and C is the pre-operative cylinder value.

High Order Aberrations

Figure 47:
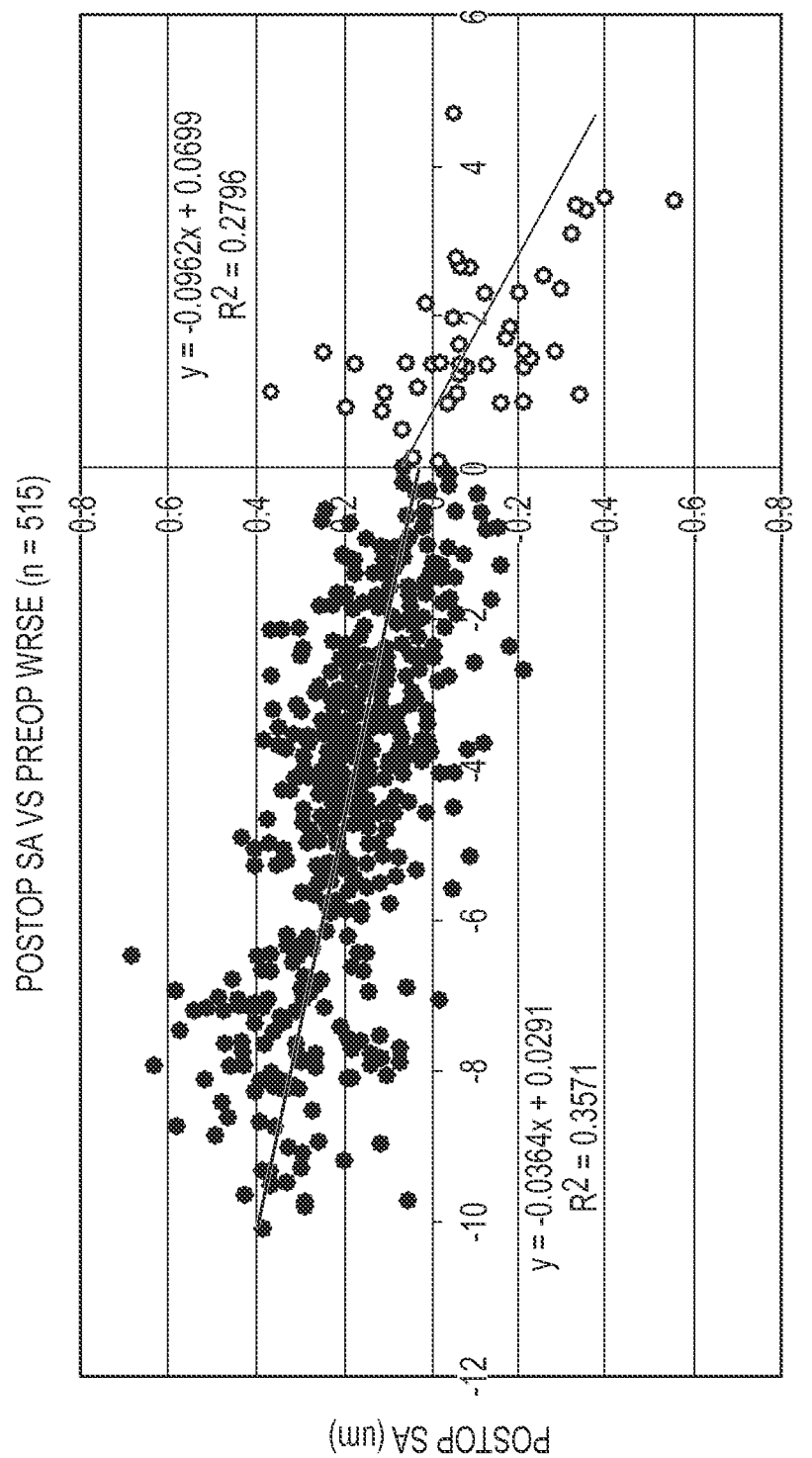
FIG. 47 illustrates aspects of treatment validation systems and methods according to embodiments of the present invention.

Laser-Assisted in situ Keratomileusis (LASIK) treatments, including convention and wavefront-guided version, can induce high order aberrations, and in particular spherical aberration (SA). FIG. 47 shows a scatter plot for a 6M post-operative spherical aberration (SA) as a function of the pre-operative wavefront refraction in spherical equivalent (WRSE), with exemplary CustomVue® treatments, for both myopia and hyperopia. This plot shows a regression slope for hyperopia (e.g. 0.0962) that is about three times the slope for myopia (e.g. 0.0364), indicating the difference in the induction strength. Without being bound by any particular theory, it is believed that this difference may be the result of a low pass filtering process, such as that described in previously incorporated U.S. Patent Application No. 61/708, 815 filed Oct. 2, 2012.

Figure 48:
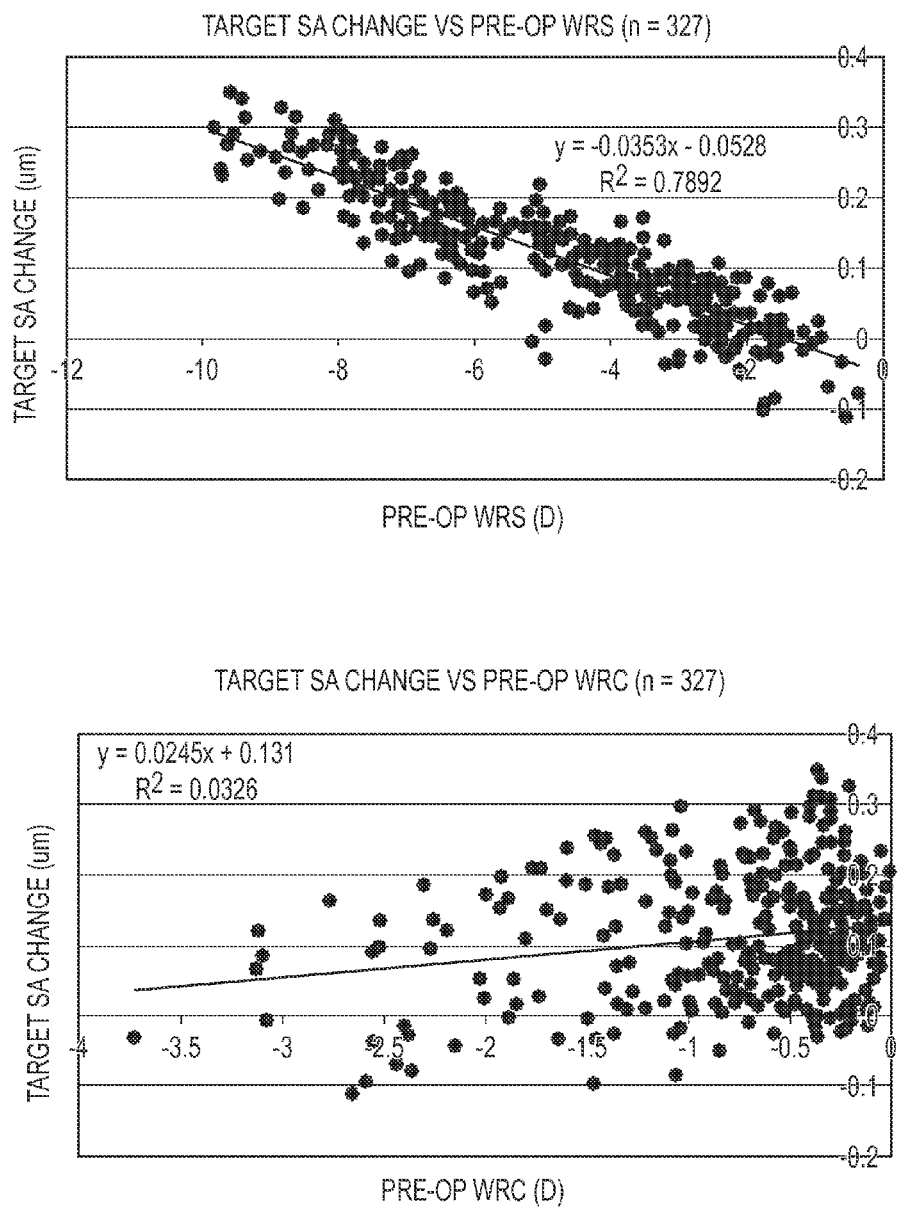
FIG. 48 illustrates aspects of treatment validation systems and methods according to embodiments of the present invention.

FIG. 48 provides plots for a target SA change (e.g. addition for SA) as a function of pre-operative WRS (wavefront refraction in sphere; upper panel) and WRC (wavefront refraction in cylinder; lower panel), according to embodiments of the present invention. These plots are based on a simulation conducted with 327 myopic eyes (e.g. simulated addition for the deconvolved target as compared to an original target for 327 simulated myopic eyes). A multivariate regression was used to obtain the following regression formula: $\Delta SA=-0.0385S+0.0364C-0.033$. This equation indicates that both pre-operative sphere (S) and cylinder (C) have an effect on the SA addition. To determine a tolerance for the verification, it is possible to consider the 95% confidence interval for all the three parameters in the equation. The 95% confidence interval for the sphere slope is [−0.0402, −0.0368], that for the cylinder slope is [0.0305, 0.0424] and that for the constant term is [−0.0428, −0.0232]. The p-values for each of them are much smaller than 0.001. The adjusted R-square is 0.857. A range of ±0.15 was determined so the upper and lower bounds can be expressed with the following equations:

$$\Delta SA_-=-0.0385S+0.0364C-0.183 \quad \text{(Equation 34)}$$

$$\Delta SA_+=-0.0385S+0.0364C+0.117 \quad \text{(Equation 35)}$$

Based on the plots in FIG. 48, it can be seen that post-operative SA can be related to pre-operative sphere, pre-operative cylinder, or both. Hence, sphere and/or cylinder can contribute to the post-operative induction of SA. The upper panel illustrates a stronger correlation for SA (high order aberration) and sphere (wavefront refraction in sphere). The lower panel illustrates a weaker correlation for SA (high order aberration) and cylinder (wavefront refraction in cylinder). Based on a comparison between FIG. 47 and the upper panel of FIG. 48, it can be determined that the deconvolved target provides good compensation, because there is a match between the plots.

According to some embodiments, validation techniques can involve comparing a revised target with an original target, and determining whether the revised target is sufficiently similar to the original target. For example, with regard to FIG. 48, it is possible to observe a trend line with a slope of −0.353 which matches the observed trend line slope of −0.0364. For a −6 D case, as an example, FIG. 48 shows SA of about 0.15 um. According to some embodiments, validation techniques can involve calculating the SA associated with a revised target, comparing that SA with the SA of an original target, and determining whether the difference between the revised target SA and the original target SA meets a certain criteria. For example, the difference can be positive, indicating an effective induction of positive SA in the revised target SA.

Figure 49:
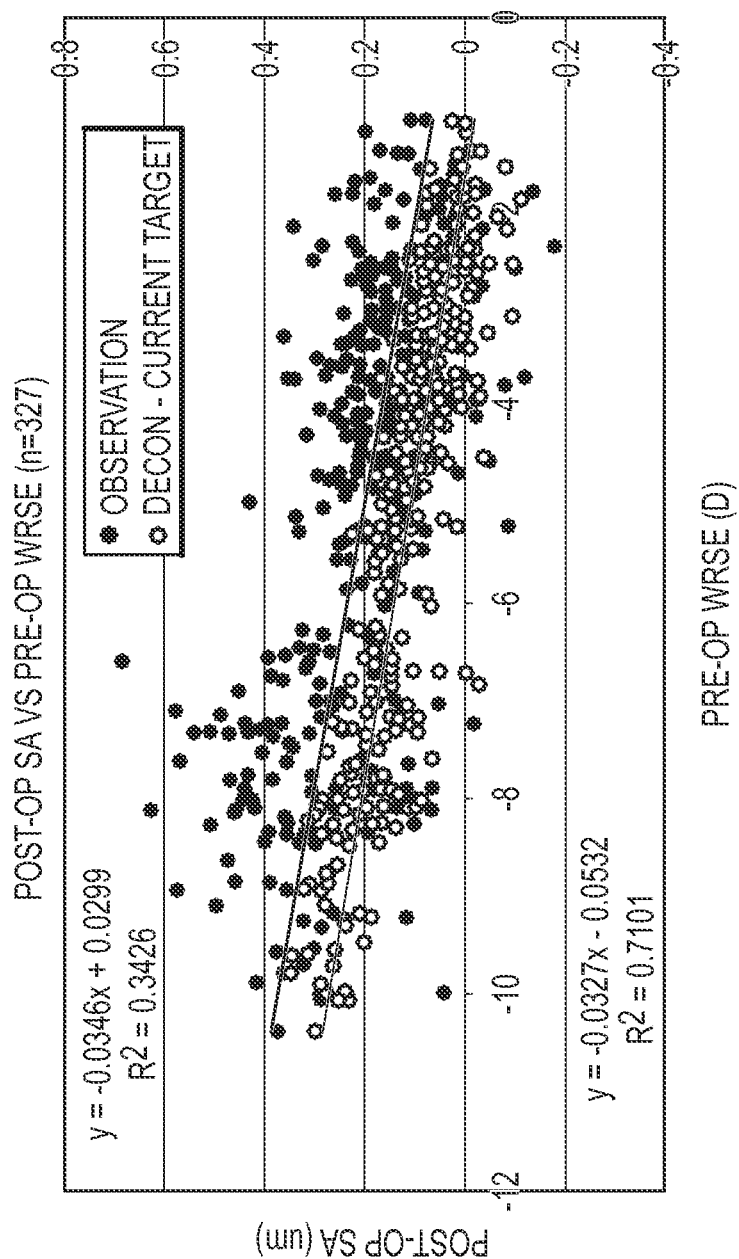
FIG. 49 illustrates aspects of treatment validation systems and methods according to embodiments of the present invention.

FIG. 49 provides a comparison between observed and expected additions for the deconvolved target as compared to an original target for post-operative spherical aberration. When Equations (34) and (35) are used for the 327-eye dataset, the additional SA obtained by doing deconvolved−[minus] original targets, is within the upper and lower bounds for all eyes. This can provide an indication of what the deconvolution is introducing into the target shape. FIG. 49 depicts the result shown as a function of WRSE. As illustrated here, the addition has a slope that is similar to the slope of the observed induction of SA, indicating a removal of this SA induction trend. According to some embodiments, it is possible to use information such as this to validate a design algorithm and/or to verify that a software code is implemented correctly (e.g. alleviate the induction of post-operative SA). For example, where an original treatment may induce positive SA, a revised treatment may counteract that effect by providing a negative SA. In some cases, a revised treatment target can have a greater positive SA for the same dioptric correction. In some cases, a revised treatment target can create an negative SA to counteract an observed clinical SA. In some cases, a kernel can be used to generate a treatment that does not induce excessive SA.

Figure 50:
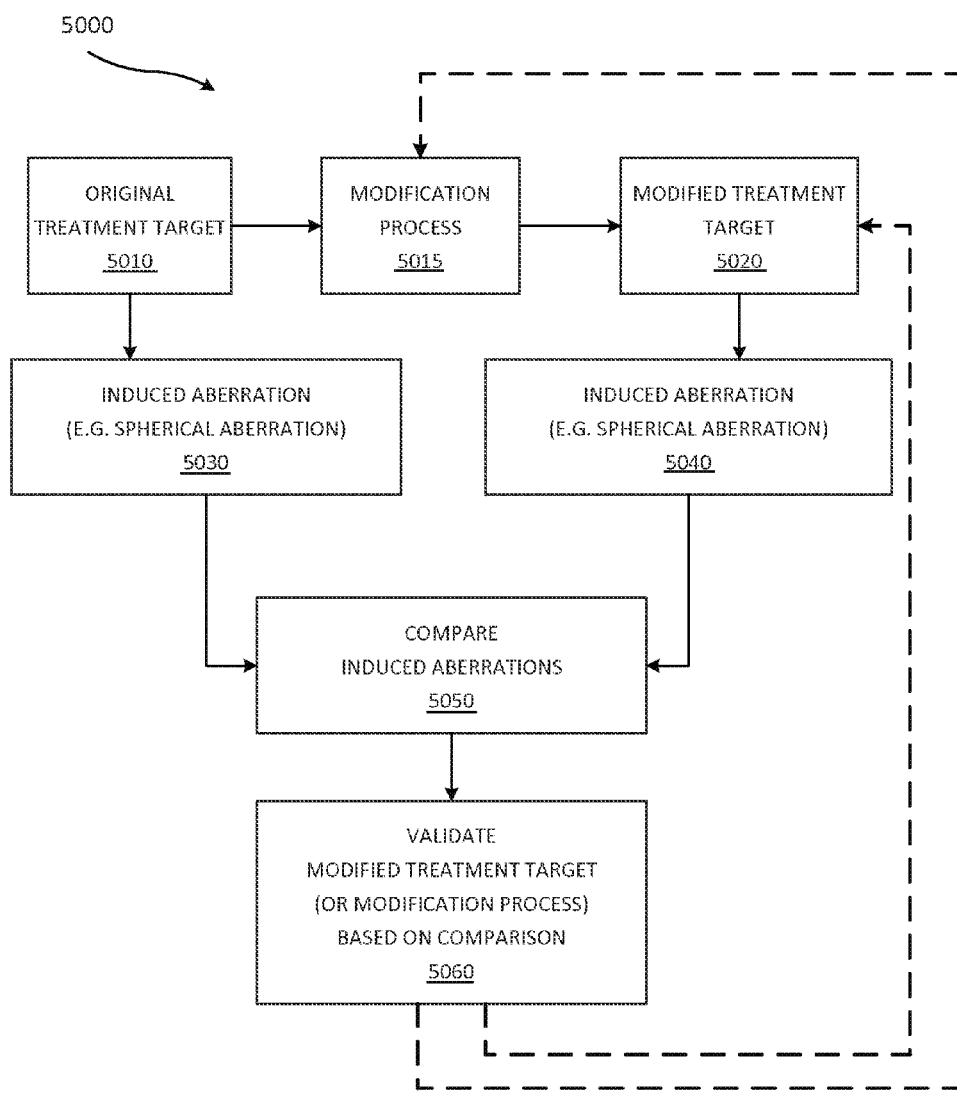
FIG. 50 illustrates aspects of treatment validation systems and methods according to embodiments of the present invention.

FIG. 50 depicts aspects of a treatment validation process 5000 according to embodiments of the present invention. As shown here, a modified treatment target 5020 can be generated based on an original treatment target 5010, for example by using a modification process 5015. In some cases, a modification process 5015 can include a deconvolution process, a low pass filter process, a scaling process, or an adjustment process, as discussed elsewhere herein, or any combination thereof. An induced aberration 5030 (e.g. a high order aberration such as spherical aberration) can be determined for the original target, and an induced aberration 5040 (e.g. high order aberration such as spherical aberration) can be determined for the modified target. According to some embodiments, the induced aberrations can correspond to post-operative induced HOAs. The induced aberrations can be compared, as indicated by step 5050. The modified treatment target can be validated based on the comparison of the induced aberrations, as indicated by step 5060. For example, the modified target can be validated if the difference between induced aberration 5030 and induced aberration 5040 meets a certain criteria or threshold. Relatedly, the modification process 5015 (which optionally may include a deconvolution process, a low pass filter process, a scaling process, or another adjustment or modification techniques as disclosed herein) for obtaining the modified target can be validated in a similar fashion, based on the comparison.

According to some embodiments, a filter can be validated based on a comparison between simulated and observed post-operative SE and SA for different data sets. For example, as depicted in the data sets of FIGS. 51 and 52, for example, there is a close match between the simulated and observed data trend lines.

Figure 51:
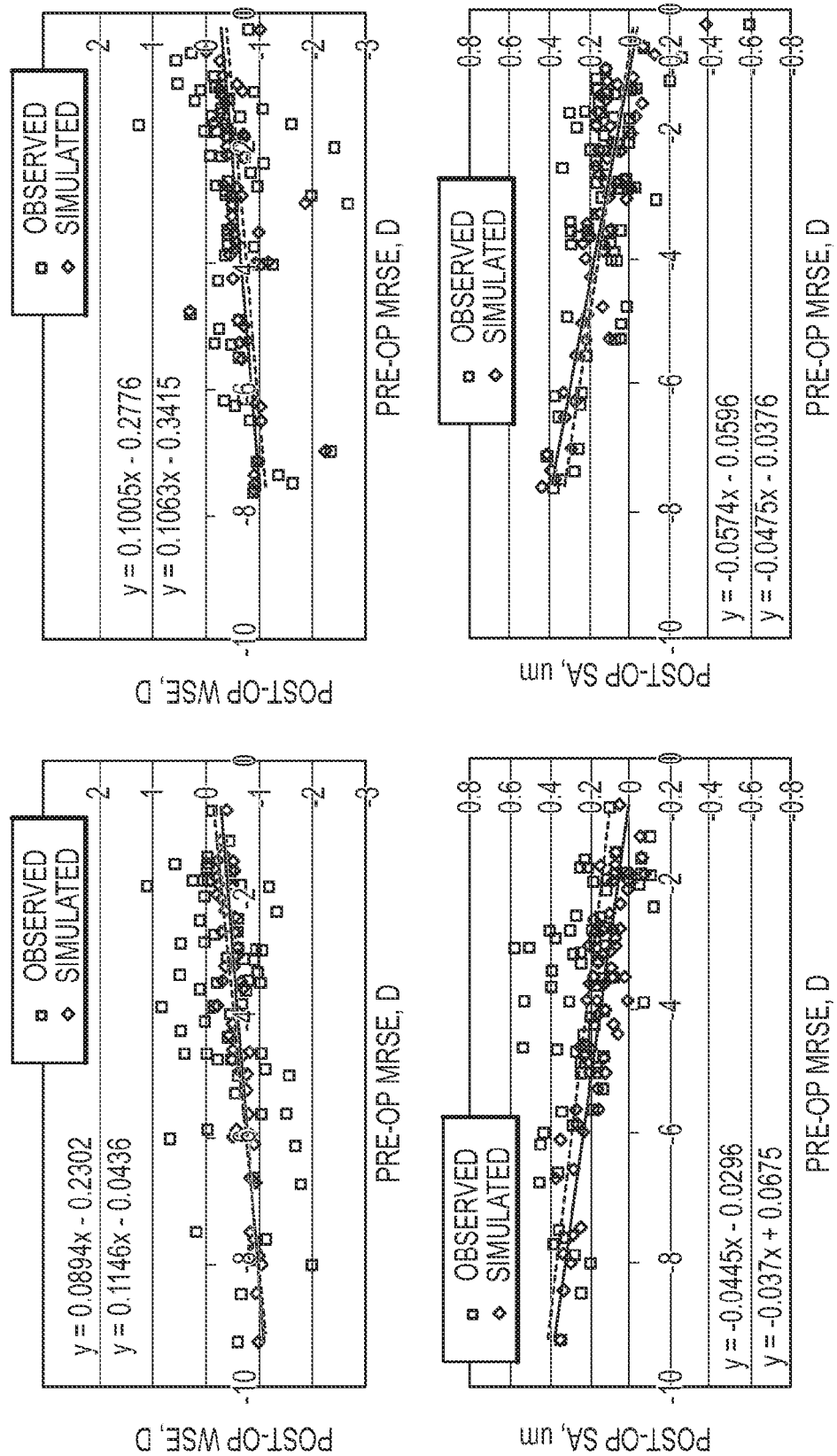
FIG. 51 illustrates aspects of treatment validation systems and methods according to embodiments of the present invention.

For example, FIG. 51 shows a comparison between simulated and observed (6M) post-operative aberrations for a clinical trial (myopic eyes, n=74) and data (myopic eyes, n=72). As shown here, it is possibly to verify the model with two clinical data sets for both SE and SA, meaning the model works very well. Put another way, FIG. 51 illustrates validation of the optimized filter model for two data sets: clinical trial data (left) and commercial data (right). As shown here, the trend lines for observed and simulated SA and SE are very close. This result confirms that the optimized filter, derived from some different data sets, provides a good model for a post-operative SA versus a pre-operative SE trend.

Some data sets show a constant shift between simulated and observed trend lines. Such shifts for post-operative SE or SA trends can be about the same for all pre-operative MRSE values, which means they may not depend on ablation depth. The data may result from aberrations, caused by the creation of the LASIK flap. Depending on the choice of microkeratome and the individual surgeon technique, the flap-induced aberrations may differ from site to site or surgeon to surgeon. Simulations of the predicted post-operative outcome for modified targets may assume no flap-induced aberrations.

Figure 52:
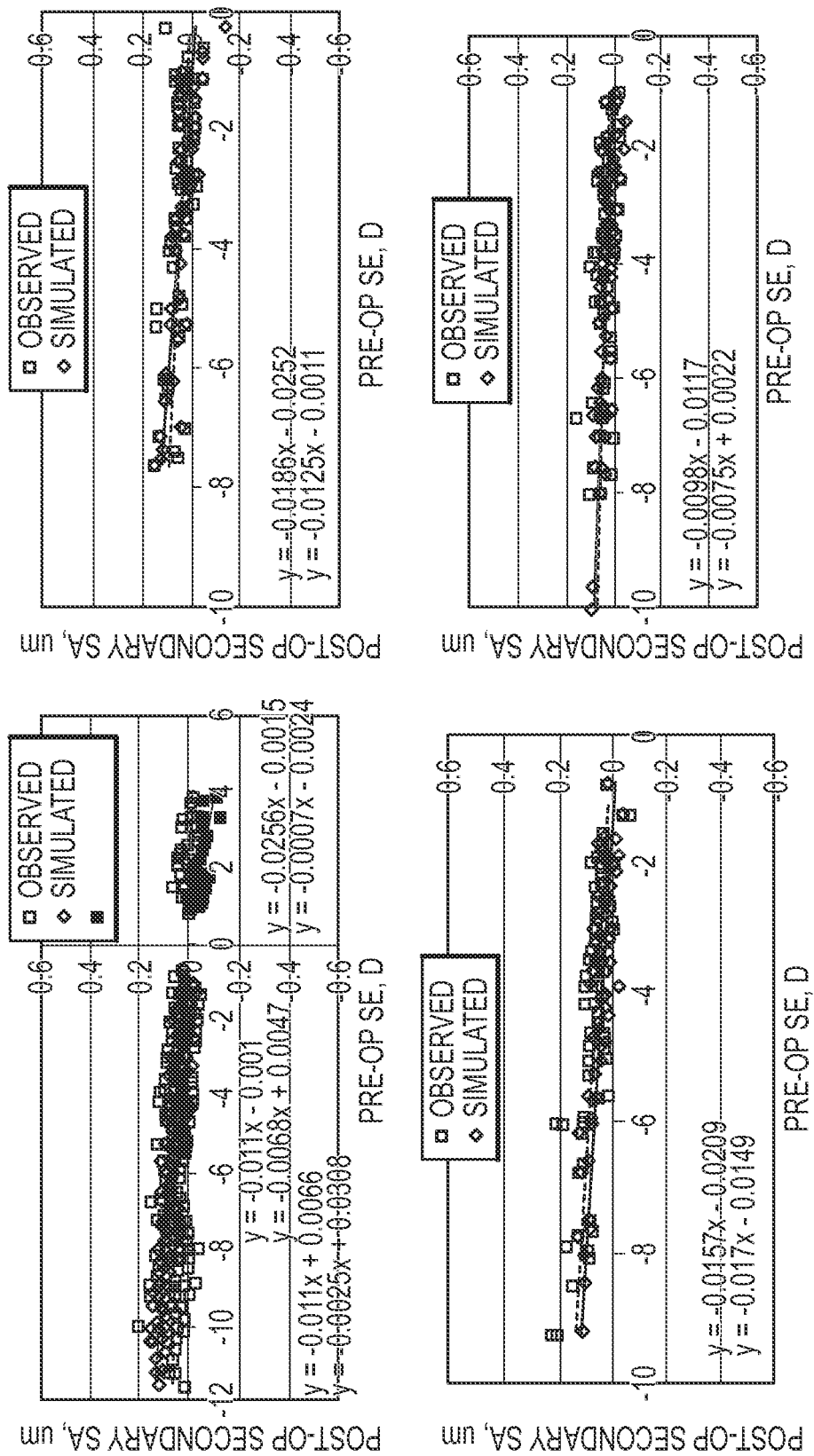
FIG. 52 illustrates aspects of treatment validation systems and methods according to embodiments of the present invention.

According to some embodiments, filter techniques as disclosed herein can provide a close match of observed vs. predicted post-operative trends not only for SE and SA, but also for secondary spherical aberration. FIG. 52 depicts plots corresponding to eye study data (n=390), myopic eye (n=74, n=72) data, and additional eye data (n=76), which provide comparisons of simulated and observed post-operative secondary spherical aberrations.

Figure 53:
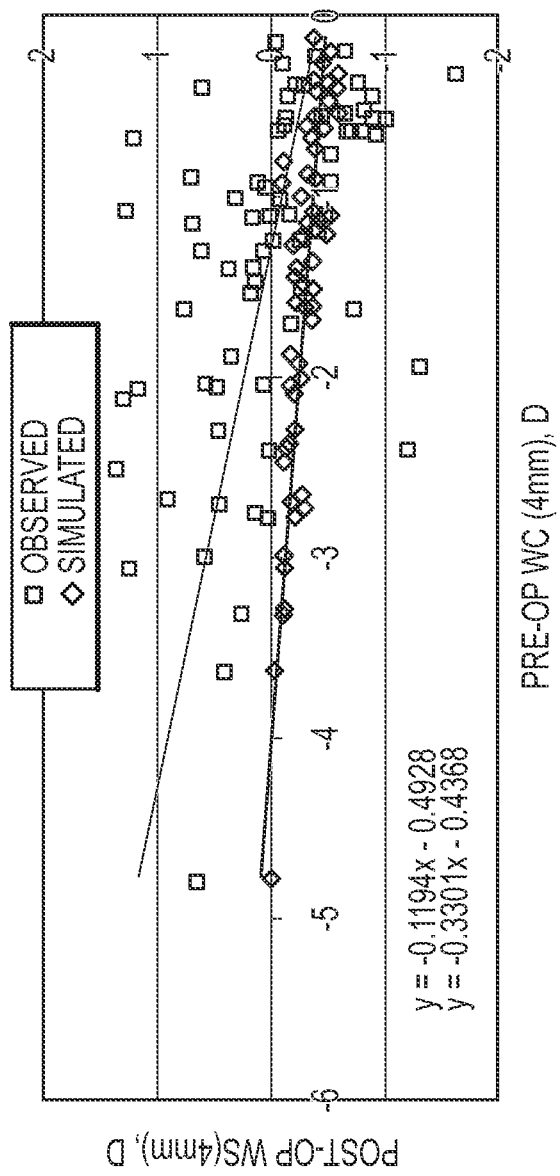
FIG. 53 illustrates aspects of treatment validation systems and methods according to embodiments of the present invention.

Techniques as disclosed herein can also explain at least partially (about one third) of a cylinder coupling effect (e.g. post-operative sphere vs. pre-operative cylinder trend). FIG. 53 depicts a comparison between simulated and observed post-operative (6M) sphere vs. pre-operative cylinder tends for myopia eyes (with WFD=6 mm), where WFD represent wavefront diameter.

It can be seen that certain vision conditions, including for example myopia, the presence of pre-operative cylinder can affect the post-operative sphere outcome. In many cases, a greater pre-operative cylinder (in the minus cylinder notation) can correspond to a greater sphere post-operative over-correction (hyperopic shift). By using certain data (e.g. clinical data), it is possible to evaluate the final outcome and make the appropriate adjustment.

Figure 53A:
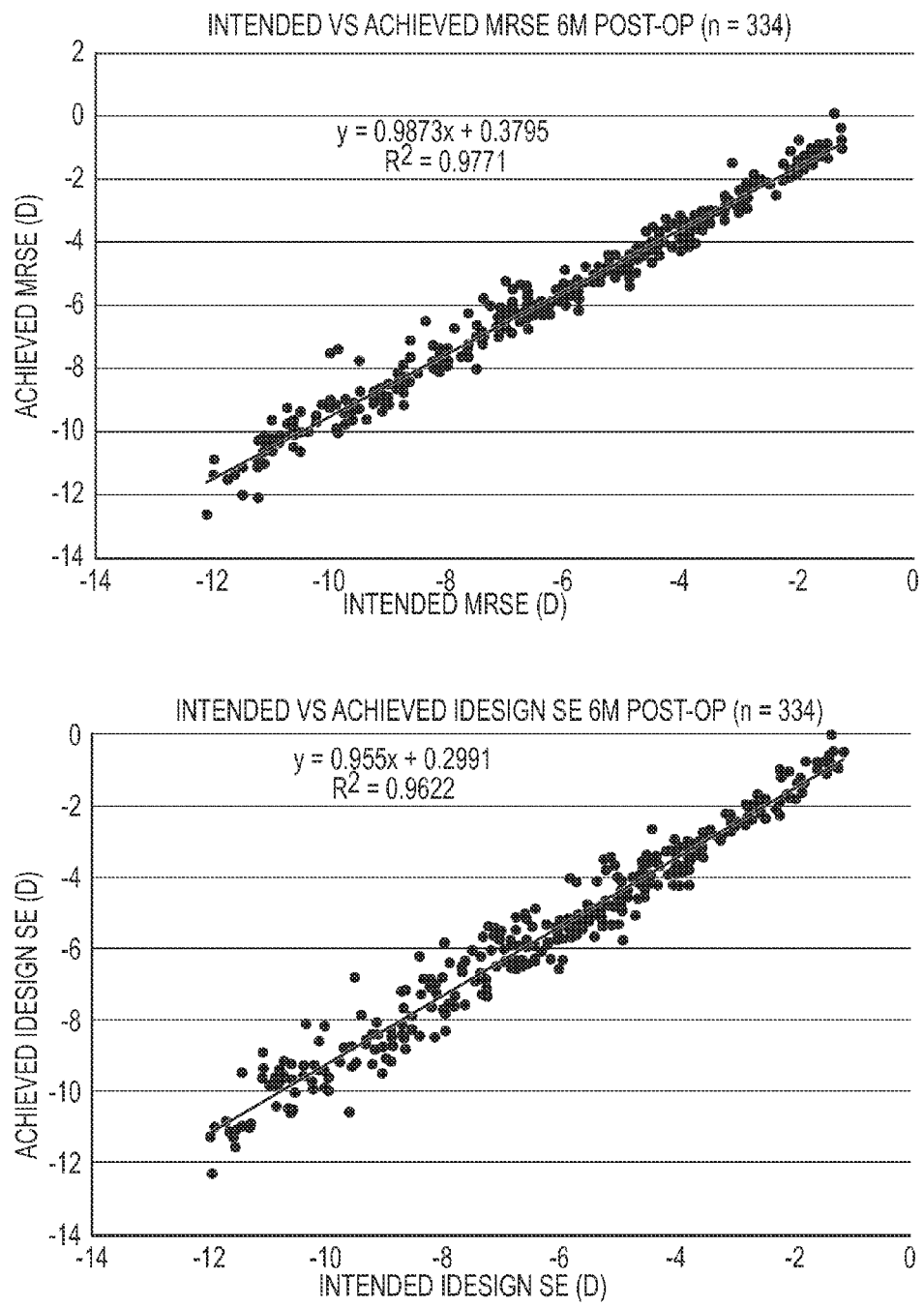
FIG. 53A depicts aspects of treatment validation systems and methods according to embodiments of the present invention.
Figure 53B:
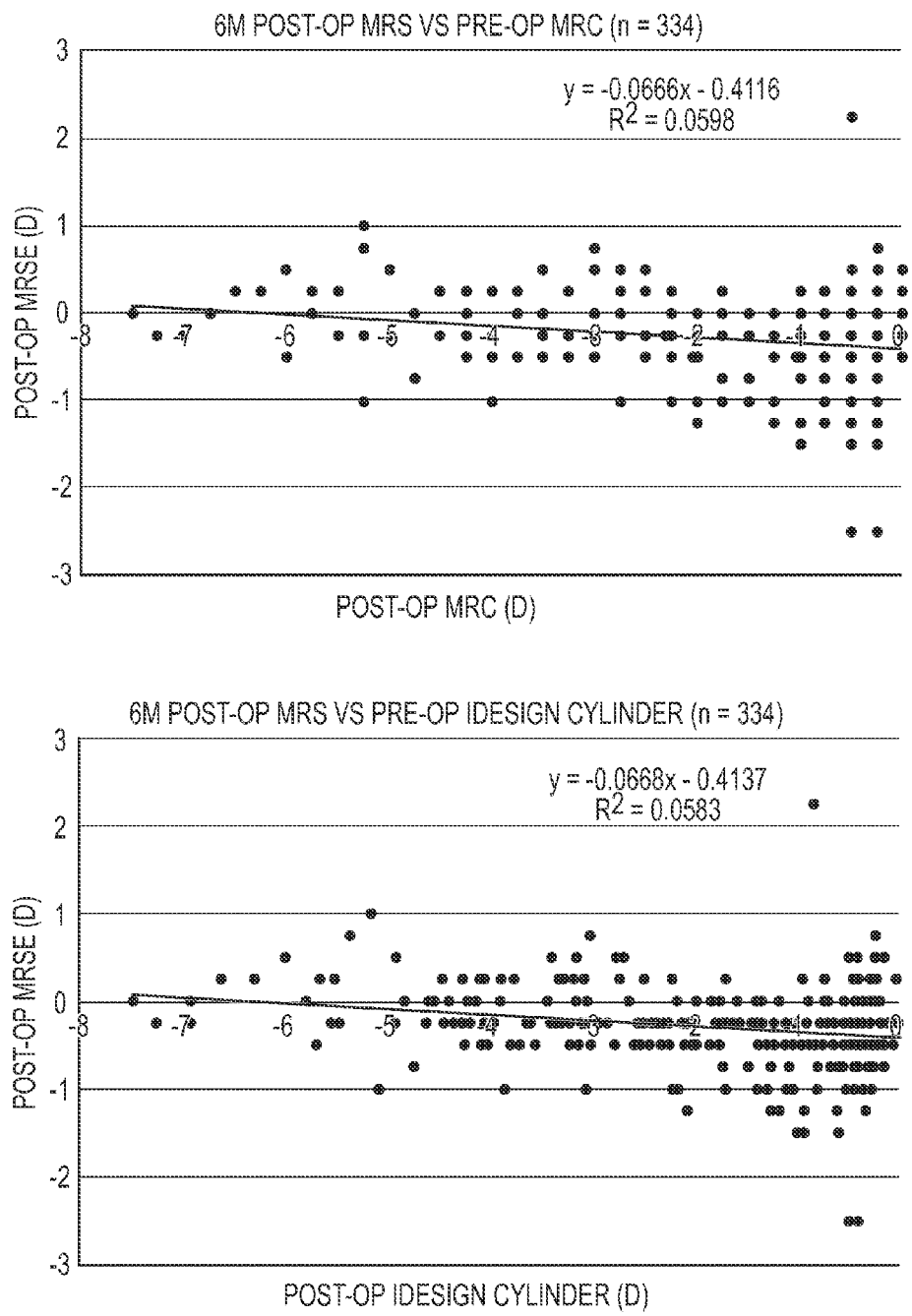
FIG. 53B depicts aspects of treatment validation systems and methods according to embodiments of the present invention.

FIG. 53A depicts results from a study involving 334 eyes. A plot of the intended versus achieved is provided for Manifest (upper panel) and iDesign SE (lower panel). As shown here, the slope is relatively close to unity but there is an offset of about 0.38 D for MRSE and 0.30 D for wavefront refraction in spherical equivalent (WRSE). In addition, a residual coupling (post-op sphere versus pre-op cylinder) can still be seen, again, with manifest and iDesign refractions. The residual slope is about −0.067, as depicted in FIG. 53B.

Figure 53C:
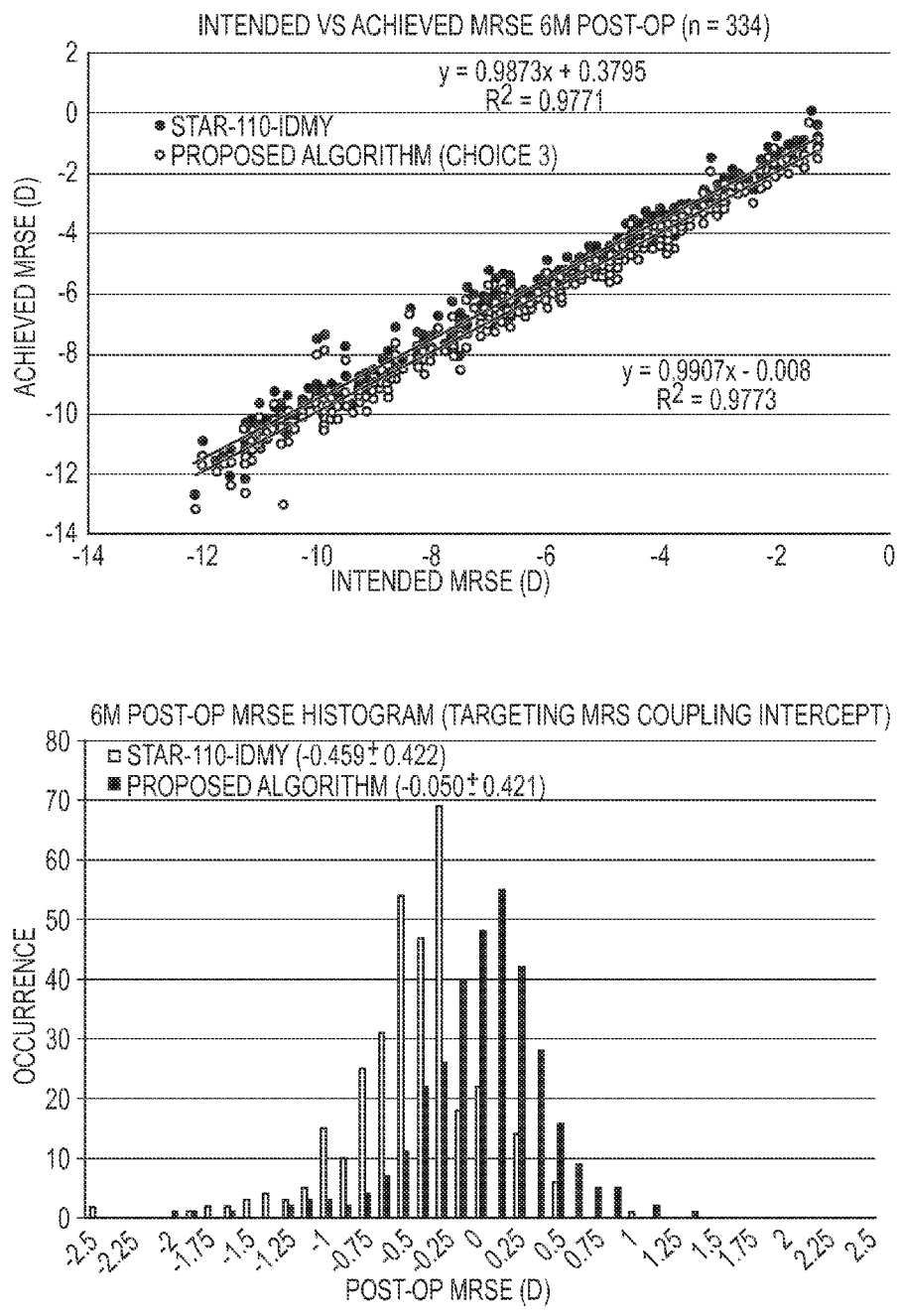
FIG. 53C depicts aspects of treatment validation systems and methods according to embodiments of the present invention.

To remove the residual cylinder coupling slope and intercept, the following algorithm is proposed, MRS target adjustment=−0.38−0.28*idc0, where idc0 stands for pre-operative iDesign cylinder at zero vertex. With this algorithm, the expected outcome as compared to the actual outcome (intended vs achieved) can be shown as depicted in FIG. 53C (upper panel). As shown here, the new slope is closer to unity and the intercept is zero or close to zero. With this algorithm, the expected post-op mean MRSE can be −0.05 D, and post-op mean MRS can be +0.12 D. The distribution of the refractive outcome can be shown in FIG. 53C (lower panel).

Accordingly, an exemplary method of determining a vision treatment for an eye of a patient can include receiving or obtaining a pre-operative cylinder value for the eye of the patient, and determining the vision treatment for the eye, where the vision treatment includes a sphere value that is based on the pre-operative cylinder value. The sphere value of the vision treatment can be determined based on the formula $S=-0.28C-0.38$, where S is the sphere value and C is the pre-operative cylinder value.

Additional Aspects Related to Reduction of Post-Surgical Spherical Aberration

Embodiments of the present invention encompass systems and methods for reducing or eliminating spherical aberration that may be induced by surgical treatments for myopia. Often, such approaches can be based on techniques that involve scaling a treatment algorithm such that with an SA reduction algorithm, it is possible to obtain a slope of unity in the intended vs achieved MRSE plot. Clinical data has been obtained which confirms such slopes are at unity or substantially at unity. FIGS. 53A-58 encompass data obtained from an iDesign™ US IDE clinical trial (e.g. which may not include an SA reduction algorithm). Embodiments of the present invention encompass the implementation of algorithms to remove or reduce a cylinder coupling effect. As discussed elsewhere herein, a coupling effect algorithm can be based on the relationship $S=-0.28 C-0.38$ for a sphere adjustment in a pre-operative refraction. Such approaches can achieve a near unity slope in the intended vs achieved MRSE plot. At the same time, it is observed that cylinder coupling is reduced or eliminated. The contents of FIGS. 53A-58 support scaling approaches such as those depicted in FIGS. 41 and 42.

As discussed elsewhere herein, diagnostic systems such as WaveScan® and iDesign™ devices can be used to evaluate spherical aberration in an eye of a patient. For example, such diagnostic devices can assess target induced spherical aberration in a post-operative patient. Spherical aberration can correspond to a fourth order rotationally symmetric Zernike term in the description of wavefront aberrations of an eye. An exemplary iDesign™ diagnostic device can incorporate multiple measurements, including wavefront aberrometry measurements, corneal topography measurements, autorefractometry measurements, keratometry measurements, and pupillometry measurements.

As shown in FIG. 54, a statistically significant trend in myopic treatments can be observed for the induction of (primary) spherical aberration following a laser vision correction procedure such as certain CustomVue® Laser-Assisted in situ Keratomileusis (LASIK) treatments. FIG. 54 (upper panel) depicts results at 6 months post-operative using a WaveScan® technique, and FIG. 54 (lower panel) depicts results at 6 months post-operative using an iDesign™ technique. As shown here, the slope for myopia can be similar, with a −0.031× value in the upper panel (WaveScan®), and a −0.0339× value in the lower panel (iDesign™)

Various mechanisms may be implicated in the induction of spherical aberration in laser vision correction, including for example (i) the induction of primary SA due to a target shape as discussed elsewhere herein, (ii) biomechanical changes such as peripheral stromal thickening or peripheral effects associated with flap cutting, (iii) peripheral underablation for example which may be associated with peripheral laser energy loss that is not property accounted for, and (iv) epithelial remodeling. According to some embodiments, reducing or eliminating the induction of post-operative SA may involve increasing the amount of ablation performed in the periphery of the target shape.

Figure 55:
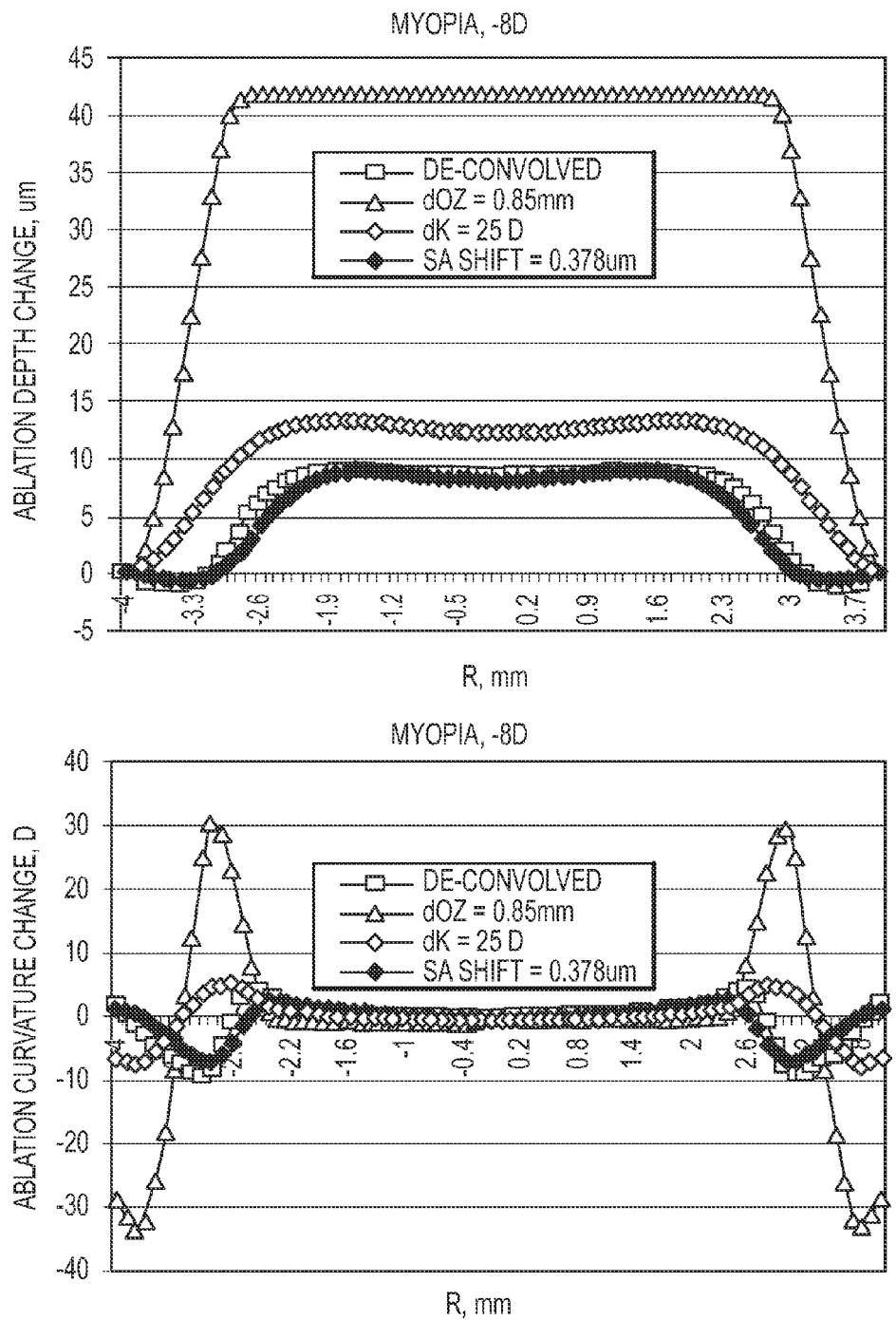
FIG. 55 depicts aspects of treatment validation systems and methods according to embodiments of the present invention.

FIG. 55 depicts aspects of differential shapes relative to a reference ablation profile, for ablation depth difference (upper panel) and ablation curvature difference (lower panel). As shown here, different shape options (de-convolved, dOZ, dK, and SA shift) can have different effects (e.g. impact on ablation depth or ablation curve) in the context of surgical procedures for reducing spherical aberration.

The dOZ line corresponds to an increase or extension in optical zone. As discussed elsewhere herein, a target shape or ablation target profile can include an optical zone and a transition zone. The aggregate of the optical zone and transition zone may be referred to as an ablation zone, corresponding to the entire corneal region covered by a laser ablation. The optical zone may refer to a corneal region which received a full intended refractive treatment. A transition zone may refer to a corneal region outside of the optical zone but inside of the ablation zone.

As an illustration, to obtain a 6 mm optical zone that has minimal or no spherical aberration, it may be desirable to extend or increase the optical zone by 0.85 mm (e.g. to 6.85 mm) and ablate a larger zone (e.g. 8.85 mm). As such, there may be a transition zone peripheral to the optical zone (e.g. transition zone of 2 mm). Exemplary OZ×AZ parameters can include based values of 6 mm×8 mm for myopia and 6 mm×9 mm for hyperopia and mixed astigmatism. As depicted here, however, increasing the optical zone can increase the ablation depth (e.g. to about 40 µm or more for an 8D ablation) to a greater extent than the other techniques. Because in some cases it may be desirable to select treatments having lower ablation depths rather than higher ablation depths, it may be preferable to use other options as an alternative to increasing or extending the optical zone. For example, the deconvolution line indicates that a deconvolution approach has a minimal impact on ablation depth (e.g. less than 10 µm) and is consistent with an expected physiological response.

Similarly, the SA shift (e.g. increase SA by 0.378 µm for −8 Diopters) line indicates that an approach involving (primary) SA shift also has a minimal impact on ablation depth (e.g. less than 10 µm). Put another way, it is possible to add 0.378 µm to an initial SA value to obtain a new SA value, where the initial SA value corresponds to pre-operative SA.

As shown in the upper panel of FIG. 55, the dK line (e.g. increase in keratometry value, for example 25 Diopters) indicates that an approach involving an increase in keratometry values can provide an intermediate increase in ablation depth, such that the ablation depth change is lower than the dOZ line and greater than the deconvolution and SA shift lines. In other words, it is possible to add 25 Diopters to an initial keratometry Diopter value to obtain a new keratometry Diopter value, and the initial value can be obtained by a keratometer or by an iDesign™ device.

The lower panel of FIG. 55 indicates that an approach involving an increase or extension in optical zone (dOZ line) can involve an ablation shape curvature change profile that is more extreme than the ablation shape curvature change profiles observed with other techniques (deconvolution, increase in keratometry, SA shift).

In some cases, it is possible to combine the use of a deconvolution kernel (as discussed elsewhere herein) with a shape option technique corresponding to the SA shift depicted in FIG. 55. The SA shift can be based on a correlation between postoperative spherical equivalent and preoperative spherical equivalent. For example, a decreased postoperative spherical aberration can correspond to an increased preoperative spherical aberration.

In some cases, it is possible to combine the use of a deconvolution kernel with a shape option technique corresponding to the increased or shifted keratometry value depicted in FIG. 55. As depicted here, for example, the increased keratometry value can correspond to an increase of 25 D to every eye.

In some cases, it is possible to combine the use of a deconvolution kernel with a shape option technique corresponding to the SA shift as well as a shape option technique corresponding to the increased or shifted keratometry values.

FIG. 55 depicts ablation depth and curvature changes for the treatments in isolation (e.g. a pure deconvolution approach, a pure optical zone extension approach, a pure keratometry increase approach, and a pure spherical aberration shift approach). As shown here, an optical zone increase/extension approach can be the most costly in terms of tissue depth.

According to some embodiments, when combining approaches, it may be possible to selectively weight or adjust the impact provided by the individual approaches. For example, it is possible to use a 25D increase in keratometry value (as depicted in FIG. 55) in combination with a percentage of the 0.378 um SA shift (also depicted in FIG. 55). For both keratometry and pre-op SA, the simulation can use the addition of keratometry value as a multiple of the pre-operative SE, for example, 0.5×, 1.0×, 2.0×, and the like. Hence, for example, where keratometry value increases by 25 D, there may be an increase, such as a percentage of preoperative SE, e.g. 0.5×, 1.0×, 2.0×, and the like. Similarly, it is possible to use a multiple for the pre-operative SA values, such as 1.2×, 1.5×, 2.0×, and the like (e.g. larger than the measured value).

Hence, FIG. 55 depicts a comparison of outcomes corresponding to various approaches of reducing SA, as discussed elsewhere herein.

An exemplary deconvolution approach can involve applying a filter (such as a low pass filter or optimized linear filter) to an original treatment target profile so as to obtain a deconvolved target profile. As discussed elsewhere herein, it is possible to generate a vision treatment based on a deconvolved target profile. According to some embodiments, a filter (deconvolution) approach is based on a biological mechanism (e.g. related to healing). In some cases, a filter approach can be implemented to address any of a wide variety of indications, including multi-focal corrections. Filter approaches are found to provide a good fit to observed data (e.g. from clinical studies). According to some embodiments, an increase in ablation depth associated with the deconvolution approach may correspond to a preservation of central curvature in the deconvolved target profile. Exemplary aspects of ablation depth are depicted in FIG. 56 (lower panel).

As shown in the upper panel of FIG. 56, (which corresponds to 6 month postoperative data) the observed relationship between postoperative spherical aberration (SA) and preoperative manifest refraction spherical equivalent (MRSE) has a slope of about −0.0353. The simulated relationship between postoperative SA and preoperative MRSE has a slope of about −0.0445. The simulated outcome can be obtained using a kernel with three parameters and two correlations. The expected values can be obtained by using the same kernel that is used to obtain the simulated values. The expected relationship between postoperative SA and preoperative MRSE has a slope of about −0.0103, which is lower than the slope for the observed data and also lower than the slope for the simulated data. As shown here, the observed and simulated slope values are similar, and the observed data values present a higher spread.

As illustrated in the lower panel of FIG. 56, the extra ablation depth due associated with a deconvolution approach can correspond to the preoperative MRSE. For example, a more negative preoperative MRSE can correspond to a higher extra ablation depth, and a less negative preoperative MRSE can correspond to a lower extra ablation depth. In some cases, a relatively small extra ablation depth can correspond to improved or enhanced safety.

In an exemplary clinical study, the right and left eyes of each patient present similar or substantially similar refraction properties. For an individual patient, one eye is treated using a test deconvolution algorithm and the other eye is treated using a reference deconvolution algorithm. In some cases, the test eye can be treated using implementation of an SA reduction algorithm, on top of a CustomVue™ algorithm. The control (or reference) eye can be treated using a CustomVue™ algorithm only. Data from an SA reduction study (e.g. implementing the deconvolution algorithm on top of a CustomVue™ algorithm) can be different from iDesign™ data from a US IDE clinical trial (which implements a CustomVue™ algorithm). A paired eye randomized comparison can be performed to evaluate the test and reference approaches. The patients of the clinical study present with a variety of myopia conditions. In some cases, patients have myopia with MRSE within a range from −4D to −12D. In some cases, patients have high astigmatism. Patients can be evaluated before treatment, and also following treatment, for example at one day postoperation, one week postoperation, one month postoperation, and three months postoperation. Treatment parameters can involve, for example, a 6 mm optical zone and an 8 mm ablation zone.

Study variables can include high order aberrations such as spherical aberration (Z4) from wavefront measurements (e.g. Zernike technique), uncorrected visual acuity (UCVA), best corrected visual acuity (BCVA), refraction (manifest and wavefront), optical coherence tomography (OCT), and subjective questionnaires. In some cases, some patients present with myopia with spherical equivalent measurements within a range from 4D to 6D, some patients present with myopia with spherical equivalent measurements within a range from 6D to 8D, and some patients present with myopia with spherical equivalent measurements within a range from 8D to 10D. Less common are patients presenting with myopia with spherical equivalent measurements within a range from 10D to 12D. The D values discussed in the paragraph are absolute values (e.g. positive nomenclature) corresponding to negative D values such as those depicted in FIG. 56. Hence, where this paragraph mentions a range of 10D to 12D, the values are −10 D to −12 D.

Figure 57:
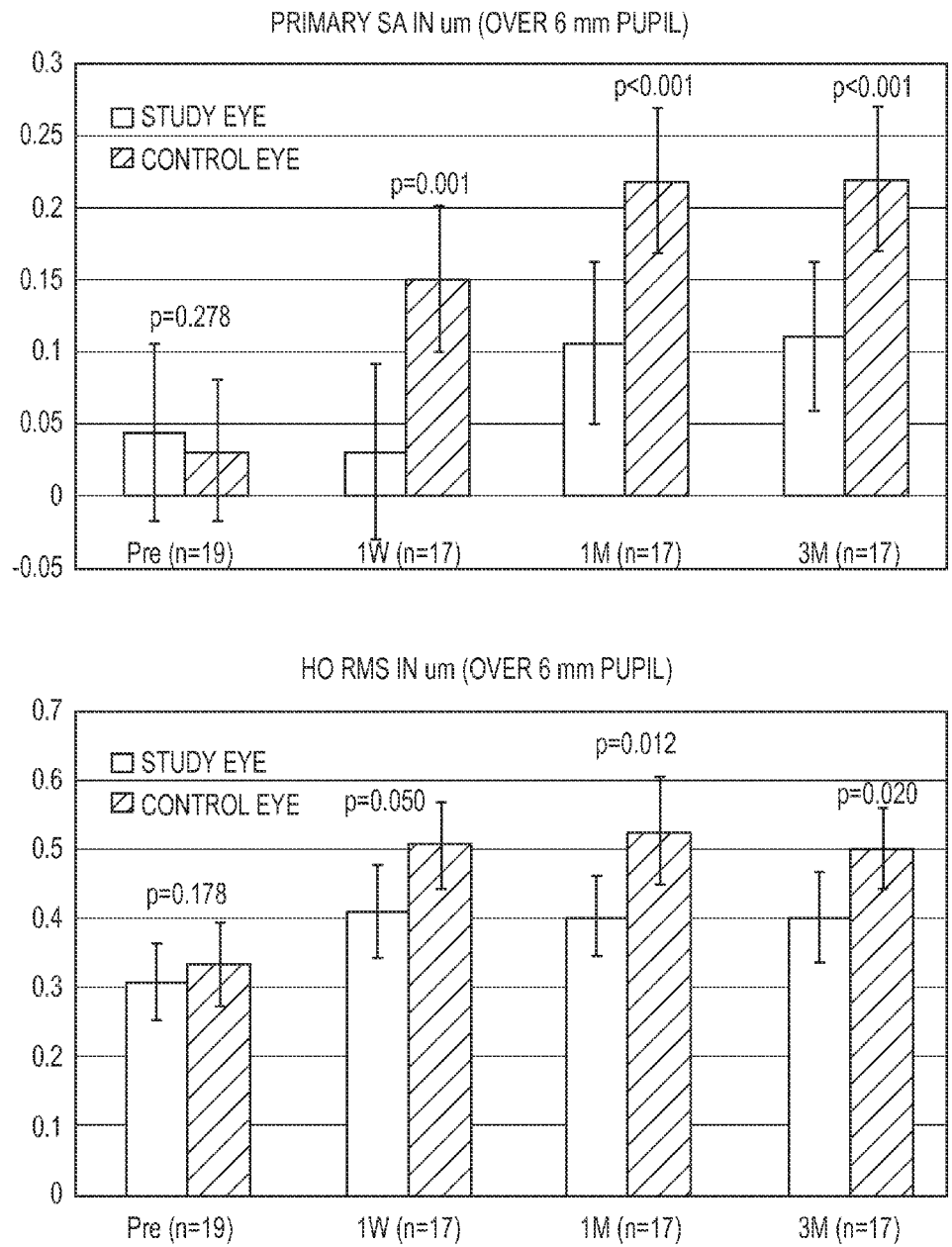
FIG. 57 depicts aspects of treatment validation systems and methods according to embodiments of the present invention.

FIG. 57 provides an analysis of postoperative diagnostic (e.g. wavefront) measurements, for example high order aberrations. The mean and standard deviation (standard error) are depicted. The error bars are 1.96× the standard error (e.g. corresponding to 95% confidence levels). The high order aberration evaluated in the upper panel include a $4^{th}$ order Zernike, and specifically the primary spherical aberration ($Z_4^0$). The high order aberrations evaluated in the lower panel include $3^{rd}$ order to $6^{th}$ radial order Zernikes (e.g. $Z_3$ to $Z_6$), which for example can include the $6^{th}$ to $27^{th}$ terms, such as secondary spherical aberration ($Z_6^0$). Zernike modes of the third order and higher can be considered as high order aberrations, whereas Zernike modes of the zeroth through second order can be considered as low order aberrations.

When evaluating the control and study eyes in the upper panel of FIG. 57, it can be seen that the primary spherical aberration ($Z_4^0$) is much lower in the study eyes as compared to the control eyes.

A comparison of the upper and lower panes of FIG. 57 reveals that the difference in postoperative high order aberrations between the reference control eyes and the test study eyes is significantly impacted by the primary spherical aberration. Hence, the other high order aberrations can have less of an impact on or contribution to the overall high order aberrations. In this way, it can be seen that postoperative primary spherical aberration can be a primary contributor to the overall postoperative aberrations, and that the test study treatment approach can produce a significantly lower amount of postoperative spherical aberration as compared to the reference control treatment approach. It is also observed (but not shown in FIG. 57) that MRSE outcomes for test and control eyes were similar at three months postoperation.

When performing a vision treatment, it is possible to create a corneal flap using, for example, a femtosecond laser or a mechanical microkeratome. The results in the upper and lower panels are obtained using a femtosecond laser. As shown here, there is an increase in primary spherical aberration when comparing the one week and one month results, and a stabilization of primary spherical aberration when comparing the one month and three month results.

As discussed elsewhere herein, it is possible to implement a kernel based on a correlation between postoperative defocus and preoperative defocus (e.g. postoperative defocus as a function of preoperative defocus). Similarly, it is possible to implement a kernel based on a correlation between postoperative spherical aberration and preoperative manifest refraction spherical equivalent. In some cases, it is possible to generate a kernel based on either or both of these correlations.

In some cases, it is possible to generate a kernel based on additional correlations. For example, a kernel can be based on a correlation between postoperative spherical aberration and preoperative spherical aberration. Similarly, a kernel can be based on a correlation between postoperative secondary spherical aberration and preoperative manifest refraction spherical equivalent.

Defocus (also known as spherical equivalent) refers to the center mode of the three Zernike second radial order aberration modes. Specifically, defocus refers to the $Z_2^0$ aberration, and corresponds with the average sphere power of the wavefront. The remaining two second order modes, $Z_2^{-2}$ and $Z_2^2$, correspond to the cylinder power. Collectively, the three second radial order aberrations can characterize the curvature or vergence of a wavefront.

Figure 58:
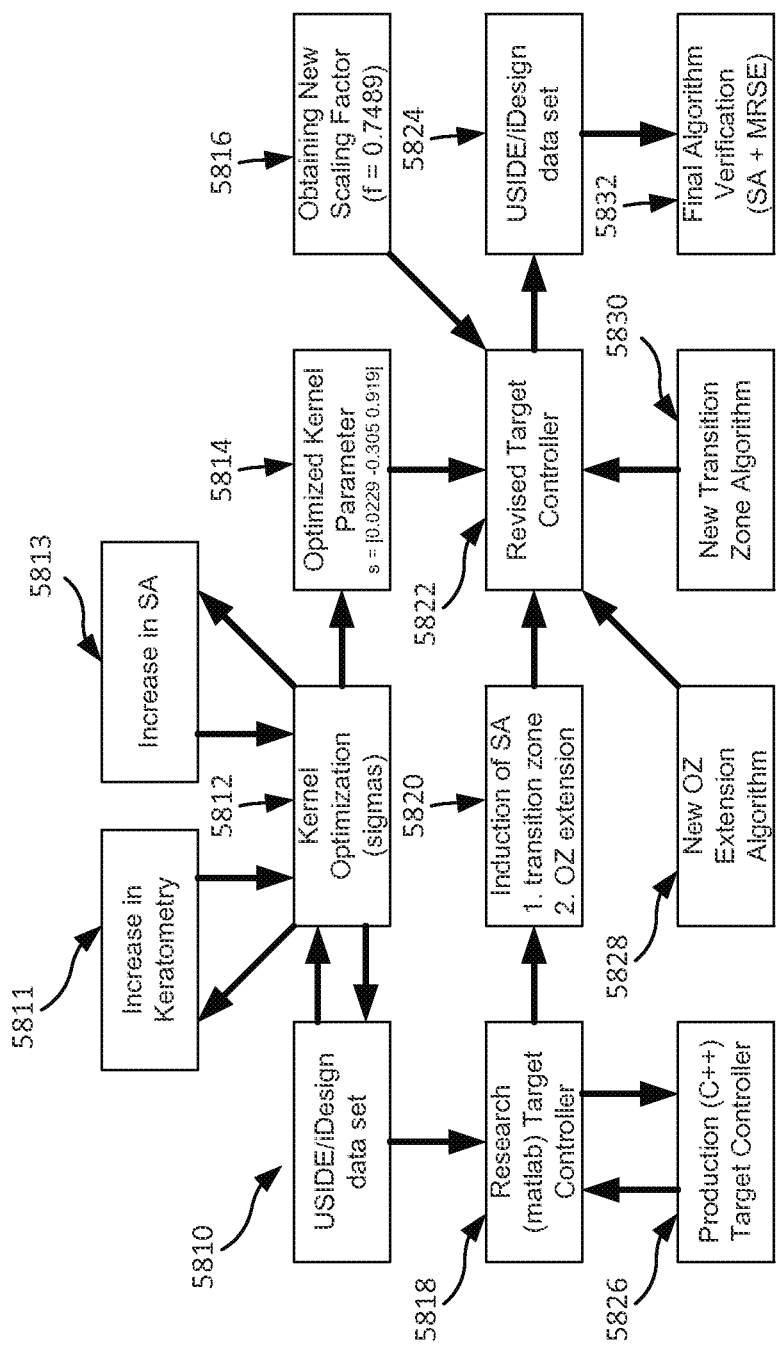
FIG. 58 depicts aspects of treatment validation systems and methods according to embodiments of the present invention.

FIG. 58 schematically illustrates techniques for obtaining and implementing a modified target shape, according to embodiments of the present invention. As shown here, study data can be used to derive parameters of a kernel for simulating a low-pass filtering process, for corneal healing and the like. Embodiments may also include optimizing the parameters by using a clinical data set. These techniques may also involve evaluating the extent to which observed spherical aberration is attributed to error, due to an imperfect optical treatment shape. In some instances, methods may also include addressing target shape induced SA by providing transition zone adjustments, optical zone extension adjustments, or both. In some cases, a deconvolution (e.g. inverse of low pass filter) may boost the total treatment depth. Techniques may also involve running a revised target controller (e.g. without a cosine effect) with a low-pass filter, to evaluate the extent to which SA for a clinical data set correlates with observed SA, or to evaluate the extent to which post-operative refractions correlate with what is expected based on the clinical data. The Optimized Kernel Parameter can be related to LPF, and sigma can represent the diffusion coefficient. Hence, as shown in FIG. 58, with a clinical data set 5810, a kernel optimization process 5812 can be employed such that simulation can be performed to obtain the optimized kernel parameter (sigma) 5814.

As discussed elsewhere herein, exemplary systems and methods can implement dual scale kernel techniques, triple scale kernel techniques, and other multi-scale kernel techniques (e.g. multiple parameters in a healing kernel). According to some embodiment, the value of sigma= [0.0229, −0.305, 0.919] was found to correspond to an optimized kernel parameter. Specifically, a three parameter case where the general optimized linear filter (OLF) formula is given by:

$$K(xi, yi) = \frac{1}{1 + (r/s2)^2 + (r/s4)^4 + (r/s6)^6}.$$

Here, s2, s4, and s6 are the three parameters, where s2=0.0229, s4=−0.305, and s6=0.919.

For a practical implementation, the clinical data 5810 can be sent to a research version of Target Controller 5818 (in matlab), which is identical to the production Target Controller 5826 (in C++). It can be derived from the Target Controller 5818 that induction of spherical aberration (SA) 5820 occurs in the target so a removal of a target-induced SA can be implemented in a revised Target Controller 5822. The revised Target Controller 5822 can implement a new optical zone (OZ) extension algorithm 5828, and a new Transition Zone algorithm 5830. With all the revisions, the Revised Target Controller 5822 can be tested with data set 5824, which can be the same as (or different from) data set 5810. The Revised Target Controller 5822 can then be verified with SA and MRSE (manifest refraction in spherical equivalent) in 5832.

According to some embodiments, an optimized kernel parameter and/or scaling factor can be modified or obtained based on techniques involving an increase in keratometry and/or an increase in spherical aberration. For example, as depicted in FIG. 58, a kernel optimization process 5812 can take into account an increase in keratometry 5811 and/or an increase in SA 5813, such that simulation can be performed to obtain the optimized kernel parameter (sigma) 5814. As shown here, values for s=[0.0229−0.305 0.919] and f=0.7489 can be implemented in a production code, for example for use in clinical trials and other treatments.

All patent filings (including patents, patent applications, and patent publications), scientific journals, books, treatises, technical references, and other publications and materials discussed in this application are incorporated herein by reference in their entirety for all purposes.

A variety of modifications are possible within the scope of the present invention. A variety of parameters, variables, factors, and the like can be incorporated into the exemplary method steps or system modules. While the specific embodiments have been described in some detail, by way of example and for clarity of understanding, a variety of adaptations, changes, and modifications will be obvious to those of skill in the art. Although the invention has been described with specific reference to a wavefront system using lenslets, other suitable wavefront systems that measure angles of light passing through the eye may be employed. For example, systems using the principles of ray tracing aberrometry, tscherning aberrometry, and dynamic skiascopy may be used with the current invention. The above systems are available from TRACEY Technologies of Bellaire, Tex., Wavelight of Erlangen, Germany, and Nidek, Inc. of Fremont, Calif., respectively. The invention may also be practiced with a spatially resolved refractometer as described in U.S. Pat. Nos. 6,099,125; 6,000,800; and 5,258,791, the full disclosures of which are incorporated herein by reference. Treatments that may benefit from the invention include intraocular lenses, contact lenses, spectacles and other surgical methods in addition to refractive laser corneal surgery.

Each of the calculations or operations discussed herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like. While the exemplary embodiments have been described in some detail, by way of example and for clarity of understanding, those of skill in the art will recognize that a variety of modification, adaptations, and changes may be employed.

The methods and apparatuses of the present invention may be provided in one or more kits for such use. The kits may comprise a system for determining a treatment for an eye of a patient, and instructions for use. Optionally, such kits may further include any of the other system components described in relation to the present invention and any other materials or items relevant to the present invention. The instructions for use can set forth any of the methods as described herein.

While the above provides a full and complete disclosure of exemplary embodiments of the present invention, various modifications, alternate constructions and equivalents may be employed as desired. Consequently, although the embodiments have been described in some detail, by way of example and for clarity of understanding, a variety of modifications, changes, and adaptations will be obvious to those of skill in the art. Accordingly, the above description and illustrations should not be construed as limiting the invention, which can be defined by the claims.

What is claimed is:

1. A method of determining a vision treatment for an eye of a patient, the method comprising:
   receiving, at an input, an original target profile for the eye of the patient;
   obtaining a deconvolved target profile based on the original target profile and a low pass filter;
   obtaining a scale factor, wherein the scale factor is based on a low order refraction measure of a test eye population and a low order refraction measure of a convolved test eye population profile, and wherein the convolved test eye population profile is based on a convolution of the test eye population profile;
   determining a scaled target profile based on the deconvolved target profile and the scale factor; and
   determining the vision treatment based on the scaled target profile.

2. The method according to claim 1, wherein the low pass filter is an optimized linear filter.

3. The method according to claim 1, wherein the scale factor has a value within a range from about 0.4 to about 0.8.

4. The method according to claim 1, wherein the scale factor has a value of about 0.7489.

5. The method according to claim 1, wherein the low order refraction measure of the test eye population profile comprises a first manifest refraction spherical equivalent measure and the low order refraction measure of the convolved test eye population profile comprises a second manifest refraction spherical equivalent measure.

6. The method according to claim 5, wherein the first manifest refraction spherical equivalent measure is a 4 mm refraction measure and the second manifest refraction spherical equivalent measure is a 4 mm refraction measure.

7. A method of determining a vision treatment for an eye of a patient, the method comprising:
   receiving, at an input, an original target profile for the eye of the patient;
   determining a first low order refraction measure based on the original target profile;
   obtaining a deconvolved target profile based on the original target profile and a low pass filter;
   determining a second low order refraction measure based on the deconvolved target profile;
   determining a scale factor based on a comparison between the first and second low order refraction measures;
   determining a scaled target profile based on the deconvolved target profile and the scale factor; and
   determining the vision treatment based on the scaled target profile.

8. The method according to claim 7, wherein the first low order refraction measure comprises a first manifest refraction spherical equivalent measure and the second low order refraction measure comprises a second manifest refraction spherical equivalent measure.

9. The method according to claim 8, wherein the first manifest refraction spherical equivalent measure is a 4 mm refraction measure and the second manifest refraction spherical equivalent measure is a 4 mm refraction measure.

10. The method according to claim 7, wherein the first low order refraction measure comprises a first sphere measure and the second low order refraction measure comprises a second sphere measure.

11. The method according to claim 7, wherein the first low order refraction measure comprises a first cylinder measure and the second low order refraction measure comprises a second cylinder measure.

12. A method of determining a vision treatment for an eye of a patient, the method comprising:
   receiving, at an input, an original target profile for the eye of the patient;
   obtaining a first healed profile based on the original target profile;
   obtaining a deconvolved target profile based on the original target profile and a low pass filter;
   obtaining a second healed profile based on the deconvolved target profile;
   determining a first low order refraction measure based on the first healed profile;
   determining a second low order refraction measure based on the second healed profile;
   determining a scale factor based on a comparison between the first and second low order refraction measures;
   determining a scaled target profile based on the deconvolved target profile and the scale factor; and
   determining the vision treatment based on the scaled target profile.

13. The method according to claim 12, wherein the first low order refraction measure comprises a first manifest refraction spherical equivalent measure and the second low order refraction measure comprises a second manifest refraction spherical equivalent measure.

14. The method according to claim 13, wherein the first manifest refraction spherical equivalent measure is a 4 mm refraction measure and the second manifest refraction spherical equivalent measure is a 4 mm refraction measure.

15. The method according to claim 12, wherein the first low order refraction measure comprises a first sphere measure and the second low order refraction measure comprises a second sphere measure.

16. The method according to claim 12, wherein the first low order refraction measure comprises a first cylinder measure and the second low order refraction measure comprises a second cylinder measure.

17. A method of determining a vision treatment for an eye of a patient, the method comprising:
   receiving, at an input, an original target profile for the eye of the patient;
   obtaining a deconvolved target profile based on the original target profile and a low pass filter;
   obtaining a scale factor, wherein the scale factor is based on a low order refraction measure of a test eye population and a low order refraction measure of a convolved test eye population profile, and wherein the convolved test eye population profile is based on a convolution of the test eye population profile;
   determining a scaled target profile based on the deconvolved target profile and the scale factor;
   adjusting a sphere parameter of the scaled target profile based on a pre-operative cylinder measurement of the eye of the patient; and determining the vision treatment based on the adjusted target profile.

\* \* \* \* \*